(12) United States Patent
Hill

(10) Patent No.: US 12,378,548 B2
(45) Date of Patent: Aug. 5, 2025

(54) METHODS AND COMPOSITIONS FOR CELL-FREE CLONING

(71) Applicant: Elegen Corporation, Los Altos, CA (US)

(72) Inventor: Matthew Hill, Los Altos, CA (US)

(73) Assignee: Elegen Corporation, Menlo Park, CA (US)

( * ) Notice: Subject to any disclaimer, the term of this patent is extended or adjusted under 35 U.S.C. 154(b) by 0 days.

(21) Appl. No.: 18/439,353

(22) Filed: Feb. 12, 2024

(65) Prior Publication Data

US 2024/0229016 A1   Jul. 11, 2024

Related U.S. Application Data

(63) Continuation of application No. 18/336,283, filed on Jun. 16, 2023, now Pat. No. 11,993,771, which is a continuation of application No. PCT/US2022/071707, filed on Apr. 13, 2022.

(60) Provisional application No. 63/174,192, filed on Apr. 13, 2021.

(51) Int. Cl.
*C12N 15/10* (2006.01)

(52) U.S. Cl.
CPC .................... *C12N 15/1065* (2013.01)

(58) Field of Classification Search
CPC .................................................. C12N 15/1065
USPC ............................................................ 506/4
See application file for complete search history.

(56) References Cited

U.S. PATENT DOCUMENTS

| | | | |
|---|---|---|---|
| 4,988,617 | A | 1/1991 | Landegren et al. |
| 5,242,794 | A | 9/1993 | Whiteley et al. |
| 5,494,810 | A | 2/1996 | Barany et al. |
| 6,582,938 | B1 | 6/2003 | Su et al. |
| 6,664,112 | B2 | 12/2003 | Mulligan et al. |
| 7,164,992 | B1 | 1/2007 | Mulligan et al. |
| 8,137,906 | B2 | 3/2012 | Schatz |
| 9,839,894 | B2 | 12/2017 | Banyai et al. |
| 10,301,672 | B2 | 5/2019 | Su'etsugu et al. |
| 10,504,615 | B2 | 12/2019 | Bagaev et al. |
| 10,632,445 | B2 | 4/2020 | Banyai et al. |
| 10,773,232 | B2 | 9/2020 | Banyai et al. |

(Continued)

FOREIGN PATENT DOCUMENTS

| | | |
|---|---|---|
| CA | 2468235 C | 5/2003 |
| EP | 1411122 B1 | 7/2008 |

(Continued)

OTHER PUBLICATIONS

Ball P. Synthetic biology: starting from scratch. Nature, (2004) 431: 624-626.

(Continued)

*Primary Examiner* — Aaron A Priest
*Assistant Examiner* — Randi Lynn Beil
(74) *Attorney, Agent, or Firm* — McDermott Will & Emery LLP

(57) ABSTRACT

The present disclosure provides methods and compositions for cell free cloning and polynucleotide production. In illustrative aspects, the methods of the present disclosure comprise the use of molecular barcodes and a dilution step. Moreover, some aspects of the instant disclosure relate to systems and kits comprising molecular barcodes for use with methods of cell free cloning and polynucleotide production.

30 Claims, 19 Drawing Sheets

Specification includes a Sequence Listing.

(56) References Cited

U.S. PATENT DOCUMENTS

| | | | |
|---|---|---|---|
| 2003/0228602 | A1 | 12/2003 | Parker et al. |
| 2010/0120038 | A1 | 5/2010 | Mir et al. |
| 2012/0258487 | A1 | 10/2012 | Chang et al. |
| 2018/0311637 | A1 | 11/2018 | Dabrowski et al. |
| 2018/0363029 | A1* | 12/2018 | Hindson ............ C12N 15/1065 |
| 2021/0254078 | A1 | 8/2021 | Hogan et al. |

FOREIGN PATENT DOCUMENTS

| | | | |
|---|---|---|---|
| WO | 2020/146425 A1 | 7/2010 | |
| WO | WO-2010148039 A2 * | 12/2010 | ......... C12N 15/1065 |
| WO | 2013/163263 A2 | 10/2013 | |
| WO | 2015/164432 A1 | 10/2015 | |
| WO | 2016/064856 A1 | 4/2016 | |
| WO | 2016/077123 A1 | 5/2016 | |
| WO | WO-2017079593 A1 * | 5/2017 | ......... C12N 15/1065 |
| WO | 2019/040599 A1 | 2/2019 | |
| WO | 2020/176548 A1 | 9/2020 | |
| WO | 2020/212391 A1 | 10/2020 | |
| WO | WO-2022087309 A1 * | 4/2022 | ......... C12N 15/1065 |

OTHER PUBLICATIONS

Chandran, S. Rapid Assembly of DNA via Ligase Cycling Reaction (LCR). In: Hughes, R. (eds) Synthetic DNA. Methods in Molecular Biology, (2017) vol. 1472. Humana Press, New York, NY. https://doi.org/10.1007/978-1-4939-6343-0_8.

Ciccarelli et al. Insertional gene synthesis, a novel method of assembling consecutive DNA sequences within specific sites in plasmids. Construction of the HIV-1 tat gene. Nucleic Acids Research. Oxford University Press, (1990) 18(5): 1243-1248.

Climie, Shane, and Daniel V. Santi. Chemical synthesis of the thymidylate synthase gene. *Proceedings of the National Academy of Sciences*, 87.2 (1990): 633-637.

El-Sagheer et al. Biocompatible artificial DNA linker that is read through by DNA polymerases and is functional in *Escherichia coli*. PNAS Early Edition, (2011) 108:28, 6 pages.

Engler et al. A One Pot, One Step, Precision Cloning Method with High Throughput Capability. PLoS One, (2008) 3(11): e3647.

Engler et al. Golden Gate Shuffling: A One-Pot DNA Shuffling Method Based on Type IIs Restriction Enzymes. PLoS One, (2009) 4(5): e5553.

Eren and Swenson. Chemical Synthesis and Expression of a Synthetic Gene for the Flavodoxin from Costridium MP*. The Journal of Biological Chemistry, (1989) 264(25): 14874-14879.

Feldman and Crutchfield. Measures of Statistical Complexity: Why? Physics Letters A, (1998) 238(4). 7 pages.

Gao et al. Thermodynamically balanced inside-out (TBIO) PCR-based gene synthesis: a novel method of primer design for high-®delity assembly of longer gene sequences. Nucleic Acids Research, (2003) 31(22): e143.

Gibson et al. Enzymatic assembly of DNA molecules up to several hundred kilobases. Nature Methods, (May 2009) 6(5):343-5.

Goldmann, T. "DNA-printing: Utilization of a Standard Inkjet Printer for the Transfer of Nucleic Acids to Solid Supports." J. Biochem. Biophys. Methods, (2000) 42: 105-110.

Gupta, et al. Studies on Polynucleotides, LXXXVII.* The Joining of Short Deoxyribopolynucleotides by DNA-Joining Enzymes. Institute for Enzyme Research, University of Wisconsin, Madison. Biochemistry, (1968) 60: 285-292.

Horton et al. Gene Splicing by Overlap Extension: Tailor-Made Genes Using the Polymerase Chain Reaction. Biotechniques, Mar. 2013;54(3):129-33. doi: 10.2144/000114017.

Hughes et al. Expression profiling using microarrays fabricated by an ink-jet oligonucleotide synthesizer. Nature Biotechnology, (Apr. 2001) 19: 342-347.

Kalman et al. Synthesis of a gene for human serum albumin and its expression in *Saccharomyces cerevisiae*. Nucleic Acids Research, (1990) 18(20):6075-81.

M. Li and P.M.B. Vitányi, An Introduction to Kolmogorov Complexity and Its Applications. DOI: 10.1007/978-0-387-49820-1_1, © Springer Science + Business Media, LLC. 2008.

Ling, et al. Approaches to DNA Mutagenesis: An Overview. Analytical Biochemistry, (Dec. 15, 1997) 254(2) :157-178.

Lipshutz et al. High density synthetic oligonucleotide arrays. Nature Genetics Supplement. (Jan. 1999) 21: 20-24.

Lockhart et al. Expressing what's on your mind: DNA arrays and the brain. Neuroscience-Nature Reviews.(Jan. 2001) 2: 63-68.

Lopez-Ruiz et al. A statistical measure of complexity. Physics Letters A. (Dec. 25, 1995) 209(5): 321-326.

Meselson, Matthew. On the Mechanism of Genetic Recombination between DNA Molecules. Journal of Molecular Biology. (Apr. 24, 1964) 9: 734-745.

Pogulis, et al. In Vitro Recombination and Mutagenesis by Overlap Extension PCR. In: Trower, M.K. (eds) In Vitro Mutagenesis Protocols. Methods In Molecular Medicine™. Humana Press. (1996) vol. 57. https://doi.org/10.1385/0-89603-332-5:167.

Qui et al. Mutation detection using Surveyor™ nuclease. BioTechniques. (2004) 36(4): 702-707.

Richmond et al. Amplification and assembly of chip-eluted DNA (AACED): a method for high-throughput gene synthesis. Nucleic Acids Research (2004) 32(17): 5011-5018.

Sandhu et al. Dual asymmetric PCR: one-step construction of synthetic genes. Biotechniques, 01 (Jan. 1992) 12(1):14-16.

Schmidt, Charlie. Synthetic gene firms evolve toward sustainable business? (Nov. 2006) 24(11): 1304.

Schofield et al. DNA Mismatch Repair: Molecular Mechanisms and Biological Function. Annual Review of Microbiology. (Volume publication date Oct. 2003) 57:579-608.

Shannon, Claude E. The Mathematical Theory of Communication. ACM SIGMOBILE Mobile Computing and Communications Review. (2001) 5(1): 3-55.

Smith, et al. Expression of a synthetic gene for horseradish peroxidase C in *Escherichia coli* and folding and activation of the recombinant enzyme with Ca2+ and Heme. Journal of Biological Chemistry. (1990) 265(22): 13335-13343.

Smith et al. Generating a synthetic genome by whole genome assembly: ΦX174 bacteriophage. From synthetic oligonucleotides. PNAS Early Edition. (2003) pp. 1-6. www.pnas.org/cgi/doi/10.1073/pnas.2237126100.

Smith et al. Removal of Polymerase-produced Mutant Sequences from PCR Products. Proc. Natl. Academy of Sciences (Jun. 1997) 94: 6847-6850.

Stemmer et al. Single-step assembly of a gene and entire plasmid from large numbers of oligodeoxyribonucleotides. Gene. (1995) 164(1):49-53.

Strizhov, et al. A synthetic cryIC gene, encoding a *Bacillus thuringiensis* δ-endotoxin, confers. *Spodoptera* resistance in alfalfa and tobacco. Proc. Natl. Acad. Sci. USA. (Dec. 1996) 93: 15012-15017.

Tian et al. Accurate multiplex gene synthesis from programmable DNA microchips. Nature. (Dec. 2004) 432 (23/30): 1050-1054.

Weiss et al. Enzymatic Breakage and Joining of Deoxyribonucleic Acid, I. Repair of Single-Strand Breaks in DNA by an Enzyme System from *Escherichia coli* Infected with T4 Bacteriophage. Biochemistry. (1967) pp. 1021-1028.

Wu, et al. RNA-Mediated Gene Assembly from DNA Arrays. Angewandte Chemi International Edition, English (May 7, 2012) 51(19): 4628-4632.

Xiong et al. Isolation, Characterization, and Molecular Cloning of the cDNA Encoding a Novel Phytase from *Aspergillus niger* 113 and High Expression in *Pichia pastoris*. Journal of Biochemistry and Molecular Biology. (May 2004) 37(3): 282-291.

Xiong et al. A simple, rapid, high-fidelity and cost-effective PCR-based two-step DNA synthesis method for long gene sequences. Nucleic Acids Research. (2004) 32(12): e98, 10 pages.

Xiong et al. PCR-based accurate synthesis of long DNA sequences. Nature Protocols (Feb. 2006) 1(2): 791-797.

Young et al. Two-step total gene synthesis method. Nucleic Acids Research (2004) 32(7): e59, 6 pages.

Zimmerman, et al. Enzymatic Joining of DNA Strands: a Novel Reaction of Diphosphopyridine Nucleotide. Biochemistry. (1967) 57: 1841-1848.

(56) References Cited

OTHER PUBLICATIONS

Au et al. Gene Synthesis by a LCR-Based Approach: High-Level Production of Leptin-L54 Using. Synthetic Gene in *Escherichia coli*. Biochemical and Biophysical Research Communications. (Jul. 9, 1998) 248(1): 200-203.
Bryksin et al. Synthetic Biology. Methods Mol Biol. (2013) 1073:31-42.
Bügl DNA synthesis and biological security. Nature Biotechnology. (Jun. 2007) 25(6): 627-629.
Xiong et al. High level expression of a recombinant acid phytase gene in *Pichia pastoris*. Journal of Applied Microbiology. (Jan. 1, 2005) 98(2):418-428.
Shabarova et al. Chemical ligation of DNA: the first non-enzymatic assembly of a biologically active gene. Nucleic Acids Research (1991) 19(15): 4247-4251.
Carr et al., Protein-medicated Error Correction for de nova DNA Synthesis. Nucleic Acids Research (2004) 32(20): e162, 9 pages.
Binkowski et al. Correcting Errors in Synthetic DNA Through Consensus Shuffling. Nucleic Acids Research (2005) 33(6): e55, 8 pages.
An et al. A rapid and efficient method for multiple-site mutagenesis with a modified overlap extension PCR. Appl. Microbiol. Biotechnol. (2005) 68: 774-778.
Peng et al. A direct and efficient PAGE-mediated overlap extension PCR method for gene multiple-site mutagenesis. Appl. Microbiol. Biotechnol. (2006) 73: 243-240.
Monge et al. Comparison of Complexity Measures for DNA Sequence Analysis. ResearchGate. (Jul. 2014) DOI: 10.1109/IWOBI.2014.6913941.
Orlov et al. Complexity: an internet resource for analysis of DNA sequence complexity. Nucleic Acids Res. (Jul. 1, 2004) (Web Server issue):W628-33.
Au et al. Gene Therapy Advances: A Meta-Analysis of AAV Usage in Clinical Settings. Frontiers in Medicine. (Feb. 2022) 8(809118): 30 pages.
Chen et al. Promoter-Operating Targeted Expression of Gene Therapy in Cancer: Current Stage and Prospect. Molecular Therapy: Nucleic Acids. (Jun. 2018) 11:508-514.
Funnell, et al. Complete Enzymatic Replication of Plasmids Containing the Origin of the *Escherichia coli* Chromosome*. The Journal of Biological Chemistry. (1986) 261:12(5616-5624).
Cloning Method Using GenBuilder™. DNA Assembly User Manual. GenScript. Jan. 30, 2018. 26 pages https://www.genscript.com/gsfiles/Cloning-methods-using-GenBuilder-and-GenBuilder-Plus-Cloning-kit.pdf.
Jiang, et al. Core Hairpin Structure of SpCas9 sgRNA Functions in a Sequence- and Spatial Conformation-Dependent Manner. SLAS Technology. (2021) 26(1): 92-112.
Jinek, et al. A programmable dual RNA-guided DNA endonuclease in adaptive bacterial immunity. Science. (Aug. 17, 2012) 337(6096): 816-821.
Su'etsugu, et al. Exponential propagation of large circular DNA by reconstitution of a chromosome-replication cycle. Nucleic Acids Research. (2017) 45(20): 11525-11534.
Kim, et al. 'Shotgun DNA synthesis' for the high-throughput construction of large DNA molecules. Nucleic Acids Research. (2012) 40(18): e140, 8 pages.
Klein, et al. Multiplex pairwise assembly of array-derived DNA oligonucleotides. Nucleic Acids Research. (2015) 10 pages. doi: 10.1093/nar/gkv1177.
Schwartz, et al. Accurate gene synthesis with tag-directed retrieval of sequence-verified DNA molecules. Nat Methods. Author Manuscript. (Sep. 2012) 9(9): 913-915.
International Search Report and Written Opinion for International Application PCT/US2022/071707, Jul. 12, 2022, 10 pages.

\* cited by examiner

Barcode 1  Barcode 2  Adapter  Target  Adapter

Adapter  Target  Adapter  Barcode 1  Barcode 2

Barcode 1  Adapter  Barcode 2  Adapter  Target  Adapter

Adapter  Barcode 1  Adapter  Barcode 2  Target  Adapter

Adapter  Target  Barcode 1  Adapter  Barcode 2  Adapter

Adapter  Target  Adapter  Barcode 1  Adapter  Barcode 2

A6 Gene

| OBC | IBC | Read Count | Error Count | Error Description | Selected for Targeted PCR | Sequenced |
|---|---|---|---|---|---|---|
| 10 | 15 | 275 | 0 | | Y | |
| 12 | 14 | 555 | 0 | | Y | |
| 20 | 14 | 1116 | 0 | | Y | Y |
| 10 | 4 | 584 | 1 | T743A | | |
| 10 | 10 | 555 | 1 | C216T | | |
| 12 | 10 | 624 | 1 | A167T | | |
| 16 | 7 | 375 | 1 | C686T | | |
| 16 | 13 | 584 | 1 | 695Del | Y | |
| 17 | 17 | 609 | 1 | T327C | | |
| 20 | 20 | 588 | 1 | 323Del | Y | Y |
| 22 | 16 | 528 | 1 | G694T | | |
| 12 | 20 | 624 | 2 | T609C, A635C | | |
| 14 | 6 | 568 | 2 | A155T, C280T | | |
| 12 | 9 | 624 | 4 | G237C, G605T, TC611, G731A | | |
| 16 | 12 | 579 | 4 | C158T, C172G, AT176, G631T | | |

| | | | | GF2B Gene | | |
|---|---|---|---|---|---|---|
| OBC | IBC | Read Count | Error Count | Error Description | Selected for Targeted PCR | Sequenced |
| 4 | 8 | 155 | 0 | | | |
| 4 | 16 | 178 | 0 | | | |
| 4 | 19 | 110 | 0 | | | |
| 4 | 20 | 270 | 0 | | Y | |
| 6 | 16 | 261 | 0 | | Y | Y |
| 6 | 19 | 224 | 0 | | | |
| 6 | 20 | 270 | 0 | | Y | |
| 8 | 7 | 247 | 0 | | | |
| 8 | 14 | 209 | 0 | | | |
| 8 | 15 | 248 | 0 | | | |
| 10 | 7 | 385 | 0 | | Y | |
| 10 | 9 | 208 | 0 | | | |
| 10 | 12 | 178 | 0 | | | |
| 10 | 17 | 180 | 0 | | | |
| 12 | 13 | 228 | 0 | | | |
| 12 | 17 | 252 | 0 | | | |
| 13 | 12 | 613 | 0 | | Y | |
| 13 | 14 | 431 | 0 | | Y | |
| 14 | 6 | 238 | 0 | | | |
| 16 | 7 | 248 | 0 | | | |
| 16 | 13 | 194 | 0 | | | |
| 16 | 18 | 191 | 0 | | | |
| 17 | 19 | 339 | 0 | | | |
| 18 | 6 | 108 | 0 | | | |
| 18 | 14 | 269 | 0 | | Y | |
| 20 | 13 | 210 | 0 | | | |
| 20 | 20 | 232 | 0 | | | |
| 21 | 13 | 219 | 0 | | | |
| 21 | 14 | 476 | 0 | | Y | |
| 22 | 8 | 245 | 0 | | | |
| 22 | 20 | 454 | 0 | | Y | Y |
| 7 | 13 | 241 | 1 | G706T | | |
| 8 | 20 | 232 | 1 | A566G | | |
| 10 | 19 | 168 | 1 | G961A | | |
| 10 | 20 | 406 | 1 | G617A | | |
| 12 | 7 | 231 | 1 | C282T | | |
| 12 | 16 | 131 | 1 | C762A | | |
| 13 | 15 | 209 | 1 | C177T | | |
| 13 | 16 | 132 | 1 | G742A | | |
| 16 | 20 | 202 | 1 | G823A | | |
| 20 | 7 | 454 | 1 | C926A | | |
| 20 | 14 | 262 | 1 | C663T | | |
| 22 | 14 | 449 | 1 | A974G | | |
| 12 | 14 | 218 | 2 | C108T, G504A | | |
| 21 | 10 | 165 | 2 | G304T, G954A | | |
| 7 | 4 | 225 | 3 | 135-219Del, 506Del, C508G | | |

SEQUENCE LISTING

```
Sequence total quantity: 46
SEQ ID NO: 1            moltype = DNA  length = 290
FEATURE                 Location/Qualifiers
misc_feature            1..290
                        note = OriC
source                  1..290
                        mol_type = other DNA
                        organism = Escherichia coli
SEQUENCE: 1
ggatcctggg tattaaaaag aagatctatt tatttagaga tctgttctat tgtgatctct   60
tattaggatc gcactgccct gtggataaca aggatccggc ttttaagatc aacaacctgg  120
aaaggatcat taactgtgaa tgatcggtga tcctggaccg tataagctgg gatcagaatg  180
aggggttata cacaactcaa aaactgaaca acagttgttc tttggataac taccggttga  240
tccaagcttc ctgacagagt tatccacagt agatcgcacg atctgtatac              290

SEQ ID NO: 2            moltype = DNA  length = 300
FEATURE                 Location/Qualifiers
misc_feature            1..300
                        note = Chromosome
misc_feature            1..300
                        note = Chromosome Desired nucleic acid sequence 1
source                  1..300
                        mol_type = other DNA
                        organism = Escherichia coli
SEQUENCE: 2
atggaagcag caaatttaag tccttctggt gcagtaatgc cgctggcgac ctcactcagt   60
ggaaataact cagtggatga gaagacagga gtgattaaac cagaaaatgg aacaaatcgc  120
accgttagag ttatagccgg attagcactt accactacgg ctctggcagc tctaggtaca  180
ggtattgcag cggcatgctc ggagacgagc agcacagaat acttagccct gggtattact  240
tctggcgtac taggtactct tactgcggtt ggcggtgcat tagcgatgaa atatgcctaa  300

SEQ ID NO: 3            moltype = DNA  length = 1521
FEATURE                 Location/Qualifiers
misc_feature            1..1521
                        note = Desired nucleic acid sequence 2
source                  1..1521
                        mol_type = other DNA
                        organism = synthetic construct
SEQUENCE: 3
ttacatgtct cgatcccact taactatctt gggctgtgac aaagtcacat ggttcacacg   60
gcaggcatac tcatctttt cagtgggggt gaattcagtg tagtacaaga datagaaaga  120
ccagtccttg ctgaaagaca agtctgaatg ctccactttt tcaattctct ctccattctt  180
cagtaagtca acttcaatgt cggatggatg aaacccagac acatagcaat tcaggaaatt  240
tgactttcca ttctctgctg gatgacgtga gtaaacctga atctttggag tacgctggat  300
agcctccagg ccagaaagag agagtagcgc gagcacgcat aaggccacgg agcgagacat  360
gggaccgggg ttttcttcca cgtctcctgc ttgctttaac agagagaagt tcgtggctcc  420
ggagcccact ttacaagctg tgagagacac atcagagccc tgggcactgt cactgcttgc  480
agcctgagag tagctccctc cttttctatc tgagctcttc ctcctccaca tcacagcagc  540
gaccacagct ccagtgatca cagctccaaa gagaaccagg ccagcaatga tgcccacgat  600
ggggatggtg ggctgggaag acggctccca tctcagggtg aggggcttgg gcaaaccctc  660
atgctgcaca tggcaggtgt atctctgctc ctgtccagaa ggcaccacca cagccgccca  720
cttctggaag gttccatccc ctgcaggcct ggtctccacg agctccgtgt cctgggtctg  780
gtcctcccca tcccgctgcc aggtcagtgt gatctccgca gggtagaagc tcagggccca  840
gcacctcagg gtggcttcat ggtcagagac agcatggtga gtcatatgcg ttttggggc   900
```

```
gtccgtgcgc tgcagcgtct ccttcccgtt ctccaggtat ctgcggagcc actccacgca   960
cgtgccctcc aggtaggctc tcaactgctc cgccacatgg gccgcctccc acttgtgctt  1020
ggtggtctga gctgccatgt ccgccgcggt ccaagagcgc aggtcctctt tcagggcgat  1080
gtaatccttg ccgtcgtagg cgtactggtg gtacccgcgg aggaagcgcc agtccgaccc  1140
cacgtcgcag ccatacatcc tctggacggt gtgagaaccg gcctcgctct ggttgtagta  1200
gccgcgcagg gtccccaggt ccactccggtg agtctgtgag tgggccttca ctttccgtgt  1260
ctccccgtcc caatactccg gaccctcctg ctctatccac ggcgcccgcg gctccatcct  1320
ctggctcgcg gcgtcgctgt cgaaccgcac gaactgcgtg tcgtccacgt agcccactgc  1380
gatgaagcgg ggctccccgc ggccgggccg ggacacggat gtgaagaaat acctcatgga  1440
gtgagagccc gcccaggtct gggtcagggc cagagccccc gagagtagca ggacgagggt  1500
tcggggcgcc atgacggcca t                                            1521

SEQ ID NO: 4              moltype = DNA   length = 3207
FEATURE                   Location/Qualifiers
misc_feature              1..3207
                          note = Desired nucleic acid sequence 3
source                    1..3207
                          mol_type = other DNA
                          organism = Homo sapiens
SEQUENCE: 4
atgcctccac gaccatcatc aggtgaactg tggggcatcc acttgatgcc cccaagaatc    60
ctagtagaat gtttactacc aaatggaatg atagtgactt tagaatgcct ccgtgaggct   120
acattaataa ccataaagca tgaactattt aagaagcaa gaaataccc cctccatcaa   180
cttcttcaag atgaatcttc ttacattttc gtaagtgtta ctcaagaagc agaaaggaa   240
gaattttttg atgaaacaag acgactttgt gaccttcggc tttttcaacc cttttaaaa   300
gtaattgaac cagtaggcaa ccgtgaagaa aagatcctca atcgagaaat tggttttgct   360
atcggcatgc cagtgtgtga atttgatatg gttaaagatc cagaagtaca ggacttccga   420
agaaatattc tgaacgtttg taagaagct gtggatctta gggaccctcaa ttcacctcat   480
agtagagcaa tgtatgtcta tcctccaaat gtagaatctt caccagaatt gccaaagcac   540
atatataata aattagataa agggcaaata atagtggtga tctgggtaat agtttctcca   600
aataatgaca agcagaagta tactctgaaa atcaaccatg actgtgtacc agaacaagta   660
attgctgaag caatcaggaa aaaaactcga gtatgttgc tatcctctga caactaaaa   720
ctctgtgttt tagaatatca gggcaagtat atttttaaaag tgtgtggatg tgatgaatac   780
ttcctagaaa aatatcctct gagtcagtat aagtatataa gaagctgtat aatgcttggg   840
aggatgccca atttgatgtt gatggctaaa gaaagccttt attctcaact gccaatggac   900
tgttttacaa tgccatctta ttccagacgc atttccacag ctacaccata tatgaatgga   960
gaaacatcta caaatccct ttgggttata aatagtgcac tcagaataaa aattctttgt  1020
gcaacctacg tgaatgtaaa tattcgagac attgataaga tctatgttcg aacaggtatc  1080
taccgtggag gagaacccttt atgtgacaat gtgaacctc aaagagtacc ttgttccaat  1140
cccaggtgga atgaatggct gaattatgat atatacattc ctgatcttcc tcgtgctgct  1200
cgactttgcc tttccatttg ctctgttaaa ggccgaaagg gtgctaaaga gaacactgt  1260
ccattggcat ggggaaatat aaacttgttt gattacacag cactctagt atctggaaa  1320
atggctttga atctttggcc agtacctcat ggattagaaa atttgctgaa ccctattggt  1380
gttactggat caaatccaaa taagaaaact ccatgcttag agttggagtt tgactggttc  1440
agcagtgtgg taaagttccc agatatgtca gtgattgaag agcatgccaa ttggtctgta  1500
tcccgagaag caggatttag ctattccac gcaggactga gtaacagact agctagagac  1560
aatgaattaa gggaaaatga caagaacag ctcaaagcaa tttctacacg agtcctctc  1620
tctgaaatca ctgagcagga gaaagatttt ctatggagtc acagacacta ttgtgtaact  1680
atccccgaaa ttctacccaa attgcttct tctgttaaat ggaattctag agatgaagta  1740
gcccagatgt attgcttggt aaagattgg cctccaatca aacctgaaca ggctatgaa  1800
cttctggact gtaattaccc agatcctatg gttcgaggtt ttgctgttcg gtgcttggaa  1860
aaatatttaa cagatgacaa acttctcag tatttaatct agctagtaca ggtcctaaaa  1920
tatgaacaat atttggataa cttgcttgtg agatttttac tgaagaaagc attgactaat  1980
caaaggattg ggcactttt cttttggcat ttaaaatctg agatgcacaa taaaacagtt  2040
agcagaggt ttggcctgct tttggagtcc tattgtcgtg catgtgggat gtatttgaag  2100
cacctgaata ggcaagtcga ggcaatgaa aagctcatta acttaactga cattctcaaa  2160
caggagaaga aggatgaaac acaaaaggta cagatgaagt tttagttga gcaaatgagg  2220
cgaccagatt tcatggatgc tctacagggc tttctgtctc ctctaaaccc tgctcatcaa  2280
ctaggaaacc tcaggcttga agagtgtcga attatgtcct ctgcaaaag gccactgtg  2340
ttgaattggg agaacccaga catcatgtca gagttactgt ttcagaacaa tgagatcatc  2400
tttaaaaatg gggatgattt acggcaagat atgctaacac ttcaaattat tcgtatatg  2460
gaaaatatct ggcaaaatca aggtcttgat cttcgaatgt taccttatgg ttgtctgtca  2520
atcggtgact gtgtgggact tattgaggtg gtgcgaaatt tcacactat tatgcaaatt  2580
cagtgcaaag gcggcttgaa aggtgcactg cagttcgaaca acacact acatcagtgg  2640
ctcaaagaca agaacaaagg agaaatatat gatgcagcca ttgacctgtt tacacgttca  2700
tgtgctggat actgtgtagc taccttcatt ttgggaattg gagatcgtca caatagtaac  2760
atcatgatgta agacgatgg acaactgttt catatagatt ttggacactt tttggatcac  2820
aagaagaaa aatttggtta taaacgagaa cgtgtgccat tgttttgac acagaatttc  2880
ttaatagtga ttagtaaagg agcccaagaa tgcacaaaga caagaaatt tgagaggtt  2940
caggagatgt gttacaaggc ttatctagct attcgacagc atgccaatct cttcataaat  3000
cttttctcaa tgatgcttgg ctctggaatg ccagaactac aatcttttga tgacattgca  3060
tacattcgaa agaccctagc cttagataaa actgagcaag aggctttgga gtatttcatg  3120
aaacaaatga atgatgcaca tcatggtggc tggacaacaa aatgggattg gatcttccac  3180
acaattaaac agcatgcatt gaactga                                     3207

SEQ ID NO: 5              moltype = DNA   length = 4094
FEATURE                   Location/Qualifiers
misc_feature              1..4094
                          note = lipase Desired nucleic acid sequence 4
```

| source | 1..4094 |
| --- | --- |
| | mol_type = other DNA |
| | organism = Aspergillus heteromorphus |

SEQUENCE: 5

```
gagatgctgg ggctattgtt tactctgcgt tctttgaagc aatccggtgg atacgcatag   60
ggagttggtc cgagttgtta tctgaacggc ctatcgcatc catatggagc aacctgtcac  120
gtggcaggcc cgcttccagc caggtgatga tgccaggtga tctccccagc atcttcagca  180
tcatcatcaa ctcaccgccc agaagctcca tgatcgccat gttcgactcc ggcagctcta  240
cccctttgact gcattgctcc tgatggtcta tacttcgtcc tgtgtctaca ctacgatttc  300
ttttgtagcg tactagaacc agatcccctt atcaccccg gttatgtctt cagctcctga  360
agcagacaga ccatcaatgt tgtctctgtc tgggatcctg gtgacctcgt catggtcccg  420
gcttcaagaa cgatttcgtg gattgttcca tggcgctgac cccagagtgt gcgtcgcatt  480
ctggttactt ggtctgataa acaatgtcct ctacgttata atcctttccg ctgccctga  540
cctggtcggg cctagtgtcc ccaagggagt tgtccttctc gcagacgtca tccctcgtt  600
tggaacaaaa ctggtcgctc cctactttat ccagagcgta ccatacctg tccgggtaat  660
gttcttgtt ttctgttccg cgacaggcat gctcctcatc gcgttgagcc cggcgtatac  720
cgatggcggt acaatatcca caaagattgc gggcatcatt ctggccagct tgtccagcgg  780
aggaggtgaa ttgagcttcc ttggaatgac gcatttttat gggccattca gcttggctgc  840
ctggggcagt ggcactgggg cagctggact ggtcggtgcc ggtgcgtatg cgctagccac  900
tacctccttg ggattcagtg tcaaggcaac gcttttggcg tcggcttgct tgccagctat  960
catgattatg agtttctttg taattctgcc aagatcgccg atgcgtttgg caggagtagg 1020
aaccgccgaa tatcgtgcaa tcagacgaga ggatcctcat gatcctctgg atgaaacgga 1080
agggctgctt agctcctccc ttcgcttggg ccagggcccc aagaaaactg acgatggtga 1140
gggaggcatt ggatggcatg ctttcaaggc caatctacag cgggctaaag gctgttcttc 1200
tccgtttatg cttccgctcc tattagtcta tgtcgccgag tacacgatca accaagggt 1260
ctccccgacc ctactctttg ccctcgagga ttcgccgttt gagcattacc gtgcttcta 1320
cccagcatac aacgcgatct accaggttgg cgtcttcatc tcgcgatcgt ccaccccttt 1380
ttttcgcatc cataatctgt acctcccctc cttgttgcag attgtcaacc tggctgtatt 1440
gaccgcgcac gccgtgattg gattcatccc aagtgtgtac atcattttg ccatagtctt 1500
ctgggaaggg ttgttgggcg ggctggtcta cgttaatacg ttcgcggaga tcggggaccg 1560
agttcccaag gaagaccgag agttctctct cggggcaaca accgtcaacc atctcctcgg 1620
gagaccgtcc accaagttcc gcaagatcca ggtcctgct gtattcctat tctggtcgct 1680
atatctattc agaggaaaca agcatggccc tcctgttgtc cgcagattct cctcccgcct 1740
ttcggaaaag ctgagcgtct ggcaaaccaa agtcatcgtc ttcctctggc tctatgtctc 1800
ccgcaacttt gcgaagatcg tcggtcttga gtgtcccgaa cccatggcaa atctgtactc 1860
gcgctcttc ttccgggcaa catggctcac cacagcgcta gatgctggct tttgacggc 1920
aatgggagtc aagccaaaat ggctcaggga tattgcctcc atggtctttt cggggtatta 1980
cattatcgca gcagagcggg cggacgagaa agtgcgccgg gtacgggcca cactgactgt 2040
ggagcatatg cgtgtatcat ggaataagag taccacacg tatctctgga cccttgctag 2100
tctggtacgc ccacgactca ccagataccc tccccgtgcg atccgaattc ctcgtccacc 2160
gtcgtcaata tacgacgagc cgaccagtgc atggctttac ttcgatggcc ctctaaccgc 2220
gctacggat caaacctgcg ttgtcttgga tatccctgga ggtggatttg tttcaatgag 2280
ccctcgccat tccgaagacc ggctgctagc atgggctgct aagacgaagg ttccgatctt 2340
gagcctcgac tataagaaag ctccggagta tccgtaccca tacgctttga acgaatgcta 2400
cgatgtgtat catactattg tatccacccg gggtcgctgc ctcggactca acgggcgaac 2460
acgccctagc gttattcttg caggcgacag tgctggcgga aatcttgcta ctggcgtcac 2520
gctgatgata ctccaatctg gcaccagtga tgcctcacac tggcagagcc aaaacgtgct 2580
tccgccacca gatgggctgg ttctggccta ccccgcattg aacatgaaaa tagagagctg 2640
gatgacagag gaacagatgt cattaatcca agagaagagc acgcggcgca cgaacgagaa 2700
cgtccttcgt aggaaggata tggactacca ccgcttgact ccttacacct ccccaggcac 2760
ctcgtttgga gatttccagc atgactcctt ttctgacgcc gatgaggagg gaagtaattt 2820
gggtgacatt gcttcaaaga aacttgcaca gcaacaaagg ctagatgtcc atgcagcgga 2880
ggcagcggcc gttgctgagc accagcccaa gcagattcgc actcgactag ccgtgtcatc 2940
agtgatctcg tatgtgagcg atcggatcct gacaccggag atgatgagag caatgatcat 3000
tctctacatt gggcctcata accgtcccga cttcaacacg gattatctgc tttccccagc 3060
gctggctccc gaggctcttc tggccaattt ccccaaaaca tacttcatca ccggagagcc 3120
cgacccccctt gttgacgaca ccgtgatctt cgccggcgg ttaagacagg ccaagctccg 3180
ccaattccaa gaacgccaag agctcggtct cgagaggtcc tatcgcttat caacgagaa 3240
agaccatgtc gaagtctcgc tactcccgg aatctcccac gggttcatgc aaatggccgg 3300
gctcttccca gatagctgga aacacatcta tcgctgcgcg acgtggatcc aggacctttt 3360
cgagatcgcc cacgccaaac ggtcctccag tctcctgcaa tccctctaca cacctccca 3420
actacccaaa ggctccaagc ccgctcttcg cggcggccgc gcccgaaacc acacccgcca 3480
tctaaccggc gaatcttccg ccgacgaaga caaaccgttg gaaatgggca tcagcaagct 3540
cacccactg acacccgtgg cccgaagcgc cagtgcccgc atcgatcaca gccaggaccc 3600
cgcaaatccc gacgctatgc acgcgaagaa cgagcgaatc gaagcgtttt cgcggggccg 3660
tcctctccgg cctggtttcg cccgaaaca acaacatctt gtccccctcca agctgagcat 3720
tccttccgcc gagggttca tctccaagcc tcggagtccc gccccttgc gcgagcgtaa 3780
ccgcagcctg accagtctcg ccagtgagga ggacttgctt gatcgtcgaa tgatgggct 3840
tgccggtctg ttgatgggca ttggggaggg cgcgagaacg ccgtagtatc tatctatatc 3900
taactctttc gcctgtttgg gatactaatc tggcaaacgg ttgcgtggaa gacccacccg 3960
acaccattga caatatgaat cctacgaccc cattttcttc tcttcgctgt acttggatag 4020
ataggttatg agcgtatgag attttattt gtgtagtaac aacaatgatc gatagaaaca 4080
atatacgcac gcac                                                  4094
```

| SEQ ID NO: 6 | moltype = DNA length = 3075 |
| --- | --- |
| FEATURE | Location/Qualifiers |
| misc_feature | 1..3075 |
| | note = chromosome Desired nucleic acid sequence 5 |
| source | 1..3075 |

```
                        mol_type = other DNA
                        organism = Escherichia coli
SEQUENCE: 6
ttatttttga caccagacca actggtaatg gtagcgaccg gcgctcagct ggaattccgc      60
cgatactgac gggctccagg agtcgtcgcc accaatcccc atatgaaaac cgtcgatatt    120
cagccatgtg ccttcttccg cgtgcagcag atggcgatgg ctggtttcca tcagttgctg    180
ttgactgtag cggctgatgt tgaactggaa gtcgccgcgc cactggtgtg ggccataatt    240
caattcgcgc gtcccgcagc gcagaccgtt ttcgctcggg aagacgtacg gggtatacat    300
gtctgacaat ggcagatccc agcggtcaaa acaggcggca gtaaggcgct cgggatagtt    360
ttcttgcggc cctaatccga gccagtttac ccgctctgct acctgcgcca gctggcagtt    420
caggccaatc cgcgccggat gcggtgtatc gctcgccact tcaacatcaa cggtaatcgc    480
catttgacca ctaccatcaa tccggtaggt tttccggctg ataaataagg ttttcccctg    540
atgctgccac gcgtgagcgg tcgtaatcag caccgcatca gcaagtgtat ctgccgtgca    600
ctgcaacaac gctgcttcgg cctggtaatg gcccgccgcc ttccagcgtt cgacccaggc    660
gttagggtca atgcgggtcg cttcacttac gccaatgtcg ttatccagcg gtgcacgggt    720
gaactgatcg cgcagcggcg tcagcagttg ttttttatcg ccaatccaca tctgtgaaag    780
aaagcctgac tggcggttaa attgccaacg cttattaccc agctcgatgc aaaaatccat    840
ttcgctggtg gtcagatgcg ggatggcgtg ggacgcgggg gggagcgtca cactgaggtt    900
ttccgccaga cgccactgct gccaggcgct gatgtgcccg gcttctgacc atgcggtcgc    960
gttcggttgc actacgcgta ctgtgagcca gagttgcccg gcgctctccg gctgcggtag   1020
ttcaggcagt tcaatcaact gtttaccttg tggagcgaca tccagaggca cttcaccgct   1080
tgccagcgca ttaccatcca gcgccaccat ccagtgcagg agctcgttat cgctatgacg   1140
gaacaggtat tcgctggtca cttcgatggt ttgcccggat aaacggaact ggaaaaactg   1200
ctgctggtgt tttgcttccg tcagcgctgg atgcggcgtg cggtcggcaa agaccagacc   1260
gttcatacag aactggcgat cgttcggcgt atcgccaaaa tcaccgccgt aagccgacca   1320
cgggttgccg ttttcatcat atttaatcag cgactgatcc cccagtccac agacgaagcc   1380
gccctgtaaa cggggatact gacgaaacgc ctgccagtat ttagcgaaac cgccaagact   1440
gttacccatc gcgtgggcgt attcgcaaag gatcagcggg cgcgtctctc caggtagcga   1500
aagccatttt ttgatggacc atttcggcac agccgggaag ggctggtctt catccacgcg   1560
cgcgtactgc gggcaaataa tatcggtggc cgtggtgtcg gctccgccgc cttcatactg   1620
caccgggcgg gaaggatcga cagatttgat ccagcgatac agcgcgtcgt gattagcgcc   1680
gtggcctgat tcattcccca gcgaccagat gatcacactc gggtgattac gatcgcgctg   1740
caccattcgc gttacgcgtt cgctcatcgc cggtagccag cgcggatcat cggtcagacg   1800
attcattggc accatgccgt gggtttcaat attggcttca tccaccacat acaggccgta   1860
gcggtcgcac agcgtgtacc acagcggatg gttcggataa tgcgaacagc gcacggcgtt   1920
aaagttgttc tgcttcatca gcaggatatc ctgcaccatc gtctgctcat ccatgacctg   1980
accatgcaga ggatgatgct cgtgacggtt aacgcctcga atcagcaacg gcttgccgtt   2040
cagcagcagc agaccatttt caatccgcac ctcgcggaaa ccgacatcgc aggcttctgc   2100
ttcaatcagc gtgccgtcgg cggtgtgcag ttcaaccacc gcacgataga gattcgggat   2160
ttcggcgctc cacagtttcg ggttttcgac gttcagacgt agtgtgacgc gatcggcata   2220
accaccacgc tcatcgataa tttcaccgcc gaaaggcgcg gtgccgctgg cgacctgcgt   2280
ttcaccctgc cataaagaaa ctgttacccg taggtagtca cgcaactcgc cgcacatctg   2340
aacttcagcc tccagtacag cgcggctgaa atcatcatca agcgagtgg caacatggaa   2400
atcgctgatt tgtgtagtcg gtttatgcag caacgagacg tcacggaaaa tgccgctcat   2460
ccgccacata tcctgatctt ccagataact gccgtcactc cagcgcagca ccatcaccgc   2520
gaggcggttt tctccggcgc gtaaaaatgc gctcaggtca aattcagacg gcaaacgact   2580
gtcctggcgt taaccgaccc agcgcccgtt gcaccacaga tgaaacgccg agttaacgcc   2640
atcaaaaata attcgcgtct ggccttcctg tagccagctt tcatcaacat taaatgtgag   2700
cgagtaacaa cccgtcggat tctccgtggg aacaaacggc ggattgaccg taatgggata   2760
ggtcacgttg gtgtagatgg gcgcatcgta accgtgcatc tgccagtttg aggggacgac   2820
gacagtatcg gcctcaggaa gatcgcactc cagccagctt tccggcaccg cttctggttg   2880
cggaaaccag gcaaagcgcc attcgccatt caggctgcgc aactgttggg aagggcgatc   2940
ggtgcgggcc tcttcgctat tacgccagct ggcgaagggg ggatgtgctg caaggcgatt   3000
aagttgggta acgccagggt tttcccagtc acgacgttgt aaaacgacgg ccagtgaatc   3060
cgtaatcatg gtcat                                                    3075

SEQ ID NO: 7            moltype = DNA  length = 4205
FEATURE                 Location/Qualifiers
misc_feature            1..4205
                        note = Desired nucleic acid sequence 6
source                  1..4205
                        mol_type = other DNA
                        organism = synthetic construct
SEQUENCE: 7
accggttcta gagcgctgcc accatggaca agaagtacag catcggcctg acatcggca      60
ccaactctgt gggctgggcc gtgatcaccg acgagtacaa ggtgcccagc aagaaattca    120
aggtgctggg caacaccgac cggcacagca tcaagaagaa cctgatcgga ccctgctgt    180
tcgacagcgg cgaaacagcc gaggccaccc ggctgaagag aaccgccaga agaagataca    240
ccagacggaa gaaccggatc tgctatctgc aagagatctt cagcaacgag atggccaagg    300
tggacgacag cttcttccac agactggaag agtcctcct ggtggaagag ataagaagc    360
acgagcggca ccccatcttc ggcaacatcg tggacgaggt ggcctaccac gagaagtacc    420
ccaccatcta ccacctgaga aagaaactgg tggacagcac cgacaaggcc gacctgcggc    480
tgatctatct ggccctggcc cacatgatca agttccgggg ccacttcctg atcgagggcg    540
acctgaaccc cgacaacagc gacgtggaca agctgttcat ccagctggtg cagacctaca    600
accagctgtt cgaggaaaac cccatcaacc cagccggcgt ggacgccaag gccatcctgt    660
ctgccagact gagcaagagc agacggctgg aaaatctgat cgcccagctg cccggcgaga    720
agaagaatgg cctgttcgga aacctgattg ccctgagcct gggcctgacc cccaacttca    780
agagcaactt cgacctggcc gaggatgcca aactgcagct gagcaaggac acctacgacg    840
acgacctgga caacctgctg gcccagatcg gcgaccagta cgccgacctg tttctggccg    900
```

```
ccaagaacct gtccgacgcc atcctgctga gcgacatcct gagagtgaac accgagatca  960
ccaaggcccc cctgagcgcc tctatgatca agagatacga cgagcaccac caggacctga 1020
ccctgctgaa agctctcgtg cggcagcagc tgcctgagaa gtacaaagag attttcttcg 1080
accagagcaa gaacggctac gccggctaca ttgacggcgg agccagccag gaagagttct 1140
acaagttcat caagcccatc ctggaaaaga tggacggcag cggaactg ctcgtgaagc 1200
tgaacagaga ggacctgctg cggaagcagc ggaccttcga caacggcagc atccccacc 1260
agatccacct gggagagctg cacgccattc tgccggcggca ggaagatttt tacccattcc 1320
tgaaggacaa ccgggaaaag atcgagaaga tcctgacctt ccgcatcccc tactacgtgg 1380
gccctctggc caggggaaac agcagattcg cctggatgac cagaaagagc gaggaaacca 1440
tcacccctg gaacttcgag gaagtggtgg acaagggcgc ttccgcccag agcttcatcg 1500
agcggatgac caacttcgat aagaacctgc ccaacgagaa ggtgctgccc aagcacagcc 1560
tgctgtacga gtacttcacc gtgtataacg agctgaccaa agtgaaatac gtgaccgagg 1620
gaatgagaaa gcccgccttc ctgagcggcg agcagaaaaa ggccatcgtg gacctgctgt 1680
tcaagaccaa ccggaaagtg accgtgaagc agctgaaaga tgactacttc aagaaaatcg 1740
agtgcttcga ctccgtggaa atctccggcg tggaagatcg gttcaacgcc tccctgggca 1800
cataccacga tctgctggaa attatcaagg acaaggactt cctggacaat gaggaaaacg 1860
aggacattct ggaagatatc gtgctgaccc tgacactgtt tgaggacaga gagatgatcg 1920
aggaacggct gaaaacctat gcccacctgt tcgacgacaa agtgatgaag cagctgaagc 1980
ggcgagata caccggctgg ggcaggctga gccggaagct gatcaacggc atccgggaca 2040
agcagtccgg caagacaatc ctggatttcc tgaagtccga cggcttcgcc aacagaaact 2100
tcatgcagct gatccacgac gacagcctga cctttaaaga ggacatccag aaagcccagg 2160
tgtccggcca gggcgatagc ctgccggagc acattgccaa tctggccggc agcccccgcca 2220
ttaagaaggg catcctgcag acagtgaagg tggtggacga gctcgtgaaa gtgatgggcc 2280
ggcacaagcc cgagaacatc gtgatcgaaa tggccagaga gaaccagacc acccagaagg 2340
gacagaagaa cagccgcgag agaatgaagc ggatcgaaga gggcatcaaa gagctgggca 2400
gccagatcct gaaagaacac cccgtggaaa cacccgagcc gcagaacgag aagctgtacc 2460
tgtactacct gcagaatggg cgggatatgt acgtggacca ggaactggac atcaaccggc 2520
tgtccgacta cgatgtggac catatcgtgc ctcagagctt tctgaaggac gactccatcg 2580
acaacaaggt gctgaccaga agcgacaaga accggggcaa gagcgacaac gtgccctccg 2640
aagaggtcgt gaagaagatg aagaactact ggcggcagct ggtgaacgcc aagctgatta 2700
cccagagaaa gttcgacaat ctgaccaagg ccgagagagg cggcctgagc gaactggata 2760
aggccggctt catcaagaga cagctggtgg aaacccggca gatcacaaag cacgtggcac 2820
agatcctgga ctcccggatg aacactaagt acgacgagaa tgacaagctg atccgggaag 2880
tgaaagtgat caccctgaag tccaagctgg tgtccgattt ccggaaggat ttccagtttt 2940
acaaagtgcg cgagatcaac aactaccacc acgcccacga cgcctacctg aacgccgtcg 3000
tgggaaccgc cctgatcaaa aagtaccta agctggaaag cgagttcgtg tacggcgact 3060
acaaggtgta cgacgtgcgg aagatgatcg ccaagagcga gcaggaaatc ggcaaggcta 3120
ccgccaagta cttcttctac agcaacatca tgaacttttt caagaccgag attaccctcg 3180
ccaacggcga gatccggaag cggcctctga tcgagacaaa cggcgaaacc ggggagatcg 3240
tgtgggataa gggccgggat tttgccaccg tgcggaaagt gctgagcatg ccccaagtga 3300
atatcgtgaa aaagaccgag gtgcagacag gcggcttcag caaagagtct atcctgccca 3360
agaggaacag cgataagctg atcgccagaa agaaggactg gacccctaag aagtacggcg 3420
gcttcgacag ccccaccgtg gccctatctg tgctggtgat ggcaaagtg gaaagggca 3480
agtccaagaa actgaagagt gtgaaagagc tgctggggat caccatcatg aaagaagca 3540
gcttcgagaa gaatcccatc gactttctgg aagccaaggg ctacaagaa gtgaaaaagg 3600
acctgatcat caagctgcct aagtactccc tgttcgagct ggaaacggc cggaagaga 3660
tgctggcctc tgccggcgaa ctgcagaagg gaaacgaact ggccctgcc tccaaatatg 3720
tgaacttcct gtacctggcc agccactatg agaagctgaa gggctccccc gaggataatg 3780
agcagaaaca gctgttttgtg gaacagcaca agcactacct ggacgagatc atcgagcaga 3840
tcagcgagtt ctccaagaga gtgatcctgg ccgacgctaa tctggacaaa gtgctgtccg 3900
cctacaacaa gcaccgggat aagcccatca gagagcaggc cgagaatatc atccacctgt 3960
ttaccctgac caatctggga gcccctgccg ccttcaagta ctttgacacc accatcgacc 4020
ggaagaggta caccagcacc aaagaggtgc tggacgccac cctgatccac cagagcatca 4080
ccggcctgta cgagacacgg atcgacctgt ctcagctggg aggcgacaag cgacctgccg 4140
ccacaaagaa ggctggacag gctaagaaga agaaagatta caagacgat gacgataagg 4200
gatcc                                                             4205
```

SEQ ID NO: 8          moltype = DNA   length = 4950
FEATURE               Location/Qualifiers
misc_feature          1..4950
                      note = Mitochondiral DNA polymerase-I Desired nucleic acid
                      sequence 7
source                1..4950
                      mol_type = other DNA
                      organism = Trypanosoma brucei
SEQUENCE: 8

```
atgcgacgta ctttcagtcg ctacgcacgg ttcgcggtgt gtcagcagtc tactggtgca   60
gggaccatag agggccctct ccgtttgcgc tcggcagatc agacagtagt gtggtgttgc  120
gccgcagctg ggcgaggtc ctggtttgc tgcttccca actcggtacg cgcggggttg    180
catgagccac gccggttcgc gtcaacgagg gccacgaatt cgcgcaaacc agcgagggtt  240
gcgcgatcgg gcgcctcttc acgagcgcca cgcaagggcc ccagacattc acaggggttg  300
aagtcatcgc aggaaagtga gggagagttt atggctacta cttcagatga tgactttgga  360
ccaatggcag agggagcagc ggaagaggag agtgcaggag attgtgatgc tggtgttggc  420
agtagtttga caggtgggcg agagacaacc gaatcatcca acgtagcgge ggcgccaagaa  480
gaagaagggg aaggagttgg cactaccgaa ggtgttgaga cggagggagg taagcctggt  540
aggagtgagg aggatccact gaatctccga gtagccacgc ttatgcagca accaggaaag  600
gcgttccgtg taattgccgt gtcatattca gctaagcggg agttaaattt tcccattact  660
tttgaggaca ttgcctctgg tacaactcta aactgtcggt tggaggacgt acacacaact  720
tacatgaatt gggttcgtca gttttgtgcg tcatgggtta tgctctttgt cccaaccctc  780
```

```
tcagcagcca gcgccgtcct actggagaat gccgtagtgt acagtagggt ggaacgtact    840
gtctctaact ctcaccgtgg ctctcctgca cccaaacagt ggggaggaacc ggatcatgtg   900
ctggtttcgt acagcaaaat gcgtgaggtg ctatgcaaag taaagcggga tgagcaggta    960
gacaaggagc ttgttagtaa cactgtactc agtgcatttg cggaggactg gaagagcttc   1020
attcactcaa cagcatcttg ctcaccggca tcaattgtga ccgcatcgtt tgatttccgc   1080
cccaacggcg ggcatctcca gttgaacaag aaattttttgc acgcacagtt gacaacagcg  1140
gcgatgacac tgttgaggca tgttgcacgt aagggatcgt ctgccagcgg cactccatgt   1200
agttcttcca ctaaggaggt tacatctggc gcgacaact ctgtagctga tgatattcgc    1260
aggaaggaat cttggttgtt aattttttgtt tcccgcacctg cggggagcgc aacgagtttt  1320
ctagggccca gagcagtcaa cttgggcgta ccacctatgc aagatcttct tactggtgag   1380
tttgtggatc cccttctcct tgggggggagg aacgtcattt acattatcgg ttccggaacg   1440
gcggcagaag ccttttcaaa aataccatct gtgcgtaagg gcaaacgtca gatatcgata   1500
ctattgaagg atatagagaa tcaactgggg ccgtttcggg cgagtcgccc gacgttaacc   1560
accacgctta tacaggcgtt agatacgttt tcgccggcaca cgtggattgg gttaatgaag   1620
gaggaggatg gcacagttcg agtgcccgg gctcctcaga gcttttgttca tctgcaccgg   1680
cgaagcgtta cgcgtgaggt gttgcctaag tttcttgagt cgacgttagg acatatttct   1740
caccacaact ccgcctatgg agtcgcagag gtgggaatgg gcggtgcggc tggcgctgcg   1800
ggtgcaaacg cgctcctgca gctgggaaag ttaaaccgca aggtagatga gcatataaag   1860
gcgattttca acaatgctga acgactcgag aaggagaagg cactccgcga gagtttgcgt   1920
cgtagcaact gtttctttgt agatgtcaag tcgcgaaca tctcggcggc acgtcgagct    1980
gacaatccct tttctacacg aaatggtata ttggagtttc acggccaact ttgggcgacc   2040
cttggcatgg gggagacggc acgagcggga aagacaacag gttgtccacc agtgaagacg   2100
ctcacagcgc agctcgctcc caatggcgac gtgcaggctt tcgttagacc cgaggaatgc   2160
attccgatgg aattacctac tggctctagt gatacaagca ccataaggca taaggggata   2220
tcattagctg catcagcatc tagtgcctct agtgggataa tcattgcatg ggacgtgaag   2280
cgtgcgctga ttttttcttcg cggcagcaac agacttcgag aatttctcct taacggtggt   2340
aggatttggt gtgcacagta cgcacagtac ctacttaaag ggttcaacaa ccacaacctc   2400
accacaatga agcggacact ccttcagtac cacacggtgc agaccaagtt gcatcctctg   2460
gagaagctga agataatttt tgagaaacaa cttgatattg cggtgaatac tcggcagctt   2520
atatcgatcg tgcatcgtat ggatggtctt cttgcttgta ctgaaatgga gttacgtggg   2580
cttcagatag ctccacaaga agacattaca gcctttgccc gtaacctgaa aaggacccgg   2640
gaggaactgg agaaggcagt taatgataaa atcatggtgt tcacggaagg aatggataat   2700
gaagtgagac gtaagattaa cgttcgctct acgcaggata tcagcacaat catctacggt   2760
ggcgcgttgt gtcggcatct gggtacgcga tacgtcac ctcacattcc ccgcattcct     2820
gtgacggcaa tcttttccaca tgcagtatgc cgcctaacaa caacccctgt ccctgagctg   2880
tacacaaacg ccgagaacct ccttggggtc aaaggaacag gcaacagcgg taacaacaat   2940
aatgctaaca agattgctga agcagcgacc attacgccca acgcagtgaa tacaacccctt  3000
aagattattg acaagtatct gaaggacaat acattggata atttgctcaa caatacggct   3060
attgtggtag tgacatgtaa ggtacggacc agtagctttc tggaggtgat caccatccat   3120
tgcccttcta gtgatcctaa tgatgaactg cggcacactg ttgcgatcga tgacgtctta   3180
ccagtaatga gctcacccga gctggttacc ataactcaac tcaaggagaa aattgccgcc   3240
tacaggcctt tacgagcgct ccaaccactc aagaagtacg gcagacgcag ttatgacctt   3300
cgaaatctcg tcattctcac tcattgttcc ttcgacaaga cggctgtgtt ggtagacacg   3360
ggcattatac agacgatcgc cgaaactgtt cttggtaaag aaaatgaaga acggtccctc   3420
ctcgaacgtg tctgtttctg tgacatcaat cgcgcctttc cacctccccc agaggggaggt  3480
gattcgtttg agaatgattt cttaggactt gtgaatggtg ctgaacaggc cggcgtgtcc   3540
tcccgcagca actgggaggc tttcacgcgg aactttgcgt cggttggagg gtttgaggac   3600
acacgcaggg cgttggtgct gcattgtgcc tcgttagttg gtacggcaag agacccattc   3660
cgtacggccc atcccttgcc ctttgcgtta gtggggttta atggtcaaca ggcgcttggg   3720
ttacatgggc aagagcgggc ctcgacgcgt gggatgctgt ggatggttac tcccgaacgg   3780
ctacacccgt tgcttcatcg ctcactgcgt ggccgcagtg cgtcatccgg cgccgacgcc   3840
attgagcgga tcaatgtgtt gctttcgaat gaaaaacagg tggatctctc cttttttcaag   3900
gcccttcagc aattgcgttt catggaaaag caaatgcagc tcttcgaaga aggtgctctg   3960
tttcgggcag ttttaccgga gtgcaaaaat cgtgttcacg gtgagttctg ccatgtcgtt   4020
actgcgacgg gtcgactttc ttcacagtcg cctaacctgc agaacattcc caaggaagat   4080
ttgaggtgcc taatcgtctc tcgcttcggt cggcgtgctg gtcgtatgat tgaggcggac   4140
tatagtcagt tggaagttgt ggtgctcgct gctctcagtc gggacgcccg catgttgcag   4200
gaacttaacg acaatgtgga tttccattgc ctacgtgttt ctctcatgac aaaagagccc   4260
tacgaggatg taatacacaa agtgaagcag gtgaaggatc cccactatat tcagctacgg   4320
cagcaggcga aaacattttc gtttcaacgt caatatggtg cagggacatc aaccatagcc   4380
acaacgacgg ggcttagtga gacggaggtt gtgcggctga ttgccgccga ggaacagcat   4440
tacaaggact gggacgcta ctataggctt gtaacggact gtgtagaggc gggtgccgat    4500
cgcttgttgc agttgcgtac attagatgca acatcttggc cccccacgat gcgtcgaatg   4560
gtgcttttga ctgaaccgat gcattatttt gtggtaccaa cgggaagcaa atttgacttc   4620
acgaaggata agaaggctgt gccacgactg aaaaattacc ccgttcaggg actggctggg   4680
gaaattgttc aaattatgtg tggaaagatt attcgtcgct tctatgcaaa acgtaactac   4740
aacgataagg cgtttcttgt taataccgtt cacgattgcg tttggattga tgcccacgaa   4800
tccgttcagg acgaggtaat ggacgacgta tccgccataa tgtcctccac ctccgaagtc   4860
attagtagtt tatggccagg cgtaaagttg gatgtcccat tcaaagcaga gattcatata   4920
ggaccatcac tagggagtt gtccaggtag                                     4950

SEQ ID NO: 9          moltype = DNA  length = 5178
FEATURE               Location/Qualifiers
misc_feature          1..5178
                      note = polyketide synthase desired nucleic acid sequence 8
source                1..5178
                      mol_type = other DNA
                      organism = Aspergillus vadensis
SEQUENCE: 9
```

```
atgagagtag tcttctttag caacaagttt ccggcgtttg acctacggga tctctcccag   60
agactccgtt tcgtctctcg atcacggagt catggactcc tgagacgttt tctggaagag  120
gcgaccattg tcgcccacga agagattcgg cgactccac cagaactaag gactctcatt  180
cctccatttc attcaatcct ggatcttgtt gattcattcg actggcatgg aggaccatta  240
accgcagttt tcgagtgcgc ttttacctgt ttatttcatc tctctctctt ccttgggagc  300
tacgagcgca acccgcagga gttcaacttc tgcaattcaa ccttcactgg tttaggtta  360
ggtctgttgg ctgctgcagg tattgctgca tctcaaacgc tattagacgt tcctcaaaca  420
gcagccgaag ctgttcggat tgctatgaga acaggctatc tgctgtacca gaagcagcag  480
gagattgagc cgcaggaact agacgctccg ccaaaaagct ggtcagtgat tgatgcctca  540
accacgggca ggctctatat cagtgttgtc gaaccagatg gcagtctgtt tgtgaatggg  600
ccaccgtcca tgctggcaaa gatatttgga aagacggggg aattggcatc ggcacgccac  660
gccgctttgc cagtgtatgg aggcccttgc catgcagctc atctctacga tcgtgctgat  720
agttcccgca tagctgaaac agtcaacccc caaattgcca atcggagagt tcctggcact  780
gtgcgcttgc tctccatggt tgatgggaag ccactggggct ctcagactgt acgtgagcta  840
tttgagtctg ccatatattg cctcctggca ggcaccattc agtggggaaa tgttgccgaa  900
gctgttttct cgtcttcgga gtggaacgac aaagctcacc tccgtctgga gtcagtcttc  960
cagtcttgtc cagttgtgaa caccctgata tcccgtgccc aggctaccta tccacactgt 1020
actgtcgatt ttcgagagca cttgcaatgg gtgttcatgg aagagaacca acctaccaac 1080
cccaccagca cggacgtcgc agtggttggt atgtcctgcc gactgcctgg cggtgccaac 1140
gacttggccg aattctggga acttctggtg gaggggcgcg acgtgcacaa gaagatcccg 1200
gccgatcgct acgatgtaga aacacatacg gacatcaccg gaaagcgcca gaataccagc 1260
cacaccccat ttgggtgctt tatagacaac cccgggctct tcgacaatgg attcttcgga 1320
atgtctcccc gggaagccgg ccaaacggat ccagcccatc gcttggcact ctgactgcc 1380
tacgaagcgc tggagcagtc tggattcgtc cctaatcgga caccatctac gatggccact 1440
cgagtgggta catactatgg ccattgttcg gacgattacc gggaggccaa tgccgggcag 1500
gatatagaca cctatttat tccaggcaac taccgtgcct ttgctcccgg tcgtatcagc 1560
tacttcttca aattctccgg tccgagctac agtgtcgaca cagcgtgctc ggccagtttg 1620
gctgcaatcc aaattgcatg ttcggccttg atacgtgagg agacggacac tgtggttgct 1680
ggaggattaa atttgttgac gggctctgac agctttgccg gcctcagtcg tggctatttt 1740
ctctccaaaa ctggaagctg taaagtcttc gatgatggag cggatggcta ttgcagagca 1800
gacggcatcg tgtcaatcgt gatgaagcgt ctatcagatg ctcaggccga taatgataat 1860
attctcggtg tgatccgagc ctctgccaca aaccatgcgg ggaatgcaag ctccataacc 1920
catcctcatg cgcctacaca ggagcatctc ttttcgcagg tcttgaacga ggcaaatgtc 1980
aatgcactgg atgtggatgt gattgagatg catggcacgg ggacgcaggc aggcgacact 2040
accgagatcg aatcgtcac aaatgtttc tgcccaggct taaagacg ctcgcaccca 2100
ttgtatgtta gctccgtcaa ggcaaatgtg ggccatggag aggcagctgc gggtattaca 2160
gcgctagtca aaacgctgct gatgttccag aagggtgcga ttccgaaaca tgttgggatc 2220
aaaacagcga tcaacaagca atttcgcgat cttgggacgt tgaatgtaca gatcccttg 2280
gaaactgttt cttgggccta tgacaaaacac cgaaggcgat acgcactggt caacaactc 2340
agcgctgcag ggggaagcac atgtttgctg ctccaggaac ctcctgtgag gagtacgccg 2400
caagcatgtc cccatccaac ccttcccgtt gccgtttcgg cgaaaagtaa agtgtctctt 2460
aagggcaaca tccggagctt gattacatac cttcagcaga acccatcatc gcaccttccc 2520
agtctgtcgt ataccactac ggcaaggcgg atgcaccata gataccgcat catcgtcaac 2580
gggggatctc cccaggaact gacccgccgc cttcagacat gtctcgatga ggtgaatta 2640
cggagaccag ttcagaagcg accatcggtt gcctttgtct tttccgggca agggtcgttc 2700
tatacaggcg ttgccgaca actatacgaa gaatacccctt catatcaaga gacgatccag 2760
cgcctggata ggttatgtct tctccacggt ttcccctcga tcatcccact catcctaagc 2820
caagaccaag acaccaccgc ggccacgcct ctaatgacgc aattattgac aacatgtgta 2880
cagattcgcc tgactgactt gtggcgtatg cttggggtga agcctgatgt agtcatcggg 2940
gcaagcctgg gagagtacgc tgcattgcat gctgctggtg tattgtctgc cagcgatgct 3000
atctttctgg tgggcagacg agctctgctt ttgcaggagc tgtgtaccat aggcacacac 3060
agcatggtta cagtacgagc atctgtcgat gagatttgcg agtgcatacc gcttgggaaa 3120
gagtacgagg tggcttgtat taacgcgcag cgtaatgtca ccattgccgg acccgtcgaa 3180
cacatgacg atatccaggc gtctctggag tcgaatgggt ataataccac caaactcaac 3240
gtcccctttg ccttccactc agctcatgtg gaaccaatcc tccagcgttt tggtgagatt 3300
tcccgaacag ttacattcca ctcgccgaag gcgtcagtcc tttcgcccctt attagcagac 3360
attgtcacta gcagagacat cttcgccgac tcatatctgg aacgggcgac acgggcaact 3420
gtaaggtttg ctgcggcact tgaaagggcg caggaggcgg gaattataca tgccaatact 3480
gcctttattg aaaattggagt ccaccaaacc tacagcaatg ctgtacgagc aactatacgg 3540
gatatgacat gcatggtccc cagcatgagg tcagatcaga gtaactggag cacatttgca 3600
gctgccatgt ctgcattgca cgaagttggg gttgagatcg actggaatga atggtatcga 3660
ccatttgagc caaatttacg cttgctgacc ctcccgtcgt accaatggga tatgaaaaat 3720
cactggatcc aatacaacgg caattggctg ctactcaaag acaaaggact caggacacaa 3780
gatggtggtg ccctagctcc agtgactcca gctttccaaa ctcctctctt gcaccaaatt 3840
ctcgaagagt cgtcaacaga gaatggccac accgttttaa tgcagtctaa cattatgaa 3900
gaccgactct tgaagataat atctggacac aaaatgtgtg gacgaccagt aatgtctgtg 3960
ttcgcatatc ctgatatggc gttatccctg gccaattaca tatataccaa acaccaacct 4020
caggttgatc ttccgtcaat ggaattttgc aacgtacaga ttcttcaggg tttagttgcc 4080
aaaaaaagcc aagcgaaacc ccagtggtta cggggtgcga cagatgcgga cctgaagaat 4140
cttttcggtcc gaatgtccctt tgagcacgcc ctggaggacg gccatggctc ccgcgaaacc 4200
ttagctacgg gagtggttac gtatggagac agccaaatct ggtcgaccaa atgggatacc 4260
caaactgagt tactcttaag cagaattgag gtgttgtatc gattggccca ggagggacaa 4320
gccagtcgcc tgtctggcaa cctggtctat actctcttca aaacgcttgt cgattactcc 4380
gagaaatacc gggaatcca gtctgtggta ctgcaccaac tggaagggt ggcgaggta 4440
tcccttccgc ctggcgagga tggatgacg gcagctccca actatatcga cagcgtttct 4500
catgtggcag gctttatctt gaacgggagc aacgcactcg acgaccacga tactgtctac 4560
gtcatggatg gttggaagtc gatgaatttt agccagccat ggtccccgg agcacgatac 4620
caatcgtaca ccagtctgaa accggcaaaa gaaaacatg gttctacat aagcgacgtc 4680
tttgtggttc gagatgggca aattgttggc caaattcgag gtatgacgat gcgtccactg 4740
```

```
cctcggattc tgctgcgccg gtttttcgat ccacctgagg aaagtccagt gtcccacaaa 4800
ggtatatcca tctcttcgac tatctctgac agcctcacgg acacacaatc accaatatca 4860
gtatccgccg gcagacctat tgcttcgatc gaacgagaca cgccaccctc tacgcccggc 4920
gatgctgaaa tcagcccgat aggccgtgac gacactaggt tgtaaaaca agccatgggc 4980
attattgcct cagagacatc tatctgcccg gaggagctca cggatgatgt cgaatttgcg 5040
aacattggag tggattcact gctgtcccta gtcctggttg aaaagtttgc gttggggttg 5100
catctgaatc ttcgggcgtc cgtatttcag gactgcccca gtgtcggtag cttcaaggag 5160
catctagtcg ctgcttaa                                                5178

SEQ ID NO: 10          moltype = DNA   length = 4940
FEATURE                Location/Qualifiers
misc_feature           1..4940
                       note = fatty acid peroxidase ppoD gene Desired nucleic acid
                       sequence 9
source                 1..4940
                       mol_type = other DNA
                       organism = Aspergillus flavus
SEQUENCE: 10
atggggtggt tgagcactac gactaagtcg tcctggaatc ccttcagtac gggttcctcg 60
ggctcatctc taggtatgtc tcctcaatac tatgtataca attggaaacc actgctgata 120
ctagaaaagt caaaaatata ttgcctgggc cttcagacag cggtggctct ttggcatcgc 180
tggccttcgg ttctaaggac caaaaatggt tccaaagcgt tcgagtaaa ttcggtttca 240
acggtgttct cgcgactgta cttagcttct ttctctatgc tctctacctc aagttcgtca 300
gccatgatga gaaaggcttg caaactttga tcaaagaaaa ggcatcccag tatctcggca 360
agatcccagg cctcaacaag ctctccttcc tgaaaggaca tctgcctttg ggtaaatttt 420
caaagtcact gattccgaag gcaacgaaag gtgcgctcga aagtattgct ggaagtagtg 480
gtggtatact gtcaaaactc aatcccttca actggaaaat cttcaacaag cggaagattg 540
ctgaggaaga ggatgatatg aggtatcaag caggtgaacc ctacgagac ccggaagttc 600
tggctcccac cctgcgcgac gatcttaaag ctgtcgggct caaggctggt gtccaagatc 660
tgaaagtgct tctggatgtc gtcaagaata agggcaaacc cattgatgat cgagatttga 720
cggtaagtcg cacgagaatc taaggatata gcgcttgcta acaggacctt agatggagaa 780
actcatcgct attgtctcgt ccctgcctcg aaactccaaa gcgagggaga agttgactgg 840
cgttctcatt gatacgctct ggcagagttt acctcatcca cccatgacct atctcggtaa 900
caaatatcaa tcggacac ctgatggaag ctacaacgtg agttataatg agcaatatga 960
tcgttattga ggttgactaa tcgatatatt agaaccctct tcaaccagac ttaggaaaag 1020
cgggcagccc ttatgcgaga aacgttccca aattgaagca catgcatggt gttcctcccg 1080
atccaggtct tcttttttgac tgtaggtgtt aaactgcatt cttcccattg aagaaactac 1140
taactcatct agtgctcatg gctcgaagcg atgaaacttt caaagaaaac ccagtcggtc 1200
tgtcatccgt gcttttctat cacgcaacga ttatcattca tggtaagata gacccgcata 1260
aaaccttgaa cagtctgctt atgtgagtta gatatcttcc ggagcaaccg atttgatcct 1320
aacatcagtg acacgtcttc ttaccttgac ctcgcccctc tgtatggatc cagcctggag 1380
gatcagatga aggttcgaac caaggtccgc ggttactaca agccagacac cttcagtgag 1440
aagagactca ttggaatgcc cccgacgtt aatgcaattc tcgtgatgta taaccgtttc 1500
cacaactatg tagccgacaa cctccttaag atcaatgagg aggacggtt ttcgctgccc 1560
gcaaccaaat ccgaggagga caagaaggct gcactggcca acaggatga agatctattt 1620
cagactgctc gactgtgagg accaaaaact gactattgat tttatatgtt tgctaatcag 1680
caaattgtct aggttacca atggtctcta cgttaatatc tcattgcacg actatatccg 1740
aggcctggcc aacgttcatc attcatcgag tgactggact cttgatcctc gagtcaagat 1800
caacaagatc tttgactcgg agggtgttcc ccgaggaatc ggtaaccagg tgtcgtcga 1860
attcaatctc ttgtaccgct tccactctat tatctcccgt cgcgatgaga aatggatgaa 1920
cgagttcttc gcagatatct tcggtcaaga caagaaggtt gaccagctca ctccacagga 1980
attcatccag ggtctttatc gcttcgaaca gagcattccc gaggatccca gtgagcgtga 2040
atttggcgga ctcaagcgtg gtgaaaatgg caaattcagt gacgccgact tagtacagct 2100
gatgaaggat agcatggagg accctgcagg ctgcttcggt gccaggatgg ttccaaaggc 2160
gctccgtgtt attgagattc tgggtatcat tcaggcaagg aagtggcagc tagcctcttt 2220
gaatgagacg cgcgacttct tcaaactcaa gcgccacgag actttcgagg atgttaactc 2280
gaatcatgag attgctgatc ttctgcgcaa gctctatgat gatcctgaca tggttgaaat 2340
gtatcctggg ctgttcctcg aggatatcaa gccacgcatg gatcctggta tacttacctc 2400
ccttactttc tgaaaatctt ttgcttacga gtagggtagg tcatggtgga tgcaccctt 2460
acaccgttgg aagagcagtg ttcagtgacg ccgttacgc tgttcgatcg gatcggttcc 2520
ttactattga ctacacggct tcgaacctca cctgctgggg ttataacgaa gttcaacagg 2580
actatgacat gtaagatcaa ttatttcctt cctttatag atgatggcta acaagaattt 2640
atctagtctg ggtggctcga tgttccacaa attgttccag cgcgctcttc ccaactggtt 2700
cccgtataac tcattgcata tcacccagcc tatgtacacc aggaagatga acgagcagat 2760
cgcccgggaa attggaacta tcgacgagta taccccttgat gacccttcgc cgcctccaaa 2820
gaccgttatc gtgaccaagc actccaccat caccaagctc tcgaaggacc aggcaaactt 2880
ccgtgttatc tgggctaagt atctgaatga gatgattccg ggtagagact tcagtggcta 2940
catgttgcta ggcgacaagc cggccaacac tgatcagaca actctcgtca aggagatcct 3000
ctacagtccc gccgagttcg tgcaattgtt gtccggaaga gcggtgctcg tggccaaaga 3060
gcaacttgcc actgagacat tgaacttgac atcggagttg caccaggttg acatcgttcg 3120
ggagtaagtt atttttttt tcttaaaaaa cactattatt ctgaattcac actaacttct 3180
ctctagcgtc gccatcccta tggtgactag gattttggcc gatcttttct gtctggacct 3240
caagaccccc gagaacccga acggaactta caacgtcgca gagctataca agtatatcat 3300
tgacgtgatc atctttggtt tcaacaatga tgatccagta ttggcttaca aacgcagaaa 3360
atgggctcgt gagggtgcag aatctcttac caagaccacg ttgagggtcg tatccaactt 3420
gcccgcttcg gagaaatctg gaagggaat cgttaagggg gccgtttcta cagccaagag 3480
catcgcctcc aaaattcctc tggtcggcaa gctggttgga gacggcaaag gcgttgaagg 3540
gcagtcgaca agtggctcgt tgcgctggta tggatacaat gtggctaaag aattaattgc 3600
ttcaggaaag actcccgcag aggttgcaga tatcagctgg atgaacgctg tcggtggtgt 3660
```

```
tggtgcaact attggagtgg ttcgtacacc tggtctacgg aaagtagtgt ctgcccgagt  3720
ctcagctgac atgagatcta gtttaccgat gtcctcaact atttcctcca ggatgagaac  3780
tcccaccact gggaagagat tcaaaagctt gctgctagct cggacttgga atcatcaaac  3840
aagtctctcc ggcagtacgt cctcgaagct caacgcttga ccagcaccca acgaagcatc  3900
cgtctctgtg cgggcaaggc cgtgattgat ggacagagct tcgaacctgg caacttggtg  3960
atctgcctat tggtatgtta gatcttaaga gtttcatgaa atcaaaacta attctataca  4020
ctagggtgcg gcgtgcaagg atcccgatgc tgtccccgac ccagaagcat tcaagcttga  4080
tcgaccatcg agcgcgtata tccacttcaa cgttggacca cacgagtgtc tcggacgaga  4140
aatcgccctg tcgtgcatca cttccctggt ccgtgtctgt gctggcctga agaacctccg  4200
agcagcccccc ggtcaaatgg gcgtcctgca gagtatcacc accggtactg aaaagcactt  4260
cctcaacgac agctggtcta cccttaccgt cgacccaacc agtaagtccc ctgactctat  4320
aattcataac atatactaat tacccatcag cctggaaaat ccacttcgaa ggccagggcc  4380
agggcattca ccatccccct aagatcccag tcaccgcagg ccgagacctc aatgccctat  4440
ccaacgcctt gaagaaacaa caccaggaca agttacaaga aactgtctca aaagtagcca  4500
acggcgtcac agccccactg accaaactca tcccatccaa tggtcccagc aacggcgcct  4560
ccaccccagg ccacctcccg ctcccatca accccttcca gaatggcaac ggtaacagca  4620
acggcgtcgc aaacggcaat acccacccaa gcctcctcca ccaagctgtg tcctcagccg  4680
ctgcgatccc acagcacgcc ctgggcacag tccacgatgt cgcccacaac accgtcggcc  4740
atttgcctgg tggccagcag gtcacagact tcactcacgg cctggtccac cccttcgctg  4800
gagctgtgtc tccgggtcaa actcaaactc cgcctcaggg tcagactcaa ccccaccagg  4860
ggaactggtt ctttctcccc catggcatgg aaaatgctgc caagcaggtt ccgggacatc  4920
tttttggtca gacagcatag                                               4940

SEQ ID NO: 11           moltype = DNA   length = 5052
FEATURE                 Location/Qualifiers
misc_feature            1..5052
                        note = Desired nucleic acid sequence 10
source                  1..5052
                        mol_type = other DNA
                        organism = synthetic construct
SEQUENCE: 11
atgaaaaaaa ttttaggatt ggatttagga accaatagca ttggttgggc actggtggag    60
attgaccacg aaaaaagaat cgtaagaatt ttagggcttg ggtcccgtat tttaaacatg   120
gattcctctg agatagcaaa gtttgaaagc ggagtcaaat ttcaagtgc tgccgcacaa   180
agaacagaga gacgtacacc tcgaaaatta aacgaacgat acctttaag aagagataga   240
ctacactgtg tgctgaacct attgaatact ttgcctccgc attataaact ttcaattgag   300
tttgaaaatg aaaaaggaaa acgaagtgga aagtttaaaa gtggtacaga agaaaagttt   360
gcctacagta aagatgagaa tgggaaagat catttccttt ttatgaatgc ctatgaaaaa   420
atggaagctg attttaaact acgtcacccg gaactatttc atcaaaagag aaatggcaac   480
ataacaaaaa taccatacga ttggacacta tattatttaa ggcataaagc tgtaaccgac   540
cccagttttg aattaacaaa agagcaattg gcttggataa cattaagttt caaccagaaa   600
cgaggctatg aaaaagttat tggacaggat gagaaagtac aaaaagaggg agaaagatca   660
gatacttta ttggcaaagt taaaagtgtt caaaaacttc aagagaaaga tatttatgaa   720
atagtactct cggatattaa taatgaagca cttgaattat ttcgctacaa agaagaatcc   780
acaattccca ttacagagat cggtgatttg aagaaattg aaagggtttc gaaattcaat   840
gataccggtg agatcgataa ctctaaaaca gaatacatag tcaacgagat tagagaatta   900
ctcattacca acgtccaaaa tacttggcaa aaaagaaaag agaatttgt tttcgagata   960
gaattagaaa caggctggat taaggaacag cagagtcgat tcactcctaa gtggaaagat  1020
accaagagag atttcattat aaagacaaag tatgatgaac aaggggatcg aatattaaaa  1080
ggtgcagaca aagggcgaaa tattgggata cctaaagaag aggattggac attgatgaag  1140
ctaaaaacag aaacttcgat aaccaatttc aacacaaaga ataatacagt aggaatagct  1200
tcttttgtct attacaatct attgcaaaat ccgagacaga gaatcaaagg tgatttagta  1260
acagttattg aacgtgatta ttacagagaa gaattggata aatatttgt aaatcaagaa  1320
aagtttcatc ctgaattaaa aaacagaata ctgtatgaac aggcaataaa actattgtat  1380
ccaaacaata ttaatcatca aaagacaatc aaagagttga attttaatta tctgattaaa  1440
gaagacattt tgatgtatca acgtgatttg aaatccaaaa aatctttaat tgccgattgt  1500
gtatatgaaa aaaggaggta cagaaacgga gaaactcatg aaatggtaga tgttccaatt  1560
aaggcaatcc ataaattcaa tccattattt caggagttca gacttggca gtttgttaag  1620
cgactcaaaa tattgaagaa acaggacgtt gtgaacaacg agacaaaatt aaacattgat  1680
gtaacatccc aatatcttaa ttcctataga atcaaagaaa aactgtttga ctatctcaat  1740
gataaggact ttgttacaga gaaaaatatt cttgattttt tgagcaaaac gtacaatgat  1800
aaaacaatta agtccgaaaa ctacaaatgg aatttagctt cagagaaaga accctgtaat  1860
accacaagac atgagtttat attaaggact aaacgtgtta atggctttga ttataagtca  1920
ttcttgtcca gtgaaacgga gtataaacta tggcatttct tctattcggt aaagagaaa  1980
gaagaattt acaaaggatt aaatagttta ttcagtcaaa tattggagaa atcaggacta  2040
tctaaagatt atctgcccga attagtgaga aactttagct cttttggagg ctatccaaat  2100
gattacgaa cttattctga aaaagcaata aaaaattac ttccgttctt acgattggga  2160
aaatactggg atgcaaaaga agttgagaac aatctaaaaa agatttacc agatgaaata  2220
agtaaaaagg taatagataa agaaagtatt aatggagaga taaatgattt ccagggttta  2280
tgggtttcaa gtgcttgcta tcttgtatat ggcaggtatt cagaagttgg ggaagttgaa  2340
ttttggaatt cacctatga tattgaaaag tatttacaga atgaattcaa acagcactca  2400
ttgaataatc ccgttgttga gaagtgctt gttgagactc ttcacttagt aaaagatgta  2460
tggaaatact atggtgaaa gttgagtgaa gatgaaaaag ggaatcctgt ttatgccaaa  2520
ttgttttgata aaattcacat tgagcttggt cgtgagatga gaaaaacaa caaacaaaaa  2580
gagaaggatg ataagcaaaa caggaaaaac cgaaaagcga acgaacgtat tattgaaatt  2640
cttaaagaac tgaaaaaaga aaatacttca cttgaagtta atccccttt ccaacaagaa  2700
aaactccgca tttagagga aggattacta tcgtctattg agtttgacaa ggatactacg  2760
gagtataatc tgccagaagg gaaatttca aaaaacaaa ttaaagaaat aaccacaaaa  2820
gagatatcga aagtaagtag aagtgatttt gaacggtaca agctttggct agaccaaaga  2880
```

```
taccaatctc catatacagg tcagatcatt aaattatcag atttattcga tagaaaaaaa   2940
tatgaaattg aacatatctt cccgcaagag agaattactt taaatgcgtt gtcaaacaaa   3000
gtaatctgtg aaactgagat caacaagatt aaaggatcaa atactggtta tggattcatt   3060
ataggtgcaa atgaaagaga aatattttgt gctgcacata atgagaagat taaaattctc   3120
agtgtggatc gatatgagca actagtcact caaaatttca ttgataagaa acgagaaatt   3180
cttttaagca aagatattcc tggtgatttc acgaatagtc agaaagttaa catgcaatat   3240
atttctaaaa tggctatgaa gcttttgagt aatgttgtaa gggatcagga tgatgattct   3300
tatcgttcga aaaacgtttt agcaacaaat ggaacaataa cttcagaact gaaaagacat   3360
tggaaactaa acgaagcctg gaatgaatta acttctccaa gatttaaaag gctgaacgaa   3420
ttaacaaact cgaatctctt tggtgattat cgaaaaataa atgggcatga tgtgtttgtg   3480
aatgatgttc ccgaagcaac taagaaagat tttgatccca aaagaattga ccatcggcac   3540
catgctatgg atgctttagt aattgcttcg acaacagaag aacatgtaca atatcttaat   3600
aatatttctt cacaagagga aaatgatgaa cagaacatga aaacccgaaa aggcttgaaa   3660
tatattttga ccaattcccg tagaggtttt aatgacgaga aagaatggta ttttctacct   3720
cctgcgcaaa caaaatcatc agatggaatt tctgaatttg aataccatta taagaggtt   3780
aaaagcaaag tatttaaaga tattgccaaa gaagctcttg ataatactgt tgcaagtttc   3840
aaacaaaaga accggattat ccgtcaacgc tggaataagt atctcaagta taatgaaaac   3900
ggacagcttg atattcacga agaagaaat ctaaaattga aaagaaata taacgtccgt   3960
caggcgttgc atttagatac ttttttatgga aaagtcaaga ttcaaaacaa tgaaaagacc   4020
aatacgaatg tagtcgaagt tgacttagga actgctatta aagataacta tgattttttt   4080
gaaacagaga ttattgatag aataagaatt cttcgtgatc aaaaacaatc taatagcgaa   4140
attatcagtt tattaagcat tgaatatccc aaagttaggg tctttgcaaa atttgttgcc   4200
tcaagatttg ggaatgaact aacctctttg gcttcatcgg atatgattct taaggcaata   4260
gaatcaatta ctgatacagg tattcagaaa attcttttaa accatctcga aaactataaa   4320
gaaaaaatag atgaagaggg aaaggaaatt gctccgcaga ctttggcttt ttcacctgaa   4380
ggaataaaag aattaaatca gaacattaaa tcattaaaaa atggtaaatc tcatcaacca   4440
atttataaag taaggatggc tgatgcgatg gggaaaaggt tcttttccagt ttcagaagaa   4500
ctagctaaat cttcgaaata cgttgcaact gctggtgata gcaatgcttt ttgtgggata   4560
tatgaaaatg gtaaaatgag aaaatactat gtgccaacat taagagagtc tcttataaat   4620
ttaaaagagg gctatgatcc ttgcccacag aaacatcctg aagatacaga ctactcgttg   4680
ttatttgtgc ttaaccccaa tgatttagtt tatgttccga caatagagga gtcagaaggg   4740
cccaaattag ttgacttcaa taatttaaac tcagaacaaa tgacacgaat atataaattc   4800
agagatggca gtattaataa acatggaggt gttcaatata attttatgcc atctaattgg   4860
gctacaatga tttttaagag tacaaaagaa ctggaaaaga taaaaatgag taatgaatcc   4920
gaattaaagg gtgaaattac gttgactaca gataaagata aatcgcagaa ttcgttagaa   4980
ggaaatcaga ttcgttctat ttgttggaaa ctaaaagtag atagattagg aaatatttca   5040
agaataaatt aa                                                      5052

SEQ ID NO: 12         moltype = DNA  length = 5430
FEATURE               Location/Qualifiers
misc_feature          1..5430
                      note = non ribosomal peptide synthetase desired nucleic
                      acid sequence 11
source                1..5430
                      mol_type = other DNA
                      organism = Naegleria gruberi
SEQUENCE: 12
atgtctggta aaccaagata ttccacactt gtggaaatgc tcgagcatgc aacacaagaa     60
agaacatcct ctctcattta cagacaatta gattactcca atgatgtggt gggggaggag    120
aagaaacttt tctctgactt attgaaacct tcaagtatca aggagattag ttattgtgat    180
ttcttaaaga aagtgaaatc tctctccact ctcattcaaa ctcaagccaa aagtggtaat    240
agagctttgc taatctttga accaggtatt aactttattg ctgctttctt tgctaccttg    300
tttgctggtg ttattgctgt acctgtctat cctccaaaga acaaggaaga attcaacaag    360
ttgagtaaga ttctggccga ttctaaacca agtttatttc tgttatccaa gtcattcat    420
caaaactttg agcaacatgg cattaacaag ttttttacca agattaattc tcaacaacat    480
gtcgagaatc aggtaataca agatgtactc agtggttgtc tggaaactta tgaaggtttt    540
agtcttttga tttcagacgc ggttgactac agtgataaac aattgtatac atattggaaa    600
cacccaaaca tcgacacaga ttcggttgct ttcctccaat atacctctgg atcaaccagt    660
gatccaaaag gtgtcattct cactcataga aaccttctca acaatcttca tgttatgaac    720
tatgccctac gatactctaa tcagaaacat gttgtgctct ggcttcctcc ttaccatgac    780
atgggtttaa ttgctggttt acttgaaatt gtctattcga attgtagtgc tactgtatta    840
tctccaatct ccttcctgga aaatccatta cgttggatgt gggcaatcaa tgaatataga    900
gccacattgc tgggtgctcc taattttggt tatgatctct gtgtaaagca ctttctagct    960
catgagaagg aatacagaga aagttttaaa ttattcagtt ttagcagttt ggaaatttgg   1020
gcatgtggtg cagaacctat cagagcagaa actatgaaa gtttcagtac actcttctct   1080
gaatttggat tgaaaaaaca agccatgtat ccatgttatg gattggctga gagtactctc   1140
tatgtcactg tgtgtaaacta tatgaaaggt ttcgactta ccacaattga caacaagaac   1200
caatacatta tcaagaatgg aacagtcgaa caaacacaaa ctcatcaaaa attcgttaat   1260
tgtggtgtca actatgatga aaatcaatcc attaaaattg tcgatccaga atcttctaca   1320
gaaatggaga atgaaaggt tggtgaagtt tggttgtcaa gtccaagtgt cgctcaaggt   1380
tattgggaga accagaact ttctcaagag gttttccatg cacgagtggt tggagatgat   1440
agggagtatc tcagaagtgg agatttgggt tcatgttga atgaaactt gtacattact   1500
ggtcgtcgta aggatgtcat tattttgaat ggtgtgaatt attatcctca agatgtagaa   1560
ttggcatgtt ctaaatgtca tgcacagatt agaactgggt ggtggtggc tgttaatatt   1620
gctgatcgtg atggacagga tcgattggtg ataattgctg aaactaaagt tgtttcgaat   1680
agtgagacac aagtattgga gagtattgta caatccatac gatctgcaat tgccgaatcg   1740
atgggaattc caatgtataa tgccctatcg accatccttc tcatgactaa aggaggcatt   1800
ctcaagacca caagtggtaa actgagacgt caaccaacta acaagcatt tctcaataac   1860
aaacttcctc caaaactaat cgttcacaga tgggatcagg agaaactctc agatagcgct   1920
```

```
tctcaaccaa gtactccaac agagattgga ttggctaaaa tttggaaaga attaacagga  1980
attgatccat cactttcgaa taactttttc cttttgggag gaagctctat gagtttgatt  2040
cagctaaaat ctagaatcca acatgttttc aatgtaatta taagtttgac tgatttggta  2100
atgtcgccaa cattgcaatt gatggctaaa ttggtcgatc aacacagcaa tcaatgtaat  2160
actagctctg tacaaatttc aaagagagaa aggacaagtg acactttaga attatcaaac  2220
tcacaaacga gattctggtt cttacatcac ttgatcgata atcctgccat tcacaatgtt  2280
tttgcaggtg ttcgtttgaa aggtgacttg gataaacaag ctttagaaaa ttccattacc  2340
aaacttgtag aacgtcatga aagtttacgt acaagctttc aagaaacaga gatgtcacca  2400
atgcaacaca ttcattctga aatttctctc aaattaaatt caattagttt gaaacatctt  2460
actagtgaag aagaaaagaa tttgaaattg aacaagtttc tctttgatga ggtgaacgaa  2520
ccattcaact tgaatgaagc tcctcttctc agagctaact tgatcgaaat gtcagagtgt  2580
gatcatgttt tggccatgac tttccatcat atcataatcg atggatggtc catgaattta  2640
cttgttgaag agctagttca atactatctg gcttttaaga atcatcaatc gccaattctt  2700
ccacaagttc ttcaatatgg tgattacaca ctgtgggagca atcaacaaca atcaatgaat  2760
gaaactcaat taaaatattg ggaagaaaaa ctctccaatt taccagaatc tatcaaattg  2820
ccaacagaag gcgaaaactt atccaaatca tttgatggat ctcatttctg gtttgcaatc  2880
ccagaaactc tcgttaactc cttaagaaag atcgttcaat caagaggagc cacactctac  2940
atgggcatgt taactctatt caatattta ctgtacagat attctgaaca gaatgatatt  3000
gcaattggaa cacctgttgt gaatagacag caacatgttg agttggaagc actgattgga  3060
ctcttggtaa atactctggt gattagaaat aatgtgaatc cagagcataa tttcattgaa  3120
actttgatgg aaatcaagtc aactgtaatt gaagcttttg aaaatcaaga tgttcctttc  3180
cagaaagttg tagaaagatt gaaagattca cgtaattcaa tggagaatcc acttttcaa  3240
gtcatgatgg ccatgcacaa cccacaacgg aaaattgtca tggataatct tgaaactgag  3300
ctagttagag ttgacaatgg atcatccatg tttaattaa cacttgaatt acaagaaata  3360
gaggatggaa gtttacaatg ttgtttcgaa tatagaactg atcttttcaa gaaggaaact  3420
attgaaagaa tggctggaaa tcttattgaa ctattgcacac tgaatcggat  3480
aacaaatcaa taagcaagtt gtctttccta tcgaattctg aagttgaaac tttgaataat  3540
tttggaaata tcaccaataa tgatctcagt tcttcagttt cgaatagatt attacacgaa  3600
ctcattgaag agcaagctat caaaacacca gacaataccg ccgtctactt ccaaggtaaa  3660
tccttctcct accaacttct cgatcaaaaa tcagaccaat tagcaaggag attacgagat  3720
atgaatcact ccaaaaatcc cttcattgcc attagcattg acagaagctt tgaattgatt  3780
gtgagtttag ttgccattct caaagctgga tttgcctatc tccctctcga tccaagctat  3840
ccacaagaac gattactcta cgtgcttgat gattcacaag caggtctgtt aataactcaa  3900
tctaattatt ctgaaaaatt caaagactat caagggaaag tgttgtctat tgatagattc  3960
gtttggtcag caagtagcac ttccacatcc tccattagta ttgagaaacc attgacatca  4020
ccaaatgatt tggcctatct catttacact tctggcagca ctggaaatcc aaaaggtgtc  4080
atgctttctc acagaaatgt aaacaatact ctcaatggtc taattaaatt gtacgaaatg  4140
aagcaagatg acaagttttat tcattacagc tcctatagct ttgatgtttc attggaagag  4200
attttccttc cactaattac aggtgcttcg attattgtgg ccaatccaaa tattcaatat  4260
cagttggagg agcttgttga cttggttgag caaacgaagg caacaatcat tggtgtcact  4320
ccaagtttgt ggcatggtat aaggtaccat gttttgagga atccaaaatc aactgaatct  4380
ttaagaattg tcactattgg aaatgaacct gttgattcga atgcagtcaa agaaatccaa  4440
caaatgtgtc ccaatgcaac agtattcaat gtatgtggga gaacagagac ttgcattgat  4500
tggtctctct tcaaggttcc aaaagattat gcacctttac aacaagtagt tcctattgga  4560
aaaccaattc ctggtgtcaa attgtatgtt tggattcga atagagagtt agttccaatt  4620
ggagtacctg gagaactcta cgttggagga aatggtgttg gaaatggata ttggaaaaat  4680
agtgagctaa cctccaagag cttttattgaa aatccattcc aaactaaaga cgaaaaacag  4740
aacaatgtta atgaaaaact attcaaaaca ggagatttgg ttaaatggtt acctgatgga  4800
aatatggtat tcatctccag attggatcat caagtgaaat taagaggatt cagagttgaa  4860
ttgggtgaaa ttcaaaatgt catgaggaag agtggtctcg tcagggaggc aattgtgatt  4920
ctccaagatg atgagaatgt cagtaacaaa caacttgttg gatacattgt tgtaatgaag  4980
ggagaaacta gaccgcactc aatcatcata cagctagtca attcctactt ggagaaacat  5040
ctgccatact atatgattcc atctcatatc atttgcattg aaaaagttcc aacaaccaat  5100
aatgaaaat tggatcgtag agctttacca agagcagttg accaccagca aactaaaaga  5160
ctagaagaaa atatgggaga ggtcgatcca gctgatattc cagagagtca ttgcaagcta  5220
agacaaattt ggtccaaagt actcaagatg aaggaggatt gcattgggtt gagtgataac  5280
ttttttgcaa ttggtggaaa ttccattctc attgcccaat tgagaagcat ggttcgtaca  5340
gagttgggta ttcagttaga gttgaagact ttctttgaaa aattaacaat ccaatctatg  5400
gctacccaca ttgaaactgt tagccaataa                                   5430

SEQ ID NO: 13         moltype = DNA   length = 5556
FEATURE               Location/Qualifiers
misc_feature          1..5556
                      note = DNA polymerase-I Desired nucleic acid sequence 12
source                1..5556
                      mol_type = other DNA
                      organism = Plasmodium inui
SEQUENCE: 13
atggttcgat gtcaattttt cctcttttgt ctgatcctta tccattatgt gttagcaatt   60
cgaaataaaa gtaggccgaa aacggatttt tacttgaaga cgaattgtga attggtgaag  120
aggggaaaga atgactccaa agtatatttc aaaaggaagg cgcggggtga ggatttgtgt  180
tcgcgggcat tctatgaccc gctaagaggg gggagaaaca accgagacag cggcgcgctg  240
cgcgccacga gcacgttcgt gtccaagtac tacaaaataa acataaacga tgtgtacagc  300
tacctgaata ggaagaagta tgagtacata gagacagacg tgaagataac tctcaagtac  360
tgccccttt gcccgccaca caagtataaa tatgacaata tgtacaaaca tgaaattttt  420
aaaaacaccg gaaatagtta ctgccacagg tgcgggtata aaggaagctt ctacgatttc  480
aaactaaaaa tgggagactt ggtaacaagc aatttcgaaa acactgttgt aagcaatacc  540
tatgaggagg aaaaaataac cttcaacgat gttaaggtgt atagcatgaa tctgttgtac  600
tcgaaggagg cagaaacggc aaggaaatat ttaatcgaag aaaggaagat aaaattagaa  660
```

```
acgctaaaaa agtattatgt aggattttct atcatggaat ttcagtcgct agagaattca    720
ggaaccthhhtg aaaaacacga atgcttaatt ttcccchttta taagaaaagc gaatgatatg    780
```

```
acgctaaaaa agtattatgt aggattttct atcatggaat ttcagtcgct agagaattca    720
ggaacctttg aaaaacacga atgcttaatt ttccccttta taagaaaagc gaatgatatg    780
aactccatgg ggttaaatgg aaataaaaac aacacgaatg aaaaagactc gtaccaaatt    840
gtccgaataa aggtaagaag cttaagggat aaaggataca tgagattata ccccaagaat    900
gtgaaagacg aaatgaaatt attctttttt ggagaccatt tggttggcaa ttccgaagag    960
attgtcctaa cggaagggga gatagatgcc atgacggtaa gtcaggagac gaattatgcc   1020
gccatttctc tgcctaatgg ttcgaagtcc cttcccatat atttgttgcc atatttggaa   1080
aggttcaaaa aaatacacct gtggctcgat tttgacaagg ccgggaaatc cagcgtcttt   1140
aattttgtca ataaaattgg gctagggagg acgaacgtaa taaccgatgc gaatgtgcac   1200
tatctggatg aacagctctt cgagagaaag aggaaaaatt tgttaaccaa aggggtctt   1260
ctcttacccc taacagttgc tgataaccct atcggcgtag cggagcagaa aaagggtgat   1320
attaaagaag atacgccaag tgacgaaaaa aatgggcaca cagagggcac ggaggatgga   1380
aagggcccga acacatctgt agatcccatg tcaggtacaa acaagtcaga tttgaaaata   1440
gccgaaaaga cgaaaaatga aggtgatagc aggaagaatc ccatttatgg tgacacggga   1500
aatacccaag aggaggcgca aaaaagagca agagaagaag gtaaagtacg aacattccac   1560
tttgtacaga acaatatcat gtatatacca acaatatcg ttgtgaagga tgccaatgac   1620
tgtctaaagc acaacataga cgtacgattt tttatagaaa atagcgaaaa ggtgaaacat   1680
agccaaatat taaacttcaa tgatttgaga caaaacattt tggaagaatt aaaaatatccg   1740
gatcgaataa atggaattaa gagtaaaact attccatcgt tgaataaatt tctatatggc   1800
ttacgcatgg gagaattatc catatggaca ggtccaacag gggtaggaaa aactacccctt   1860
ttgtcccaac tttcgctaga ttattgcatc caggggggtgt ctaccctatg ggggtcgttc   1920
gaaattaata acataaaatt aggaaaagta atgttaaatc agttttgtgg aaaaaactta   1980
gaaaaaaata ttgacctatt tgacctatat gcagataagt ttgaattatt gccactaaaa   2040
tttctaaagt ttcatggaag cacaaatatc gaccaagttt tggatgccat ggattatgca   2100
gtctatgcct acgatgtgaa gcatatcatt attgacaact tacagttcat gttaaatata   2160
aataaatttt ctgacatata tgaactacaa aatattgcta ttgataagtt tagatcgttt   2220
agcacaaata aaaatgtgca catcactttg gttgttcacc caaggaagga ggacaacaac   2280
cttctctcca ttgcttccgt cttttggtagc gtcaaatcta cacaagaagc cgataacgtg   2340
tttatcattc agagacatgt gtctaaaacg aatgaaactg ttttttttat agacattaaa   2400
aagaaccgat tcaagggcag cttggggaga atcccctacc tctacaataa agaaaaatatg   2460
accatcaagg agatgtccat tggctactta aatgatgcca tttcgggtag cgcctaccga   2520
tccactggtg ccaccccttc tgctaacact tttgtgccga gcgttgggcc acttcccgat   2580
ggtcccccaa gcgatggcct agacttcacg ctttgtgatg agtacgacta tatgaagcag   2640
ttagccgacg aatacgagtc gaagcacgca gtacgcaggt atcgccttgg cgctgatgga   2700
agggttagca gtgtggggag tggaagtacg aacaggcctg acgcttcatc atcgaacgat   2760
gccccaaacc aaagtaggga cagtagcggg tcggtggact cctcgcgcaa taatcaaaat   2820
aaagataaca agtcagtcaa ccaagtaggc ggcgcagaga atgaccctac gagaaataac   2880
tgcttagtta gtccaagcag caagagcgaa aaaggaagca taaaaaacct attgaaggga   2940
gtcgaccaag gaagcacaac aatttctgta ggaagaactc caaaaagtga aaaactaagt   3000
ggtgatagca ttcatgtggc caaccctgct gacccgaacg gggagaagca agaagcaccc   3060
tcagatgtgt ccaagaaaaa tgtatcatcc taccgattga gcactgaagg gataataaaa   3120
ctatgcgaag aaataaaaga caacacaaat gaaaaactaa aagatagagt gataaccata   3180
tccatgagga actgtgttat aaataaagat tcaatgataa ggacattcg aaacttttata   3240
aagacaaaca agttaaacat aaaaacggct gggaagaacc taaaaaaggt agatgtttt   3300
attgccattc tgcagagtat tccgaaggag tacataacga ttacatatgg aggagggggac   3360
gtagagaaag aggatccgga caacaacagt gtcagcaaca cgtgtggtga aatgtagaa   3420
cgaggcagac tgaatagcac cctcgcagga aataataaca atgtgaacat tgggggaagc   3480
cgttccagcg cattaccaat tagggggggcc accaggaata atttcaacat tgttccgact   3540
gtgcaggaat tctgtgcgaa cagccataac attgcccata gttcaagtgg ttatccgatt   3600
gacccctcaaa aaggggaggc caaatcggga cagcaataca gtgaagatga tataaaatcg   3660
gtatacgggg aggaagttac aaaaaggtac atccaggaca atataatcaa cgtagatgac   3720
aacattgtta agcggaatgg cacattcaaa ttggaaggag acaacaaaat ggttagtagc   3780
gaaaaattgg agtactacga accggtgaaa aaattcgacg acgatattga gtcgagattt   3840
tttctcataa atgacaataa ttataacgaa aaggttaatc ttatctacaa gaacgtaacg   3900
cactgcggat tagacattga gacaaccggg ctggaggtgt ttgacgagaa aatccgcctc   3960
atccagatcg ccgtggagga ttacccagta atcatttacg atatgtttaa catcacgaag   4020
gagaagatct tgactggcct acgagaaatc ctaagaaatg gacaagtggt aaaaattata   4080
caaaacggaa aatttgacgc gaaattctta atgcacaaca attttgaagt ggaaaacata   4140
ttcgacacgt acatagctag caagcttttta gacaaaaata aaaatatgta cggatttaag   4200
ctgaataata ttgtagagaa atatttaaat gtaaccctag acaagcaaca gcaaaatagt   4260
gtatggaata attcgctgct gaacaataat caactgttt acgcagcaag agactccagt   4320
tgtttactca agttgtacaa aaaactgaag tccgaaattt gtagggaaaa tatgagaact   4380
gtgaacgata ttgaaaataa gtgcattttg cccatttgtg atatggagct taatggcatc   4440
aaggtggacc tggagagctt aagcaaaagc acgaatgaaa ttttaagaga attaaatgga   4500
gagacgagca aattgaaagc agagctgaag gatgaagaaa ttaacgtaaa ctcgcagcaa   4560
caggtgctaa aagcattaca aaataataac gtgagggatg tttcgaataa gcttatcgaa   4620
aatacatcgg actcaaattt gaagaacttc ctcaaccata gggaagtagt cctattaaga   4680
aattacagaa gattgtataa gctgtactcc gccttttact taaagttacc acaacacata   4740
aacaaaaaaa cgaacaaaat acacacgacg tttaatcagt taaaaacttt ctccggcaga   4800
tttagcagtg agaaacccaa cttacagcaa atcccaaggc agaaaaatat aagggaaatt   4860
ttcatccccc aagaaaacaa catatttata atcgccgact ttaagcaaat tgagctaaag   4920
atagctgccg aaatcaccaa tgacgatatt atgctgaaag cgtacaataa caacatcgac   4980
ctgcacacac tcacagctag cattatcacg aagaaggcca tacctgatat aaataaggaa   5040
gacagacaca ttgccaaggc cataaacttt ggcttaatct acggaatgaa ttacgtcaat   5100
ctgaaaaatt atgcaaacac atattacaac ctaaatatga accttgatca atgccttttat   5160
ttttacaact ccttttttga gcactataag gggatataca gatggcataa tcaagtaaaa   5220
cagatgaggg cctttagagta ctctactctt tccaacagga aagttatatt cccctacttt   5280
tccttcacca aggcgttgaa ttacccagtg cagggcacct gtgctgacat tttgaaactg   5340
tccttagttg agctgtataa aaatctgaga cccatcaatg ggaaaatcat cctctgtgtc   5400
```

```
cacgatgaaa ttataatcga ggttgacaaa aaatatcagg aggatgcctt aaaaatcctc   5460
gtggaatcga tggaaaattc cgcttcgttc tttttgaaga aagtcaagtg cgaagtttcc   5520
gtgaagattg cgcaaaactg gggctccaag gagtag                            5556

SEQ ID NO: 14           moltype = DNA   length = 5361
FEATURE                 Location/Qualifiers
misc_feature            1..5361
                        note = polyketide synthase Desired nucleic acid sequence 13
source                  1..5361
                        mol_type = other DNA
                        organism = Aspergillus lentulus
SEQUENCE: 14
atgaggccag tagactttac ccctcgtcc gaatctccca cagcagagaa aggaatgaag    60
gttgtctact ttggtaacga gctgcctcaa gacggcctcc aaggcatctg tcgacgacta   120
cacgcctaca ccaaagaccg gcgttacccg ctcctcgccc gattcatcga ggagagcacc   180
tgggcagtcc gcgatgaggt tcggcagcta catgccgcgc aaagagcctt ggtaaccccg   240
ttcgagagcg tcctccatct tgctgagcag ccggagctgt gcaaaggacc tctctgcggg   300
tcgattgagg gcgttcttct ttgtgttatt cagttgggaa cctttattgg ctactacgaa   360
acttcacgga atgaatacgc ctttgaatcc gcacacacct atctcacagg cctgggactt   420
ggctgttga cgtcgacggc tgtctctctc tccccgacgc tggcagacct cccctagct    480
ggggccgagg tcgtgcagt ggcttttccgt cttggtgtgc tggttgccga tgtctctcag   540
aatctcgaac ctgctgcatgc ggcaggcgat cgaggctgat gggcttacgt gattcccaac   600
atcacaccta gtgaagcaga agaggagctt actgctatcc acaagcgaga aaatactccc    660
gaagctagcc ggatatttat cagcgcaatc agtcggacgt cagtgacgat cagtgggcca    720
ccggctcgac tcaagcgcct ctttcggctg tctgatttct tccgtgaccg caccttcata    780
gctcttcctg tgtatggagg cctgtgccac gcaaaacaca tctacagctc gcagcatgcc    840
cggtcggtgg ttcagggccg gtcaatagcg gccttggaca cgcgctttat tgggagatac    900
ccgatcctct cgactggcag cggcgagccc ttccccacag ccacgacggc gacggagctg    960
ttcgaacatg ttattaccga aatcctcacc caagccattg agtgggagaa tgtcatccag   1020
ggagtagttg aacgggccaa gctgctctcc gtgtccaggg tcgaggttca ggtcttccga   1080
atctcacttc ctgttcacga tctcctgtca gccttgcaga cctccataag ggaaggagtt   1140
gaggtgacta tcaaggacct agatccatgg atcacaaagg caatagatga cgagcaatcc   1200
acaccgcgcg gcaccgcgca atccaagatc gcaatcgtcg gcatgtcgtg ccgcatgccc   1260
agcggagcga ccgatacgga gagattctgg gaaattctgg aacaggggct ggatgtccat   1320
cgcaagatcc ctccagaccg attcgacgtg gatagccatt atgaccccgc ggggaaacgc   1380
gtcaacgcta gccacacacc atatggttgc ttcattgacg aaccaggtct gttcgatgcc   1440
cccttcttta acatgtcgcc ccgagaagct cagcagaccg atcccatgca gcgtctcgcc   1500
attatcaccg cctatgaagc cctcgagcgg gcaggatacg tggcgaaccg cacccccatcg   1560
tccagcaaac accgcattgg cacgttctac ggccagtcgg gtgatgatta ccgcgaggtc   1620
aactcggcac aggagatcag cacctacttc atccccggtg gctgccgtgc attcgggccc   1680
ggacggatca attacttttt caaactctgg gggccgagct ttagcatcga cacggcctgc   1740
tcctccagct tggccaccat tcaggcagcc tgtaccgcgc tctggaacgg tgacacggac   1800
acggttgttg ctggaggaat gaatgttctg actaattcgg acgccttcgc ggcctcagc    1860
cacgggcact tcctgaccaa gactcccaac gcatgcaaaa catgggactg tgaggcggat   1920
ggctattgcc gtgccgatgg agtggcctct atcgtaatga gcgtctggga gacgcggaaa   1980
gcagacaatg acaacatctt agggggttatt cttgggggccg caacaaacca ctctgctgaa   2040
gcctctccca tcacccatcc ccatgccgga gcccagtctt ttctgagccg gcaggtcctc   2100
cgcagtgctg catcgatcc aatgacgtc agctacgttg agatgcacgg aactgggacc   2160
caggccgggg acgcggagga atgaagtca gtcagtgatg tgtttgcccc ggctgcgaag   2220
cggcgcagtt ccaagcagcc agtgttcatt ggtgcagtca aggccaacgt cggccacggg   2280
gaagctgtag caggtgtcac cgcgctggtg aaggttcttc tcatgttcca gaaagaggcc   2340
atccccccgc atgtcggcat taaaaatagc atcaatcccg gattccctaa agacctgaaa   2400
cagcgcaatt tgcatattcc ctacgagaaa cagcccctggc cccgcatccc cggcagcaag   2460
cgcatcgcga tggtcaacaa cttcagtgct gccggcggca attcgacctt ggcagtagag   2520
gaagggcccc ttcgaccaaa accgactggc gagatccgcc ccgttcttc tcacctggtc   2580
gctgtctcgg caaagagcaa ggtctccctg aaagggaacc tcgaacggct gctgggcttt   2640
ctggacgctc atccggatgt ggtcttgtct gacctggcgt acacgaccac cgcacgccgt   2700
caccaccata atcatcgaat cgctgtggct acttcggatg tcatgcacct gaagaagcag   2760
ctgtccgcaa gcctcgaatc cgactctgtc aacaccctc aaccgatttc tgctacgggc   2820
ccgccccca ttgcctttgc ctttaccggc cagggatcct catacaaatc atggaacctc   2880
cagctcttcc acgactcgcc gtactttcgt gcgcagatcc tccatttgga catgctggcg   2940
caggggcaag ggttcccttc ttttgtccct gcgattgacg ttcctactcc cgggatcac    3000
gcacactccg ccatcatcac acagctagca ctggtctgca ctgagattgc tctggcaaaa   3060
tactgggcct cactaggtgt gaagccgat gtggtggtgg gccatagtct ggtgagtac    3120
gcggccttgc acatcgctgg agttctctct gccagcgatg cgatctttct tgtttgggcag   3180
cgtgcgtgcc tgcttagaga tagatgccac cccagtagcc atcagatgat ggcagttcgg   3240
gcgtccctgc cgcagattga gcagttcgcg ggaccctgc catacgaggt tgcctgtgtc   3300
aatggaccta gggaaatggt cctcagcggc acccgcgagg agatgcggc ggtggctaaa   3360
cccttgaag tcgaaggtt caaatgtatt gttctggag tagcctttgc ttttcactcg   3420
gcgcagatgg atcccatcct cgaagaattt gaggcgctgg cggcgtcggg cgtcgtcttc   3480
caggcaccta acttgccggt gatctcgccg ttgttgagta aggtggtctt tgatgagcat   3540
acgatagatt cgctctacat gcggcgggcg acgcgcgaga ctgtcaactt tctttctgcg   3600
atggagacg cgcacaagat ctccactatt gacgatgcca ccgtgtgggt tgaaatcggt   3660
ccacatcctg tctgtgtaaa cttcgtcaga tcctcgctcc cgtgacagtg            3720
ccgtcattac gccgcggaga ggataactgg gtgacgctca caaacagttt agggggctctc   3780
cactgcgccg gagtgcctgt ggactggaat gagttccacc agccgttcga acgcgctcta   3840
cggctgttag acctaccgac ctatagctgg aatgaaaaga catactggat ccaatataag   3900
gggaattggg ccctccaaa ggaaacacg ttctatgatg acgaggtccc acaaaccaat   3960
gccgttgcgg gactggcatc ggagctgaga acgtccaccg tccagcagat catccacgag   4020
```

```
cagttcgatg gaacagctgg gtcggtcgtc atgcagtcag acctcatgca gccggacttc    4080
ctagcggcag cgtatggcca caaaatgaat gggcgaggag ttgtcacctc gtcgatccac    4140
gccgatatcg cgttcacact cggtggatat ctctataaaa agctaaatcc caatcaggaa    4200
gcgcatatga atatcgccaa tctgaagtt cttaggggtc ttgtggcgca ggagaacacc    4260
aagtcaccac agctcatcca agtgtctgcg agcaccgaca atccggtcg ggacaggca    4320
catctgaagt ggcacaacgt gatcaacggg tctattgagg agccattcgc cagtgcgact    4380
atctactacg aggaagcaag cgagtggctg gcatcctggc gccctgcgac acatctcgtg    4440
cagggccgga tccatgcgct ggagcggctc gcagaagacg gcgtggccaa ccgcttcacc    4500
cggcgcatgg cctacggact gttgccagt agcctggtcg actatgcga caagtaccgc    4560
ggcatgcaat cagttgtgct gcatgagctc gaggcatttg cggatgtcgt cctcaccaat    4620
gagaaagggg gtacctggac cgttcccccc tatttcattg acagtgtggc ccatctggct    4680
gggttcataa tgaatgttc cgacgcgaat gatacgaatg ccaatttctg tgttaccccc    4740
ggatggagct cgatgcggtt tgcggcccct cttgtcgcgg gaacaaata ccggtctat    4800
gtcaagatga tccctactgt cgaagcaac aatatctatt tgggtgacgt ctacatcctc    4860
cagaacgaga ctatcgtcgg catggtcggg ggaatcaagt tccgccggta tcctcgtatc    4920
ctcctcaacc ggtttttctc agccccggat gcggatggcc gaaagtctac gcctgctgtg    4980
cctgcacctg cgcctgcttc tactcctgct cctcctgcta aattggaagc cgtgcagccc    5040
aaagtggcac cgaccagcac tccagcttct ccagcaccag ccaatccgcc gaccactaac    5100
ggagtcgagg cagccgctga gcctgacgcc aacagtaccg ccgccaaagc gattgctcta    5160
gtggctacag aggccgggct cgggctgggt gacctcaagg acagtgccag cttctctagc    5220
ctagggatca acagtctgat gagtctggtg atttctgaaa agttccggga ggcgctgggg    5280
gtgacagtga cgggcagcct gttcttggag tatccgacta ggggatttt gaagagctgg    5340
ctactggagt attacagctg a                                               5361

SEQ ID NO: 15          moltype = DNA   length = 5349
FEATURE                Location/Qualifiers
misc_feature           1..5349
                       note = polyketide synthase Desired nucleic acid sequence 14
source                 1..5349
                       mol_type = other DNA
                       organism = Aspergillus fumigatus
SEQUENCE: 15
atgaggccag tagactttac cccctcgtct gaatctccca cagcagagaa aggaatgaag    60
gtcgtctact ttggtaacga gcttcctcaa gatggcatcc aagcatctg tcgacgacta    120
cacacctaca ccaaagaccg gcgataccg ctcctcgccc gattcatcga ggagagcacc    180
tgggcagtgc acgatgaagt tcgacaacta catgccgcgc aaaaagcctt ggtgagtccg    240
ttcgagagcg ttctacatct tgccgagcag cccgagctgt gcagaggacc tctctgcggg    300
tcgatcgagg gcgttcttct ttgtgttatc cagttgggaa cgtttatcgg ttactacgaa    360
gactcaccga atgagtacac cttcgactcc gcaaacacct atctcacagg cctgggactt    420
ggcctgttgg cgtcgacggc tgtctctctc tccccgacgg tggcggacct tcccttggcc    480
ggggcagagg tcgtgcgcgt ggctttccgt cttggagtgc tggttgccga tgtctctcag    540
aatcttcaac ccgctgatgc gacaggcgaa cgagactcat gggcctatgt gattcccaat    600
gtcgctccta aggaagccga agaggagctg gctgttatcc acacgcgaa aaatactcc    660
gaggcgagcc ggatcttcat cagcgcaatt agtcggacgc cagtgaccat cagtgggcca    720
ccggctcgac tccggcgcct cttccgaatg tctgatttct tccgtgaccg caccttcgtt    780
gcgcttcccg tgtatggggg gctgtgtcat gcaaacaca tctacaattc gcagcatgcc    840
cggtcagtgg ttcaaggccc gtcaatagcg gcgttggata cggcctttat cgcccgatac    900
ccgatcctct cgactggcag cggcgagccc ttcccgacag ccacgacggc gacggagctg    960
ttcgaacatg tcatgactga atcctcacc caagccattg agtgggaaa tgtcatccag    1020
ggagtagtag aacgggccaa gctgctctcc gtgtccgagg tccaggtcca ggtcttccgc    1080
aactcacatc cggttcaga cctcctgtcc gccttgaaa cctccctaag ggaaggagtc    1140
gaggtggcta tcaaggacct cggcccatgg atcacaagga cgcgagacga ggagcggcct    1200
ccaccgcgcg gtacgctca atctaaaatc gccatcgtcg gcatgtcctg tcgcatgccc    1260
agtggagcga ccgatacgga gaattctgg acattctgg aacaggggct ggatgtccat    1320
cgcaagatcc ctccgaccg attgcgtg gacagtcact atgatcccgc ggggaaacgg    1380
gtcaacgcga gccacacacc gtatggttgc ttcattgacg aaccaggcct gttcgatgcc    1440
cccttcttca acatgtcccc ccgggaagct caacagaccg atccaatgca gcgtctcgcc    1500
attgtgacgg cctacgaagc cctggagcgg gcaggatacg tggcgaaccg cacccgatcg    1560
tccaacaaac accgcatggg cacgttctac ggccaagcca gtgacgatta ccgcgaggtc    1620
aactcggcac aggagattag cacctacttc atccccggcg gctgtcgtgc attcgggccg    1680
ggacggatca actactttt caaactctgg gggccgagct tcagtatcga tacagcctgc    1740
tcctccagtc tggccaccat ccaggcagcc tgtacggctc tctggaacgg cgacacggac    1800
acggtggtgg ccggaggaat gaatgttctg acaaactcgg atgccttcgc cggcctcagc    1860
cacgggcatt tcctgaccaa gactcccaat gcgtgcaaaa cctggacctg tgaggcagat    1920
ggctattgcc gtcgggacgg agtggcctcc attgtaatga gcgtctgga agacgcggaa    1980
gcagacaatg acaacatctt gggagtgatt cttggggccg cgacaaacca ctctgcggag    2040
gccatctcca tcactcatcc acatgccggc gcccagtcct gtctcagccg acaggtcctc    2100
cgcagcgccg gcatcgatcc aatggacgtc agttacgtgg agatgcatgg aactgggacc    2160
caggccgggg acgcggaaga aatcaagtca gtcagtgatg tctttgccc tgctgttaag    2220
cggcgcagtt cccagcagcc cgtgttcatt ggtgcgtca aggcaaacgt cggccacggg    2280
gaagctgtcg cgggtgtcac tgcgctgtg aaggtgcttc tcatgttcca gaggaggcc    2340
atccccccgc atgtcggcat caagaatagc atcaatccgg ggttcccgaa agacctggat    2400
cagcgaaatt tgcgtattcc ctatgaaag aagccctggc ccgacgccc cggcaggag    2460
cgcatcgtga tggtcaacaa cttcagtgcc gccggtagaa attcgacctt ggctatagaa    2520
gaagggccgc ttcgaccaaa gccggctggc gcgatcgacc ccgttcttc tcacctggtc    2580
accgtctcgg caaagagcaa gatctccctc aagggaacc tcgaacggct gctgagcttc    2640
ctggacgccc atcggacgt cgcgttgtct gacctggcgt acacgaccac ggcacggcgt    2700
catcaccata tcatcgagt cgccgtgcc acttcggata ttgcggatct caaggctcag    2760
ctgtgcaaaa ccctcgaatc cgactcggtc aataccctg aaccgatttc tgccacgggc    2820
```

```
ccgccccca ttgcctttgc ctttaccggt cagggatcct catataaatc atgggacctc  2880
cagctcttcc agcactcgcc gtactttcgc tcgcagatcc tgcatttaga caccctggcg  2940
caggggcaag ggttcccttc ctttgtccct gccattgacg gctcctatcc ccgggaccat  3000
gcccattgtc ccgtcatcac acagctagca ctggtctgca ccgagatagc tcttgcaaag  3060
tactgggtct cgctaggcgt gacgccggat gtggtggtgg gccatagtct gggtgagtat  3120
gcggccctgc acatcgctgg cgttctgtct gctagcgatg ccatctttct tgtcggacag  3180
cgtgcgtgcc tgcttcaaga gcggtgccag cccagtagcc atcagatgat ggcggtccgg  3240
gcgtctctcg agcaaattga gcagttcgca gggagcctgc cctatgaaat tgcttgtgtc  3300
aatggaccca gggaaatggt cctcagcggc acccgcgagg agatggcggc ggtggccagg  3360
ctcctggaag ccgagggatt caagtgtatt gtgttagagg tagcctttgc ctttcactcg  3420
gcgcagatgg atcccatcct ggacgagttt gaggcgctgg cggcatcggg cgtcgtcttc  3480
caggcgccga acttgccggt gatctcacca ttactgagta aagtggtctt cgatgagcat  3540
acgatagatt cggtatacat gcggcgggcg acgcgcgaga ccgtccactt cctctctgcg  3600
atgaagatgg cgcacaagat ttccaccatt gacgatgcca ccgtgtgggt tgaaatcggc  3660
ccacaccctg tctgtgtcaa cttcgtccga tcctccctcc cctcgaccag cgtgaccgtg  3720
ccgtcgttcc gccgcgggga ggataactgg gtaacgctca cgagcagttt agggatcctc  3780
cactgcgccg gggtgcctgt ggactggaat gagttccatc agccgttcga acgggccctc  3840
cggctattgg atctgccgac atacagctgg aatgaaaaga catactggat ccagtaccag  3900
ggaaattggg ccctcaccaa gggaaacacg ttctacgatg acgaggcccc gcaaaccaag  3960
gcccttgcgg ggctggcatc ggagctgagg acgtccaccg tccagcagat catccacgag  4020
cagtacgacg gtgcagctgg gtcggtcgtc atgcagtcgg atctcatgca gccggatttc  4080
ctagcggcag cgtatggcca caagatgaat ggacggggag ttgtcaccct gtcgatccat  4140
gccgatattg cgttcacgct gggtgaatat ctctataaga agctcaatcc caatcaggaa  4200
ccacacatga atatcgccaa cctggaagtc gtcaaggctc tggtggcgca ggagaacacc  4260
aagtcaccac agctcatcca agtgtctgcg agcactgaca atatccgatc cagacaggca  4320
catctgaaat ggcacaacgt gatcaacgga tctattgagg aacctttgc cagtgcgact  4380
gtctactacg aggaagcgag cgactggctg gcgtcctggc gtcctgcgac ccatctcgtg  4440
cagggccgga tccatgcgct tgagcagctc gcagaagacg gcgtgccaaa ccgcttcacc  4500
cggcgcatgg cctacggact gtttgccagc agcctggtcg actatgctga taagtaccgc  4560
ggcatgcagt cagtggtgct gcacgagctc gaggcattg cagatgtgt cctcaccacc  4620
gagaaaggcg gcacctggac cgttcccccg tacttcattg acagtgtggc ccatctggcc  4680
ggcttcataa tgaatgtctc cgatgcgaac gatacgaatg ccaatttctg cgtcactccc  4740
ggctggagct cgatgcggtt tgcggcgccc ctccttccgg ggagcaaata ccgctcttat  4800
gtcaagatga tcccgacggt tgaagacaac aatatctatc tgggtgacgt ctacatccgt  4860
caggacgaga cgattgtcgg catggtcggg ggaatcaaat tccgcaggta tcctcgtatc  4920
ctgctcaatc gattcttctc cgccccggat gcggatgcca gaaagtctac gcctgctacc  4980
tccgcgcctg cacctgcacc tcctgctgga tcagaggccc tgcagcccaa agcggcaccg  5040
gccagtactc cggccgctcc agcatcagcc gatgcgccga ccaccaacgg agtgaaggca  5100
gccgctgagc ccgacgccaa cagtaccgcc gccaaagcga tcgctctggt ggctacggag  5160
gccggactcg ggctgagtga cctcaaggac agtgccagtt tctctagcct agggatcgac  5220
agtctgatga gtcggtgat ttccgagaag ttccgggaga cgctgggggt gacagtgacg  5280
ggcagcctgt tcttggagta tccgactgta gggggatttga agagctggct actggagtat  5340
tacagctga                                                          5349
```

| SEQ ID NO: 16 | moltype = DNA  length = 5394 |
|---|---|
| FEATURE | Location/Qualifiers |
| misc_feature | 1..5394 |
| | note = polyketide synthase Desired nucleic acid sequence 15 |
| source | 1..5394 |
| | mol_type = other DNA |
| | organism = Aspergillus eucalypticola |

SEQUENCE: 16

```
atgtctgcac ccacaaagct ggtcttcttc ggaaacgaat tcccaatga cgatctcaag    60
tccctcttcc gcggtctgca ccgacacggc aaggaccggc gctttcgcca gctggcaacc   120
ttcctggagg agtccactcg cgtactccag aatgaagttg cccagcttcc cgagccgctg   180
aagaagctgg tgccccattt cgaaaatctg atgcccctaa ccgaggtcga ctttcgtcaa   240
ggccctctgg agccgctat ggaaagcgcc ctgctgacca ttctggaact gggaatgttt   300
attggccact acgaggctga ggagcgtgtc tgggacctct ccgcagaccg aaccaccttg   360
gctggtctta gtattggcct gcttgccgcc gccggtgtcg cattgtccac tcacttggct   420
gaggtggttc agaacggtgc tgagtgtgtg cgggtctcct tccgcctggg agtctacgtc   480
catgacatct cccgcaagct ggaagctccc caggcagacg gcagcttgct cagctgggct   540
catgttgtca ccggcgagtc cgcatccgac ctccaagagg aactgtcgcg atacaacacg   600
gaaacgagca ctcccgagct gctcaaggtg ttcatcagtg ctgccgacaa gacttctgtg   660
agtgtcagcg gccctccctc gcgcatccgt gccgcctcc cgccctctca ggaccgtgct   720
tactctaagt tccttgccct tcctgtgtat gatggtctct gccatgcggc ccatctctat   780
gacgaggaga ccatccatcg tgttcttcac cccgatggat ccgtcatcc cacctctcgg   840
ccggtgcagc tggcactact ctcgtcgcgg tctggacagc cctttgaggc caccacggcc   900
gctgagctgt tccgcgccat cagcacagag ctgttgactg gcactatctt cctggacaat   960
atcacggccg gtatcctcga ccgtacggaa cgatgtgccg atgccacaca gtgccagatt  1020
gagacctacc gcacttcgct ggtattcaag ggtctgctga aagccctgga ggcatgcttc  1080
cctgaccgga ccatcaacac caccgatctc atccctgggg tattccagga ctacggtgcg  1140
cgccagccca agtcatacgc agactcgaaa ctggccattg tcggcatggc ctgccgcatg  1200
cccggcggtg ctaatgatct cgacctcttc tgggagctgc ttgcacaggg tcgcgatact  1260
cacacgacgg tgcctgcgga tcgctttgac cttgaaacgc actacgacct gactgggag  1320
accgagaacg ccacgcgcac tccctttgcc aacttcatcg accagccgg gctcttcgat  1380
gccggattct tcaacatgtc ccccgggag gctgagcaga ctgaccccat gcaccgtctt  1440
gcccttgtca ccgcttacga agccctggag atggcaggtg tggtctctgg ccgcacgccc  1500
tcgtccaacc ccaagcgcat tgccaccttc tacgacagg ccagtgacga ctggcgtgag  1560
ctgaacgcgt ctcagaatat cggcacctac gccgtgcctg tggtgagcg tgcctttgcc  1620
```

```
aacggtcgca tcaactactt cttcaagttt ggcggcccgt cctttaacct ggacacagcc   1680
tgctccagcg gtttggctgc cgtccaggcg gcttgctctg ccctgtgggc cggtgaagcc   1740
gatactgtcc tggccggcgg actgaacatc attactgacc ccgataacta cgctggtcta   1800
ggaaacggcc acttcctgtc acgcaccggc cagtgcaagg tttgggatca gtctgctgac   1860
ggctactgcc gtgccgatgg tgttggctcc gttgtgatca agcgactcga ggatgcggaa   1920
gcagacaatg acaacattct ggctgtcgtg ctatccgctg ccaccaacca ttcggcggga   1980
gctatctcca ttacccaccc ccatgctggc gcccagaagg agaactatac ccaggtgctg   2040
caccaagcgg ctgtcaaccc gctggatgtg agctatgttg agctgcacgg caccggtacc   2100
caggcaggtg acgctcagga ggctgaatcg gtgttggatg tcttcgctcc ccggactcat   2160
cgtcgtcgga ccgaccagcc gctgtacttg ggagcggtga aaagtaacat ggtgacatgt   2220
gaggcggccg ctggtattgc ctccctgctc aaggtgctgc ttatgtatca gaagaacgag   2280
atccctgctc acatcggtat ccccactgtc atcaacccgg ctattcccac ggatctcgag   2340
cagcgccagg ttcatttgcc tcgaagcaag actgcctggc cccgggctgc aggccagatt   2400
cgacgcgcca ttgtgaactc tttcgtgcg cacggtggta acacaactct ggtattggaa   2460
gatgcccctg agaagcaggt gactgtggcc cgagaggagc gctcgacgca cccggtagtc   2520
atctccgcca agtcgaagaa gtccttggct gccaacttgg agactctcct tgcctacctc   2580
gacgagaagc cggaaaccga tcttggtgac ctatcttaca cgacctgtgc gcggcgcatg   2640
caccacagct ggcgcgttgc cactgctgtc agcgatattc ccgccctgcc aaaagttcctg   2700
cgcaacgccg tgaacaacga cgccgtgtct caaatccggc ctattcccac cgaagctccc   2760
cctgtggtgt tcactttcac cggccagggt gcatactacg ctggactggc acagggtctc   2820
ttccaggctc tgccttcctt ccgcgctgaa gtgcgccagc ttgaccacct gtcccagcga   2880
ctgggatttc cctctattgt gccggtcatc ctcggcaggg tggaagaggg aactgctacg   2940
gccctggtca cgcagctcag cattgtgatc gtggagattg ccctggctcg gctctgctgca   3000
ctcctcctgg gaattcctgc tcctcacgcc gtgatcggcc acagtctggg cgaatatgcc   3060
gccctggctg tcgccggcgt gctctccacg gcggatgctc tctacctggt tggccaccga   3120
gcccagctca tcgaggaaca ttgcaccccg ggcagccacg ccatgctctc ggtgcgcgct   3180
accgtcactg acattgagcg tctggttgga accggccctg atgcacccac ttacgagctg   3240
tcctgccaga acacacacca ggacaccgtc atcggcggat cgatcccaga ccttaatgcc   3300
atccgcaaga gcctcgagcc tgaaggcatc aagtgtgtca aagtcgatgt tccctttgcc   3360
tttcacaccg cgcagatgga cgccgtctgg gaacgcctcg ccaaggccgt cgccagcgtg   3420
cccttcaaga cccccagcgt ccccgtcctc tctccctgt gggcagcgt cgtcttcgac   3480
ggtaagtcca tcaccccaga gtacattgtg cgggctaccc gcgagcccgt ccagtttgcg   3540
gctaccatcg acgccgccca ggagctcggc atcgtcaatg accagaccct ctgggtcgac   3600
atcggcccgc accccatctg cgccagcttc gtccgcagcc tggtgcctgg cgcacgtatc   3660
gtctcctcct gccgtcgaaa cgaggacaac tttgccacca tggccgaagag tctctgcacg   3720
ctgcacttgg ctgccgcac cccttcttgg gccgagtact tccgtcccga cgagcaggcc   3780
tactcactgc tccgcttgcc caagtaccgc tggaacgagg tcaactattg gatccagtac   3840
ctgggaacct ggacccggga caaggcgcat atcaagaacg gcagcagcca gaagcgcgct   3900
gtcaccgatg ttccatctgt ctcttctctg cgcacctccc tcatccacca ggtcaccgag   3960
gaaaccgtcg acaagaccac tgccactttc aaggccatct ccgacatcca gcaccccgac   4020
ttcctcgagg ccgtgcacgg tcacaccatg aacaactgcg gcgtcgccac ctcctccatc   4080
tggacggaca tggccatgac cgtcggcgag cacctgtacc gtcgcctggt tccgggcacc   4140
gacaacgtcc tcatggacct gtgcgacttc gaagtccaac acgccaagt tgccaacacc   4200
agctccaaca ccccacagcc attggcccctt gaagcccacc tcgaccttcc cacccgccac   4260
atgtccctcg cctggtacga tgtttgatgcc accaccaaca agcgtgccgc aacccccttc   4320
gccaccggca gcattaagta ccctgccgac ccagccggtg cagcctggtc tactgaatgg   4380
tctcgcatca cccacctcat ccaggccgcc atcgacgccc tgcagcacct ggccgccggag   4440
aacaaagcca gcacactctc caagccgctc gcttacgccc tcttcaagaa cgtcgtcgac   4500
tacgccccc gctaccgtgg catggatcgg gtcgtcatcc acgaccacga agccttctcc   4560
gacatcaccc ttaccaccga ccgccacggc acctggcaca cccctcccca ctggatcgac   4620
agcgtctcgc acctggtcagg cctggtcatg aacggcagtg atgcctccaa cactagggac   4680
ttcttctacg tcacccctgg ctgtggcagc tgccgcatga cggagcccttt ggttgccgga   4740
ggcaagtacc ggaactatgt ccgcatgttc cccatgccgg acgaggccca catgtacgcg   4800
ggcgacttgt acatcctccg tgagggcaag atcatcggtg tcgtgaaaca gctcaagttc   4860
cgtagagtgc cccgccttgtt gatgatcgg ttcttctcgc cgaacaagaa cgccgttgcg   4920
catgctgctc ctgctcctgc tcctgccgct gctccggtgg tgaagaagca atctcctact   4980
cctacaccca cagacactac cacttcccag caggccaaga cagagcagaa gcaagtccga   5040
ctccaacttc ccaatctcac ctctgctgca ccctcgacag ctagcagctc gtcttctccc   5100
tcctccagcg gcgtcgcaac ccccaccact gaacaggagg ctcccgtcgc cgatcgatca   5160
gcagttaccg gtgtgagctgg caaatgtctg gaattaattg ccaacgaaac aggcctgggt   5220
gtggcagagc ttactgcgga cgcgacattc gtgcagctgg gtgtggattc actcatgtca   5280
ctggtgctgt cggagaagtt gcgcagtgag atgggactag aaatcaagag ttcgttgtc   5340
ttggaatgtc ctactgtggg ggacttgacg ggatggttgg agcaatactg ctga         5394
```

SEQ ID NO: 17   moltype = DNA length = 4983
FEATURE     Location/Qualifiers
source       1..4983
          mol_type = other DNA
          organism = Babesia bigemina
SEQUENCE: 17

```
atgcaaggac cacttccgcg gctgccgcgc cagagggcgt tggcgacgct gctgggactc    60
gctggcggca tgcacgatcg atcaacatca gcggcacgcg gagcaggcct aaaaggaaaa   120
acagcgctgc gtgccataag cagccacgtg gccccagctt tcatgtgcgg cagccctgct   180
ggtggtggtt cgtcagattc agttgtaaaa ggcgtcatac ccaacggcca tggtcgtatcc  240
ggtgacattc taggcgccgg gaagatatcg caactcaatg aagtcgaggc agcgtgtgcc   300
cgcggggtcg ggccgtggtc gagcctgttc gcttacggcg ccgactacgg ctacacgcgg   360
agtgactacg atggcagcgc gtacggttcg cgcggcgttc agacgatgcc cgagccgagc   420
gaatacacga ccttcgtgtc gcaccactat cgcatcttaa cgggcgacat tgtggagtac   480
ctgcgtcgta agcgcatgga gtacgtcgag agcccgatca agctgacgct caaattttgc   540
```

```
ccgttctgcc cgcctcacaa atacaagagc gacaacctgt acaagcacga aatcttcaag    600
aactcgggca actcctactg ccatcgttgc ggctacaagg gcagcctcta cgacttcaag    660
gcggccatgg gcgaccttcc cggcgggatg atcgaggagg cgatgaaccc gtcgttcagc    720
ggcaacccgt tcagcctgcc catggtctcc gagcccgccg tgacgctgac caacatcgcc    780
cagtacgagc acaacctctt ccacgacgag cggtacaaac ctgtgctgga ctacctgacg    840
gagacccgcg ggatttccat cgagaccctg aagcgctacc gcgtgggcgc aggcgagttc    900
agtttcagtc tcggcgttgg caagggcgag agcgagctct cgtcgtgtt ccctggctg    960
atggggaagg ccagcagcgg caactccgag ctggttgtta accgcataaa ggtgcgctcc    1020
attcaagaca aatcacgcat gaaactggtg ccgcgcggcg gcggctgggg catgttcggc    1080
gagcacctgc tggcgtccga gctggccaag tcgggcgaag gcccgtcctc cgtggtgctg    1140
accgagggcg aattcgacgc gatggttgtg aaccaaacaa ccggtcgcgt ggcagtgtcg    1200
ctacccaacg gctctaattc gctgccggtt gcactgttgc ctcggctgga gaaggtcgac    1260
cagatctacc tctggatgga cttcgacgct gccggcaagg gtagcgtgga ccacttcgcc    1320
agcaagctgg gcatccagcg cacgcgggtg atccgcgatg tgttcgagct tccgagggac    1380
agcaacgcca gtcgcccgcc caaagacgcc aacgagatat tcctgcgcgg cctcagcgtg    1440
cagagctacg tggacgctgc agcgcccatg tcccactccc agattttgaa cttcaacgac    1500
atccgccaga acgtcttcga ggagctctcc aacccctgcg cgacgtccgg gataacctcc    1560
atcacgctgc ccgggttgtc ccagctgctg aagggccacc ggcgtggcga gctgaccgtg    1620
tggactggcg ccactggctc cggcaagacc accatcctgt cgcagctttc gctggactac    1680
tgcatgcagg gcgtgagcac gctttggggt tcgttcgaga taaacaatgt gcgtttggcg    1740
aagacgatgt tgcggcagtt cagcggccgc aacctcgaga cgtccctgga ggatttcaac    1800
tactacgccg acaagttctc cgagctgccg ctgcggttca tgaagttcca cgggtcaact    1860
tccatcgacc aggtcatcga cgccatggac tacgcggtgt acgtgcatga cgtgcgccac    1920
atcatcatcg caaacctgca gttcatgttg agtggccaga actcgcgcgt cggtgagatt    1980
tgggagatcc agaacaaggc catagagaag ttccggcgct tcgcgacgaa caaaaacgtg    2040
cacgtttcgc tggtggtgca cccgcgcaag gaggccgacg gcaccgccct gggaatgtcg    2100
agcgtcttcg ggtcggtgaa atccaccag gaggcggaca acgtgctgat tttgcagaac    2160
gtcgtggggc agaaccgttg cattgatgtg aagaagaacc ggtttgctgg taaccttggc    2220
cgcgtaacct tccgattcga ccccttgagt ctaaccgccg aggagctgaa ggtcaccgag    2280
ttcgttttgg aggcgtcaaa gaacacccaa acggaggtca aaccgtccgc gaaggcattc    2340
gacaagctgc gccctcccga acccaagcgt tccgctgcca aggtggccgg taccatcgat    2400
cgctctacgc atccgctggc ctacgccagc acgtctcccg cattcaccgg atcgcagctt    2460
gtcgctggca atgttggaca ctcaacggct cgtccgatgt ccacgtaccg tctgaacagc    2520
gtgatgcacg acgagcgcaa ccagacgggc ttcgttcacg attctgacct cgaggaaaac    2580
cagaacccag gctgcttcgc actgggagat cttttcgtgt cgcccagtga cagccctact    2640
tccgatgagt cgagttcgtc gtccgtcgtc gcccaaggtt ccgccgcctc caccgctgca    2700
tctgccgcct catcagcgga caaccccgct gccaatggcg gcactgcagc ggcgcccaaa    2760
cgtggtcgca agcccaaagt gaccgaggcc acagccgagg ttgacgagga gaccataacc    2820
atgcgcggca agtccgtgac gcggtcctcc tccattaagg agtaccggga attcatcaag    2880
gccaacggcc tgggcgagtt gatcaagacc gccgggaagg gtattgtgaa agccgacatc    2940
tacgacaaga tcaagcagca cgtgccgcct tccagcattt ctagcggtgc ccagcatgcc    3000
gcggcaccttt cgccagcggc atcaaccacc agctcgctgg atttcggcgt gtcgacagtg    3060
gagcctctgc tcactcgtaa ggaagttgat gtggatatct tcgacgacat cgacgacttc    3120
cgtgcgcgca tgctgcgtcg cactggtccc ggcgccttgc tatcgaaggc tggcgtgaaa    3180
cccgtgggca ctgtgaagct gccggtgcac actctcgtgg agggcacgga cgagctgctc    3240
cccaagggca taatatacgt gcgggatgtc gagttgttgg agcgttttggc tccgctgttc    3300
gagaacacca agctctgtgc gctggatatc gagaccaccg gcctggacca cgcaacgac    3360
cacatccgtc tgctgcagat atcaacgccc gaccagcccg ccgtgatcat cgacgtcttt    3420
aaggtgtcct tggaggctat gcgggaatgc cgctggctgc gttcgctgct gagctcctcc    3480
gccgtgaagg ttctgcacaa cgggaagttc gacataaact tcttgtcctt caacgggctg    3540
cccgtgaagg gcgccgtgtt cgacaccatg atcgccgcga agtcgctcag cgccacgcgc    3600
ttcaactgga gttgcaagtt gggccacgtc gctgagcgct acctgaacat tgcgctggac    3660
aagtcgcagc aattttccga ctggacgctg gagccgctgt ttgaggagca gctgatatac    3720
gcgtctcgcg atgctgcagt gctgcttccg ctgtacttcg tgctgcagga gaagctgaaa    3780
agcgcgcggt tggactccat agcgtcgatt gagaacaagt gcgtgctggc ggtctgccaa    3840
atggagcaga acggcatccg cgtcgaccgg gcgaggctgg agtcgctgca gcgcgagctc    3900
aacagcgaga atgaggtggc catgaagcgg ctgggggagg cgctgggcgt gtccggcaac    3960
gccaacttca actacaactc gcagcggcag atactgcaag cgctgcagaa cctgaacgtg    4020
atggacaagt cgcgccgcat gttgatccag gacacctccg agcgaacgct cgccgcgcac    4080
acctaccacc cagcgataga ggcgctacgg gagtaccgca aggcaacaa ggccgtcacg    4140
gcgttcaccg agaagatccc gaaccacatc gacgccacca ccggcaggat ataccccaac    4200
atcaaccaga tcggcgcgga aagtggccgc ttcagctgcg acaaccccaa cctgcagcaa    4260
atcccgcgtg accataggtt ccgcgagtgc ttcgttgccg accccgggca aagttcgta    4320
atcgccgact tctcgcagat cgagttgcgc atccgcgctg acatcgccga gaccgacaag    4380
atgatagagg cgtacaacag cgggcaggat ttgcacgccc tgacggcgag cctggtcaag    4440
ggcaagccca tcgccgaggt gaccaaggac gagcgccagc tggcaaggc cgtgaacttc    4500
ggcctgatct tcgggatgtc gctggccggc ttccgcaact acgccgaggt gggttacggc    4560
gtgcgtctcg gcatgaacga ggctcgtgaa atctacgatt cgttttttccg caactatagc    4620
ggcatcgcca attggcacga gcgcatgaag aacagcaagc cgatgtcgct gcgcacgctg    4680
agcaaccgct tgtccatatt cgaccagttc tcgttcacgc gttcgctgaa ctaccccgtc    4740
cagggcacat cggctgatat cacgaaggag gccatgcgc tgctggtcga ccgcgtcgag    4800
gccttttggcg gccgaatggt gctctgcgta cacgacgaga tcatactgga ggtgccggac    4860
gagcacaccg aggaggcgct gcgcgtgcta gtagggacca tggaggccgc tggaaacaag    4920
ttcctccgct acgtgccctg cgaggccgtg ggctccgtgg cggcagctg ggctgagaag    4980
tga                                                                  4983
```

SEQ ID NO: 18      moltype = DNA  length = 1269
FEATURE            Location/Qualifiers
misc_feature     1..1269

```
                          note = strain Y5 cellulase gene Desired nucleic acid
                           sequence 17
source                    1..1269
                          mol_type = other DNA
                          organism = Bacillus cereus
SEQUENCE: 18
atgtgtgtaa aatataaaga gaaagaagga aaagttgtga aaaaagtttt gccaattgtt  60
gcgttattag gcatgatgag ttttggagta caggaaatga atgtaagagc tgatacatac  120
cacaagggcg attcaaaaat tagtttttgg gattcgaaaa gaaagggtac taatttcatg  180
aatagtacgt cattacctga aaactataaa agtgcaaaag aagctaatat tgaatatgta  240
cgtttagcac ctgataaatg ggcaaaagat aaagattttc tatttgagga taaaccagat  300
acttctggaa aggattttct gataggtaat gcagataact atcggggatt agtaaaggaa  360
gatctagaaa aattaaaggc ggatttagat gccgcacaat cacaaggaat gaaagtcgtt  420
cttacaatgt tatccttacc tggtgatcga tggcgccaat ttaataataa taagaatgac  480
tacagaatat gggaagaaga gaagtatcaa gaacaagcaa gtcaattttg gaaggacctc  540
gctctggaac taaaagatca ccccgcggtg gttggttata atattataaa tgaaccacat  600
ccagaaacag ctaaaaataa tagatataat gatttttgga cggaagatta cgagaaatgg  660
tatgcaaaag taaaaggaac gacagctgat ttaaacagat tttatgaaaa ggtgattaac  720
tccattcgtg aagtggacaa agaaacaccg attattttag attcaggttt atatgctact  780
ccatgggcct ttaaatattt aaaaccagta gaggataaaa aaacactata cgcatttcat  840
atgtatgaac catatgaatt aacgagccaa ggtgaaaaac aaaacaagga atatcaatat  900
ccaggattag taaaagtagg ggatttagag aaacctgtaa tgtggaatag acagggatta  960
gagaagtttt tgaagccaat tcaacaatgg tctaagaaaa atcatgtacc atctaatcga  1020
attattgcag aggagtttgg aattaaccgt actgttccag gtgctaccca atacatgcaa  1080
gatcttattt ctatctttaa ccaaaaagga tggcataaat cattctatgc attccgtgaa  1140
gacacatgga cagggatgaa ttatgaattg ggaacagaaa aaataaaatg ggatgaagag  1200
ggtaaaccga tgcgtcaaga taattcactc tgggatgtaa taaaaaaaga tttacaaacg  1260
cgtaaatag                                                          1269

SEQ ID NO: 19             moltype = DNA  length = 1134
FEATURE                   Location/Qualifiers
misc_feature              1..1134
                          note = Desired nucleic acid sequence 18
source                    1..1134
                          mol_type = other DNA
                          organism = synthetic construct
SEQUENCE: 19
ttgagaaaat ggttaaaagg tacagcttta tttttagtag cagttttagc attttcctta  60
acatttggag gagtaagtgc gaaagaaaat aacgaagctg caaaaaaaga atacttaatt  120
ggttttaaaa caggaattga cagtaatgca aagaaatcag taacaactgc tggaggatcc  180
gtattacatg aattccagta tatgaacgta ttgcatatcg aattgcctga aaaagcagta  240
gcagcattaa aaaataatcc aaatgtagag tttattgaac ataatgcaga agtacaaaca  300
tacgcacaaa ctactccgtg gggagttaca catattaatg cacatagagc ccatagttca  360
ggtgtaactg gatcaggtgt taaagttgct atattagata ctggaataca tgcgagtcac  420
cctgatttga acgttagagg tggagcaagt tttatttctg gagaatccaa cccttatatt  480
gattcaaatg gtcatggtac ccatgtggct ggtacagtag cagcattaaa taatacagta  540
ggagtattag gtgttgctta taacgcggag ttatatgcgg taaaagtact tagtgcatca  600
ggaagtggta cgttaagtgg tattgcacaa ggggtggaat ggtcgattgc aaacaaaatg  660
gacgttatta acatgagttt aggaggaagc tctggttcaa cagcactcca gcgcgcggtt  720
gacaacgctt acagaaataa tatcgttgta gtagctgcag caggaaatag tggagctcaa  780
ggtaatcgta atacaatcgg atatcctgca agatattctt cggttattgc ggttggggca  840
gttgattcca ataataaccg agcttctttc tcaagtgttg ggtctgaatt agaagtaatg  900
gctcctggtg ttagtatttt aagtacagta cctggcagtt cttatgcttc ttataacggt  960
acatcgatgg catctccaca tgtagcaggt gctgccgcat tactaaaagc taaatatccg  1020
aactggtccg ctgcacaaat tcgtaacaaa ctaaacagca cgactactta tttaggaagt  1080
tcgttctatt acggtaatgg tgtcattaat gtagaaagag ctttgcagta ataa        1134

SEQ ID NO: 20             moltype = DNA  length = 951
FEATURE                   Location/Qualifiers
misc_feature              1..951
                          note = neutral protease (NP) gene Desired nucleic acid
                           sequence 19
source                    1..951
                          mol_type = other DNA
                          organism = Bacillus cereus
SEQUENCE: 20
gtaacaggaa cgaataaagt aggaactggt aaaggtgtat taggagatac gaaatcgctt  60
aatacaacgt tatctgggtc atcttactac ttgcaagata atacgcgcgg ggcaacaatt  120
ttcacatatg atgcgaaaaa ccgttcaaca ttaccgggaa cattatgggc agatgcagat  180
aatgttttca atgcagcgta tgatgcagca gcagtagatg ctcatttcta tgctggtaga  240
acatatgatt attataaagc tacatttaat agaaactcta ttaatgatgc aggagcacca  300
ttaaaatcaa cagttcatta cggaagtaag tataataatg cattctggaa cggttcacaa  360
atggtatacg gagatggtga tggtgtaaca ttcacttcat tatctggtgg aattgatgta  420
attggtcacg aattaacgca tgctgttacg gaaaatagct cggatttaat ttatcaaaat  480
gaatcaggag cgctaaatga agcaatttct gatatctttg gtactttagt agaatactat  540
gataatcgta atccagattg ggaaattggt gaagatattt acacgcctgg taaagcagga  600
gatgcacttc gctctatgag tgatccagcg aaatatggtg acccagacca ttattctaag  660
cgttacactg gtactagtga taacggtggg gttcatacga acagtggtat tattaacaag  720
caagcttatt tattagcaaa tggcggtacg cattctggtg taactgtaac tggtattggt  780
```

```
aaagataaat taggtgcgat ttactaccgt gcaaatacac agtatttcac gcaatctact  840
acatttagtc aagctcgtgc tggtgcagta caagctgcag cggatttata tggtgctagc  900
tctgcagaag taaatgcagt gaagcaatca tttagtgctg ttggtattaa c           951

SEQ ID NO: 21              moltype = DNA   length = 1224
FEATURE                    Location/Qualifiers
misc_feature               1..1224
                           note = strain MP11 polyketide synthase S (pksS) gene
                            Desired nucleic acid sequence 20
source                     1..1224
                           mol_type = other DNA
                           organism = Bacillus subtilis
SEQUENCE: 21
atgcaaatgg aaaaattgat gtttcatccg catggtaaag agtttcatca caatccttt   60
tcagttttag gacgatttag agaggaagag cccattcacc gatttgaatt aaaacggttc  120
ggagccacat atccggcctg gttaattacc cgatacgatg attgtatggc ctttttaaaa  180
gacaatcgaa ttcaagaga cgtaaaaaat gtgatgaacc aagaacaaat caaaatgctc  240
aacgttagtg aagatatcga ttttgtatcc gatcatatgc tggcaaaaga cacacctgac  300
catacccgcc tgagatcact tgttcatcaa gcatttactc cccgaaccat tgaaaatctg  360
cgcggcagca ttgaacaaat tgctgaacag ctttttagatg aaatggaaaa agaaaataaa  420
gcggatatca tgaaatcctt cgcttcccct ttgccttta ttgttatatc tgaattgatg   480
ggaatcccaa aagaagatcg gtcacagttt caaatcgcat ccaatgcgat ggttgatacc  540
tctgaaggta atagagagct gacaaatcag gctcttcgtg aatttaaaga ttatatcgcc  600
aagctgatcc atgacagaag aataaagcca aagacgatt taatcagcaa acttgtgcat   660
gctgaggaaa acgcagcaa gttaagcgaa aaagagctct attcgatgct gttcttgctc   720
gttgtagccg gccttgaaac aactgttaac ttactcgttg caggcaccct gcattgctg   780
cagcacatga aggaatgtga gaagctcaag cagcagcctg aaatgatcgc tacagcggtt  840
gaagaattgc tgcgatacac ctcacctgtc gttatgatgg caaatcggtg ggccattgaa  900
gactttacat ataaggggca ttcgatcaaa agaggagaca tgattttat aggcattgga  960
tcggccaatc gcgacccgaa tttttttgag aacccgtaga tattaaatat aaatcggtcg  1020
cctaacagac atatttcttt cggttttggc attcatttct gcttaggagc gcctcttgcc  1080
aggctggaag gccacattgc atttaacgca cttttgaaga gatttcctga tattgaactt  1140
gcggttgcac ctgatgacat tcaatggaga aaaaatgtct ttttaagagg attagaaagt  1200
ctcccctgttt cactttcaaa ataa                                        1224

SEQ ID NO: 22              moltype = DNA   length = 963
FEATURE                    Location/Qualifiers
misc_feature               1..963
                           note = ARSEF 3297 DNA polymerase II large subunit-like
                            protein partial mRNA Desired nucleic acid sequence 21
source                     1..963
                           mol_type = other DNA
                           organism = Metarhizium brunneum
SEQUENCE: 22
atggattcgg acgactcaga attctatggg agcccagacg agaggcggca gctccaaacc  60
cgcgttgaca gattcgacgc ccatgcctgg gccgagcaac acagcgtctg gggattcggt  120
tctccttgca gaagcccagc ggtcgcgggcc aagtctacaa agctacacaa cccttacgct  180
ggaattagct acgcgtggca gctctctgaa acactggatg atttcttgtc gaggctacct  240
cctgaatcga ctgacgggag tgaggacttg ccctggattt tcatatgcaa cccatacgtt  300
tcgcgaaagg agaagcacga ggaaaatggc ggatacatga agggaacga gtgcgaagct  360
ccgacggaga aggacagcca cgtcggcctc gtggttgaga gcggaatgga gagattggag  420
cttcttgcag atttcaggca aaagttggag ctgtcaggca gatcgaccac attttttgaag  480
caagagctat acaagaaca gaatcaggct gtggtcgata ttctccgtct agcccaagcg  540
ggcaaggttc gaagcggcaa gtggatgctc tttttgctcgc cttccgaggt caacgaaatt  600
tggggcttgg ttgccaaagc tacggcacaa aacgagctcg gtatagcagc caaggtaaac  660
cctaggtcgc aattcgatga ttttcgcaaa gacagggtca tctgcatata tcggccgat   720
ttccaagaca aatccgacgt cgggcgtgtc ttgcaacagt tgaagaggct caagcttgtt  780
gggccagggc taccaaccat gtactacaag cccggtgagt caacatcgcg gggtaactgc  840
aagacgatgc caccgccgca tcatgctgac gacgagtcag atatatttac ctacattggt  900
atttcgcatg gaaaccctg gggactcgct gcttcgatct acagttcgaa atcatttcag  960
taa                                                               963

SEQ ID NO: 23              moltype = DNA   length = 1141
FEATURE                    Location/Qualifiers
misc_feature               1..1141
                           note = CBS 112811 lipase 2 Desired nucleic acid sequence 22
source                     1..1141
                           mol_type = other DNA
                           organism = Aspergillus piperis
SEQUENCE: 23
cccagttcat ctgatctata aagggggcca cgccaccgta ggtaaatctc tagaaagtcg  60
cagatctttc ccaagaatat ccagcgctgt attacctggc tctcaagatg ttcttccgca  120
gggaatttgg ggttttgtca gccctatctg tgctggccca tgctgctccc gcacctgctc  180
cgatgcagcg tagagacatc tcctctaccg tcttggacaa catcgacctc ttcgcccaat  240
acagcgcagc agcttactgc tcctccaaca tagaatccac cggcacgact ctgacctgcg  300
atgtaggcaa ctgcccctct tgtcgaggcag ccggtgccac gactattgat gagtttgacg  360
acagcagcag ctacgcgac ccgactgggt tcatcgccgt tgaccctaca aacgagttaa   420
tcgttctggc tctccggggt agttccgaca tctcgaactg gattgccgac ttggacttcg  480
gcctcacctc cgtaagcagc atctgtgatg gctgtgagat gcacaagggc ttctacgagg  540
```

```
cctgggaagt catcgccgac accatcacat ccaaggtgga ggctgctgtc tccagctatc   600
cagactactc catcgtgttc accgacacag gctacggcgc tgcattggcg gccattgcgg   660
ccactgtgct ccgaaacgcc ggatacactc ttgacctgta caacttcggc caacctcgta   720
tcggcaacct tgccttagcc gactacatca cggaccaaaa catgggcagc aactaccgcg   780
tcacccacac cgacgacatc gtgcccaagc ttcctcccga gctgctgggc taccaccact   840
tcagcccgga gtactggatc accagcggca atgatgtgac ggtgactacg tcggacgtga   900
ccgaagttgt gggggtggat tcgacggacg ggaatgacgg cacccctgct gacagtacga   960
cagctcatag atggtatacg atctacatta gtgaatgctc gtagagcatt actggtgcag  1020
tacagtgata atctggactg gatatagcta agatggaatg aatttgtaca tagttttcaa  1080
tagtaactgg cgaagtacat atgctagtct gattttgaaa gagttcgtga ggcatgtttt  1140
g                                                                 1141

SEQ ID NO: 24        moltype = DNA  length = 1133
FEATURE              Location/Qualifiers
misc_feature         1..1133
                     note = IBT 23096 AhpC/TSA family thioredoxin peroxidase
                     Desired nucleic acid sequence 23
source               1..1133
                     mol_type = other DNA
                     organism = Aspergillus steyniI
SEQUENCE: 24
gaacgaggaa gcaggaaggg gatgatctct tcgcaacgaa gccgagatcg tcccccgccg    60
ggtaaatgcc tggggcacca cacgatgcca agcaccgcca aggccggtgc caaggcgcat   120
tacatcatcg cgcggccgtc ggcaaattcc cccaaatcaa atctctccgt ccgtcggttc   180
atccgctgca tccccagctt cttgacactc cgtcatacca tttacccata ccaacacaat   240
ggcctcaatt atccccccgtg ccggcctccg cgccttcacc gctcttcccc gggcactcc   300
cttgaccagg accactttg cctccaagct tccccgcacc cagccgttct cgcagccctt   360
cgctcgccga ttcctcgcaa ccgtcccgca ggagcagccc cgaatccgtc ttggatcgac   420
cgcccccaac ttcaaggcga ccacgaccca cggcgagatc gatttccacg aattcatcgg   480
cgacagctgg gccattctct tctcgcaccc ggccgacttc accccccgtc gcaccaccga   540
gcttggcgcc tttgccaaac tcaagaatga gttcgaccag cggggcgtta agatgatcgg   600
gctgagtgcc aacgacctcg gctcccacga caagtggatc gacgacatca acgaggtgtc   660
caacaccagc gtccaattcc ccatcatcgc cgacgccgac cggaaagtcg ccttcctgta   720
cgacatgatc gaccagcagg atctggataa catcggagg aagggcatcg cgttcaccat   780
tcgctcggtg ttcatcatcg atcccaccaa gaaggtcgc ttgaccatga tgtacccgcc   840
ttcgacgggc cgcaactcag cggaggtgct gcgcgtcatt gattcgttgc agaccgcgga   900
taagaagggc atcgcgaccc cgatcaactg gaatgtcggc gaggatgtga tcgtcccgcc   960
gtcggtgtcg acgaggatg cgcggaagaa gttcggcgag gttagagagt tgaagcctga  1020
cctgcggtac actaagcact agatgtagga tagatagcgt gttagatggt gtataacagt  1080
acagcttttg ctgttttact tggtcggatt tatgttgtag tggactaatg gag         1133

SEQ ID NO: 25        moltype = DNA  length = 1380
FEATURE              Location/Qualifiers
misc_feature         1..1380
                     note = putative lipase Desired nucleic acid sequence 24
source               1..1380
                     mol_type = other DNA
                     organism = Aspergillus candidus
SEQUENCE: 25
atgagattcg gtcaccctgt atctacggcg ctgctgtcgt ggctggtcac ctgcccggct    60
gtgttaggag cagctctccc ccgagccgat tcgtcctccg acaacgacct ggaatccatc   120
ctcgccggtc acgccaacgg aagcgacgac cggacgtcac gaaccgccgc cgccctcgcg   180
tccaggatcg cagatgccaa caaccagccg gacccaggag accggtccat gcaccaggcc   240
tggggaaaga tcgaatccat cttcaaccac accgatcgcg ccgatcaacc ggacctcttc   300
gactatgctg atggtctggt ctcgctggac ctgatcccgt cgcacatcct ttccttcctg   360
aacggctacc tcgactggag catcaattcc atccacacc ggaacccagc cgtgcccgac   420
gccggcatct acccgtccaa ggatcccgcc gatgcgccct atagcgtcgc cgaggccgac   480
ctacgcgcgc ccatccacat cccggaggat ttctcctacg gccggcaggg caaaagcc   540
gtcatcctgg taccgggcac ggccatcccg gccggcaccc ctaccactt caacctgggc   600
cagcttggc atgccgccc cgaggccgac gtggtgtggg tcaatatccc ccaggcctcg   660
ctgcgcgacg cccaggagaa cgccgagtac gtggcctacg ccatccacta catcgccgcg   720
ctgtcccaca cctccgtctc ggtcatctcc tggtcccagg gcggcctgga cacccagtgg   780
gcgctcaagt actggccgtc gacgcgggcc caagtggaag acttcatcgc cgtcagcccc   840
gactttcgcg gcacgcggt ccgtcccatc gtctgcccgg ccctagacct gcttgtctgc   900
acccatcgc tctggcagca gggctgggag accgagttca tccagacggc gcgggccgac   960
ggcggcgact cggcatatgt ccccacgacg acgatctact cgacctttga cgagattgtg  1020
cagccccaga gcggcgacga cgcctcggcc cttctcaaag acgcgcgctc catggggta  1080
tccaacaacc acctccagac cgtctgcgcg aaccgccccg ccggcggcat ctacacgac  1140
gaaggcacgc tgtacaaccc gctcacgtgg gcgctcatca tcgacgccct cacccacgac  1200
ggaccgggtg atgtatcccg cctgatctg gacgccatca gccaacaggt gctgcccaag  1260
acctgggat tggatgatat tctcggcacc gaggggatcc tgctggtggc ggttgccgaa  1320
ctgctccttt acgtgcccaa ggcttttaaa gaaccccgca ttgcagacta tgccgcctag  1380

SEQ ID NO: 26        moltype = DNA  length = 2070
FEATURE              Location/Qualifiers
misc_feature         1..2070
                     note = Chromosome Desired nucleic acid sequence 25
source               1..2070
                     mol_type = other DNA
```

-continued organism = Saccharomyces cerevisiae
SEQUENCE: 26

```
atgtttggct ctgggaatgt tctgcctgtt aaaattcagc ctccgctgct taggccactg   60
gcgtatagag ttttatcaag aaaatatggt ttatcaatta aatctgatgg actgtctgct  120
cttgcagaat tcgttggcac taatataggt gctaactgga gacaagggcc tgctacaata  180
aaatttctcg agcaatttgc tgcagtatgt aaacaacaag aaagaggcct tttcatcgac  240
cagagcgggg ttaaagaagt tatacaggag atgaaagaac gtgagaaagt cgaatggagt  300
catgaacacc ctattcaaca tgaggagaat atcttgggac ggacagatga cgatgagaac  360
aacagtgacg atgaaatgcc gatcgctgct gattcatcct tacaaaatgt ttcattatct  420
tcacccatgc gacagcccac cgaaagagat gaatataaac agcctttcaa gccagaaagc  480
tccaaggcgt tggactggag ggactacttc aaagttatca atgcttctca gcaacaaaga  540
ttctcataca atccgcacaa aatgcaattt attttcgtcc ccaataaaaa gcagaatggg  600
ctaggaggca ttgcgggttt tctaccagat atagaggaca aagttcaaat gttcttgaca  660
agatattacc tcacgaacga cagagtcatg agaaatgaaa acttccaaaa cagtgacatg  720
tttaatccat tatcatctat ggtgtcttta caaaatgaac tgtccaatac taaccgacag  780
cagcaatcca gcagtatgag tatcaccccca ataaaaaacc tactaggtag ggatgctcaa  840
aactttctac tattggggct cttaaataag aactttaagg gcaattggtc actggaagat  900
ccgtctggat ctgtcgaaat tgacattcc caaactatcc ctacacaagg ccattactac   960
gtgccaggtt gcatggttct tgtggaagga atatactatt ctgtaggaaa taaattccat  1020
gttacctcca tgactttacc ccctggtgag agaagagaaa ttacattaga aacgataggt  1080
aatctcgatc tcttaggaat acatggcatt tctaataaca atttcattgc tcgtttggat  1140
aaagatttga agattagatt acaccttttg gagaaagaat taacagatca taaatttgta  1200
attctcggcg caaatttgtt cctagatgat ttgaaaatta tgactgcact cagcaaaatt  1260
ttgcaaaaat taaatgatga cccaccgacc ctattaattt ggcaaggttc tttcacttca  1320
gttcccgttt tcgcatcaat gagtagccgg aatataagta gttccactca atttaagaat  1380
aatttcggta ccttggcgac gcttctgtca agatttgaca atttgaccga aaataccaca  1440
atgatattta ttccaggtcc taacgattta tgggggtcga tggtgtcatt ggggcaagt  1500
gggacattac cgcaagatcc aattcctagt gcgtttacca aaaaaatcaa caaggtctgt  1560
aaaaacgttg tatggagctc aaatccaact agaatagcat acttatccca agaaatagtc  1620
attttcaggg acgatttatc cggaagattc aaaagcacc gtttggaatt cccattcaac  1680
gagagcgaag atgtttatac tgaaaacgat aacatgatgt ctaaagacac cgatattgta  1740
ccaatcgatg aattagttaa agaaccagac cagttaccac aaaaggttca agaaacaaga  1800
aaactcgtta aacaatact agaccagggt catttatcgc catttcttga ttccttgcgc  1860
ccaatttcat gggatttgga ccacacttg acactttgcc caataccatc gacaatggtt  1920
ctttcgaca ctacttctgc acaatttgat ttgacataca acggttgtaa agtaattaac  1980
cctgaagtt tcattcataa tagacgtgct aggtatatgg agtacgttcc atcctcaaag  2040
aaaactatac aagaagagat atatatctaa                                    2070
```

SEQ ID NO: 27        moltype = DNA  length = 2073
FEATURE            Location/Qualifiers
misc_feature       1..2073
                     note = Dpb2 Desired nucleic acid sequence 26
source             1..2073
                     mol_type = other DNA
                     organism = Saccharomyces paradoxus
SEQUENCE: 27

```
atgtatggtt ctgggaatgt tctgcctgtt aagattcagc ctccgctact caggccattg   60
gcatatagag ttttatcaag aaaatatggt ttatcgatta aatctgatgg gttgtctgct  120
ctggcggaat tcgttggcac taatataggt gccaactgga gacaagggtc tgctacagtg  180
aaatttctcg agcaatttgc tgtcgtatgg aaacaacaag aaagaggact tttcatcgac  240
cagaacgggg ttaaagaagt gattcaggaa atgaaagaac gtgaaaaagt tgaatggagt  300
catgaacact ctacccaaca tgaggaaaat atactgagac ggacagatga tgatggcaac  360
aacagcgacg atgaaatgcc catggcagct gattcatcct tacaaaatgt ttcgttatct  420
tcaccaattc cgcagcctac taataaaaac gaatatgaac agccttttaa gccagaaagt  480
tctaaaatat tggactggag ggactatttc aaagttatta atgcttctca gcaacaaagg  540
ttctcataca atccacacaa aatgcaattc atcttcgtcc ccaataaaaa gcagaatgaa  600
ctgggaagcg ttgcaggatt tctacctgat atggaagaca agttcaaat gttcttgaca  660
agatattacc ttaccaacga cagagtcatg agaaatgaga cttccaaaa cagtgacatg  720
tttaatccat tatcctccat ggtgtcttta caaaatgaac tatccaatac taaccagcac  780
cagcagcaat ccaacagcat gagtatcacc ccaataaaaa atttactagg tagggatgct  840
caaaattttt tactattggg gctcttaaat aagaactta agggtaattg gtcactagaa  900
gatccgtctg gatccgtcga aatcgatatt cccaaacta tccccacaca aggtcattat  960
tacgcgccag gttttatggt tcttgtgaaa ggaatatatt attcggtagg aataaaattc  1020
cacgttactt ccatgacttt gccccctggc gagaggagag aagttacatt agagacgata  1080
ggtaatctag acctcttggg aatacatgga atttctaaca ataacttcat tgctcgttta  1140
gataaagatt tgaagattag attacacctt tggagaaag aattaattga tcataaattt  1200
gtaattcttg gcgcaaattt attcctagat gatttgaaaa ttatgactgc actcagcaaa  1260
attttgcaaa aactaaacga tgacccaccg accctattaa tttggcaggg ttctttcact  1320
tcagttcccg ttttcgcatc aatgagtagt cggaacataa gcagttcaac ccaataaag  1380
aataatttcg acgccctagc gacacttctg tcaagatttg ataatttgac cgaaaatact  1440
acaatgatat ttattccagg ccctaacgat tgtggggg cgatggtgtc actgggca  1500
agtgggacat accacaaga accaattcct agtgcgttta ccaaaaaaat caacagggtt  1560
tgtaaaaata ttgtatggag ttcaaatcca acaagaatag cgtacttatc tcaagaaata  1620
gtcattttca gagatgattt atccggaaga ttcaaaagac accggttaga attcccattc  1680
aacgaaagtg aagatgtcaa taccgataac gatgaaatgg taaccaaaga cactgatatc  1740
gtgccaattg atgaattagt taagaaacca gaccagttac cgcaaaaggt tcaagaaaca  1800
agaaaactcg ttaaaacaat actagaccag ggccatttat caccatttct tgattctttg  1860
cgcccaattt catgggattt agaccatact tgacgctct gcccaatacc atcaacaatg  1920
attctttgcg acactacttc tgcacaattt gatttgacat acaacggttg taaagtcatc  1980
```

```
aaccctggat cattcattca taacagacgt gctaggtata tggagtacgt tccatcctca  2040
aagagaacta tacaggaaga gatatatatc taa                               2073

SEQ ID NO: 28          moltype = DNA  length = 2039
FEATURE                Location/Qualifiers
misc_feature           1..2039
                       note = neutral protease (NPRC) gene Desired nucleic acid
                        sequence 27
source                 1..2039
                       mol_type = other DNA
                       organism = Bacillus cereus
SEQUENCE: 28
ctgatattgt tggtcaacaa gctaaaactg ttgaacaagt taatttataa tctccccccc  60
tttccaaccg gaaaggggtt tttcaatatt tgttcctcaa aattctacaa aacttgagaa  120
aaaaattatt tgaattttta gtatattaat agtggaaaca taatgctaat atgaaacact  180
ctttttcaaa aaaatttttt attaggggga aggttcatga aaaagaaaag tttagcgtta  240
gtgttagcga caggaatggc agttacaacg tttggaggga caggctctgc atttgcggat  300
tctaaaaatg tgctctctac gaagaagtac aatgagacag tacagtcacc tgagtttatt  360
tctggtgatc taactgaagc aactggcaag aaagcagaat ctgttgtgtt tgattactta  420
aacgcagcaa aggtgatta caagctaggg gaaaagagtg cacaagattc tttcaaagtg  480
aaacaagtga agaaagatgc tgtaactgat tcaacagtag tacgtatgca acaagtttac  540
gaaggagtgc ctgtatgggg ttctactcaa gtagctcacg taagtaaaga cggttcttta  600
aaagtattgt ctggaacagt tgcacctgat ttagacaaaa aggaaaagtt gaaaaataaa  660
aataagattg aaggcgcaaa agcaattgaa atcgcgcagc aagatttagg ggtaacaccg  720
aaatatgaag tagaaccaaa agcggactta tatgtatatc aaaacggtga ggaaacaaca  780
tatgcatatg ttgtaaatct aaacttctta gatccaagcc caggaaacta ctactatttc  840
attgaggcag acagcggtaa agtattaaat aagtttaata caattgatca tgtgacgaat  900
gatgataagt caccagttaa gcaagaggct cctaaacagg atgcgaaagc tgttgtaaag  960
cctgtaacag gaacgaataa agtaggaact ggtaaaggtg tattaggaga tacgaagtcg  1020
cttaatacaa cgttatctgg atcatcttac tacttacaag ataatacacg cggggcaacg  1080
attttcacat atgatgcgaa aaaccgttca acattaccag gaacactatg ggcagatgca  1140
gataatgttt tcaatgcagc gtatgatgca gcagcagtag atgctcatta ctatgcaggt  1200
aaaacatatg attactataa agctacgttt aatagaaatt ctatcaatga tgcaggagcg  1260
ccgttaaaat cgacagttca ttacggaagt aattataaca atgcattctg gaacggatca  1320
cagatggtat acggagatgg tgatggtgta acgtttactt cattatctgg tggaattgat  1380
gtaattggtc acgagttaac gcatgctgtt acggaaaata gttcaaatct aatttatcaa  1440
aatgaatcag gggctttaaa tgaagcgatt tctgatattt ttggtacttt agtagaattc  1500
tatgataacc gtaacccgga ttgggagatt ggtgaagata tttacacacc tggtaaagca  1560
ggagacgcac ttcgctctat gagtgatcct acgaagtatg gtgatccaga ccattattct  1620
aagcgttaca ctggttcaag tgataacggt ggtgttcata caaacagcgg cattattaat  1680
aaacaagctt atttattagc aaatggtggt acgcattatg gtgtaactgt aactggtatc  1740
gggaaagata aattaggtgc gatttactac cgtgcaaata cacagtattt cacgcaatct  1800
actacattta gtcaagctcg tgctggtgca gtacaagctg ctgcagactt atatggtgca  1860
aattctgctg aagtagcagc agttaagcaa tcatttagtg ctgttggtgt aaactaaggc  1920
tttaaggaag agctagtaat aaaatacctc aaaaataaag aaggagcata ggctccttct  1980
ttattttttt ctccattttt tccacaaata aaacaatcca ataacgcctg cgattgtta   2039

SEQ ID NO: 29          moltype = DNA  length = 2289
FEATURE                Location/Qualifiers
misc_feature           1..2289
                       note = Phenylalanine ammonia lyase (PAL) mRNA Desired
                        nucleic acid sequence 28
source                 1..2289
                       mol_type = other DNA
                       organism = Botrychium virginianum
SEQUENCE: 29
atgtcaaagt caagctagac gtagccactg cgaaggaaag agttgatgag agttcggaat  60
gggtgatgaa ccatgtcatg aaaggaacgg atacctatgg agtgacaacg ggttttggag  120
caacctcgca ccgcagaacc aagcagggca ttgagcttca gaaggagctc atccgttttt  180
taaatgctgg aattcttagt ggcgacaagg aagaatgctc tacgttgtcc gtgtctgctg  240
ttcgcgcagc aatgcttgtt cggacaaaca ctctcatgca gggctattct ggcataagat  300
gggagattct ggaagcaatg ggaagcttc tgaacaatca aatcactcca agactgccac  360
tgaggggcag cataactgcg tcaggtgatc ttgtccctct ttcttatatt gctggtgtgc  420
ttacagctcg tcccaattct gcagctgtga cagccgaagg aaaagaagtg acaggtaaag  480
aagctcttga gttggccgga gtggctgaac catttgagct caaaccgaaa gagggtcttg  540
ctcttgtcaa tggaacagct gtgggctctg gtcttgcttc cttagtatgt tatgatgcca  600
acattctagc acttcttgct gaagtattat ctgctttatt ctgtgaagtg atgcaaggga  660
agcctgagtt caccgatcat cttacccatc gattgaagca tcatcctgga cagattgaag  720
cggcagcaat catggaatgg cttctggatg gcagctctta cgtgcaaaca gccgcgaaat  780
tgcacgaagc ggatcccttg aaaaaaccca aacaggacag atacgcattg cgaacgtctc  840
cacaatggtt ggggcctcaa gtagaggtga ttcgtcttgc aacgcatgct attcagcggg  900
aaattaattc tgtgaatgac aacccattga ttgatgtagc aagagacaag gctcttcatg  960
gtggtaattt tcagggaact ccaataggcg tctctatgga caacatgaga ttggccatcg  1020
ctgccatagg caggctcatg tttgcccagt tctctgagct tgtgaatgat ttttacaata  1080
atgggttacc ctcaaatttg agtggaggcc caaatcccag tttagactac ggttttaagg  1140
gagcagaaat tgcaatggct tcatacacat ctgagttgca gtacctcgca aatcctgtga  1200
caacccatgt tcaaagtgca gagcagcata accaagatgt gaactcactg ggtcttatat  1260
cagctcggaa aactaaagaa accgttgaca ttctgaagat gatgtcttcc acatttatgg  1320
tggccctttg tcaagccgtt gatcttagac atttggaaga gaacatgacg gcagttgtga  1380
```

```
agcatgtggt atgtcaagtg gcaagaagaa cattgtattc tgatcagaat ggattacttc  1440
ttccttctcg attttgcgaa aaggagttgc ttcaagtggt ggaacatgag ccaatattct  1500
cctacataga tcatgcctct gcggatacgt ctactctgat gcagaagcta aggcaagtgc  1560
tggttgacca tgcattgaaa aatgtggcga aggagaaact agattctgcc aatgtgttaa  1620
ataggattat cagtttcgag gaattgctaa agattcgttt gcaaatagaa atccctaggg  1680
catgggagag ttttgacaag ggacaatgtg ctgtccttaa taggatacag aattgcagaa  1740
cctatccttt gtataaactc gtgcgtgatc tgttggatac gcagatattg agtggtgcta  1800
agaagcaatg tccaggccag gattttcaga aggttttga ggctatctca gaagggaagc   1860
tagctgctcc attgcttgag tgcatgaatg gttggactgg tcgtccgggg ccatttgcac  1920
cctcgcagca gaaaaattct tctacagaga tatgtaatcc ctccggttgg atctggtttg  1980
atcaacttat tgcttccaaa ccacgaggtg gtgccacggg atattttatg ctttccatgg  2040
tgtgatttgg atgaatcatg ttttgtttcg ctcttgataa ttggatctgc agaaatgcac  2100
aataattgtt ccttcttcga ggtgttagga ctgtacttgg actagatgat tgcttatggg  2160
gttagccagc catgtgtctg ctattgggat ggtatctcca gaagtttcaa gatctggtat  2220
taggtgatta acgaacatgt aacagtttgt tggtaatgat gtagccagct acgtgccaaa  2280
aaaaaaaaa                                                          2289

SEQ ID NO: 30           moltype = DNA  length = 1990
FEATURE                 Location/Qualifiers
misc_feature            1..1990
                        note = CCAP 1055/1 cryptochrome photolyase family 1 Desired
                        nucleic acid sequence 29
source                  1..1990
                        mol_type = other DNA
                        organism = Phaeodactylum tricornutum
SEQUENCE: 30
cgtttcccag cttttaatct atcgctatcg tggaaaaacg aaaatatcaa gcgaattcgc   60
aatcgctctg ttgggaacga gctgttcatc tctatgcaag tgacagccta tcagacgaaa  120
agcgcaaaac ggagatgcgc tcggaagaaa gccactactc accgtatatc aattcttcct  180
agcgtgtttc caagctgatt gctccacttt tccaactatt gctcttgtcg gccccatccc  240
cgttccgtcg ttatcaaatt cgcaggttcg ccgccactgt gctcgggatg gctaaatcgg  300
aagagaaaaa acacgacgtt gccatccatt ggttccgcaa tggtctccgc ttccacgaca  360
acccttgttt gctggatgcg tgccaaaaat ccgaatcact ccttccgatt tacgtagtcg  420
accctgaatt tcccttcgcg caaactgctg ggtgccgcgc cggtacaatt cgtgccaatt  480
tcttactcga atcgataaac gaagtcgacg aaaaactccg gaaaatgggt agtcagctga  540
tcgttgttct cgggaagagt cacgaagtct tacccgaaat tgtcgccacc acacaggcta  600
aggcattgtt ctatgaacaa gaagcagccg ctcctgtgcg agagcaagac gccgagacga  660
tccaagccat caagaatcgt ttgaaaaggg acggtaaaaa ttacgagtgc aaatttgaag  720
cctatgcaac gcatacgctt catcccatgg aacggtattc atgcagtgc aaaagaccata  780
cggcaccgtc gacgtatgga agttttacga gattttcaa caaatgagt gttgcgaaag    840
aagtgaacga agtcaaggag gtaccatcgt tgccaaacaa gtcagttaaa cttcttgaaa  900
aatcgtttgc agaggctttg cgaatgccta cgttaaaaga tcttggatac gcagctgctg  960
ctgatgatat gaagaacagc ggcaaaggag ggtatgcttt tgcaggggga gaaaacgccg  1020
caatcgagct tcttgcaaag aacatgcgcg gctcgcagtg ggtagcaacg tttgaaaaac  1080
caaagacaag cccaaatgat gccacacgac caagcactac tgctttgagt ccttacgtca  1140
agcacggctg tatatctccg cgtcgctttt atcatgagtt gtcgaaggtg tactcaaaat  1200
acaatagcaa agaaacatcg aagccaccag tttcgctcta tggacaacta atgtggcgcg  1260
acttcaatta tctggtcgga tacagcactc caaactttga caaaatgatc gacaatccta  1320
ttgctcgaca aattccatgg gacgacgatc cggatctttt gctagcctgg aagatgtcga  1380
agacgggata tccttacatc gatgcgatca tgacccaact acgggaaacg ggctggattc  1440
accacctagc tcgtcattcc gttgcttgct tcctcactcg aggggatcta tggcaaagct  1500
gggaagatgg cgctacagtc ttcgaagaat atttgattga cgctgattgg agcatcaaca  1560
acttcaactg gcaatggctt tcttgcactg cccatttcta tcagtatttt cgatgctatt  1620
cgccaattgc tttcggtaaa aagacggacc caaatggcga ttacattcgc aaatggttgc  1680
ctcagttcaa ggacatgcca gcaaagtata tctacgaacc ttgggaagct cccattgaac  1740
ttcaaaagaa agttggggtg attgtccggtg aaaactaccc tcatccaatt gttgaccaca  1800
agttggtcag taaaaacaat atgtcaccgga tgaaggaagc gtacgatgca cagaagaatc  1860
gggagcctat gccagccaac gaatcgcata gtagcggttt gaatcgtgat acttcaccaa  1920
agcgacaacg tcgcaactaa cagaaagtgc aaagaatcgt tttttataa caaatgggat   1980
tcataaccga                                                         1990

SEQ ID NO: 31           moltype = DNA  length = 2172
FEATURE                 Location/Qualifiers
misc_feature            1..2172
                        note = flap structure-specific endonuclease 1 (Fen1)
                        Desired nucleic acid sequence 30
source                  1..2172
                        mol_type = other DNA
                        organism = Rattus norvegicus
SEQUENCE: 31
gcggcgaagc tggaaacgat ttcggctcga cattgtaaga acaggcttgt ggctgtccac   60
agaacactgg ggatccaaac cactgctagc taggtgaagc ctcgtgcact cgaggcggag  120
tgaggtctcg cggaagcgtc tccgagacg gcgagggccg cgagagcaac accaagcagc   180
ccggggcttg ggctattctc actgatccga acatctctct tcgctggtag gaagaagcca  240
ttgctcctgt gttaccatgg gaattcaagg ccttgccaaa ctaattgctg atgtggcccc  300
cagtgccatc gtgagaatgc acatcaagag ctactttggt cgcaaagtgg ccattgatgc  360
ctccatgagc atttaccagt tcctgattgc tgttcgtcag ggtggggacg tactgcagaa  420
cgaggagggg gagaccacca gccacctgat gggcatgttc taccgtacca tccgcatgat  480
ggagaatggc atcaagccgg tgtatatctt tgatggcaaa ccaccacagc tgaagtcggg  540
```

```
ggagctggcc aaacgcagtg agcggcgtgc agaggccgag aagcagctgc agcaggctca    600
ggaggcgggg gcagaggagg aggtggaaaa gttcaccaag cggcttgtga aggtcaccaa    660
gcaacacaac gatgagtgca aacacctgct gagcctcatg ggcatcccat accttgatgc    720
gcccagcgag gcagaggcca gctgtgctgc cctggcaaag gctggcaaag tctatgccgc    780
agccacggag gacatggact gcctcacttt tggcagcccc gtgctaatgc gacacttaac    840
tgccagtgag gccaagaagc tgccatcca agagttccac ctgagccgcg tcctgcaaga    900
gctgggtctg aaccaggagc agtttgtgga tctgtgcatc ctgctgggta gcgactactg    960
tgagagtgtc cgtggcattg gacccaagcg ggctgtggac ctcatccaga agcacaagag   1020
catcgaggag atcgtgaggc ggctggatcc cagcaagtac cctgttccgg aaaactggct   1080
ccacaaggaa gcccggcagc tcttcctgga gccggaagta ctggacccag agtctgtgga   1140
gctgaagtgg agtgagccaa acgaagaaga gttggtcaaa tttatgtgcg gtgaaaagca   1200
gttttctgag gagcggattc gtagtggggt caaacggctg aataagagcc gccaaggcag   1260
cacccaggga cgcctagatg atttcttcaa ggtgacaggc tcactctcct cagccaagcg   1320
caaggagcca gagcccaagg ggcctgccaa gaagaaagca aagactgggg gagcaggaaa   1380
gttcagaagg ggaaaataaa tgtgtccttc cctccactgt cccttggccc caggacagtg   1440
ttttgtaccc tcagctagag cacatccctc tcgcccgcg tcttgaggac aagttcattg    1500
cttcccagcg ctgcccttca gagctttccc tcgcttgacc ctgtgtcagg aagcccgtag   1560
ctctgctttt cctcattttt agctcaggaa agatgtcagg ctcaaaccac ttctcaggtt   1620
aatggaccct gtccgttgct ctgtgcaact gctagcagta ttttaaggga aagataagg    1680
cagggagaga gtaggaggta atttcccagc tggccagctg gtgggggaca ggtgactaga   1740
gcgcggctgc cgactgctct ttctaatttc actgtgccct ggaagacagc catcagtctg   1800
ggattagctg atgagagagc cgcaaagaga aacagagag ttcggcgaca acagatttaa    1860
tactgactgg ctgtttttgtg gacttgctgt ctggtgagcc cagtagttgc gcaagggagt   1920
gaaaacacag tgtttaggtt taggtttgta gtgtttggtt ttgtgcctcc cctctccagt   1980
gttgggaatt gaacccaggg caaaggcatt aagtgtacca ctgacctgta gctccaagtg   2040
atgttctgag gctccaagtg atggcctttc tgaggcagtc aatttaattg aggttttgga   2100
agaaaaact tgttcatggg ctgtttctat tttaaaagat gtgaagaaaa aaaacaataa    2160
aattataaaa gc                                                       2172

SEQ ID NO: 32         moltype = DNA  length = 2112
FEATURE               Location/Qualifiers
misc_feature          1..2112
                      note = Desired nucleic acid sequence 31
source                1..2112
                      mol_type = other DNA
                      organism = synthetic construct
SEQUENCE: 32
atgttccatg tgagcttcag gtacatcttc ggactgcctc ctctcatcct ggtcctcctc    60
cccgtggcca gctccgactg tgacatcgaa ggaaaggatg gcaagcagta cgaaagcgtg   120
ctgatggtga gcatcgatca gctcctggat tccatgaagg aaatcggctc caactgcctc   180
aacaatgagt tcaactttt aagaggcat atctgcgacg ccaacaagga gggcatgttt    240
ctgttcaggg ccgccaggaa gctgagacag ttcctcaaga tgaatagcac cggcgacttc   300
gacctccatc tgctgaaggt gtccgaggga accaccatcc tgctgaactg caccggccaa   360
gtgaagggaa gaaaacctgc tgccctgggc gaggctcagc ctaccaagag cctcgaggag   420
aacaaaagcc tgaaggagca gaagaagctg aacgaccgt gcttcctcaa gaggctcctg    480
caggagatta agacctgttg gaacaagatc ctgatgggca caaggagca cggatccggc    540
gtgaagcaga ccctgaactt tgacctgctc aaactggccg gcgacgtgca gtccaatcct   600
ggacctatgg ctctgctgct cgccctgagc ctgctcgtcc tctggacctc ccctgctcct   660
accctgagcg gcaccaatga cgctgaagac tgctgcctgt ccgtgaccca gaagcctatc   720
cccgatata tcgtgaggaa ttttcattac ctcctgatca aggacggctg tagagtgccc    780
gccgtcgtgt tcacaaacact cagaggcagg cagctgtgtg ctcccccga ccagccttga    840
gtggagagaa tcattcagag actgcaaagg acctccgcta agatgaagag gaggtccagc    900
ggcagcggag tgaagcagac actgaatttc gacctgctca agctggccgg cgatgtggag    960
agcaaccctg gacctatggc ttcctacccc ggacatcagc acgcttccgc cttcgaccag   1020
gccgctagaa gcagaggaca ctccaataga aggacagccc tgaggcctag aggacagcag   1080
gaggccaccg aggtgaggcc cgagcagaaa atgcccaccc tgctgagagt gtatattgat   1140
ggaccccacg gcatgggaaa aaccaccaca acccagctgc tggtggctct gggaagcagg   1200
gatgatattg tgtacgtccc cgaacctatg acatattgga gggtcctcgg cgcctccgag   1260
accatcgcca acatttacac cacccagcac aggctggatc agggaagat ctccgccgcg    1320
gatgctgccg tggtgatgac cagcgcccag atcactatgg gtatgcctta tgccgtgacc   1380
gacgctgtgc tggctcctca cattggcggc gaagccggat cctccatgc tccccctcct    1440
gccctcacac tgatctttga cagacatcct atcgccgctc tgctgtgcta cccgccgct    1500
aggtacctga tgggcagcat gacccctcag gccgtgctgc ttttgtggc cctcattccc   1560
cccacactgc ctggcacaaa tatcgtgctc ggcgccctgc ctgaggacag ggcacatcgat   1620
aggctggcta agacagagag acccggagag aggctggatc tcgctatgct ggccgccatc   1680
aggagggtgt acgcctgct ggccaacacc gtgagatatc tccagtgtgg cggatcctgg   1740
agggaagact ggggccaact gagcggcaca gctgtgcctc ctcaaggcgc tgagccccag   1800
agcaacgctg gacccagacc tcacatcggc gatacctgt tcaccctgtt tagagccct     1860
gagctcctgg ccctaacgg cgacctgtac aatgtgttcg cttggtgcct ggatgtgctc    1920
gccaagagac tcaggagcat gcacgtcttc attctggact acgaccagtc cccgctggc    1980
tgcagagatg ccctgctcca gctgacctcc ggcatggtgc agaccacgt gaccacccct    2040
ggaagcatcc ccacaatctg cgacctggcc aggacctttg ccagagaaat gggagaagcc   2100
aactgagtcg ac                                                       2112

SEQ ID NO: 33         moltype = DNA  length = 2169
FEATURE               Location/Qualifiers
misc_feature          1..2169
                      note = FGSC A4 CATB_EMENI Catalase B Desired nucleic acid
                      sequence 32
```

```
source                  1..2169
                        mol_type = other DNA
                        organism = Aspergillus nidulans
SEQUENCE: 33
atgcgagctc tcggcctggt cggccttgtt ggcgtcgcca atgccgtctg tccgtatatg   60
acaggcgagc tcggccgtcg cgataccaac cccgatgcta ccgaggccac tgaggaattt  120
ctgtccgagt actaccttga cgacacggac tcgtacctga cgactgacgt cggcggccca  180
attgaggacc agcagagtct caaggccggt gcgcgcgggt ctaccctgct ggaagacttt  240
atcttccgtc agaagatcca gcgattcgac cacgagcggg tccccgagcg tgccgtccat  300
gctcggggtg caggtgccca cggtgtcttc acctcgtacg gcgacttctc caacatcacc  360
gccgcctcct tcctctctgc tgagggtaag gagacccccg tcttcgtccg gttctcgacc  420
gtcgccggca gtcgtggcag ttctgacctc gcccgcgatg tccacggttt cgccacccgc  480
ttttacactg acgagggcaa ctttgatatc gtcggtaaca acattcccgt cttttttcatc  540
caggatgcca tccagttccc cgacctgatc cacgccgtca agccaagggg cgatcgtgaa  600
atcccgcagg ctgccacggc ccatgacgcc gcctgggatt tcttcagcca gcagccctcg  660
actcttcaca ccctgctctg ggccatggcc ggtcacggta tccgcgttc gttccgccac  720
gtcgatgggt tcggtgtgca cactttccgg ctcgtcacgg aggatggctc caccaagctc  780
gtcaagttcc actggaagac cctgcaaggt ttggcaagta tggtctggga ggaagctcag  840
caaatttctg gcaagaaccc cgactacatg cgccaggatc tgttcgagtc gattgaggct  900
ggccggtacc ctgagtggga gcttaacgtg caaatcatgg acgaggagga ccagttgcgc  960
tttggcttcg acctttttcga ccctaccaag attgtccctg aggaatacgt cccattgacc 1020
ccgctgggca agatgaccct caaccgcaac ccccgcaact actttgcgga gactgagcag 1080
gtcatgttcc aacccggcca cgtcgtgcgt ggtgttgact tcaccgagga tcccttcctt 1140
cagcagggac gtcttttcag ctaccttgac acccagctca accgcaatgg tggcccgaac 1200
tttgagcagt gcccatcaa ccagccgcgc gttgctattc acaacaacaa ccgtgacggt 1260
gctgcccaga tgttcattcc gctgaacccc gatcgtacga gcccaaacgc gctgaaggga 1320
tcaaccctca aacaggccaa ccagactgcg gtcgcggat tctttactgc tcctgaccgt 1380
actgccaacg gcaatcttgt gcgtgccaag agctccacct tcgatgatgc ttggtcgcag 1440
ccccggcttt tctggaactc tcttcttccc gccgagaagc agttcgtggt caacgccatt 1500
cgcttcgaaa acgccaatgt gaagagcgat gtcgtgaaga acaacgtcat cgttcagctt 1560
aatcgaatct cgaacgacct tgccaccgc gttgccaagg ccatcggtgt tgatgctccc 1620
gagcccgaca cacttacta ccacgacaac acgacctcca acatcggtgc gtttggccac 1680
cgactccaga gcttggctgg cctgaagatt gccgtacttg cttctgttga cgcagaggaa 1740
tccttcagcg cggctactgc tctgaaggcc gagctccaca acgacaacct ggacgtcatt 1800
gtcgtcgctg aacgcttctc caacggcgtg aaccagaccc actctgcctc tgacgccatt 1860
cagtttgacg ccgtcgttgt tgcccctgga gcggagaagc tcttcggtgc caagtccgcg 1920
gccaactcca gctcaaccct ctaccctgcc ggccgtcccc tcgaaatcct cgttgatgct 1980
ttccgcttcg gtaagccagt cgctgctctt ggcagcggct ccactgcttt cgacaacgct 2040
ggtatcaaca ccgccgtcga gggcgtgtac gttgccgatg ccgtgaacga gagctttgcc 2100
aacaacctcg aggagggtg gaccgtgttc aagttcttgg atcgctttgc cctggactcg 2160
gatgaatag                                                         2169

SEQ ID NO: 34          moltype = DNA   length = 1968
FEATURE                Location/Qualifiers
misc_feature           1..1968
                       note = NRRL 1 extracellular phytase, putative Desired
                        nucleic acid sequence 33
source                 1..1968
                       mol_type = other DNA
                       organism = Aspergillus clavatus
SEQUENCE: 34
atgaggttcc tttggatctc cggggtgtca gtcctcgtct cgtgcgccca tgctcagacc   60
tttcagcggt tgggtggttg cccgacccta ggctgtgttt tccctccgga ccaagcggac  120
ttccttccag gtcaatattt cgatatccga ctggaagtcc attccccgt caacgggtcg  180
gaggctcgcg tcggtgaacc cgacccaaat ttcaaattta ccatccacaa gaagggtgag  240
aagggtgtga agccagtacc tgccaccgag tactttggcc ttcaggagcc ccagctcgag  300
agatggaact tcacttggta tgaagatctg tttgcggagg acgcaaagaa accctctctc  360
gtcaatgtca cttccaaggc atacagaagg gtggcgctgc atgagccggg agagtacgag  420
gcgactttga cctactacgg aaaccagaca accaaggcca actggctggt gcgtgatctc  480
tccaagaagc gtcgtgcgaa gaatgtcatt ctgttcgtcg gcgacggaat gaccaccaac  540
atgatcaccg ccgctcgtct cattgctcac cagagcatta acggcaagta tgtgtccaag  600
atgcagctga acaagttccc cgtgctgggc catcagatga cgcattcgat ggactcgttc  660
atcacggact cggccaactc tgcgacggct ctctactcgg ccacaagac gaccgtcaat  720
gcgctgaacg tttatgttga ctcgtcgaag gatcccttcg acgacccaa gtttgagacg  780
attgtgggaga tcttccgccg ccggtacccg ggcgttggtg ttggtatcgt ctccactgcc  840
ttcctggcgg atgcgacacc ggccggtctg ccgcgcacca ccagcaagcg tggcgagtat  900
gagcatgtca tcgatgccta ctacgagggc ctgaccaagt acgagtggac caacctggat  960
ggccccgatg tgatcttcgg ggcgggtgcg gagaactcc tgaagagcaa ggatgcgtcg 1020
cgggactact ataagctgtt cgcggacaag ggctacagca tcagctggaa caacacggcg 1080
ctgcatgcgg ccccccaacaa caccaaggcg ctgggtgtct tccagacctc caacctggcc 1140
acatggctgg accgcaacgt ctaccagtcc aaccttctga accagaccaa ctacccggat 1200
ggctccggcc gcgacgccga ggacctgcct ggcctcaagg atatgactct caaggcgatc 1260
gacgtgctga atgcccggca cggcaagcag ggctggttcc tcatgtcgga ggcggccagc 1320
atcgacaaac agatgactac gaccggcgtgc tgggtgacg gctggagctg 1380
gacgacacg tgcgcgcgac gatgagaag ctcaaggcgc tgggccagct ggaagacacg 1440
ctgatcctcg tgacggccga ccacggccac gggtcgacg tcacgggcgc cgtcgacacg 1500
gagtacctcca ccacacacgc ccacgactcg gaccgccaga gcggcgggc ggtcggcacg 1560
tacgagaggt cgggtctctc acagtacacg tggcggat ccaacagcct gcgctactcg 1620
gagggcgtcc acttcccgc gcggtgggat ccccggtaca ccctgcactc gggcctggcg 1680
```

```
gcgtatcccg atcaccggga gaactaccag gtccacaagg gagggccacg caagccggct   1740
tccggcagcg gtggcgacta cttcgccaac tacaaggatg cggtgacggg attcctggtg   1800
aacggcacgt tgcccgtgga cgcgagccag ggcgtgcact cgctgaccga tgtgccggtg   1860
ttcgcgcagg gtccgtgcca ggagctgttc ggcggcgtgt ataattcgat tgatattttc   1920
ttccatatgg ccgagtgcct ggggttgtcc gagaccaaga agccttaa                1968

SEQ ID NO: 35          moltype = DNA   length = 2934
FEATURE                Location/Qualifiers
misc_feature           1..2934
                       note = Desired nucleic acid sequence 34
source                 1..2934
                       mol_type = other DNA
                       organism = synthetic construct
SEQUENCE: 35
atgtcagttc gatgtggttt atcattttt  cataaaactt ggccaattac tactacacga    60
tggtatacag tagaagtaaa ttcaccagaa caaccgtcaa catcaaagag aaatgcttca   120
tttagtttga aaaagattga tttggtaccg aacgattac  atcgtcattt gtttggtaat   180
tatccaattc ctgaaaacac cttaaaagat gatccatttg aaatgcttga tttaccacac   240
ctggaaggtt caaatttgtt agatcatttt caaaagactg ctatgaagca gtttgaacca   300
tatcatcgcc ttctcattga agcaactact attgaaggt  tacctgttat gccaaaggaa   360
tggaattttc atcctggttg gacaagatat gaaataaaca aatcaccaaa acaggttgat   420
aagccacttg aagattgat  attttttgat gtcgaggtat gcgttcgtga tggattacta   480
ccaactcttg ctactgctgt aacaccaaaa gcatggtatt catggtgtag tgatcgtttg   540
gtaaatggtg gagacatacc tgagctttac cgtttgaatc atttaattgc atttgaagca   600
aatgaaaaar acttaaaaca tcgtttaatt attggacata atgtagcttt tgatcgctca   660
agagttcgag agcagtatta tagaaagggg acgaataac  gattctggga tacaatgtca   720
atggcaatac ctatatatgg aatggcagat catcaagtga ccctgtatga aagaaaagat   780
acggaagtag atgattccgg accaattggt tggattgatt attggcgatc gcttgtgtgt   840
aaaaattcat taagtgcatt gcacgaaaaa ttatgtggta ctactaattc gttgaagcca   900
ttgaacaaat cactacaaac atttttcgtg aaagaaccta ttgacgaaat acgtcggtca   960
tttcaggatc ttacaacata ttgtgcttat gatgttgtag cttgttttga attgttaccaa  1020
gttttatatc ctgaatttac aaaaagattt cctcatccag taacatggca aggaatgctt   1080
gaaattggca atgtttattt accggttaca agaattggc  ggaaattttt cgacaataat   1140
gaaactcgtg cgaataatga gaataagatt gctgcaattg gagtagtata tgcagcacgt   1200
gaattggtgg aaaaattgga agagccgatt caatcataca aaaatgatcc atggatgtgg   1260
tcggttggatt ggagcagtcg gaaaggagaa gagtttccca tatggtatga atcattgcta  1320
cgtactagga gccttcttca tatgccagtt gaagagttat ctcaggcaga tgtgaaattg   1380
aaaagccgtg ttgtaccacg attattcgga cttttgttggg gaccatatcc attacactac  1440
aaaactgata agggttgggg attttttggtt ccaaaagatc gtcgtattgc tttatctgga  1500
gtgccagaaa tggacgaagt tgtattaaga cgaggtgtaa aagccacgat tcctgtgaaa   1560
gcaatcctta gcctaataca acaaaatata gcagaaggta ttggagatgt tctgttgacg   1620
cattcgcatt catcatcaac aacaattagt atcttcaatt ttcacaaatt gccacatcct   1680
aatggtgaac atgataatgt tggtgatcca attcaaaagg cattccaact ggaaattgat   1740
gaaggtgttt tatggcctgt gcggtacaag aaggagtttt cagatttata tcgtgcaaga   1800
aataccacac gattttggaa caattataga gatcggtttc aagtcaagt  aacaatttgg   1860
ctggatgaaa atggtgatga aggagctatt gcgccatcaa ttattccagc tggtacagta   1920
acaagacgag ctgttcataa acttggttg  acagctata  atccaaaaga tgatcaaatg   1980
ataggtacca atttgaagtc aatggtagaa tgtcctgaag attggcatat agttggtgca   2040
gatgttgatt cacaggaaca atggatagca gcaatgytag gtgattgttg tgttggaaaa   2100
ggtacagctg gtgtaactcc ttttagcaat atgcttttag caggatctaa atctgataac   2160
agtgatttgc atagtgttat tgcgaaggaa gttggtatta gcagagataa agcaaaggta   2220
ttgaattatg cacgacttta tggttctgga atagtacatg cagctgaatt tctcattcaa   2280
tcaggaatga atgctacgaa agcattaaat gtaagcaaca aattattcgc tacaaccaaa   2340
ggcaaacgat tcaattttt  gaaattaaat gaaagttaca atgattattt tcgttggtac   2400
atcgataata tatgcccttc aaagatgaaa gcagattatg tgtatgcaaa tggtacttat   2460
ttcttaccgg aatatcgcat tcgacagggg aaactgacgc taaactttga agactgcgtt   2520
tatgaaagtc tatggaataa actcgtgaaa atggacagg  atgaagtggt acaatcaagt   2580
gctgttgatt ttttacatct acttattgta tgtatgaaat ggctttgtga aatttatagt   2640
attaaggctc gatttgctct ttccattcat gatgactggg ttgcattctt cagccaagtt   2700
gatatcgatc gtgtacttcg aaaagaggtt aatttagtgt gcacaacgcc aagcggtgaa   2760
tgcattccac caggtgaagc attggatatg aatgctattt tggtgaaaac tggtggtacg   2820
ttgaaaaaag ttgcaaatgc atcctttacc gccaatgcgg cagttcaaca acaaatagta   2880
ttagggaaaa tagtgaaatc tgataagaat cgaaacaaaa agagattatc ctaa          2934

SEQ ID NO: 36          moltype = DNA   length = 3180
FEATURE                Location/Qualifiers
misc_feature           1..3180
                       note = cellulase (CelA) gene Desired nucleic acid sequence
                       35
source                 1..3180
                       mol_type = other DNA
                       organism = Bacillus sp. NBL420
SEQUENCE: 36
gcatttcttt aagtagtacg tgtatatgtt gtgcatgccc cttcaggaag ggtatagtca    60
ttggtcactt ttctcagttc cttcaagatg ctgcctgcgg cttcatgctc ttgttcaagg   120
acgtcgatcg cctgaaccgc ttctgccagg ctgtccattg atcgcgtctc ttcataggtc   180
gtcactttcg ggaaaatgag ttcctcttcc tgaaagagat ggtgttccag ttcagttttc   240
agctgatgga acaattgatg gacctgggcg agttccggat gatggatgcc gtgaacccgg   300
tagacttttg tgacaaagcc tgatagttca ggaagcacct catacaggta agcatggtgc   360
```

```
gtatgaatca catggtcgat cagctgtgaa tacggggctt cactccagtt cgtctcttttt   420
gcgttcaatg cctttgtctc ttgatataat gtattgattt ttgctaagat ctcttcttca    480
tttaaatcct gttctttat cgcttcaccg atcgggcggt tgcccccgca gcaaaagtcg     540
atgcgatatt ctttcagcaa ccggctggct cttggaaaac gcgtaacaat atcacctgtt   600
tttgtgtttt gattgttttt gacaagatca cggagtttat ccggaaaccg ttcatgaaga    660
aaaagcagac ggttgatgaa caagggcatg tataaacgaa aaaagtgccg aaatcaaact    720
tcggctattt gctgaattgc tattggtgcg cagggatatg gtgcgctttg atcatcgctg    780
tcgggtatct gattgtccca aaaacgatat tcccgttaat tttaattta tcggtcgcag    840
gtggacaggc gattcttgaa acgtttgtcg gtgtcgcaac aaaacttgtc agcttttct   900
ctgatttaaa gaaataaacc attccaagcg gatggtttta ttttttgac aataaagtga    960
cacaaacagc agagagaaca tgtccgcttt gtgaactttt tacagcgatt tttccccggt  1020
tgccgcattt taggcagagg gaagacatta ttttgaagaa gaatcaggtt ttaaaatttt   1080
gaattgagag aaaaaggaag cacaaagtcc ccggtcatac tttttagct tttcatcatt   1140
agcattcaga cctcccattt catacgaaaa gaggaaata atagatttc aaaacgaaaa    1200
aaacgtgaaa tatggttgat agacaatcaa tgaatagttt ttttacaatc agtaacgtgc  1260
tacaagccaa gaaaggggtg aaaatgtctg ccagaaagtg ttttggaaa ataacatcat   1320
tggaggaaaa agaatgtcat acatgaaacg ttccatttct gtcttcatcg cctgcttcat  1380
ggtagcagca ctcggcatca gcggtatcat cgcacctaaa gcgtctgccg cttctcaaac  1440
acccgttgct gtaaacggac agctcacctt gaaaggtacg cagctcgtca atcaaaaagg  1500
aaaagcggtt cagctgaaag gaatcagttc acacgggctg cagtggtatg gcgattatgt  1560
caacaaagac tcgttaaaat ggctgagaga cgactggggc atcaatgtct tccgcgcggc  1620
tatgtatacg ggtgaaggcg gctatattga caatccgtcg gttaaaaaca aagtgaagga  1680
agccgtcgaa gcggcaaaag aactcggaat ctatgtgatc atcgactggc acatactgag  1740
cgacggcaat ccaaaccaaa acaaagcgaa agcaaaagag ttttttcaacg aaatgtcaag  1800
gctttacggc aagacgccaa acgtcatttt tgaaattgcc aacgagccga acggcgatgt  1860
caactggaac cgtgacatta accccttacgc tgaaagcatt ttgtccgtga tccgcaaaaa  1920
ttctccgaaa aatattgtga tcgttgggac aggcacttgg agccaagatg tcaacgatgc  1980
ggcggacaat cagctgaaag acggcaatgt tatgtacgcg ctccatttttt atgcgggtac  2040
gcacggtcag tctttgcggg ataaagcaga ctatgcactc agcaaaggag cgccgatttt  2100
cgtcacagaa tggggaacga gcgatgcttc cggaaacggc ggtgtctacc tcgaccaatc  2160
cagggagtgg ctgaaatatt tagacacgaa aaaaatcagc tgggtaaact ggagcttgtg  2220
cgacaaacaa gagtcgtcag ctgctttaaa ctccggcgcc tctaaaaagg gaggatggtc  2280
tcaatccgac ttatcctcat caggtaaatt cgtcagggaa aacatccgca gcggatcaaa  2340
cggttcgtca ggagactctg gatcggattc gaaagggtca gatcaaaaag accagaaaaa  2400
ggatcaggat aaaaccaggtc aagacgcgg cgctgcagcc aacacgatag cagtacaata  2460
cagagcgggg gacaacaatg taaacggcaa ccaaatccgc cctcagctca acattaaaaa  2520
caacagcaaa aaaaccgtgt ctttaaatcg aatcactgtc cgctatggta taaaacgaat  2580
cacaaaggac aaaaattttga ctgcgactat gcccaaatcg gctgcagcaa actcacgcac  2640
aaattcgtcc aattaaaaaa agcggtaaac ggagcagaca cgtatcttga agtaggattt  2700
aaaaacggta cattagcgcc gggtgcaagt acaggcgaaa tccagatccg tcttcacaat  2760
gacaactgga gcaattatgc ccaaatcggc gactattcat tttcttcagg ttcaaacaca  2820
tttaaaaata cgaaaaaaat cacgttgtat gagaatggaa aactgatttg gggcgctgaa  2880
cctaaataac ggcactttaa cggacaccga atttggtgtc cgttttcgta tatattataa  2940
tggaaggaat gaggaatatt tttgtaaaca tgaaaggaga tggatgtatg aatgaaacat  3000
tgcagcaata catgatgctt gtcaaggaaa actacgacac gatcaatgga cctgattacg  3060
caggcaaaga ggaagacatt gaaaagcgaa aaaacaaat cgagctttac gccaaaacgc  3120
tccagcaagg ttttttcaaca gatgacgact atgagaattc gtaatcaggt catagctgtt  3180
```

SEQ ID NO: 37      moltype = DNA  length = 3603
FEATURE             Location/Qualifiers
misc_feature      1..3603
                    note = Desired nucleic acid sequence 36
source              1..3603
                    mol_type = other DNA
                    organism = synthetic construct
SEQUENCE: 37

```
aatgacatcc actttgcctt tctctccaca ggtgtccact cccaggtcca agtttgccac     60
catggagttt cagacccagg tactcatgtc cctgctgctc tgcatgtctg gtgcggccgc    120
agatgttgtg atgacccaat ctccagcttc tttggctgtg tctctagggc agagggccac    180
catatcctgc agagccagtg aaagtgttga tagttatgac aataattta tgcactgtta    240
ccagcagaaa ccaggacagc cacccaaact cctcatctat cgtgcatcca acctagaatc    300
tgggatccct gccaggttca gtggcagtgg gtctaggaca gacttcaccc tcaccattaa    360
tcctgtggag gctgatgatg ttgcaaccta ttactgtcag caaaataatg aggatccatg    420
gacgttcggt ggaggcacca agctggaaat caaacggact gatgcacc caactgtatc    480
catcttccca ccatccagtg agcagttaac atctggaggt gcctcagtcg tgtgcttctt    540
gaacaacttc taccccaaag acatcaatgt caagtggaag attgatggca gtgaacgaca    600
aaatggcgtc ctgaacagtt ggactgatca ggacagcaaa gacagcacct acagcatgag    660
cagcaccctc acgttgacca aggacgagta tgaacgacat aacagctata cctgtgaggc    720
cactcacaag acatcaactt caccccattgt caagagcttc aacaggaatg agtgttagag    780
acaaaggtcc tgagacgcca ccaccagctc cccagctcca tcctatcttc ccttctaagg    840
tcttggaggc ttccccacaa gcgacctacc actgttgcgg tgctcaaac ctcctcccca    900
cctccttctc ctcctcctcc ctttcttgg cttttatcat gctaatattt gcagaaaata    960
ttcaataaag tgagtctttg cacttgatag ttattaatag taatcaatta cggggtcatt   1020
agttcatagc ccatatatgg agttccgcgt tacataactt acggtaaatg gcccgcctgg   1080
ctgaccgccc aacgaccccc gcccattgac gtcaataatg acgtatgttc ccatagtaac   1140
gccaataggg actttccatt gacgtcaatg ggtggagtat ttacggtaaa ctgcccactt   1200
ggcagtacat caagtgtatc atatgccaag tccgccccct attgacgtca atgacggtaa   1260
atggcccgcc tggcattatg cccagtacat gaccttacgg gactttccta cttggcagta   1320
catctacgta ttagtcatcg ctattaccat ggtgatgcgg ttttggcagt acaccaatgg   1380
```

```
gcgtggatag cggtttgact cacgggatt  tccaagtctc caccccattg acgtcaatgg  1440
gagtttgttt tggcaccaaa atcaacggga cttcccaaaa tgtcgtaata accccgcccc  1500
gttgacgcaa atgggcggta ggcgtgtacg gtgggaggtc tatataagca gagctcgttt  1560
agtgaaccgt cagatcctca ctctcttccg catcgctgtc tgcgagggcc agctgttggg  1620
ctcgcgggtg aggacaaact cttcgcggtc tttccagtac tcttggatcg gaaacccgtc  1680
ggcctccgaa cggtactccg ccaccgaggg acctgagcga gtccgcatcg accggatcgg  1740
aaaacctctc gagaaaggcg tctaaccagt cacagtcgca aggtaggctg agcaccgtgg  1800
cgggcggcag cgggtggcgg tcggggttgt ttctggcgga ggtgctgctg atgatgtaat  1860
taaagtaggc ggtcttgaga cggcggatgg tcgaggtgg tgtggcagg cttgagatcc  1920
agctgttggg gtgagtactc cctctcaaaa gcgggcatta cttctgcgct aagattgtca  1980
gtttccaaaa acgaggagga tttgatattc acctggcccg atctggccat acacttgagt  2040
gacaatgaca tccactttgc ctttctctcc acaggtgtcc actcccaggc caccatgaag  2100
ctgcctgttc tgctagtggt gctgctattg ttcacgagtc cagcctcaag cagtgagttt  2160
cagctgcagc agtctggagc tgagctggtg aagcctgagc cctcagtgaa gatctcctgc  2220
agggcttctg gctacacatt cagtacctac tggatacagt gggtaaagca gaggcctgga  2280
catggccttg agtggattgg agagatttta cctggaaata ttagtactaa ctacaatgag  2340
aagttcaagg gcaaggccac attcactgca gatacatcct ccaacacagc ctacatgcaa  2400
ctcagcagcc tgccatctga ggactctgcc gtctattact gtgcaagatt gaggctcggc  2460
tatgctatgg actactgggg tcaaggaacc tcagtcaccg tctcctcggc gcgcccaaca  2520
gccccatcgg tctatccact ggcccctgtg tgtggagata caactggctc ctcggtgact  2580
ctaggatgcc tggtcaaggg ttatttccct gagccagtga ccttgacctg gaactctgga  2640
tccctgtcca gtggtgtgca caccttccca gctgtcctgc agtctgacct ctacacctc  2700
agcagctcag tgactgtaac ctcgagcacc tggcccagcc agtccatcac ctgcaatgtg  2760
gcccacccgg caagcagcac caaggtggac aagaaaattg agcccagagg gcccacaatc  2820
aagccctgtc ctccatgcaa atgcccagca cctaacctct gggtggacc atccgtcttc  2880
atcttccctc caaagatcaa ggatgtactc atgatctccc tgagccccat agtcacatgt  2940
gtggtggtgg atgtgagcga ggatgaccca gatgtccaga tcagctggtt tgtgaacaac  3000
gtggaagtac acacagctca gacacaaacc catagagagg attacaacag tactctccgg  3060
gtggtcagtg ccctccccat ccagcaccag gactggatga gtggcaagga gttcaaatgc  3120
aaggtcaaca acaaagacct cccagcgccc atcgagagaa ccatctcaaa acccaaaggg  3180
tcagtaagag ctccacaggt atatgtcttg cctccaccag aagaagagat gactaagaaa  3240
caggtcactc tgacctgcat ggtcacagac ttcatgcctg aagacattta cgtggagtgg  3300
accaacaacg ggaaaacaga gctaaactac aagaacactg aaccagtcct ggactctgat  3360
ggttcttact tcatgtacag caagctgaga gtggaaaaga agactgggt ggaagaaat   3420
agctactcct gttcagtggt ccacgagggt ctgcacaatc accacacgac taagagcttc  3480
tcccggactc cgggtaaatg atctagacac gtgattaatt aaggatcccc cgacctcgac  3540
ctctggctaa taaggaaat ttatttcat gcaatagtg tgttggaatt ttttgtgtct    3600
ctc                                                               3603
```

SEQ ID NO: 38         moltype = DNA   length = 3156
FEATURE               Location/Qualifiers
misc_feature          1..3156
                      note = siamense Non-canonical non-ribosomal peptide
                      synthetase FUB8 (FUB8-2) Desired nucleic acid sequence 37
source                1..3156
                      mol_type = other DNA
                      organism = Colletotrichum siamense
SEQUENCE: 38

```
atggccacga ctcagtacgg aaagcgcttg atccctcagg tgctcgacga gatcgccaag   60
tcagaccctc acgccgaagt cctctcagtt ccccgctcat ccaaccccaa agatggatgg  120
aggaagatca cctacaagca gctcgccaac gcggtgaaca gcatagctca cagaattatc  180
gacaagaggg gcaagcctga acccgaaagc ttccctactc tcacctacat cggccccagc  240
gatgcccgct acatgattgt catgattgcc tgtatcaagg ctggatacaa ggcgctcctg  300
atctccccca ggaattcgca tgagggccag atgaaccttt tcgagaagac ggactgcaac  360
atcatctgct tcgactcatc attcaaggat gtcatccagc cccttttgag agaacgccag  420
atggatgcca tcatggtgag ctccgccgat gcctggctcg acgagacgga agtccccac   480
ttcccttacg ataagacctt cgaggaggct aagatggacc ccgtcgtcgt tctgcacacg  540
agtggtagca ccggcctccc gaagcccatc gtcgcccgtg tgggcatgtg tgctgtcgcc  600
gatgcattcc acgacctccc ggatttcatg ggttccgaga gcgatcatcaa gtctatcatg  660
cttggcgagc gcatcttcct gccgatgcc ctattccacg ccgcggatg ctacatgtcc    720
acctttgccg ccatctactg gaagcaccct gtcgcattgg gcttcattga ccgccctctc  780
accccctcaga ccgtcttgga cgctgttgaa tacgccaaga tcgacaacat catccttgcc  840
cctgccattc ttgaggagat ggctcacatg cccgaggta tcgaggctct caagaagctt  900
aagcgcgtga actttggtga tggtaacctc gcgcgcaagg caggcaacat tctcacaaag  960
gctggcgtca aggtctgcag tgtcatcgcc ttcactgagg ctgctcccct cccgtactt   1020
ttccagaaga acttggacct ctggcaatgg ttcatcgtcg actccgagcg tctgggcgtg  1080
gaatggcgcc aggccagcgg tgaggacgag gacatttacg agcaggtcat cgttcgtaag  1140
gataaggagg atcctctcca gggtattttc tacaccttcc ctgacgccaa ggagtactcc  1200
accaaggatc tttaccgcaa gcacccttca cttcccaacc actggatgta ctacggccgt  1260
gccgacaaca ttatcgtctt ctccaacggt gagaagctga accggtcac cattgaggag  1320
atcgttactg gtcaccccgag agtcaagggt gccgttgttg ccggagctat gcgcttccag  1380
ccgctgctga ttatcgagcc catggaggat ctcaagacag aagaggagaa ggagaagttc  1440
attgacgatg tctggcccct ggttgtgaag gcgaacaagg aaaccgttgc ccacggtcag  1500
attggtgcc agttcatcgc cgtcaccacc cctgacagc cattccctcg gcgccgaaag   1560
ggcaccatcc aacgtcctat ggcactgaag ctgtacaagg aggagctcga cgagtggtac  1620
cagaaggcca aggacggttc tgactccgtt ccgtccaca tcgatgtcag ctctcagcag   1680
accctcatcg actccatcga gaagctcttc cagcagactc tcggcagcag agcgctctcc  1740
gccgactccg atttcttcag tgccggtatc gactccatgc aggtcatcaa cgcctcccgt  1800
ctcctccgca aggtcttga ggccgccggc gccaacatta ccgccgacgc tatcgccacc  1860
```

```
cgtgttatct acgcccaccc gacacccaga cagctggctt cttacctctt ggaccgtgtc  1920
agaaagaaca ctggggtcaa cggcgaagat gaatctgaag gccccaacca tgacatcgcc  1980
gccatggagg cccagcttca gaagtacacc cgcgacctgc cccagaagca gggcaacaag  2040
cccggtccta acgaccaggg ccagaccatc ctcatcaccg gtaccacggg tgctctcggc  2100
tcgtacatgc tcgacttcat ggagtccaac ccggccgtca agaaggtcgt ctgcctcaac  2160
cgtagcgagg acagcgataa gcgccaggtc aagatgagcg ccgagcgcgg cctcaagacc  2220
gatttcaaaa aggccgagtt cctctgcgcc gatatgtcca agagcaacct cggcctcgag  2280
cccgaggttt acgacagact gctcaaggag gctgaccgcg tcatccacaa cgcctggccc  2340
gtcaacttca acatctccgt cgagacctttt gagcctcaca tccgcggtgt ccgccactgg  2400
gtcgacttct ccctgcgcgc cgccaagaac gtccccatca tcttcatcag cagtatcggt  2460
actgtcgact cctggcctgg tcctggcccc gtccctgaga acagactcat ggacctgtct  2520
cttcccagca ctggctacgg tcgctccaag atggtcagtt ccctcatcct tgacgaggct  2580
actcagcgct ctggtgttcc caccgccatc gtccgtgtcg gccaggtcgc tggccctcag  2640
tccaagtctg gcgtcctggaa ccgtcaagag tggctcccga ccatcgtcgc cagctccgcc  2700
taccttggtc tcctgcccaa ggaccttggc gccatgggtc tggtgaactg gactcccatc  2760
gagggcattg ccagcctcat tctcgaggtc tccggtatcg ctgagcctgt tcccctgcag  2820
aacatcaggg gttacttcca cggtgtgaac ccgcgcaccg tcgagtggga gaagcttgcc  2880
gaggcggtca agtctttcta cggcgaccgc atcaagaagg tcgtttcctt caaggagtgg  2940
gtcaaggctc tggaggagag tgcctcttcc accgacgacg ttgacaagaa ccctggtgtc  3000
aagcttcttg acttctacca gggcctggct tacgcggag gaaagggtgt cgacttctcg  3060
atggagcgca ctgtgaagca cagcaaggcg atgaaggaga tgcaggccgt cacgcctgag  3120
ctgatgcaga actggtgcag acagtggggc ttctaa                           3156

SEQ ID NO: 39        moltype = DNA   length = 3090
FEATURE              Location/Qualifiers
misc_feature         1..3090
                     note = CBS 114.51 Pro-apoptotic serine protease Nma111
                     Desired nucleic acid sequence 38
source               1..3090
                     mol_type = other DNA
                     organism = Aspergillus japonicus
SEQUENCE: 39
atggatatga atggtgacgc aggcgccaag cgcaagcgcg gctcgatcgc cgcgcccgcc  60
gagcggcccg caaagcatct ccgtcccgaa accagcacat taacgcctgg cgactccact  120
cccgcgaatg gaactgttta cgacgtggag gaagaggagg atgtggtcg gttgttgccc  180
ctgggagctg cacaggccga ctcgcctgag tggcaggcca ccattgagga ggtcgtgaaa  240
agcgttgtgt cgatccactt ctgtcagacg tgctccttcg acacggaact gtcgatgagc  300
agccaggcga ctggttttgt ggtcgacgcg gagcggggtt atatcttgac aaatcgcacc  360
gtggtgtgtc caggaccctt ctggggatac tgtatctttg acaaccatga agagtgtgat  420
gtccgtccga tttaccgaga ccctgtgcac gacttcggaa ttttacagtt cgacccgaaa  480
gcaattcgat atatgaactt gaaggaattg aaactacaac cggatgcggc caaggtcgga  540
tcggagattc gtgtcgtggg taacgatgca ggagaaaagc ttagtattct gtctggtgtc  600
atcagtcgtt tggatcgaaa tgctccggaa tacggcaggg gatacagtga tttcaacacc  660
aattacattc aggccgctgc ggcagcgagt ggtggcagtt ccggcagtcc tgtcgtgaac  720
atcgatggcc atgcaattgc tttgcaggct ggtggtcgcg ctgatggcgc agctacggat  780
tacttcctcc cgttggaccg gccgttcgt gcgctggaat gcatccgtcg cggtcagccg  840
gtcacgcgag gaaccattca gacacaatgg atttctcaac cattcgacga gtgtcgtcgg  900
ttgggcctga cgcctgagtg ggaggccacc gtgcgcaagg cagctcccac ggagaccagc  960
atgctggtgg ccgagatcat cctgccgag ggcccggcag atggaaagct cgaggaggga  1020
gacgtgcttc tggaggtcaa cggggagctg ctgactcagt tcattcggct ggacgacatc  1080
ctggattcga gcgtcgggca gacggtcgt ctgctcgtgc aaagaggcgg tcaagatgtg  1140
gaggtggagt gccaggttgg cgacctgcat gccatcacgc ccgaccgctt cgtgacagta  1200
gcgggaggca cgttccataa tctgtcttac cagcaggcac gtctgtatgc catcgctacc  1260
cgcggcgtct atgtctgcga ggctgccggg tctttcaagc tggaaaacac cttgtcggga  1320
tggctgattg actccgtgga taagcggcca acgcggacac tggatgagtt tgtggaggtc  1380
atgaagacga tccctgatcg ctcgcggggt gtcatctcgt atcgccacat ccgcgatctc  1440
cacacgcgcg gtaccagcat tgtctatatc gaccgacact ggcacccgaa gatgcggttg  1500
gcggtgcgga atgattccac tgggctctgg gacttctctg atctcgcgga ccccgtcccc  1560
gccctgcctc ctgtgccgag gaaagccgat ttcatccgat ttgatgggt gagtcagcct  1620
gctgccgcag ccattgtgcg cagcttcgtg cgcgtgtcgt gcacgatgcc tctcaagctg  1680
gacggctatc cccaagccaa gaagacggga ttcggtctgg tcgttgacgc tgagaaggga  1740
ctggtcgtgg tttcgcgtgc cattgttccg tacgacctct gcgacatcaa cgtcaccgtg  1800
gccgactcga tcattgtcac cgccaaggtg gtgttcttgc atcctctcca gaattacagc  1860
atcattcagt acgacccccag cttggtccag gctccggttc agacgccaca gctcagcact  1920
gagtacatca gcagggtca ggacaccatc ttcgtcggct tcaaccagaa cttccgcatc  1980
gtggtggcca agaccgccgt caccgatatc accaccgtat cgattccggc caatgcctcg  2040
gccccgcgct accgcgcgat caatctggac gccatcacgg tagacactgg tttgagcgga  2100
cagtgctcca atggtgtact ggtcggcgag atggcacgg tgcacgcact ctggctgaac  2160
tacctcggtg aacgcacagg gaactcgcac aaggacgtcg agtaccaact gggtttcgcg  2220
acgccgtctc ttctgcctgt cctgtccaag gtgcagcaag gcgagatgcc cacgctgcgg  2280
atcctgaaca tggagagcta cgtggtcag atgagccagg cccgcatcat gggcgtgtcc  2340
gaggagtgga tcgagaaagt gacacggcg aaccccgccc ggcatcaact gttcatggtc  2400
cgcaaggtcg actgtccgcc tccggggcttt gcctccgagg ccgtagacag ctttgaggaa  2460
ggcatatca tcctcacct gggcgggcag ctgatctcgg atgtctcgga gtcgacatg  2520
atgtacgaga aggaatctct ggaggcgctc atcgtgcgca acgttcagga gatgcgcatc  2580
caggtcccca cggtgccgac ggaggatctg gaaaccgacc gcgccgtggt cttctgcggc  2640
gctgcctcc agaagcccca tcacgccgtc cgccagcaga tctccaaact ccacagcgag  2700
gtgtacgtca gcgctaggag ccgcggttcc ccctcctacc aatacggcct ctcgcccacg  2760
aacttcatca ccgccgtcaa cggcaccccc accccgaacc tggaccgctt cgtcgaagag  2820
```

```
gtccgcaaga tccccgacaa cacatacttc cgtctccggg cggtgacctt cgacaacgtc 2880
ccctgggtgg tgaccatgaa gaagaacgac cactacttcc ccatgtccga atacctgaaa 2940
gacccatccg ccccgcaagg ctggcgcacc gtgtcccacg ataatgacaa gcaccgcgac 3000
ggcgctgcgc cggatgcggc gaacctgaac cccgatgcca tggacgaggg cttcgatggc 3060
gtcagtgatg ttgagccgga ggccgagtga                                  3090
```

| | |
|---|---|
| SEQ ID NO: 40 | moltype = DNA  length = 3903 |
| FEATURE | Location/Qualifiers |
| misc_feature | 1..3903 |
| | note = Synthetic construct Cpf1 gene AND Desired nucleic acid sequence 39 |
| source | 1..3903 |
| | mol_type = other DNA |
| | organism = synthetic construct |

```
SEQUENCE: 40
atgtcaattt atcaagaatt tgtgaacaaa tatagcctga gcaaaaccct gcgttttgaa   60
ctgattccgc agggtaaaac cctggaaaac attaaagcac gtggtctgat tctggatgat  120
gaaaaacgtg ccaaagacta caaaaaagcc aaacaaatca tcgataaata ccaccagttc  180
ttcatcgaag aaattctgag cagcgtttgc attagcgaag atctgctgca gaattattcc  240
gacgtttatt tcaaactgaa aaaagcgac gatgataacc tgcagaaaga tttcaaaagc  300
gccaaagata ccatcaaaaa acaaattagc gagtatatca agacagcga gaattcaaa   360
aacctgttca accagaatct gatcgatgcc aaaaaaggtc aagaaagcta tctgatcctg  420
tggctgaaac agagcaaaga taatggcatc gaactgttta agccaacag cgatattacc  480
gatattgatg aagcactgga aatcatcaaa agctttaaag gttggaccac ctactttaaa  540
ggctttcacg aaaatcgcaa aaacgtgtat agcagcaatg atattccgac cagcattatc  600
tatcgcatcg ttgatgataa tctgcctaaa ttcttgaaa ataaagccaa atatgaaagc  660
ctgaaagaca aagcaccgga agcaattaac tatgagcaga tcaaaaaaga tctggcccgaa  720
gaactgacct ttgacattga ttacaaaacc agcgaagtta accagcgtgt ttттагсстг  780
gatgaagttt ttgaaattgc caacttcaac aactacctga tcagagcgg tatcaccaaa  840
ttcaatacca ttatccggtgg caaattcgtg aatggcaaa ataccaaacg caaaggcatc  900
aacgaataca ttaatctgta tagccagcag attaacgata aaacgctgaa aaaatacaaa  960
atgagcgtgc tgttcaaaca aattctgtca gataccgaaa gcaaaagctt cgtgattgac 1020
aaactggaag atgatagtga tgttgttacc accatgcaga gcttttatga acaaatcgca 1080
gcgtttaaaa ccgtggaaga gaaatccatt aagaaaccc tgagcctgct gtтттgатgат 1140
ctgaaagcac agaaactgga cctgtccaaa atctacttca aaaacgataa атсссгasc   1200
gatctgagcc agcaggtttt cgatgattat agcgttattg gcaccgcagt tctggaaatt  1260
atcacacagc agattgcacc gaaaaatctg gataatccga gcaaaaaaga caagagctg   1320
atcgccaaaa aaaccgagaa agcgaaatat ctgagcctgg aaacaattaa actggccctg  1380
gaagaattta caaaacaccg cgacattgat gaaacagtgc cgtttgaaga aatcctggca  1440
aattttgcag caatcccgat gatctttgat gaaattgcgc agaataaaga taacctggca  1500
cagatcagca tcaaatatca gaatcaggga aaaaaagacc tgctgcaagc aagtgccgaa  1560
gатgатгтта agcgattaa agatctgctg gатсагасса ataacctgct gcataaactg  1620
aaaatctttc acattagcca gagcgaggat aaagcgcac tttctgataa agatgagcac  1680
ttctatctgg tgттттgаaga gtgttatttt gagctggcaa atattgtgcc gctgtataac  1740
aaaatccgca actatattac ccagaaaccg tatagcgacg aaaaaattcaa actgaacтттт  1800
gagaatagca ccctggccaa тggтттggдат aaaaacaaag aaccggataa taccgccatc  1860
ctgttcatta aagatgataa атасттатстg ggcgtgataa caaaaaaaaa caacaaatc   1920
ttcgacgata aагccатcaа agaattaaa ggcaagggtt acaaaaaat cgtgtacaaa   1980
ctgctgcctg gtgcgaataa aatgctgccg aaагтgтттт ttagcgccaa atccatcaaa  2040
ттсatатаасc cgагсgаaga тaттcтgcgт аттcgтааtc атагсассса taccaaaaат  2100
ggтагтcggc agaaaggcta tgaaaattc gagttcaaca ttgaggatt ccgcaaattc  2160
atcgacttct acaaacagtc cattagcaaa catccggat ggaaagactt tggttttcgt  2220
tttagcgata cccagcgcta tacagcatt gatgaattt atcgcgaagt ggaaaaccag  2280
ggctataaac tgcattttga aacatcagc gagagctata ttgatagcgt tgtgatcag   2340
ggtaaactgt ccttgttca gatctataac aaagatttta gcgcctatag caaggctgt   2400
ccgaatctgc ataccctgta тggaaагсa стgттсгатg aacgtaatct gcagatgtt  2460
gtctacaaac tgaаtggтga agсagaaстg тттттатсгса аасagagтat сссgaaаaa   2520
atcacccatc cggcaaaaga gсаатсгсgс aacaaaaaca aagataaccc gaaaaaaaga  2580
agcgtgttcg адтатgатст gatcaaagat aaacgctta ссgаагатаа аттсттттс   2640
cattgcccga тсасссатсаа ссттааadгc адcggтgсga acaattca сgатgааaтс  2700
aатсгстgсгс гgаaагаааа адссаасгат gттсататс тgаgсатгgа тстgгтгааа  2760
cgtcatctgg cctatacac ссtggттgат gгтаaаggca ататгатсаа асаggасасc  2820
ttcaacatta tcggcaatga tcgtatgaaa асcаасгасс atgataaact ggсаgссатг  2880
gааааагатс gtgatagcgc acgtaaagat tggaaaaaca taacaacat taaagaaatg  2940
ааgаагgст acctgagcca ggttgttcat gaaatcgcca асгggтgат tgaatataat  3000
gccатгgтgg tgttcgagga tctgaacttc ggттттcaaaс gtggtcgttt сaaагттgаg  3060
aaacaggtgt atcaaaaact ggaaaaaatg ctgatcgaaa actgaatta ссгggтгтг   3120
aaagacaacg ааттcгатаа aaccgttggt gттстgсгтг catatcagct gасссгсасст  3180
ттгaaассг tcaaaaaat gggтaaасаg ассggсатса тстатгтт ссggсаggт   3240
ттгассгсcа aатттgтcс ggгтасcggc тттгттаатс агстстатсc gааататgаg  3300
аgcgттаgcа аагссаага gгтттттcаgс ааагттгата aатстgcта acсctggас   3360
aaaggctact tgaattcag cтттgасгат аааааcттг cgataaagc agccaaaggc  3420
аатгggассa ттгсаagсгг тggтагсcгг стгатааст ттcгтааcаг сgасаaaааc  3480
сатаасстga атасссгga агтттатсг асcааagаgс тggaaаасгс гсгgааaат   3540
тасадссатгg aatatggtca tggcaatgt атгааadссg саттгттgg тгаgтссгас  3600
ааааааттст гgсаааааст gаccagcgгг стgаатассa ттгтсадат gсgтаатаgс  3660
aaaaccggca ссgаасгggа ttatctgatt agtccggttg cаgатgгаа cggcaattt   3720
ттсgатагcc gтсаggсгcс gаааатагг ccgcaggatg сагатgсааa тggтгccтаг  3780
саттаттгgсс tgaaaggtct gатгстgстg ggtcgcatta aaaacaatca agaaggcaaa  3840
```

```
aaactgaacc tggtgatcaa aaacgaagag tattttgagt tcgtgcagaa taggaataac   3900
tag                                                                 3903

SEQ ID NO: 41           moltype = DNA  length = 4008
FEATURE                 Location/Qualifiers
misc_feature            1..4008
                        note = strain CL Brener DNA polymerase I alpha catalytic
                         subunit partial mRNA Desired nucleic acid sequence 40
source                  1..4008
                        mol_type = other DNA
                        organism = Trypanosoma cruzi
SEQUENCE: 41
atggagccat gggaaagttg tcgcacgaag gatcaaaaaa gagagacagc ggcaatggtc    60
tctcttttt ccgagacgga ggaagaacag tggcaaagat taaaggagga ggcgatgatc    120
gactcggatg aagatgatgc caacatcaca gatggtaggg ccttggtgct accacaggac   180
gcaaggaaac ggaaacccaa gaagagtaag aagtcaacag tcttttccaa agctgctcat   240
atacaacaaa agaagctgac ccagtctata agtacgtctg acatggagaa tctcctgaaa   300
aagtatcggg gggctgttgc ggatgaggag gatgagattg gaatagacgt caccaagttc   360
ctacaggatg atgcattgga gagtggagag gaggaagagg gtgtcaccgc tgacgaactt   420
atatcttcgt tgttgacgac aaagaataca ggcgcatcaa aatcagtaga acgacgcca    480
agcgttcctt tggtaagtct caacgatgag attttttctt acgaaaagaa atcggttgca   540
cggcaagctg ttgtaaacaa gaagcaaaat ggacatggga gtgaagccaa ttacgttgtt   600
aaagatccat tttcagggga tctaaacatc gtcactgaac ttccgacgca ggcactaagt   660
aaattgaagc agagctccga taacgccaat aaggggtacc catctagtgg agtgttttat   720
tggtttgatg cgaaagaaca gccccatact ttatcggaac ctggtactat atttcttttt   780
ggtaagttt atgagaaaaa aagagaaaaa gtcagttttt cttcttgttg tgttcgtgtc    840
aaaaacgttt accggtgtac atttctactt cctcgtgagg ggtcatctga tacgaaaatt   900
atcaaggaga taaacgacgt gtgtcaaaaa catggtatag gagagcgacg gataaggttt   960
gtggaaagat attatgcctt tgaagaacct ggtataaggc gtgagaagaa tcgttgggca  1020
aagcttcgtt ttccaggtaa atatccaggc tttcctatta tggggggaatt taagcacatt  1080
cgagctgtta tgggtgcatc ccgttcgtta attgagcttt tcttgataaa gaagaagctt  1140
atggggcctt catatctttc catggagaac tttttttcctg caacagaacg tttatcccat  1200
tgtgaattgg aatttgtggt ggattccccg aaaaacatca aggttgacga tacagcgaga  1260
ccctcgccac tcttcacact tgcaagtata caactgccata ctcagttgga cagcaaggggt  1320
gtaacaaatg aggttgtggc tgcatcgatt gctgtttatc gtgatgttaa cattgattcg  1380
ggcatgaaga cagaagtttc ggaatgcttt acaggaatca gacaaatttc atcggttgcg  1440
gctttaccgt taaatttgga ggcttattgt cagtcaaaag gttacctgg tgtaaagaat    1500
tttgaaatg aaagagcttt actcacatgg atggcgtcaa ccttgggaa tttggaccct    1560
gacattgtag ttgggcacaa tttcattggg tacacgattg atattctttt gaatcgctat  1620
catgaactga atataccttcg gtggtcgacg attggacgtc ttgatatcaa acgttttcca  1680
cgttcacaaa atgggaattc taatctgtcg aatgaaaaag aggcgtgtat tggtcgtctt  1740
gttgttgaca cataccttct ttctagggaa tactacaaga gtacaaacta caaactgaaa  1800
tctttgggcta ctcagatggg agttgcaggt attacagatg gccgtggttc atttgaacct  1860
ggattaactg ttcttgggaa tgatattatg aaatcttcca aagacctttt tcacgttctt  1920
ttacaacttc ttaattgtgc ggtacttttc gtgcgtgtgg tagcctttct ggacgcgatt  1980
ccacttacca aacggttaac tacattgcaa ggcaatttat ggagccgaac tttgtatggg  2040
gcgcgttctg aaagaattga gtatcttctt ttgcacgcgt ttcatgatct taaatttgtg  2100
acgccagata agaaaagatt tgatgggaaa aggggggcgac aggatctgga ggatgaaacc  2160
aaacgcaaaa cgaagtatca gggtggtatg gtattggagc ccaaaagtgg actttactcg  2220
gattatattc ttcttcttga ctttaattcg ctttatccct ctcttattca ggagtttaat  2280
atctgctata ctacaattga acgggatgga aacacgtat ctgccgagat tcctccacct   2340
gagaggctaa tttgcacctc ttgtgcggct gcgggtttac cgtctccgtg ctcacacaaa  2400
tgtgtcttac cgaaggtcat tcgagggctt gtggagagta gacgagaaat taaacgtttg  2460
atgaagacgg agaggatcc aaacaatctt gctaccttgg agattcgtca gaggtctctt  2520
aaattaaccg ctaacagtat gtatggctgt ctttggttttg aacactcccg cttctatgct  2580
cagcctcttg ccgaacttgt cacgcggcaa ggtcgtattg ccttacagaa tacagttgag  2640
ttgattccac aaatttcgcc attgttgcgt gttatttacg tgacacggga ttctgtcatg  2700
atccaaaccg gtatcaaaga cgacatcagg aaagtgcgtg aacttggttt tgaaataaag  2760
aataaagtta atcaacgata ccaaagcctg gaattggaca ttggtggcat ttttaggggct  2820
atgcttctcc ttaaaaagaa aaaatatgcg gcattaagtg tgtggattg gcaaaatgat    2880
ggcaaaacgt acaagaaaga agtaaaaggt ttggatatgg ttcgtaggga ttggtgtcct   2940
ctctctcaaa aggtctccga ggctgtgctt agcagagtgt tgaatgccga ggcaggtgaa   3000
gatatcctag actacgtgat gacccacatg aaaactgttt ccgaccatgt gcgtgctgga  3060
aattattacg gacttgagga tttttgtcatt tccaagagct taacaaaaga gcctgagtct  3120
taccgtggga ctgcgtttcc ccacgctgcg gttgcgcttc gtatgaaaca aagaaaagaa  3180
aatgttcgtg ttggagacct tatcccttat gttatttgcg agggcgaaca tcttaatgac  3240
aaggcgtatc acgtggatga ggtacgaaga accaaggaa tccgaatcga tgtggagtgg   3300
tatttgtcat cgcagttgta ccctcctgtg atgcggttgt gtgaacacat tcaagggttt  3360
tctccggagc agttgagtga agtcatgggg gttgcgtgtc atgtgcgaac tgaacggaaga 3420
attcaggaga cgctcattgt ggacgacttt tcacattgtc cactattcaa gagccgcgat  3480
ctctccgagt gcttccccac cgcagtgcct cttcaggttc aatgtacgcg gtgccatcag  3540
gttgttccca tcgatccaca caagtacatc aatgacatgt ttagtgcttc caagacttcc  3600
tttccaaatg aacccttga actgtacaat tgcgtcaact gtggccaatc tcttctctgtt  3660
acatacctga caactgtct gactcagatg tgtcacaaga taatacagca gttttacata  3720
tcaggcggta atgccgcggc ggtacgggcg gtgcgagcac agtttacata ttttagagct   3780
ttgtttgacg ttccgcatgc tcctggatgc tctccggcaa ttaaagccgc ccaccgcaat  3840
cttgctttgc gttgccttgg cacgatcaa aaattgtaca cactctctgg agctgcccgt  3900
gctgtggacg tggagcctgt ggatcatttg tttttttgcg cggatagttt ttacaggaga  3960
atggatcatt tgtttctcaa cgttggaaat ttatttgtct caatataa               4008
```

```
SEQ ID NO: 42          moltype = DNA  length = 4032
FEATURE                Location/Qualifiers
misc_feature           1..4032
                       note = ARSEF 2860 non-ribosomal peptide synthetase Desired
                       nucleic acid sequence 41
source                 1..4032
                       mol_type = other DNA
                       organism = Beauveria bassiana
SEQUENCE: 42
atgactacag gtagcaaaga agcacactac tctgcgacgt cttcgggcac ttcttctaca   60
ctatctctat cctctgcacc ctcatccgtc acacaggatt cctcgaaata tgccctgtac  120
ccgtacgaag aagctgccaa ggaaagaact ctcgttgata tctttgctgc ttccagcaag  180
ttgtttccag aagaacttgc gctcgataac ggctccgata gtttgaccta tgccgagttg  240
accgacgctg ttggcatcct cgtcgatcgg ttgcatgaag ctggcatcgg ccctggcgat  300
agagttggca tccgcgtcac ctctggcaca gcagagctat acgttggcat cctggccatt  360
ctcaaagccg gagctgctta cgttcctgtg gatgttgatg accccgatga gcgcgccaag  420
ctcgtcttct ccgaagcagc cgtctgcgct gtcattaccg accacaatac aattacactg  480
caagacacga agccaatcgg caacacagca tcacgcaaat gtccttgtcc tgacaatgac  540
gcttggatca tcttcacatc tggctcgact ggcaagccga aggcgtcgc cgtcacgcat  600
cgcagcgcag ctgcctttgt cgacgccgag tcgcacctct cctcccaa aaaacctctt  660
gccccgggtg accgtgtcct tgccggccta tctgtggctt ttgatgcctc ctgtgaagag  720
atgtggctag cctggcgcca cggcgcgtgt ctcgtgccgg cgtcgcgcgc gctagtcaag  780
gctggcgcg agctgggcac gtttcttacc gccaacgca tatccgtcgt ttccaccgtg  840
ccgacgctgc cggcgctgtg gccaacagaa gcacttcatg gcttcgtct actgatcctc  900
ggcggcgaag cgtgctcccc cgagttggcc aacaggctg ctggcgccgt cggcgccgtt  960
tggaacacct acggcccac cgaggcgacg gtagtctcgt gcggcgcccc actcaccgtc 1020
ggcgatccgg tggtgcggat cggcctgccg ctagccgggt ggcggctggc tgttgtcgga 1080
gccgatggcc atcccgtccg ctggggcgaa gaaggcgagc ttgtcattgg cggtgtcgga 1140
atggctcgct acttggaccc cgaaaaggac aaggtcaaat ttacaccctc cccagccttt 1200
ggcggcgagc gcgcctactg cagcggcgac ttggtgcgcg ccgaaaggga aggcctcttg 1260
ttcgttggtc gaaatgatga gcagattaag ctgggtggcc ggcgcattga gctcggtgaa 1320
attgatgcgc cgatgatgac attacctggt gtgaagagtg ctgctagcgc cattcggcgc 1380
accgacacgg gcaatcaggt cctcgtcggg tatgtggtga gggacaacag tgctgccacc 1440
acgtctgata ggacctttct gaagcgtgtt taccgccaa ctttaattcc catgctcatt 1500
accgtcgaca atatccctgt tcgcacttct ggcaaggttg accgcaaagc ccttccgtgg 1560
ccaccgcccg agtcatcctc ggctgcaact gccgagggaa ctaccatggg ctgggtgtcc 1620
agccagtggc gcgccgttct tggtgcatct ggcgcgttac cagagtccaa cttctttgag 1680
ctcggtgcca ccagcctggc cgccgcgcag ctggtctcgc agctgcgcca gaagtgccaa 1740
accttgtccg tggcggacgt ctacgagcat ccaaccctgt ccgccatgac agagcgcatt 1800
gacgagctgc taggcaccac gatcgtgatg cgcgaggtca agctcagccc ccgctgggtc 1860
atctttatcc agagcatcgt gctcattgcc gttttttctca tcgagggcct gcgtctcatg 1920
atgccgctgt tcatatccca gaagattttc caagcactct tgaaggaga ctattgggcg 1980
acgagacaca cgctgccttg gtccgctgtg gctgtgctct gggtcgtctt catgacgctg 2040
ccgggccgtc tcctgacgac tgtcttgatt gtgcgctcca tcaccgttgg cattcgtccg 2100
ggcgagtatc gccgcgccgg cctgacgcat ctccgcctct ggacagcgga cagggttgtt 2160
ggacttggca ggctgacggc catggccggt accaattgga cccggtggca cgcttggctc 2220
atgggctgcc atgtcggtcg cgatgtgcag ctgcataccc tcgcgcctac gaccggactg 2280
gctagctttg gcgacggcgc tgccctggag cccgaggtgg acattgccgg ctactggctc 2340
gatggtgacg tgttgcatgt cggcagtatt actgtaggcg agggtgccag agtcggagcg 2400
cgcaccatgc tcatgcccaa ctccgttatc gagccgtatg ccactgttga gcctggtctt 2460
tctatccagg gcaccgtcaa gtcacccctt ccaccgtcgg cttcctcgtc ggaccaggga 2520
tccaaccccg atagttcatt caagccgact ccgggaagct ttcgcatggc tattctctat 2580
actcttgccc tcatactcct cgacttcatg gccgtcttgt tgtatgctcc catttggggt 2640
ctgatgccta tcattgtcaa agaatacaca aatttcagc agctcagcat tggaattatt 2700
gcaatgacgg ctcccggaac agtctttgga atctttctct acaccgctgc tgttgtcctc 2760
attgtcggc ttgccaacct cggcattcgc cctggctcgc actcgtggaa cagctggact 2820
gcgttttgcg cttggcttat tcacttcctc atgatggaca ttcgcacgag catgtttccc 2880
atgtttgcca gcttattcac gcccgtctgg ctgcgcctgt tgggtgccaa aattggccgc 2940
aacgtggagt cgtctaccgt ggtcccatg ccgtctcttc tcaccgtgca tgacaatgca 3000
ttccttgccg acgacgtgct tattgcgcca tatgagctca gcggggacg catgcacctc 3060
ggccctgtga cggttggaaa taagactttt ctcggcaatt ctgcgattgt tgacccagac 3120
atcagcgtcc ctgccaattc gctcattggt gtgctgggct ctgcgccggg tggcctgggc 3180
gagaagcaga tgcaggctgg ctcctcgtgg cttggtcgcc ttcctatgcc acttcctcg 3240
aaaatcgact ccaacattga caatgcgctc acttttgcac ccccgaagaa gctggtcctt 3300
gctcgggctc taattgagtc ttgccgcgcc atccctctta ttctcaatgg cttcatcccc 3360
tccatgcgca gcctcggcac gctttggttc ttgtggcggt ttggcattgg ctgggccatc 3420
ctcgcatctg gagggtttct cgtcggcact gcatttattg ccgccatcat caccattgcc 3480
gccaagtgc tcgtgacgcc caacgtcaag gccggcagca cacatccgct ctggagctca 3540
tttgtgtggc gcaatgagct tgccgactcc ttcctgcagt ccatggccgt tccctcatg 3600
gtgcgctact tttacggcac ccctgtgctg gccatgttct tccgcgctct cggtgccaag 3660
attgccacg tacgtggat cgagagccat ctactaccg aagcggatct ctgcatcgtt 3720
ggcaacggcg ctacaatcaa cagaggtagc ttgctgcaga cgcacctgtt tcacgaccgg 3780
ctgatgcgtc tggatgaggt ccagctctgc gatggtgcta cactggggtcc cctcacagcg 3840
tcgcttcctg gtactcggat tggtgccggc tcgacagtgt accgggtctc gtcgtgatgc 3900
agaggcgagc atctaccggg gagtacacaa tggcgaggca atcctgtgcg accgtggagc 3960
gagggcacag acgagaaatg ggtgaacaag ggttcgcgaa gtacgagctg ggactcgccg 4020
acgccagtat aa                                                    4032
```

```
SEQ ID NO: 43           moltype = DNA  length = 4023
FEATURE                 Location/Qualifiers
misc_feature            1..4023
                        note = Chromosome Desired nucleic acid sequence 42
source                  1..4023
                        mol_type = other DNA
                        organism = Leishmania chagasi
SEQUENCE: 43
atgtcgggcg gcaatgatgg agcatcgtgg cggctgtctc gcaagcccaa tgctcccaac  60
tttgacgaga cacaggagga tcagtggagg tcgttgaggg aagaggtgct tcagtctgat  120
gaggacgaga atatcccgga gtccggcgac cttactattc cacagctccc ctcagcgaag  180
aaagcagcga aaaaactgag aaagccccca tcgggtgcaa aaccgacccc aaagccgaag  240
cagcagactc ttgcccagtc tatgagcgac atggacatgg agcgcttgtt gaagcggtac  300
cgcattgacg aggatatcga tatcgcagag gacatcgaca tgtcacacct gctgcagctc  360
cacagtgatt ccgacgatgg cggcgatgcg caagaggcaa ctctgaccgc cgacgagttc  420
ctagcgagac tggcgagggc agaggcagcg ccggcagcga gcattgccaa agaaaagcgc  480
aagagcggag agaacgtgac tgtggttgca ctgaaagatg agttgttcaa tgttgaaaga  540
gaccaaagtg caaagccgct tcgcccaagg ccagcaccag gagcaggcgg tggtgcgggc  600
taccgaaatg aggaaacgcc aaagcaagcc attgagctta ccgcaacgtt ggcaccacag  660
atggacgctg cgcagttcgt gtcgccagcg gtgccataca agtcggggga aatgactgaa  720
ggcctttttt actggttcga tgctcgtgag caacctcaca cactttccgt cgaccctgga  780
tcgctgtttc tctttgggaa gatggcggtg gagaagaacg ggcgcacctc ctacctatcg  840
tgctgcgtgc gcgtgcgcaa catgtaccgc agcgtttttg ttctaccgaa agcgggctcc  900
tcgcaggagg atgtcgtgaa ggaaatcaac gacatctgcc gcaaccaggg aatagagcag  960
cggcgcatca aatttgtgga gcgctactac gcttttgagg tgccaggcgt tccccacgaa  1020
aagacgcaat gggcgaaact gcgatatcct ggccgctacc caccactgaa tgcgaagggg  1080
ccgtttcgcc atattctgat catcatgggc gcttcctcgt ccctactgga gctatttttg  1140
atcaagcgaa agttgaaagg gcccagcttt ctgcgcatca gcggccttgt cgcgtcggcg  1200
aatcgcattt cgcactgcgc tcttgagttt agtgtcgact ccccgaagaa ccttcgcgca  1260
gaggacacaa agctaccggt tccaccgttt acgctggcaa gcattcagat acatacccag  1320
ctcgacagca aaggcgcctg caacgagatt ctcatcgcat cagttgccat ctacaaagac  1380
gtcaacatcg agaacacgat ccgctacatt cctgacaata ttctgactgg cgtgcgccct  1440
gcctcaatga gcacccctct gccgatcgac ctggaaagct actgcagcgc caaaggtcta  1500
cccggcgtgc gccgctttgc caacgagcgc gcactgctcg actggctcgc acagcaactc  1560
ggcaagatcg atgcagacat gatgattggc cacaactttc tgggcttcac actggatata  1620
cttctccgtc gataccagga gctgagcatc tcgtcgtggt ccaccattgg ccgcctggac  1680
ctgaaacgac tgccgcgctt ccagggaacc gccactaacg tgaatcagga aaaagagacg  1740
tgcattgggc gccttgtcgt ggactcctac tcactctcgc gcgagcacta caagacggtg  1800
aattacaggc tgctgtcgct tgcagaccag atgcagctgc aggggattac gaagggcagc  1860
aacaacttcg agcctggcac ctcggtgctc acacctgcga tgctgtcggc atcgcgcgac  1920
atctacgatg tgctgctgca ggtgtgcaac tgcgctgtgt tgtccacagc ggtcgtctca  1980
catctcgatg tgattcgact gaccaagcgc ctcaccacga ttgcaggaaa cctgtggagc  2040
cgtactctct tcggtgcccg ctccgagcgc atcgagtacc tcctgctgca cacgttccac  2100
gacctcaagt tcattacccc tgatcgctat gtgcagaact tcaagcgggg ccgcgacgac  2160
gaggaggagg aggatgggaa gcggaaggcc aagtaccaag gcggcatggt gctcgacccc  2220
aagtgcggcc tttactcgga ttacattctc ctcctcgact tcaactccct gtacccgtcg  2280
ctgattcagg agttcaacat ttgcttcacc accgtcgatc gcgaaagtgg gagcgagatt  2340
gacgtaccac caccagagaa cctcatctgt gcttcgtgcg ccgcagcagg cctctccgct  2400
ccgtgcttgc acaagtgtgt gctgccgaag gtgatcaaga gtctcgtaga cagccgtcgc  2460
gaggtgaagc ggttgatgaa gatagagaag gacgcgaaca acctggcgct gctggagatt  2520
cgccagaagg cgctgaagct gacggcaaac agcatgtacg gctgcctcgg cttcgagtac  2580
tcacgctttc acgctcagcc gctcgccgag cttgtcacgc ggcaaggccg tctggctctg  2640
cagagcacgg tagacctcat cccccagctg aacccttccc tgcgcgtgat atacggcgat  2700
accgactccg tcatgatcca gacgggaatc aagaacgaca tcaaggctgt cagggacctc  2760
ggactagacc tgaaggcaaa gatcaacaag cgctaccaaa gcctcgagat cgacattgat  2820
ggcgtctttc gcgctattct gctgctgaag aagaaaaagt acgccgcact gacggtgacg  2880
gactggcagg gcgagggcaa gacatacaag aaagaggtga aggggctcga tatggtgcgg  2940
cgtgattggt gcccgctctc aaagtgtgtg tgcgactcgg tgctgagtcg cgtgctgaac  3000
gcggagggca gcgaggacat tctggactac gtcatgaact acatgcggga tgtgtcggag  3060
aaggtgcggg ccgggcgcta cacgctcgac aactttgtca tctcgaagag cttgacgaag  3120
gagccggagg cgtaccgtgg caacagcttt cctcacgcca ctgttgcgct gcggatgaag  3180
cagcggaagg agctggtgcg cgtcggtgac ctgatcccgt atgtcatctg caccggcgac  3240
cggctgagcg acaaggcgtt tcatgtggag gaggtgcggc agaacagcca gttgcaaatc  3300
gactcggagt ggtatctgtc cgtgcagatc tatcccccag tcatgcgcct gtgcgagcac  3360
attcagggct tctcaaacgc gcagctgagc gaggcaatgg ggatcgcctg ccacaccggc  3420
gccaagctgg aggaagaaga ggcggaaacg atgaacgact tctcgcacag ctccctcttt  3480
cagagtcgaa agttagagga gtgcttccca gcagccctgt cgctgcaggt ggcatgcaca  3540
cattgccgcc tcatgacccc aatcaatccg cacacgcgcg tgatggaggt gctcgctgac  3600
caggaaaggc aacgagaccg gtttgacctg tacgtgtgcg tcagctgccg caagtcgctg  3660
ccggtagact acgtcgccaa ctgcttcacc cagacgtgct acggcattat ccggcagttt  3720
taccagtgcg gcggcagcgc ggctgccgtc aaggcagtgc gaacacagtt cacgtactac  3780
cgcgcgctgt ttgatgtgcc gcacgcgcca ggctgcccgg cgcgggtgaa ggatgcccac  3840
tactaccaag cgcgccgctg cctcggcgtg gatcgccggc tgtacacgtt agcggaggcg  3900
gcagacccgg cggtacagga ggtggccgac ccagtcgacc ccctcaacgc tgctgcggag  3960
actatataca agcgcatcga ccacctgttc ataaatctcg actccctctt cgccggcatc  4020
taa                                                                4023

SEQ ID NO: 44           moltype = DNA  length = 4260
FEATURE                 Location/Qualifiers
```

| misc_feature | 1..4260 |
| | note = mitochondrial DNA polymerase I protein B Desired nucleic acid sequence 43 |
| source | 1..4260 |
| | mol_type = other DNA |
| | organism = Leishmania panamensis |

SEQUENCE: 44

```
atgcgtcgtc gactgagcga ctcccggcca catgtgctgt tccaatcact gcgctcgacc   60
tgcactgtgc agtcactgac gaaggcccaa gcagcgctcg caagagggaa ggctccgtcg  120
gtggatgccg ctgccgaata cgcagagttc tttcgcgtcc ccatctcact agactccggt  180
gtcgtgcgta gtacccagga atactacaga aacattcaga agctggccga cgctaagcaa  240
agcaccgatg cgcagcatag ctcgccgaag aatggcttcg accaaagcag cgtggcgact  300
ttcctggcgg ggtaccactt tccaacagcg accttcaca tcttctccat cgccgcggac  360
aaaattgtgt gtagcgtgga cacgagccgg ggggctgcag agatgtgaga tttagcgagt  420
gagctcgtgg cccatatgaa cggcaaatcg ccgcagcttg ctcttatacc cgttgtggag  480
acggagcagg agcggaagag tctgcaggtg cctctccaaa agctcacggc cttgttgagg  540
tccagcgggc tgcaggtggt tgctcacgtt gacaccctcg agctgagctc cgcgctgtgc  600
cgcgatcctc cgtcgccggg tgatatcaca cgcaatgctg tgtctggtgt gtctccgact  660
cccgtgactc tcaaatggtt tcaggcgcat tgggcgttca tccgcactgc ggcttgccag  720
gcaaagccga cggacccgct gcagacactg agcacgtacg tgctgccccg ctttgccgtc  780
taccttattc acctcgtgca tgccggcact cgcgggctta acgtgtcact ctgggatccg  840
gtgcgtgccg gccgcttttc cgccaagggc atgctctcag gctactcgc tgcctgcttt  900
gatacgcgct ccagccagat gattttggtg cccacgcacc gcaccgaccg cgctgcgctc  960
ttccgctgcc gcaccgccgt catgaaggct ggccatgatt gcgtcgtcgt gtacgcgtcg 1020
gaggtgagcg accgcctgcg tggctgctac cagtccgacc caatgcgata ctggggcgtg 1080
atgaaggaga ctgcaggttt cctgaagcag gatttgctat tcaacatcta catatccgtc 1140
ggcaacacac tccgcagtta tcagcgcaag aagctcaccg agaaccagtc atgccaccac 1200
ttgagtctgt tgaccagctc ctcggatgag ggggtggagt ccccacagat tgtgctcgac 1260
tgggtccgct acttcacgca tcccaagcgc gttgcagccg agaaggcgga gctgcgccac 1320
tatgacaagt tcattgccat cgcctacgtc gccaccagtc acatgtgca cggccagccg 1380
atgaaccccg tggcgagat taatcacgtg ttgagtgcgt gcatcaccga ccacgcgaat 1440
cagacagtgg agccgtgggc tatctacacc aagcgcggac agttctgctt accctgtctt 1500
gacggataca acgtgctcgt cacgcacgat gccaagtcgt tattgctgct gctgtcgggt 1560
gacgccgaac ttcacaagtt catccaacgc ggcggccgtg tttggtgcgt gacgctagcc 1620
gagtatcttc tagaggcgca gcgatgcacc agcagcagta acagccttca cgatttggcc 1680
cttcgtcacg gtgtgcagct gccgccgttg tcgcgtgtgg gtacgccaaa cgatcgtctc 1740
ccgtttgcct atcagcggca gtttcttcgt cacacaacgc ctgcggtggt gaaggtgttt 1800
gcggggcagc tcaagcgtgc acttgagcag tgccaggtgc tgagcctggc gcatcgtatg 1860
gactccttgc tggcgatgac gagcatcgag aatgctggta tccacatgca gcgggaagag 1920
gcagcgcggc agacgcttc cttgaagagc gctgcatctg tgctagacgc ggcgatggag 1980
gcctacgtcc cgcgcgaggt accactcgac atgaggatgt atttgactgg ggcgtctctg 2040
caacagcagc acgcctactt cttttggcggt accgttacgc tgggtcaccg gacccaagtc 2100
cgcgatacgc ctctatggac gtcgaatctg gttcatctct gccaccgctt tggcactttc 2160
acccatatgg ttggggagct acacctgcag cgttacgcgg cccaatgtgc gctgcccacg 2220
acagggccgt tgcctgcccg tatccatcag tacatcgagg ctcagggatc gcagaagctg 2280
aagacgtacc gcattgtctt cttcgacatc gagacaacag ggctcaaccc aagtacggac 2340
gccattgtgg aggtggccat gttcgacccc atcgagaaca gcacgttttca cacactcgta 2400
aacccgcagc gccccatctc gccacggact gttggcattc accacatcac gaacgaaatg 2460
gtgcgcgatg cgccgactgt ggacgtggtc gcaaagagta tcggccagta cctgcgcctc 2520
gacatggcgt cgtacaaccc gcatgagatt ttggtgctgg tgggtcacaa cgtcttctcc 2580
ttggaccagc cgatgctgcg ccgtgcgctg gagtgttacg gccggagtg ccagctggac 2640
ggcgttctgt tctgtgactc gctggcgttg cttaattccc accgaagcgt gctgcgatgg 2700
cgcttgcgcg gaaaccgtgc gaatcaaccc ctcatggagg ccctcgcatc ctctctgcgc 2760
ctcagtcgac tgatcacagc gctcaacgtg cggccgagg gagacctgca tcgcgctgac 2820
acagacacaa aggcgctctg gtacgtgcta gtcaacattc tcggcgttgc cggcaaagaa 2880
cccacggtgc agcgtgacaa aatttttgctg gaggccgcca actgcttcct gcgcgctccg 2940
tcgatcgggt gctttgtgcc agcagagcgt caaagtcgcc ttgtaaaggt gcgtcttccc 3000
ggcgtagccg ccgactacat cagtaacgcg aagctgattg caagtctgca aggtaaagtc 3060
ttctccgacg ctgtgctgac gtccttgtac gcacacggcg tgaagccgac cggcctgctc 3120
ctgcagcggc agctgctcaa ccgtcacacc tccacctcc tgcaaccgag cgcaaacgga 3180
cggctggcca ttctgcatcg agacggtaga gtgcaccagc atatcgacat gaccgccacg 3240
acaacgtcgc gcactgtcag tgcctaccca agttgccaga atattcccaa ggacgataag 3300
tcgtctgtgc ggcgtctctt cgtgtcccgc ttcggctccc aagggcgctg cgtcgaggtg 3360
gactactcac agctggagat cgtggtgctg gcgattctgt gcaacgacgc gaactgaca 3420
catgacctca atcacggcgt cgacttccac gtgaagcggg cagcgttctt tagcgggcta 3480
ccgtacgacg agatctatca gggctataag cgaaatgttc ccaagtatgt caagctgcgc 3540
aggacgcgca agcagttttc ctttcagcgt ctgtacggcg ctggggtgcc actgctgcac 3600
aagacaactg gcattccagt aaaggacctt gaggcgtcga ttcagagaga aacgaggac 3660
tacccccgga tcgcgcagtt tcatcgcact atccggtctg tcgcgcttcg cccgaacaac 3720
ccagggctgc ccaccagctt cattgccgag atgccgacag ggttgcggat gagcctcgcc 3780
acgcgggatg tggtgctgaa cctgcctcct atcaagaact acccaattca gggctacggc 3840
gcggagctgc cgcagatgat gctcggccgg ctcttccgac actttatgcg gagggacttc 3900
tacaagaacc gcgcgtttct catcaacttt gtgcacgact cggtgtggat ggattgccat 3960
gtcgatgtac tgcgtgagtg tgtgacagac acgtgccgca ttcggctc ggctcacgag 4020
tacgtcccga aggtgttccc tggggtgaag atcagcgtgc cgctgcaagt ctctgcgtcg 4080
tgcggggtag acatgtgctc tatggagaac atcaggggtg acgactacac gtttgtgttg 4140
aagcagcgca agacgaggtc agcggaggtg caggactttt tggacctgac gacggccaag 4200
tcgaacttct cggcggtgat ggaggagagc gtcgcgtccg aggaggaggc gaccgtgtga 4260
```

| SEQ ID NO: 45 | moltype = DNA length = 3205 |
|---|---|
| FEATURE | Location/Qualifiers |
| misc_feature | 1..3205 |
| | note = Desired nucleic acid sequence 44 |
| source | 1..3205 |
| | mol_type = other DNA |
| | organism = synthetic construct |

SEQUENCE: 45

| | | | | | |
|---|---|---|---|---|---|
| ctgcagtgtg | cgcggcccgg | gacgagcgac | ggggtctcga | ggactcgtcc | accatgctcg | 60 |
| ccgatccggg | gggcagacga | aaagacaatg | agttgagtga | atgaggcgta | actgaatcta | 120 |
| gactagtggg | ggcctgtcgg | gttgtccaga | gcgtgtcgtc | gcgcgcagga | aagcgtcaaa | 180 |
| aatcaactgc | cgcaacgttt | gctccggaat | gaggcagctc | ccctgttgcg | cccatgcggg | 240 |
| ggagtctgcc | ctctggatcc | cccgtgcgag | aggcaacaaa | atcttaacag | gtcacgaagt | 300 |
| catgacctat | tgacctatcg | ggattgtggt | gtttaaggtt | ggtgacccaa | gccacaagga | 360 |
| ggcaatgcga | tggatggtat | ccacgatctg | ggcgggcgcg | ccggtctggg | ccggtcaat | 420 |
| cccgaacccg | gtgagccggt | ctttcattct | cgttgggagc | ggtcggtttt | gacgatgttt | 480 |
| ccggccatgg | cgttagccgg | ggcgttcaac | ctcgaccagt | tccggggcgc | gatggaacag | 540 |
| attcccccgc | acgactatct | gacctcgcag | tactacgagc | actggatgca | cgcgatgatc | 600 |
| cactacggca | tcgaggcggg | catcttcgac | ccgaacgagc | tcgaccgtcg | cacccagtac | 660 |
| tacctggagc | atccggacga | agacccgccc | ctgcggcagg | acccgcagtt | ggtggagacg | 720 |
| atctcgcagt | tgatcatgca | cggagccgac | taccgaaggc | cgaccgacgc | cgagggcgtc | 780 |
| ttcgcggtgg | gcgacaaggt | cgttgtgcgg | tcggacgcct | cgccgaacac | ccacacccgt | 840 |
| cgcgccggct | acatccgtgg | acgcaccggt | gagatcgtcg | cagctcacgg | cgcctacgtt | 900 |
| ttcccggaca | ctaacgccgt | cggcgccggc | gaacaccccg | aacacctgta | cacggtgcgg | 960 |
| ttctcggcga | ccgagttgtg | gggcgagacc | gccacctcca | acgcggtcaa | ccacatcgac | 1020 |
| gtgttcgaac | cctacctgct | gccggcctga | ccggagcgtc | cgatacaacc | tcgctgatac | 1080 |
| ccccactgcc | ccgcctacgg | aaacgagttc | acccgatgac | cgcccacaat | cccgtccagg | 1140 |
| gcaccttccc | ccgatcgaac | gaggagatcg | ccgcccgcgt | caaggccatg | gaggccatcc | 1200 |
| tcgtcgacaa | gggcctgatc | tccaccgacg | ccatcgacta | catgtcctcg | gtctacgaga | 1260 |
| acgaggtcgg | tcctcagctc | ggcgccaaga | tcgccgccca | tgcctgggtc | gatcccgagt | 1320 |
| tcaaacagcg | cctgctcgcc | gacgcaaccg | gcgcctgcaa | ggaaatgggc | gtcggcggga | 1380 |
| tgcagggcga | agaaatggtc | gtgctggaaa | acaccgacac | cgtcaacaac | atggtcgtgt | 1440 |
| gcaccctgtg | ctcgtgctac | ccgtggccgg | tgctcggatt | gccgcccaac | tggtacaagt | 1500 |
| accccgccta | ccgcgcccgc | gccgcccgcg | accgcgagg | ggtgatggcc | gagttcggct | 1560 |
| ataccccgc | ctcggacgtc | gagatccggg | tgtggagact | gagcgccgaa | ctgcgctact | 1620 |
| gggtgctgcc | gcagcgcccc | gccggcaccg | agaacttcac | cgaagagcag | ctcgccgccc | 1680 |
| tcgtcacccg | cgactcgctc | atcggcgtgt | ccgtccccac | cgcaccgaac | aaggcctgac | 1740 |
| atgccccaac | tcaacgaaca | acccagccag | gacctcaagg | accgcctcga | cggcctggtg | 1800 |
| cagaacctac | cgttcaacga | gcagattccc | cggcgtccgg | cggaggtcgc | cttcgaccat | 1860 |
| gcctgggaga | tccgcgcttt | cagcatcgcc | accgccctgc | atgcccaggg | ccggttcgag | 1920 |
| tgggacgaat | tccagtcccg | cctgatcgac | tcgatcaaac | agtgggaaac | cgaacacacc | 1980 |
| accaccgagg | agtggagcta | ctacgagtgt | tggatgctcg | cactcgaaga | gctggtgcgg | 2040 |
| gacaaggggc | tggtcgccgg | tgatgaactc | gagcaccgca | ccgagcaggt | gctggccacc | 2100 |
| ccggccaacg | cccaccacca | acacgctgta | cgccgacccca | ttgccgtgca | caccagcgaa | 2160 |
| gtacctactg | ctcagtactc | ccggtagccc | ctggggcctc | gccttcacgg | aggtggaact | 2220 |
| ctcgtgtaaa | ggctcctggg | ctctgcgacg | tagagatacc | accgatcttt | ctcttgggct | 2280 |
| cccccaggagc | cgaagacgca | tccctgatat | ggcaactcgg | acctggccgg | gcgcgcagac | 2340 |
| acaacgtgcg | agcgccccgg | aacttccaag | cctctggcgt | attcggaaga | cgctgcgaat | 2400 |
| tagtcgaagg | acaagggttt | gaccagtacc | gcaatgacac | cgcaccgcat | gggcggtgcg | 2460 |
| tggactcgta | cagagcgcca | gcggctggca | tcggttgtcg | gcgccgtcgt | gatcctgcat | 2520 |
| gtattgcgcg | tggccctgta | tgtgggatac | tccggtaatc | cagcagccgc | cggaggcctc | 2580 |
| gccggatccg | gtgtgctcgc | ctacgtgctc | ggcgtccgcc | acgcattcga | cgccgatcac | 2640 |
| ctcgctgcca | tcgatgacac | cacgcgcctg | atgctgttgc | gcggacgccg | tccggtcggg | 2700 |
| gtcgggttct | tcttcgcgat | gggacactcg | accgtcgtca | ttgtccttgc | tctggtcgtg | 2760 |
| gcgctgggcg | ccagctccct | gaccacgagt | gagctcgagg | gggtccagga | gatcggcgga | 2820 |
| atggtcgcga | cggtcgtcgc | cgtagccttc | ttgctggtcg | tcgccggact | caacagcgtg | 2880 |
| gtcctgcgca | atctgctctc | cctgcccga | cgggtgcgga | ccggggcgga | catcgcaggt | 2940 |
| gatctcgaga | gcagcctcag | cgagcgtggg | ttgttcgccc | ggctgctcgg | tgcccgctgg | 3000 |
| cgtggactga | ttcgttcgtc | ctggcacatg | tatccggtcg | ggctgttgat | ggggctcggg | 3060 |
| ctcgagaccg | catccgaggt | caccctgctc | actctcactg | cttcggcggt | gaccggggc | 3120 |
| accttgtccg | tggctgcagc | gggctcacgg | acggatcggc | cgccagatag | tcgctcgcgg | 3180 |
| tgcgcgccag | atgccagttc | tgcag | | | | 3205 |

| SEQ ID NO: 46 | moltype = DNA length = 4374 |
|---|---|
| FEATURE | Location/Qualifiers |
| misc_feature | 1..4374 |
| | note = DNA-directed DNA polymerase alpha catalytic subunit |
| | POL1 Desired nucleic acid sequence 45 |
| source | 1..4374 |
| | mol_type = other DNA |
| | organism = Kazachstania barnettii |

SEQUENCE: 46

| | | | | | |
|---|---|---|---|---|---|
| atgagtgata | aactatcgaa | gttgaagaaa | ctacaagctg | ccagaaatgg | cggttctgtc | 60 |
| gaagatgatc | tagaagattc | ctatgatgac | cataagttat | atgatgaagt | tgatgagaaa | 120 |
| gaatatagaa | acagaaagcg | taaagagttg | ctacaagatg | attttgttgt | tgacgatgat | 180 |
| ggtgtaggtt | acgttgatcg | tggtattgaa | gaacaggaag | aatattacag | tgacgactat | 240 |
| agtgacgacg | atcagaataa | gacatcttcg | aaactgaaga | agaagacgaa | acagcagtct | 300 |
| aaggtaaagt | caactcatca | gattagtaat | atgttacgag | cccattcatc | taagaccgca | 360 |
| gatccaaaga | agaagaaaat | agaaattgat | gaatttgatg | atatccttgg | tgaattcgat | 420 |

```
agtggaatat caaataaaat tcaacctact atgagttcgt cgtcgagacc tccatcctct    480
ccttctaacc gtcctgagaa aaagagacca ctagtcgtag catcagatat agaagtgaat    540
ttaaagaagc ctagggctgc acctcaaagc agcactaact tttctaataa tttaatgaat    600
tcctctccgt taaagaaaca tattaaacta gatgatgata tggatgattt attggaagac    660
gtagcagtct caccgacaat gaaaaaagtt cctaccggtt taacagacaa ctctaatgac    720
acatctatga ccaacgatat cgaggaagat ggaatgagta gtgacgatga tattgtagtt    780
agaaggagaa ctgttaggag cgcagcagct accaaacaga tcaatttgaa ttcaaaaagt    840
aatccaggat catccccatt tgtcactgca ccaggtacac ctcttgatct gaagtccact    900
attaggaagc cggcatcatc aatgaatagt gcaccattgc aattctcaaa taagtataca    960
aaagcacaag ttgtcaaccc ggagaccgat tccttccaaa tgtattggtt ggattatgca   1020
gaaattaata acacattgat actttttggt aaagtaaaaa cattggataa tagtatggta   1080
tcagctatgg ttcagattaa cggttagag agggattat attttttgcc tcgtgaagga    1140
aagacaccaa gcgatattca tgaggagatc gtcccacttt tgatggagaa atatggattg   1200
actaatattc gtgccaaacc tcaaaaaatg aaatatgcat ttgaattgcc aggtattcct   1260
catgaagctg actacctaaa ggtgttatta ccgttcaata ccccaaaagc atcttacgat   1320
ttgattcccc ctgatttatc aagtgaaact ttccatcatg ttttttggtgg taacacaaac   1380
atcctagaac aatttttaat tcaaaataag atcatggggc catgttggct agaaattacg   1440
catggggact ttaatgcatt gcaaaatgca tctcattgct cgttagaagt tgcggtatct   1500
aaaccagcta atatcaaagt attgaatgat attaaaacaa cagctggact aaattgtacc   1560
tcacttgcaa tccagacgat gatgaattcc aaggaaaata acaggaaat tgtttctatt    1620
tctatatcaa catacaataa tgtaactcta gatatcccaa tcccagagga tttgaaaccg   1680
gatgcagttg ttacattagt gaggccacct caaggctcag attttgcggt tggtctagct   1740
acccttgtga aacagaagct tccgggaaat gttcgtttat ttaataatga aaaagctttg   1800
ttagcttgct tctgtgcgat gatgaaaaca tctgatccag atgtcttaat tggtcataga   1860
cttgacagta tttatttaga tgtcctagta cacagattgt atgatctgtc tgttccgact   1920
ttcagttcat taggtcgtcg tgctagaaaa gaatggcctg ataaatttgg tagaggtcac   1980
aacaatatga atcatttttt cattcgtgac attgttgctg gtaggttaat ttgtgatatt   2040
ggtaatgaaa tgggtcaatc tttgacacca aaatgtcaga gttgggattt gtctgaaatg   2100
ttccaggtca cttgtcaaca agaacataaa gcgcttgata ttaattatca aaatgctcaa   2160
tatcagaacg accctaatat tatgacaatg gctttgcaag aaaatattac aaattccatg   2220
attactgcta caatttcttt tagaatacaa atgttatctt taaccaagca acttacaaat   2280
ttggctggta atgcatggtc tcaaacattg ggaggtacaa gagcaggtag aaacgaatat   2340
attttgcttc atgaatttgc aagaaatggt tatatcgttc cggacaaaga aacgagaaag   2400
atgaaggctc atagacttgc taatactgaa gatggtgaaa atgaaaataa tgatacacca   2460
acatcttcta agaaagcgaa atatcaaggt ggtttggtgt ttgaaccaga aaagggacta   2520
cataaaaact acattctagt catggatttc aactctcttt acccatctat tattcaagag   2580
tttaatattt gtttcactac cgtcaagaga aacgtgaacg atattgagga attaccagag   2640
gttcctccta gcgatatagg acaaggtgtt ttgccacgat tacttgccac tttagtggat   2700
cgtcgtcgtg aagtcaagaa gatcatgaaa actgaaacag atcctcataa acgtgtccaa   2760
tgtgacatta gacagcaagc attgaagttg acagccaatt cgatgtacgg ttgtctgggt   2820
tatgtccaca gtagatttta tgcaaaacca ctagcaatgc tggtcacaaa caaaggtaga   2880
gaaattttga tgaacaccag acaattagca gagagtatgg tcttactgt tgtgtacggt    2940
gatacagatt ctgtcatgat tgataccggg tgtgaaaatt atgaagacgc aattaagatt   3000
ggggtagaat ttaaaaaact tgttaatgaa cgttatggt tgctagagat tgatattgat    3060
aatgttttta gaaagctgtt actacatgca aagaagaagt atgctgctct taatgtcacc   3120
attggtaaag atggtaagga acaaacagtt ttagaagtga aaggtctgga tatgaaacgt   3180
cgtgagtatt gtccactgtc caaggatgtg tcgacacatg tattaaacac cttactttca   3240
gataatgatc cagaatcatc tttacaagag atatatgggt acctggagaa tattagaagt   3300
aaggttgagt cgaacgaaat tagaattgat aaatacaaga taaatacacg attatctaag   3360
gatccaaagg catatcctaa tggtaaaact atgccagctg ttcaagttgc tatgagaatg   3420
agaaaagctg ggagagtagt aaaagccggt accgttatca cttttgttat tactaaaggt   3480
aaaggatccg aagaggatag cacagataag gatgtgactg atagtgcaca ttttgcatca   3540
agagcttatg cactaaacga tgttatggtt aaaagcaaca atcttgttcc agatccaaat   3600
tactatctgg aaaaacaaat attttgctcct gtggaaagat tgttggaaag aattgaaagt   3660
ttcgatgttg ttcgtttgag tgaagccttg gactagtaga gcaggaaatt cgctagacgt   3720
tttgcagatg ataaaaatag cagtggtatt cataatttgg aacccttgga gaccactata   3780
tctgatatgg aaagattcaa ggattctgct aaattcgaat taaattgtcc aaattgttca   3840
catttgttcc catttggtgg tattattgct tcgaactttt ataagatgtg ttataatggt   3900
gtccaatgta agaactgtga tcatgtatttt aatatgattc agtttacgag tcaattagaa   3960
tctgttatca gatcccatat ttcgttgtat tatgccggtt ggttgtattg tgatgattcg   4020
acatgcagga acgttactag acaaatatct gtcttcggaa aacgttgttt aaatgacggt   4080
tgtactggtg tcatgcaatt caagtatacc gataaacaat tatacaacca attattatat   4140
ttcaattcct tatttgatat ggaaaaaaat aagaagcaac tattgaaacc actatattat   4200
gaaggtgaca tcgattatcc atccgaacag ttagctgagt ccgcaatctt agcattgact   4260
gaacaaaata gaaagctatt cgaaattagt cagggtgtta tagataaaata tctagacaat   4320
tgcggccgtc gttacgtaga catgggtgcg attttgatt tcatgatgaa ctaa          4374
```

METHODS AND COMPOSITIONS FOR CELL-FREE CLONING

CROSS-REFERENCE TO RELATED APPLICATIONS

This application is a Continuation of U.S. application Ser. No. 18/336,283 filed on Jun. 16, 2023, which is a Continuation of International Application No. PCT/US2022/071707 filed Apr. 13, 2022, which claims priority to U.S. Provisional Application Ser. No. 63/174,192 filed on Apr. 13, 2021. All of the applications cited in this paragraph are incorporated by reference herein in their entireties.

SEQUENCE LISTING

This application hereby incorporates by reference the material of the electronic Sequencing Listing filed concurrently herewith. The materials in the electronic Sequence Listing are submitted in XML format entitled "119922-0050_SUBSEQ.XML" created on Aug. 14, 2023, which has a file size of 200,891 bytes, and is herein incorporated by reference in its entirety.

FIELD OF THE INVENTION

The disclosure relates to the field of nucleic acid synthesis and assembly.

BACKGROUND

Cloning is a key step in molecular biology, yet the time and cost inefficiencies associated with cloning result in a significant bottleneck for many molecular biology processes. In general, traditional cloning in molecular biology includes isolating and copying single nucleic acid molecules of interest by inserting them into a vector, e.g., a circular DNA vector; inserting the vector comprising the nucleic acid of interest into a living cell, e.g., E. coli cells; isolating and growing colonies from single transformed cells (clones), wherein each cell in the colony is derived from a first single progenitor cell having taken up a single original copy of the vector and thereby the inserted nucleic acid molecule of interest. Cells from these clonal colonies comprising nucleic acid of interest subsequently can be expanded by growth in a larger culture, which can create a corresponding larger number of copies of the vector carried by each cell. After culturing for a desired time period, these vectors can be isolated from the cells by various means known in the art. This process enables the production of quantities of the single vector and the inserted nucleic acid molecule of interest that are useful for characterization of the inserted nucleic acid molecule of interest as well as for use in downstream processes, e.g., expression and purification of a molecule of interest encoded by the nucleic acid of interest.

Typically, the source nucleic acid for insertion into a vector is a mixture of molecules, only some of which comprise the desired sequence. This mixture of nucleic acid molecules is very common and occurs whether the source nucleic acid molecules are generated by PCR, direct nucleic acid synthesis, and/or by isolation from some other source of nucleic acid. When cloning, characterization and confirmation that the nucleic acid insert is the desired nucleic acid, rather than another nucleic acid from the mixture of molecules that does not comprise the desired sequence, is essential. To ensure success in identifying at least one clone having the correct nucleic acid of interest, it is typical to select 2-10 clones for expansion and analysis, though in some instances more than 10 clones may need to be selected to identify the desired clone. The number selected is variable and can vary based on the process used to generate the source nucleic acid.

Nonetheless, there is considerable cost, effort, and time involved in preparing, selecting, expanding, and analyzing even one clone. If more clones are evaluated, the cost, effort, and time necessary for analysis is correspondingly amplified. As such, studies involving the use of variants, for example, encoded by multiple different nucleic acids of interest are greatly hindered by the time and cost needed to generate the vectors comprising the nucleic acids of interest, where each nucleic acid of interest that has been cloned has the correct nucleic acid sequence.

Approaches that do not involve traditional cloning have been devised for assembling and/or identifying target polynucleotides. However, such methods can: 1) be limited to polynucleotides of less than 300 base pairs; 2) require complex tagging and sequencing of a large number of molecules; 3) require large or randomized sets of barcodes (barcoding libraries); 4) require complex and time-consuming steps; and/or 5) be unable to synthesize many different polynucleotide sequences. As such, there is a recognized need in the field for methods and compositions to decrease the cost, effort, and time necessary for cloning, as, for instance, many molecular biology processes utilize cloning.

BRIEF SUMMARY OF THE INVENTION

The inventors unexpectedly discovered that the methods described below can result in: reducing the amount of time it takes to synthesize desired polynucleotides, increasing the accuracy of the resulting polynucleotides, and decreasing the cost of the synthesized polynucleotides. In particular, the inventors unexpectedly discovered that using a relatively small library of barcodes could improve in vitro synthesis of polynucleotides. The inventors further unexpectedly discovered that substantially diluting a sample of polynucleotides during polynucleotide synthesis could also improve in vitro synthesis of polynucleotides.

In one aspect, provided herein is a method of generating a population of product polynucleotides, wherein the method comprises:
   a. diluting a subvolume of a source sample comprising candidate nucleic acid molecules to form a diluted sample having a target number of the candidate nucleic acid molecules isolated from the source sample, wherein the diluted sample comprises one or more tagged candidate nucleic acid species derived from one or more of the candidate nucleic acid molecules, wherein each nucleic acid molecule of a candidate nucleic acid species has an identical nucleic acid sequence comprising the nucleic acid sequence of the one or more candidate nucleic acid molecules from which it was derived and a tag comprising at least one barcode from a set of barcodes,
   b. determining the sequence of at least some of the tagged candidate nucleic acid species; and
   c. enriching a desired uniquely tagged nucleic acid species by amplifying one or more candidate nucleic acid molecules of the desired uniquely tagged nucleic acid species, using one or more primers that bind to one or more barcodes on the tag associated with the candidate nucleic acid molecules of the desired uniquely tagged nucleic acid species to generate a population of product polynucleotides.

In one aspect, provided herein is a method of generating a population of product polynucleotides, wherein the method comprises:
  a. diluting a subvolume of a source sample to form a diluted sample having a target number of the tagged candidate nucleic acid molecules isolated from the source sample, wherein each tagged candidate nucleic acid molecule has a tag comprising one or more barcodes,
wherein the diluted sample comprises one or more tagged candidate nucleic acid species derived from one or more of the tagged candidate nucleic acid molecules, wherein each nucleic acid molecule of a tagged candidate nucleic acid species has an identical nucleic acid sequence comprising the nucleic acid sequence of the one or more tagged candidate nucleic acid molecules from which it was derived;
  b. determining the sequence of at least some of the tagged candidate nucleic acid species, wherein at least 1 of the tagged candidate nucleic acid species is a desired uniquely tagged nucleic acid species; and
  c. enriching the desired uniquely tagged nucleic acid species by amplifying one or more tagged candidate nucleic acid molecules of the desired uniquely tagged nucleic acid species to generate the population of product polynucleotides.

In one aspect, provided herein is a method of producing or generating a polynucleotide or a population of polynucleotides, a method for production of such a polynucleotide or population, or in certain illustrative embodiments, a method of cell-free cloning of such a polynucleotide or population, wherein the method comprises:
  a. diluting a source sample comprising source nucleic acid molecules and/or tagged nucleic acid molecules derived therefrom, to form a diluted sample by isolating a target number of the source nucleic acid molecules and/or the tagged nucleic acid molecules away from the source sample,
    wherein the diluted sample comprises one or more tagged nucleic acid species derived from one or some of the source nucleic acid molecules, wherein the tagged nucleic acid molecules from each tagged nucleic acid species have an identical nucleic acid sequence;
  b. determining the sequence of at least some of the tagged nucleic acid species, wherein at least 1 of the tagged nucleic acid species is a desired uniquely tagged nucleic acid species, wherein the desired uniquely tagged nucleic acid species comprises the desired nucleic acid sequence; and
  c. enriching the polynucleotide having the desired nucleic acid sequence from the diluted sample by enriching one or more polynucleotides of the desired uniquely tagged nucleic acid species, to generate the polynucleotide or the population of polynucleotides.

In certain embodiments, the method further includes before the diluting step:
  assembling at least two nucleic acid molecules of an initial source of nucleic acid molecules to produce the source sample of nucleic acid molecules.

In certain embodiments, at least 2 different desired polynucleotides enriched using the methods provided herein are assembled into a subsequent polynucleotide having the nucleotide sequences of the at least 2 different polynucleotides.

In some embodiments, the error rate in the population of polynucleotides is at most 1 in 10,000. In some embodiments, the error rate in the population of polynucleotides is at most 1 in 15,000, the error rate in the population of polynucleotides is at most 1 in 30,000.

In another aspect, provided herein is a method of fulfilling an order for a population of desired polynucleotides, the method comprising:
  a) receiving an order for the population of desired polynucleotides from a customer, wherein the desired polynucleotide has a desired nucleic acid sequence; and
  b) fulfilling the order by generating the population of desired polynucleotides with a quality threshold, wherein the quality threshold is the minimum percentage of nucleic acid molecules in the population of desired polynucleotides that comprise a sequence that is sequence-perfect to the desired nucleic acid sequence.

In some embodiments, fulfilling the order is performed using a cell-free process. In some embodiments, fulfilling the order is performed using an automated production system.

In some embodiments, the desired polynucleotides of the population are:
  i) between 500 and 1,999 bp in length, and wherein the quality threshold is 98%;
  ii) between 2,000 and 2,999 bp in length, and wherein the quality threshold is 95%; or
  iii) between 3,000 and 50,000 bp in length, and wherein the quality threshold is 92%.

In some embodiments, the desired nucleic acid sequence is a non-natural sequence.

In some embodiments, the method from receiving the order to fulfilling the order is performed in between 2 and 7 days.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein. Further details regarding aspects and embodiments of the present disclosure are provided throughout this patent application. Sections and section headers are for ease of reading and are not intended to limit combinations of disclosure, such as methods, compositions, and kits or functional elements therein across sections.

BRIEF DESCRIPTION OF THE DRAWINGS

FIG. 10A presents sequencing-based analysis of 15 different A6 tagged nucleic acid species in accordance with Example 1. OBC=outer barcode; and IBC=inner barcode.

FIG. 10B presents sequencing-based analysis of 46 different GF2B tagged nucleic acid species of in accordance with Example 1. OBC=outer barcode; and IBC=inner barcode.

DETAILED DESCRIPTION OF THE INVENTION

I. Terminology

Figure 1A:
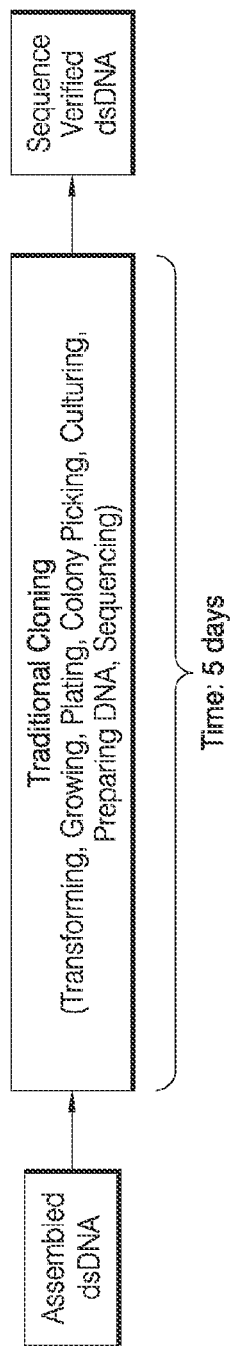
FIG. 1A-FIG. 1B present schematic diagrams of traditional cloning (FIG. 1A) and an illustrative embodiment of cell-free cloning in accordance with the present disclosure (FIG. 1B).

As used in the present disclosure and claims, the singular forms "a," "an," and "the" include plural forms unless the context clearly dictates otherwise.

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can mean "includes," "including," and the like; "consisting essentially of" or "consists essentially of" are open-ended, allowing for the presence of more than that which is recited so long as basic or novel characteristics of that which is recited is not changed by the presence of more than that which is recited, but excludes prior art aspects.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, otherwise analogous aspects referring to the specific numeric value or range are also provided.

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures).

As used herein, "no more than" or "less than" is understood as the value adjacent to the phrase and logical lower values or integers, as logical from context, to zero. When "no more than" is present before a series of numbers or a range, it is understood that "no more than" can modify each of the numbers in the series or range.

The term "nucleic acid" as used herein refers only to the primary structure of the molecule. Thus, the term includes double- and single-stranded DNA, as well as double- and single-stranded RNA. A "nucleic acid," is generally understood by the skilled person as a molecule comprising two or more covalently linked nucleosides. Such covalently bound nucleosides can also be referred to as nucleic acid molecules or oligomers. Polynucleotides can be made by means known in the art, such as recombinantly, enzymatically, synthetically, e.g., by solid-phase chemical synthesis followed by purification, by the methods described herein, and/or any combinations thereof. When referring to a sequence of the polynucleotide or nucleic acid, reference is made to the sequence or order of nucleobase moieties, or modifications thereof, of the covalently linked nucleotides or nucleosides.

As used herein, the term "synthetic" means produced, prepared, and/or manufactured by the hand of man. Synthesis of polynucleotides or polypeptides or other molecules of the present disclosure can be chemical and/or enzymatic.

As used herein, the terms "adapter" and "adaptor" are used interchangeably and refer to a nucleic acid molecule that can be used for manipulation of another nucleic acid molecule. In some aspects, an adaptor comprises at least a portion of at least one molecular barcode. In some aspects, an adaptor comprises at least one molecular barcode. In some aspects, adapters are used during assembly of two or more nucleic acid molecules. In some aspects, adaptors are used for amplification of one or more target nucleic acids. In some aspects, adaptors are used in reactions for sequencing. In some aspects, an adaptor comprises, consists of, or consist essentially of at least one priming site. In some aspects, a nucleic acid molecule can be tagged with an adaptor by, e.g., an amplification reaction using a primer comprising the adaptor. Further characteristics of adapters are discussed infra.

As used herein, the term "tagging" refers to any means of associating two molecules, such as associating a molecular barcode and a nucleic acid molecule. In some embodiments, a nucleic acid molecule can be tagged with one or more molecular barcodes, one or more adaptors, and/or one or more adaptors comprising one or more molecular barcodes by any means known in the art. For instance, such tagging can be accomplished through ligation reactions, PCR-based strategies, Splicing by Overlap-Extension strategies, and/or Click chemistry. In some embodiments, a nucleic acid molecule can be tagged with a molecular barcode by ligating the molecular barcode and the nucleic acid molecule. In some aspects, a nucleic acid molecule can be tagged with a molecular barcode by PCR, such as using primer comprising an adaptor during PCR. In some aspects, a nucleic acid molecule can be tagged with a molecular barcode by Click chemistry. In some aspects, a nucleic acid molecule can be tagged with a molecular barcode by overlap-extension (e.g., Splicing by Overlap Extension (SOEing)). In some aspects, tagging comprises linking one or more nucleic acids with one or more adaptors and/or one or more molecular barcodes.

As used herein, the terms "molecular barcode" and "barcode" refer to a nucleic acid sequence, or a combination of nucleic acid sequences, that can act as a 'key' to distinguish or separate a plurality of sequences in a sample. For instance, two nucleic acid molecules can each be tagged with a molecular barcode having a unique nucleic acid sequence, such that the two uniquely tagged nucleic acid molecules are distinguishable from one another based on their respective molecular barcodes during nucleic acid sequencing. Moreover, each of two or more different nucleic acid molecules can be tagged with two or more molecular barcodes, wherein the combination of molecular barcodes used to tag each of the two or more different nucleic acid molecules distinguishes the different nucleic acid molecules. In some aspects, at least one molecular barcode is incorporated into the nucleotide sequence of at least one adaptor and/or at least one primer. In some aspects, at least one molecular barcode is used to tag at least one nucleic acid molecule. In some aspects, molecular barcodes are used for amplification of one or more target nucleic acids. In some aspects, the molecular barcodes are used in reactions for sequencing. In some aspects, a molecular barcode comprises, consists of, or consist essentially of at least one priming site.

As used herein, the term "complementary" refers to any two or more nucleic acid sequences (e.g., portions or entireties of nucleic acid molecules, target sequences and/or primers) that can undergo cumulative base pairing at two or more individual corresponding positions in antiparallel orientation, as in a hybridized duplex.

As used herein, the term "partition" refers to an isolated volume of fluid. Each partition can be and/or include a fluid volume that is isolated from the fluid volumes of other partitions and/or isolated from a sample. The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), or the like. Accordingly, the partitions may be formed serially, in parallel, or in batch. The partitions may have any suitable volume or volumes.

As used herein, the terms "droplet," "microdroplet," and the like refer to an isolated volume of fluid that is surrounded by an immiscible carrier fluid, e.g., oil. Droplets can be generated using any means known in the art. For example, in some instances droplets can be generated using microfluidics, e.g., microfluidics from Elegen as disclosed in WO2019/040599A1, WO2020/146425A1, and WO2020/176548A1, all of which are incorporated by reference herein.

The terms "linked" and "fused" as used herein refers to a first nucleic acid molecule or polynucleotide covalently or non-covalently joined to a second nucleic acid molecule or polynucleotide. The first nucleic acid molecule or polynucleotide can be directly joined or juxtaposed to the second nucleic acid molecule or polynucleotide or alternatively an intervening nucleic acid molecule or polynucleotide can covalently join the first nucleic acid molecule or polynucleotide to the second nucleic acid molecule or polynucleotide. The term "linked" means not only a fusion of a first nucleic acid molecule or polynucleotide to a second nucleic acid molecule or polynucleotide at the 5' or the 3' end, but also includes insertion of the whole first nucleic acid molecule or polynucleotide (or the second nucleic acid molecule or polynucleotide) into any two nucleotides in the second nucleotide nucleic acid molecule or polynucleotide (or the first nucleotide nucleic acid molecule or polynucleotide, respectively). The first nucleic acid molecule or polynucleotide can be linked to a second nucleic acid molecule or polynucleotide by a phosphodiester bond or a linker. The linker can be a nucleotide or a nucleotide chain or any chemical moiety. The term "linked" is also indicated by a hyphen (-). Such linkage can be accomplished using methods of assembly of two or more nucleic acid molecules and/or polynucleotides provided herein. When such assembly is assembly of single-stranded oligonucleotides, this can be referred to herein as "primary assembly", which can be all or part of a first assembly in certain embodiments disclosed herein. In some embodiments, the two or more single-stranded oligonucleotides that are assembled in a primary assembly are synthetic oligonucleotides.

As used herein, the term "detecting" generally refers to any means of identifying the presence or absence of a target, such as, for example, a desired nucleic acid sequence and/or a molecular barcode. For example, the presence of a desired nucleic acid sequence and/or molecular barcode can be identified by, for instance, nucleic acid sequencing.

As used herein, the term "barcode-targeted PCR" generally refers to PCR comprising use of primers complementary to at least one barcode of a nucleic acid molecule. In some aspects, barcode-targeted-PCR comprises two PCRs: a PCR having a first primer that binds to a first molecular barcode, and a second PCR having a second primer that binds to a second molecular barcode.

II. Methods of Polynucleotide Production

Figure 1B:
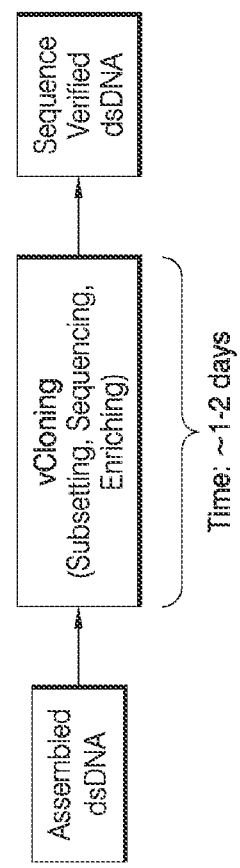

As discussed supra, there is a long felt need in the art for cloning methods and compositions, e.g., cell-free cloning methods and compositions, that can reduce the time, cost, effort, and equipment as compared to the present methods while also increasing the throughput as compared to the presently available methods and compositions. Furthermore, there is a need for cloning methods that are more easily automatable, and flexible enough to accommodate the production of polynucleotides, or highly enriched populations thereof, that can be a wide range of sizes, from hundreds to millions of base pairs. As illustrated in FIG. 1B, the cell-free cloning methods provided herein, meet such long-felt needs. The time required for traditional cell-based cloning, as illustrated in FIG. 1A, is substantially reduced by the cell-free cloning methods provided herein, as illustrated in the non-limiting embodiment shown in FIG. 1B. Such cell-free cloning methods, in some embodiments, can reduce the time for cloning a target or desired polynucleotide or nucleic acid sequence down to 1-2 days from the time from a first assembly or an order is received from a customer for a desired polynucleotide, such as a desired sequence-perfect polynucleotide, to the time that the desired polynucleotide is enriched, generated and produced. Furthermore, it is believed that illustrative cell-free cloning embodiments provided herein, with optimization and automation, can be performed in 1 day or less than 1 day. Such automation can be high-throughput and include a conventional liquid handler and PCR instrumentation, eliminating the need for lower throughput incubators, manual or automated colony pickers, shakers, and centrifuges. Such cell-free methods can be referred to herein as vCloning methods.

Such vCloning or cell-free cloning methods provided herein typically include a vCloning/cell-free cloning module, step(s), process, or subprocess and yield a cell-free cloned polynucleotide, or typically a population of cell-free cloned polynucleotides. As discussed herein, vCloning modules provided herein typically include a subsetting step or submodule, a sequencing step or submodule, and an enriching step or submodule. Cell-free cloning/vCloning methods can be referred to herein as methods for polynucleotide production; and methods for producing, generating, or enriching (e.g., isolating) a nucleic acid molecule, a polynucleotide, a population of polynucleotides, a population of desired polynucleotides, or a population of product polynucleotides. Disclosure provided herein related to any one of such vCloning methods applies to all of these methods unless otherwise noted. Furthermore, a vCloning method provided herein can include, in addition to a vCloning module, an assembly module performed before and/or after the vCloning module. Cell-free cloning/vCloning methods typically include one or more tagging steps either as part of the vCloning module or as part of an assembly module performed immediately before a vCloning module. Furthermore, vCloning methods provided herein can include an assembly module before and after a vCloning module, and can include multiple rounds, where each round includes performance of an assembly module, which can assemble polynucleotides generated from a previous vCloning module, followed by performance of a vCloning module, which optionally can be followed by a final assembly module. Thus, vCloning methods provided herein provide considerable flexibility that helps to make these methods more robust to different desired nucleic acid sequences and to producing polynucleotides, or populations thereof, having a wide range of sizes.

Figure 2:
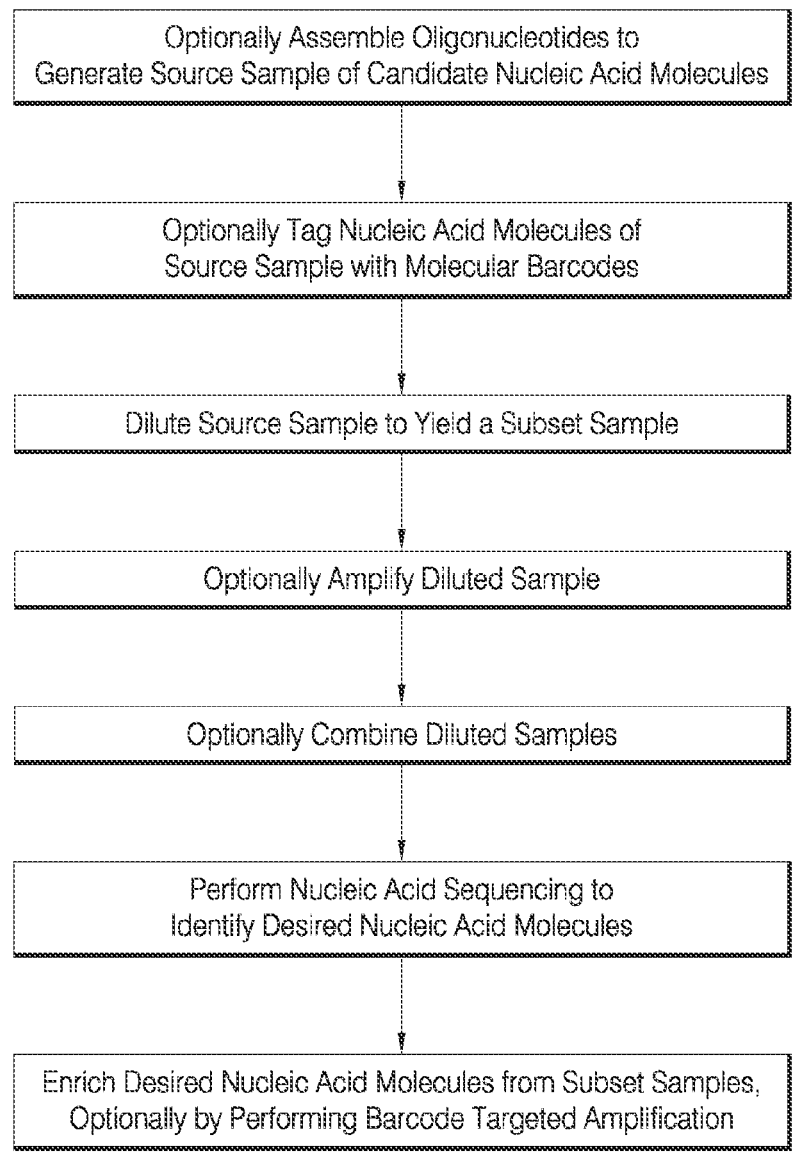
FIG. 2 presents a schematic diagram of a method of polynucleotide production comprising diluting a source sample to yield a diluted sample in accordance with the present disclosure.
Figure 3:
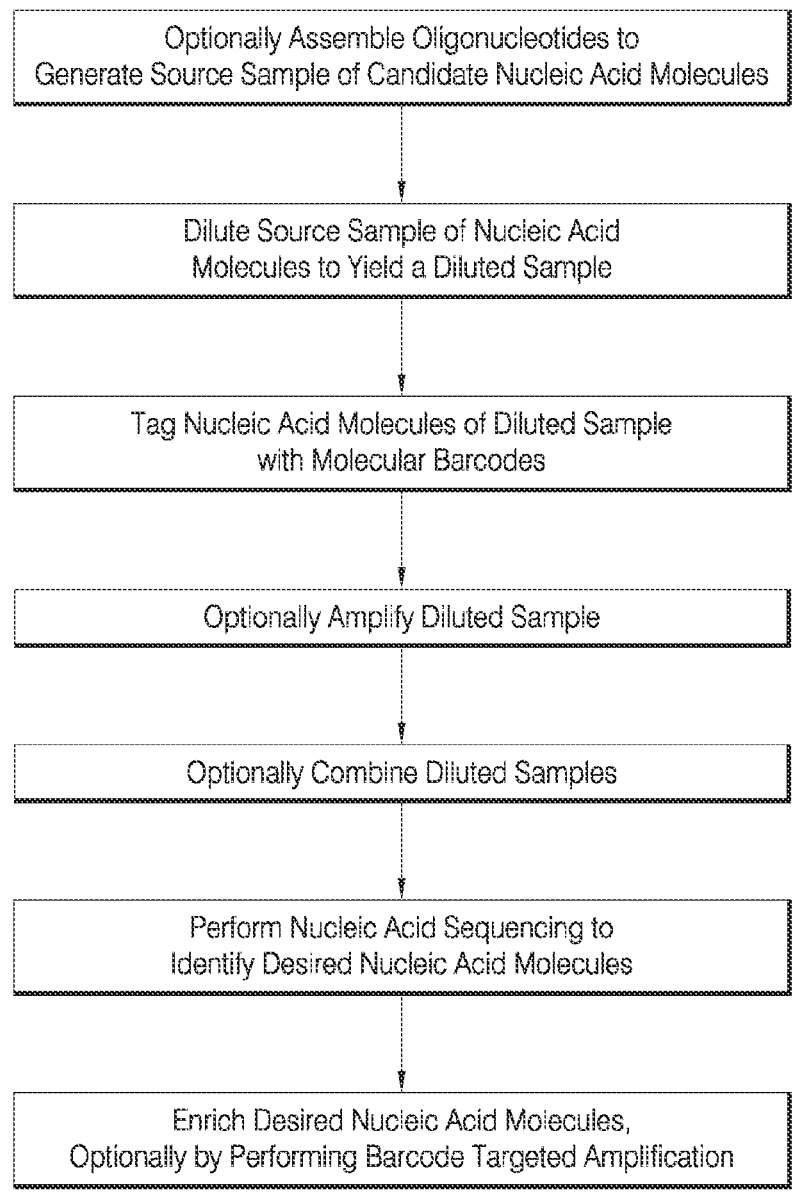
FIG. 3 presents a schematic diagram of an alternative method of polynucleotide production comprising diluting a source sample to yield a diluted sample in accordance with the present disclosure.

FIG. 2 and FIG. 3 provide flow diagrams of non-limiting examples of such vCloning methods of polynucleotide production. As indicated, the non-limiting examples set out in these figures provide certain steps that are performed and certain optional steps. In a related aspect, provided herein is a method of producing or generating a polynucleotide or a population of polynucleotides, a method for production of such a polynucleotide or population, or in certain illustrative embodiments, a method of cell-free cloning of such a polynucleotide or population, which in illustrative embodiments is a partially or fully automated method, wherein the method comprises:

a. diluting a source sample comprising at least $1\times10^5$ source nucleic acid molecules and/or tagged nucleic acid molecules derived therefrom, to form a diluted sample by isolating a target number of the source nucleic acid molecules and/or the tagged nucleic acid molecules away from the source sample, wherein the diluted sample comprises one or more tagged nucleic acid species derived from one or some of the source nucleic acid molecules, wherein the tagged nucleic acid molecules from each tagged nucleic acid species have an identical nucleic acid sequence,
wherein at least one, or in illustrative embodiments at least some of the tagged nucleic acid species in the diluted sample are uniquely tagged source nucleic acid molecules;
b. determining the sequence of at least some of the tagged nucleic acid species, wherein at least 1 of the tagged nucleic acid species is a desired uniquely tagged nucleic acid species, wherein the desired uniquely tagged nucleic acid species comprises the desired nucleic acid sequence; and
c. enriching the polynucleotide having the desired nucleic acid sequence from the diluted sample by enriching one or more polynucleotides of the desired uniquely tagged nucleic acid species, to generate the population of polynucleotides.

In illustrative embodiments, the target number of source nucleic acid molecules and/or tagged nucleic molecules isolated or sampled from the source sample is between 10 and 100,000 nucleic acid molecules. In illustrative embodiments, at least 25% of the polynucleotides in the population of polynucleotides comprise the desired nucleic acid sequence, and wherein the desired nucleic acid sequence is at least 25% identical to a sequence-perfect desired nucleic acid sequence.

In some aspects of any of the methods provided herein the method is performed at least 1, 2, 3, 4, 5, 6, 7, 8, 9, 10, 15, 20, 25, 30, 40, 50, 60, 70, 80, 90, or 100 times to enrich at least 1, 2, 3, 4, 5, 6, 7, 8, 9, 10, 15, 20, 25, 30, 40, 50, 60, 70, 80, 90, or 100 different polynucleotides having 1, 2, 3, 4, 5, 6, 7, 8, 9, 10, 15, 20, 25, 30, 40, 50, 60, 70, 80, 90, or 100 different desired, in some embodiments sequence-perfect, desired nucleic acid sequences, or to enrich at least 1, 2, 3, 4, 5, 6, 7, 8, 9, 10, 15, 20, 25, 30, 40, 50, 60, 70, 80, 90, or 100 different populations of polynucleotides having 1, 2, 3, 4, 5, 6, 7, 8, 9, 10, 15, 20, 25, 30, 40, 50, 60, 70, 80, 90, or 100 different desired, in some embodiments sequence-perfect, desired nucleic acid sequences. In some embodiments, at least 25%, 30%, 40%, 50%, 60%, 70%, 75%, 80%, 85%, 90%, 95%, 96%, 97%, 98%, 99%, 99.5%, 99.9% or 100% of the polynucleotides in each population comprises a respective desired nucleic acid sequence. In some embodiments, the respective desired nucleic acid sequence is at least 25%, 30%, 40%, 50%, 60%, 70%, 75%, 80%, 85%, 90%, 95%, 96%, 97%, 98%, 99%, 99.5%, or 99.9% identical to each respective sequence-perfect desired nucleic acid sequence. In some aspects of any of the methods provided herein at least 2, 3, 4, 5, 6, 7, 8, 9, 10, 15, 20, 25, 30, 40, 50, 60, 70, 80, 90, or 100 different polynucleotides having 2, 3, 4, 5, 6, 7, 8, 9, 10, 15, 20, 25, 30, 40, 50, 60, 70, 80, 90, or 100 different sequence-perfect desired nucleic acid sequences, respectively, are enriched from one subset sample or from one combined sample comprising multiple subset samples. In some embodiments, the sequence-perfect desired polynucleotides are 2, 3, 4, 5, 6, 7, 8, 9, 10, 15, 20, 25, 30, 40, 50, 60, 70, 80, 90, or 100 populations comprising the sequence-perfect desired polynucleotides, wherein the populations comprise at least 95%, 96%, 97%, 98%, 99%, 99.5%, or 99.9% sequence-perfect desired polynucleotides. In some aspects of any of the methods provided herein, the method is performed in solution, e.g., the nucleic acid molecules and/or polynucleotides are not attached to a solid-phase during the method.

In some embodiments, methods herein are cell-free methods that do not include the use of cells for one or more or all of the recited steps of the method. Such cell-free methods can include methods wherein nucleic acid molecules and/or polynucleotide having the desired nucleic acid sequence never enter a cell, for example, never cross the membrane of a cell, for example, the membrane of a bacterial cell. In some embodiments, a cell-free method is one where, for example, source nucleic acid molecules, subsequent polynucleotides, final polynucleotides having the desired nucleic acid sequence, and all intermediate nucleic acid molecules never cross the membrane of a cell during the method. However, it should be noted that before a dilution step herein, or after the polynucleotides are generated using methods herein, the polynucleotides can then be inserted into cells.

a. Assembling Nucleic Acid Molecules

In some aspects, the method includes an optional assembly step, before a subsetting (e.g. dilution) step, such as that provided in any of the methods, sometimes referred to as vCloning methods, provided herein. The assembly step can involve a series of substeps and can also be referred to as an assembly module, an assembly subprocess, an assembly method, or an assembly submethod. It will be understood that reference to an assembly step, unless in the context of a single step, can refer to a series of steps that make up such an assembly module, an assembly subprocess, an assembly method, or an assembly submethod. Furthermore, such assembly step can be referred to herein as a first assembly step, which in illustrative embodiments is a first assembly step before a first subsetting step, in a method provided herein, such as a vCloning method provided herein. The product of an assembly step can be referred to as an assembled nucleic acid molecule.

Accordingly, in certain illustrative embodiments, the method can include before a subsetting (e.g. diluting step), assembling at least two nucleic acid molecules of an initial source of nucleic acid molecules to produce the source sample of nucleic acid molecules. Such assembling can include, for example: performing an assembly reaction in a reaction mixture comprising a plurality of nucleic acid molecules, to generate a plurality of assembled nucleic acid molecules, a population of candidate nucleic acid molecules, or a population of candidate polynucleotides, some, most, or all of which typically have a desired nucleic acid sequence. The exact sequences of candidate nucleic acid molecules typically have not been determined by sequencing. In some embodiments, candidate nucleic acid molecules are generated from synthesis or assembly reactions or isolated from a cell, and in illustrative embodiments generated from synthesis or assembly reactions. The assembled nucleic acid molecules can be single-stranded, double-stranded, and/or comprise both denatured strands of a double-stranded nucleic acid molecule. Typically, at least one, and in illustrative embodiments two or more, or a plurality of the population of candidate nucleic acid molecules or polynucleotides having the desired nucleic acid sequence, have or comprise a nucleic acid sequence that is sequence-perfect with respect to the desired sequence.

In certain illustrative embodiments, the nucleic acid molecules that are assembled into the longer candidate nucleic acid molecules or candidate polynucleotides, in illustrative embodiments to form a source sample, are synthetic oligonucleotides, for example between 10 and 100, 150, 200, 250, 500, or 1,000 kb, or between 50 and 100, 150, 200, 250, 500, or 1,000 kb in length. Assembly reactions for assembling nucleic acid molecules are known in the art. In some aspects, the assembly reaction assembles single-stranded nucleic acid molecules. In some embodiments, the assembly reaction generates a desired polynucleotide comprising between 100 and 10,000 nucleotides in length, for example between 500 and 5,000 nucleotides in length. In some aspects, the assembly reactions can include ligation of hybridized oligonucleotides and/or polynucleotides, for example synthetic oligonucleotides. In illustrative embodiments, single-stranded synthetic oligonucleotides are generated and then hybridized before or during the assembly reaction. In some embodiments, the oligonucleotides comprise 1, 2, 3, 4, 5 or more barcodes and/or an adaptors, at least one of which can comprise the one or more barcodes. In illustrative embodiments, the oligonucleotides comprise one or more non-degenerate barcodes. Such assembly reactions include, as non-limiting examples, polymerase cycling assembly (PCA) (Stemmer et al. Gene. 1995 Oct. 16; 164(1):49-53), isothermal assembly, e.g., Gibson assembly (Gibson et al. Nat Methods. 2009 May; 6(5):343-5), ligase cycling reaction (LCR) (Au et al., 1998; Chandran. Methods Mol Biol. 2017; 1472:105-10), overlap extension PCR (overlapping PCR, PCR SOEing, PCR sewing) (Young and Dong, 2004; Bryksin and Matsumura. Methods Mol Biol. 2013; 1073:31-42; and Horton et al., BioTechniques 2013 54:3, 129-133), PCR incorporating 5' sequences, PCR stitching, enzymatic gene synthesis, annealing and ligation reactions (Climie and Santi, 1990; Smith et al., 1990; Kalman et al., 1990), simultaneous synthesis of two genes via a hybrid gene, shotgun ligation and co-ligation (Eren and Swenson, 1989), insertion gene synthesis (Ciccarelli et al., 1990), gene synthesis via one strand of DNA (Chen et al., 1990), template-directed ligation (Strizhov et al., 1996), microarray-based gene synthesis (Zhou et al., 2004), Blue Heron solid support technology, Sloning building block technology (Ball, 2004; Schmidt, 2006; Bugl et al., 2007), Golden Gate assembly (Engler et al. (2008) PLoS ONE, 3(11): e3647; Engler et al. (2009) PLoS ONE 4(5): e5553), RNA-mediated gene assembly (Wu et al., 2012), the PCR-based thermodynamically balanced inside-out (TBIO) (Gao et al., 2003), nonenzymatic chemical ligation, two-step total gene synthesis method that combines dual asymmetrical PCR (DA-PCR) (Sandhu et al., 1992), PCR-based two-step DNA synthesis (PTDS) (Xiong et al., 2004b), successive PCR method (Xiong et al., 2005, 2006a), or any other suitable method known in the art, or any combinations thereof.

A ligase cycling (or chain) reaction (LCR) can be used method for synthesis of polynucleotides (Au et al.; 1998). Fragments can be assembled from several oligonucleotides via ligation, using a ligase, for example Pfu DNA ligase. After LCR, the full-length gene can be amplified with the mixture of fragments which shared an overlap by denaturation and extension using the outer two oligonucleotides.

In enzymatic gene synthesis, enzymes that repair single-stranded breaks in double-stranded DNA, first discovered in the 1960s in *E. coli* and in T4 bacteriophage infected *E. coli* cells (Meselson, 1964; Weiss and Richardson, 1967; Zimmerman et al., 1967), can be used to join chemically synthesized oligonucleotides, such as deoxyribopolynucleotides, to form continuous bihelical structures (Gupta et al., 1968a). In another example, DNA polymerase I (Klenow) can be used to join oligonucleotides to longer polynucleotides. Oligonucleotides can further be joined together via ligation, for example using a ligase, such as using phage T4 polynucleotide ligase. In some cases, oligonucleotides can be ligated hierarchically, forming longer and longer polynucleotides in each step. In annealing and ligation reactions, both strands of the desired sequences can be divided with short cohesive ends so that adjacent pairs of complementary oligonucleotides can anneal (Climie and Santi, 1990; Smith et al., 1990; Kalman et al., 1990). The synthesized oligonucleotides can be phosphorylated, for example using a kinase, and annealed before ligation into a duplex.

The shotgun ligation approach comprises the assembly of a full gene from several synthesized blocks (Eren and Swenson, 1989). Accordingly, a gene may be sub-assembled in several sections, each constructed by the enzymatic ligation of several complementary pairs of chemically synthesized oligonucleotides with short single strands complementary to that of an adjacent pair. Co-ligation of the sections can achieve the synthesis of the final polynucleotide.

Insertion gene synthesis (IGS) (Ciccarelli et al., 1990) can be used to assemble a DNA sequence in a stepwise manner within a plasmid containing a single-stranded DNA phage origin of replication. The IGS method is based upon consecutive targeted insertions of long DNA oligonucleotides within a plasmid by oligonucleotide-directed mutagenesis.

Gene synthesis via one strand refers to a method to synthesize a gene via one stand (Chen et al.; 1990). A plus-stranded DNA of the target gene can be assembled by a stepwise or single-step T4 DNA ligase reaction with several, for example six, oligonucleotides in the presence of multiple, for example two, terminal complementary oligonucleotides and multiple, for example three, short interfragment complementary oligonucleotides. The use of fewer synthesized bases, in comparison to the double-strand or overlap methods can reduce costs.

Template-directed ligation refers to a method to construct large synthetic genes by ligation of oligonucleotide modules, by partial annealing with a single-stranded DNA template derived from a wild-type gene (Strizhov et al.; 1996). Oligonucleotides comprising only one strand can be synthesized, in contrast to other technologies that require synthesis of two strands. A ligase, such as the Pfu DNA ligase, can be used to perform thermal cycling for assembly, selection and ligation of full-length oligonucleotides as well as for linear amplification of the template-directed ligation (TDL) product. Due to its reliance on a homologous template, this method is suitable to the synthesis of only a limited number of sequences with similarity to an existing polynucleotide molecule.

Microarray-mediated gene synthesis, as a general concept, is based on the capacity to immobilize tens of thousands of specific probes on a small solid surface (Lockhart and Barlow, 2001). For the production of arrays, DNA can either be synthesized directly on the solid support (Lipshutz et al., 1999; Hughes et al., 2001) or can be deposited in a pre-synthesized form onto the surface, for example with pins or ink-jet printers (Goldmann and Gonzalez, 2000). The oligonucleotides obtained can be used in ligation under thermal cycling conditions to generate DNA constructs of several hundreds of base-pairs. Another microchip-based technology for accurate multiplex gene synthesis, the modified array-mediated gene synthesis technology (Tian et al., 2004), is similar to amplification and assembly of chip-eluted DNA AACED), a method developed for high-throughput gene synthesis (Richmond et al., 2004). Pools of thousands of 'construction' oligonucleotides and tagged complementary 'selection' oligonucleotides can be synthesized on photo-programmable microfluidic chips, released, ligation amplified, and selected by hybridization to reduce synthesis errors (Tian et al., 2004).

The Blue Heron technology, developed by Blue Heron Biotechnology, is based on a solid-phase support strategy based on the GeneMaker platform and enables automation (Parker and Mulligan, 2003; Mulligan and Tabone, 2003; Mulligan et al., 2007). The GeneMaker protocol may generally comprise a user sequence data entry, an algorithm designing suitable oligonucleotides for the assembly of entered sequence, oligonucleotides synthesis and hybridization into duplexes, automated ligation based solid-phase assembly through automated sequential additions inside a column on a solid support matrix, and/or cloning and sequence verification. The Blue Heron technology relies on the sequential addition of building blocks to lower errors that occur with other gene assembly methods based on non-serial pools of building blocks, such as PCR methods.

Sloning building block technology (Slonomics™; Sloning Biotechnology GmbH, Puchheim, Germany) is another method using a ligation-based strategy for chemical gene synthesis (Adis International, 2006). The Sloning synthesis method consists of a series of parallel iterative and standardized reaction steps (pipetting, mixing, incubation, washing) (Schatz and O'Connell, 2003; Schatz et al., 2004; Schatz, 2006). In contrast to ligating oligonucleotides specifically designed and synthesized for a given gene construct, Sloning technology uses a library of standardized building blocks that can be combined to form any desired sequence with a series of standardized, fully automated, cost-effective reaction steps (Schatz and O'Connell, 2003; Schatz, 2006).

The Golden-gate method (see, e.g., Engler et al. (2008) PLoS ONE, 3(11): e3647; Engler et al. (2009) PLoS ONE 4(5): e5553) offers standardized, multi-part DNA assembly. The Golden-gate method can use Type IIs endonucleases, whose recognition sites are distal from their cutting sites. There are several different Type IIs endonucleases to choose from, for example BsaI. The Golden-gate method can be advantageous by the use of a single Type IIs endonuclease. The Golden-gate method is further described in U.S. Patent Pub. 2012/0"258487, which is incorporated herein by reference in its entirety.

In some embodiments, RNA-mediated gene assembly is used to assemble RNA transcripts from DNA elements, optionally immobilized to a surface forming an immobilized DNA array. DNA elements are designed to include an RNA polymerase (RNAP) promoter sequence, such as a T& RNA polymerase promoter sequence, toward the 5' end. Hybridization of an oligonucleotide encoding the promoter sequence, such as the T7 RNAP promoter sequence, to a DNA element can yield a double-stranded promoter. Addition of RNAP may affect the transcription from these optionally surface-bound promoters yielding many RNA copies. These amplified RNA molecules can be designed to allow self-assembly to yield a longer RNA. Briefly, the DNA elements can be designed to encode "segment sequences", which are the sections of the desired full-length RNA transcript, and "splint sequences", which are complementary RNAs that serve as templates to direct the correct assembly of the RNA segments. The DNA elements encoding RNA segments or splints may be chosen to optimize one or more reactions during the synthesis of assembled polynucleotides. For example, the DNA elements may be constructed such that the 5' end of each RNA transcript corresponds to a GG dinucleotide, which is believed to affect higher efficiency of transcription exhibited by T7 RNA polymerase (T7 RNAP). GGG trinucleotide sequences at the 5' terminus may in turn be avoided, to avoid giving rise to a ladder of poly G transcripts in which the number of G residues can range from 1-3, attributed to "slippage" of the enzyme during coupling of GTP. Assembly can be affected via RNA:RNA hybridization of the segments to the splints. Nicks can be sealed chemically or enzymatically, using a suitable enzyme known in the art. In one example, the assembly of the RNA segment sequences into the full-length RNA transcript includes ligation with T4 RNA ligase 2. Triphosphorylated transcripts, such as those generated by 17 RNA polymerase can be "trimmed" to their monophosphorylated analogues before ligation. Trimming can be accomplished by treatment of the transcript pool with RNA 5' pyrophosphohydrolase removing a pyrophosphate group from the 5' end of each RNA. The transcript, once synthesized, can be copied by reverse transcription polymerase chain reaction (RT-PCR) to yield the corresponding gene. The assembled RNA sequence or its DNA equivalent may be amplified using a suitable nucleic acid amplification method, including those described elsewhere herein. The method is further described in Wu et al. (Cheng-Hsien Wu, Matthew R. Lockett, and Lloyd M. Smith, RNA-Mediated Gene Assembly from DNA Arrays, 2012, Angew. Chem. Int. Ed. 51, 4628-4632), which is herein incorporated by reference in its entirety.

Other approaches include, nonenzymatic chemical ligation of DNA, for example with cyanogen bromide as a condensing agent, as described for the synthesis of a 183 bp biologically active mini-gene (Shabarova et al., 1991). In some embodiments, assembly of oligonucleotides comprises the use of CLICK chemistry. Suitable methods to link various molecules using CLICK chemistry are known in the art (for CLICK chemistry linkage of oligonucleotides, see, e.g. El-Sagheer et al. (PNAS, 108:28, 11338-11343, 2011). Click chemistry may be performed in the presence of CuI.

TBIO synthesis requires only sense-strand primers for the amino-terminal half and only antisense-strand primers for the carboxy-terminal half of a gene sequence. In addition, the TBIO primers may contain identical regions of temperature-optimized primer overlaps. The TBIO method involves complementation between the next pair of outside primers with the termini of a fully synthesized inside fragment. TBIO bidirectional elongation is completed for a given outside primer pair before the next round of bidirectional elongation takes place.

DA-PCR is a one-step process for constructing synthetic genes. In one example, four adjacent oligonucleotides of, e.g. 17-100 bases in length with overlaps of, e.g. 15-17 bases are used as primers in a PCR reaction. Other suitable oligonucleotide and overlap sizes are within the bounds of the invention as further described herein. The quantity of the two internal primers is highly limited, and the resultant reaction causes an asymmetric single-stranded amplification of the two halves of the total sequence due to an excess of the two flanking primers. In subsequent PCR cycles, these dual asymmetrically amplified fragments, which overlap each other, yield a double-stranded, full-length product.

Successive PCR is a single step PCR approach in which half the sense primers correspond to one half of the template to be assembled, and the antisense primers correspond to the second half of the template to be assembled. With this approach, bidirectional amplification with an outer primer pair will not occur until amplification using an inner primer pair is complete.

PDTS typically involves two steps. First individual fragments of the DNA of interest are synthesized: In some embodiments of the invention, 10-12 oligonucleotides, such as oligonucleotides of length of about 60, 80, 100, 125, 150, 175, 200, 250, 300, 350, or more nucleotides, with about 20 bp overlap are mixed and a PCR reaction is carried out with a polymerase, such as pfu DNA, to produce longer DNA fragments. And second, the entire sequence of the DNA of interest is synthesized: 5-10 PCR products from the first step are combined and used as the template for a second PCR reaction with a polymerase, such as pyrobest DNA polymerase with two outermost oligonucleotides as primers.

In some aspects, nucleic acid molecules can be assembled such that the assembled nucleic acid molecule is a circularized nucleic acid molecule. In some aspects, the assembly reaction can include components for amplification of circularized nucleic acid molecules, as disclosed elsewhere herein. In some aspects, the assembled nucleic acid molecule includes an origin of replication. In some embodiments, the origin of replication is OriC. In some embodiments, the OriC is derived from E. coli. In illustrative embodiments, the OriC can bind to an enzyme having DnaA activity. In some embodiments, the OriC includes the sequence of SEQ ID NO:1.

In some embodiments, between 2 and 100, 90, 80, 70, 60, 50, 40, 30, or 20 oligonucleotides and/or nucleic acid molecules can be assembled into a circularized nucleic acid molecule. In some embodiments, between 10 and 100, 90, 80, 70, 60, 50, 40, 30, or 20 oligonucleotides and/or nucleic acid molecules can be assembled into a circularized nucleic acid molecule. In some embodiments, between 25 and 100, 90, 80, 70, 60, 50, 40, or 30 oligonucleotides and/or nucleic acid molecules can be assembled into a circularized nucleic acid molecule. In some embodiments, between 25 and 75 oligonucleotides and/or nucleic acid molecules can be assembled into a circularized nucleic acid molecule, also referred herein to as a polynucleotide having a desired nucleic acid sequence. In some aspects, the length of assembled, circularized nucleic acid molecule can be at least 500, 750, 1,000, 2,500, 5,000, 7,500, 10,000, 100,000, 250,000, 500,000, 750,000, 1,000,000, 2,500,000, 5,000,000, 10,000,000, 20,000,000, 30,000,000, 40,000,000, 50,000,000, 75,000,000, 100,000,000, 200,000,000, or 300,000,000 bases. In some aspects, from about 0.1 kilobases (kb) to about 500 megabases (Mb), about 0.1 kb to about 250 Mb, about 0.1 kb to about 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, 15 kb, 10 kb, or 5 kb, or about 0.01 kb to about 30 kb, about 0.1 kb to about 30 kb, about 0.5 kb to about 100 Mb, 75 Mb, 50 Mb, 25 Mb, 20 Mb, 15 Mb, 10 Mb, 5 Mb, 500 kb, 250 kb, 100 kb, 75 kb, 50 kb, 30 kb, 20 kb, 10 kb, 5 kb, or 4 kb.

In some aspects, the assembling includes a reaction mixture, wherein the reaction mixture can include a 5' exonuclease, a polymerase, and a DNA ligase. In some embodiments, the assembling is performed at an isothermal temperature. In some embodiments, an isothermal temperature is held within 0.1° C., 0.5° C., 1° C., 2° C., or 5° C. of a target temperature. In some embodiments, the target temperature can be 15° C., 20° C., 25° C., 30° C., 35° C., 37° C., 42° C., 45° C., or 50° C.

Serial combinations of these assembly methods can be used in a single assembly step or module. For the sake of clarity, providing a reaction mixture for an assembly reaction and performing an assembly reaction, are optional steps that are performed in certain illustrative embodiments, of methods herein. In some aspects, less than or equal to 99%, 98%, 97%, 96%, or in more illustrative aspects less than or equal to 95%, 90%, 80%, 75%, 70%, 65%, 60%, 55%, 50%, 45%, 40%, 35%, or 30%, or between 25% and 95%, 90%, 80%, 75%, 70%, 65%, 60%, 55%, 50%, 45%, 40%, 35%, 30%, 25%, 20%, 15%, 10%, 5%, 4%, 3%, 2%, or 1%, or between 1% on the low end of the range and 2%, 3%, 4%, 5%, 10%, 15%, 20%, 25%, 30%, 35%, 40%, 45%, 50%, 55%, 60%, 65%, 70%, 75%, 80%, 90%, 95%, 96%, 97%, 98%, or 99%, on the high end of the range, or between 1%, 2%, 3%, 4%, 5%, 10%, 15%, 20%, 25%, 30%, 35%, 40%, or 45% on the low end of the range and 50% on the high end of the range, or between 75% and 95%, 90%, or 80% of the nucleic acid molecules in the source sample are sequence-perfect with respect to a corresponding portion of the desired nucleic acid sequence. In some aspects of any of the methods provided herein that include an assembling nucleic acid molecules step, the step can be performed in solution, e.g., the nucleic acid molecules and polynucleotides are not attached to a solid-phase during the step.

In some aspects, including as non-limiting examples, methods for producing, enriching, or generating a polynucleotide having a desired sequence, the length of the desired nucleic acid sequence or polynucleotide produced, generated, or enriched is at least 100, 200, 300, 400, 500, or 750 bases or 1 kb, 2.5 kb, 5 kb, 7 kb, 10 kb, 100 kb, 250 kb, 500 kb, 750 kb, 1 Mb, 2.5 Mb, 5 Mb, 10 Mb, 20 Mb, 30 Mb, 40 Mb, 50 Mb, 75 Mb, 100 Mb, 200 Mb, or 300 Mb bases. In some aspects, the length of the polynucleotide is from about 0.1 kb to about 500 Mb, 250 Mb, 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, 15 kb, 10 kb, 5 kb, or from about 0.2 kb to about 100 kb, about 0.1 kb to about 30 kb, or from about 0.5 kb to about 30 kb, 20 kb, 10 kb, 5 kb, or 4 kb. In some aspects, the polynucleotide is from about 0.1 kb to about 30 kb in length. In some aspects, the length of the polynucleotide is from about 1 kb on the low end of the range to 2 kb, 3 kb, 4 kb, 5 kb, 10 kb, 15 kb, 20 kb, 25 kb, 30 kb, 40 kb, or 50 kb on the high end of the range, or from about 1.5 kb on the low end of the range to about 3 kb, 4 kb, 5 kb, 10 kb, 15 kb, 20 kb, 25 kb, 30 kb, 40 kb, or 50 kb on the high end of the range, or from about 2 kb on the low end of the range to about 3 kb, 4 kb, 5 kb, 10 kb, 15 kb, 20 kb, 25 kb, 30 kb, 40 kb, or 50 kb on the high end of the range, or from about 2.5 kb on the low end of the range to about 3 kb, 4 kb, 5 kb, 10 kb, 15 kb, 20 kb, 25 kb, 30 kb, 40 kb, or 50 kb on the high end of the range, or from about 3 kb on the low end of the range to about 4 kb, 5 kb, 10 kb, 15 kb, 20 kb, 25 kb, 30 kb, 40 kb, or 50 kb on the high end of the range. In some embodiments, the size ranges for polynucleotides produced are any of the ranges provided herein for subsequent polynucleotides. A skilled artisan will recognize that methods provided herein are flexible and can produce polynucleotides of a wide range of lengths depending on the number and length of the nucleic acids in the source sample.

In some aspects, the polynucleotide produced, enriched, or generated comprises one or more desired nucleic acid sequences. In some aspects, the polynucleotide comprises one or more nucleic acid molecules each comprising one or more desired nucleic acid sequences. In some aspects, the polynucleotide comprises one or more assembled nucleic acid molecules, each comprising one or more desired nucleic acid sequences.

In some embodiments, the desired nucleic acid sequence comprises at most 1, 2, 3, 4, 5, 6, 7, 8, 9, 10, 15, 20, 30, 40, or 50 errors, or 50 or more errors relative to the sequence-perfect desired nucleic acid sequence. In illustrative embodiments, the polynucleotide produced, enriched, or generated comprises a desired nucleic acid sequence that is sequence-perfect, i.e., has 0 errors relative to the sequence-perfect desired nucleic acid sequence. In some aspects, the population of polynucleotides produced, enriched, or generated comprises sequences can have an error rate of 1:10,000, 1:15,000, 1:20,000, 1:25,000, 1:30,000, 1:35,000, 1:40,000, 1:45,000, 1:50,000, 1:60,000, 1:70,000, 1:80,000, 1:90,000, 1:100,000, 1:110,000, 1:120,000, 1:130,000, 1:140,000, 1:150,000, 1:160,000, 1:170,000, 1:180,000, 1:190,000, 1:200,000, 1:210,000, 1:220,000, 1:230,000, 1:240,000, 1:250,000, 1:300,000, 1:350,000, 1:400,000, 1:450,000, 1:500,000, 1:600,000, 1:700,000, 1:800,000, or 1:900,000 or lower. In some embodiments, the sequences in the population can have an error rate that is greater than 1:1,000,000, 1:2,000,000, 1:3,000,000, 1:4,000,000, or 1:5,000,000. In some embodiments, the sequences in the population can have an error rate between 1:10,000, 1:15,000, 1:20,000, 1:25,000, 1:30,000, 1:35,000, 1:40,000, 1:45,000, 1:50,000, 1:60,000, 1:70,000, 1:80,000, 1:90,000, and 1:100,000 on the low end of the range and 1:30,000, 1:35,000, 1:40,000, 1:45,000, 1:50,000, 1:60,000, 1:70,000, 1:80,000, 1:90,000, 1:100,000, 1:110,000, 1:120,000, 1:130,000, 1:140,000, 1:150,000, 1:160,000, 1:170,000, 1:180,000, 1:190,000, 1:200,000, 1:210,000, 1:220,000, 1:230,000, 1:240,000, 1:250,000, 1:300,000, 1:350,000, 1:400,000, 1:450,000, 1:500,000, 1:600,000, 1:700,000, 1:800,000, or 1:900,000 on the high end of the range In some aspects of any of the methods provided herein, including as non-limiting examples, any method that includes an optional assembly step, including as non-limiting examples, methods for producing, enriching, or generating a polynucleotide having a desired sequence, and in illustrative embodiments having a sequence-perfect desired nucleic acid sequence, the method is performed in four days or less, three days or less, two days or less, 48 hours or less, 46 hours or less, 44 hours or less, 42 hours or less, 40 hours or less, 38 hours or less, 36 hours or less, 34 hours or less, 32 hours or less, 30 hours or less, 28 hours or less, 26 hours or less, 24 hours or less, 23 hours or less, 22 hours or less, 21 hours or less, 20 hours or less, 19 hours or less, 18 hour or less, 17 hours or less, 16 hours or less, 15 hours or less, 14 hour or less, 13 hours or less, or 12 hours or less. In some embodiments, the method is performed in from 8 hours to 6, 5, 4, 3, 2, or 1 day, or from 1 day to 6, 5, 4, 3, or 2 days.

In some aspects, the method from subsetting (e.g., diluting) a source sample to enriching a polynucleotide is performed in three days or less, two days or less, 48 hours or less, 46 hours or less, 44 hours or less, 42 hours or less, 40 hours or less, 38 hours or less, 36 hours or less, 34 hours or less, 32 hours or less, 30 hours or less, 28 hours or less, 26 hours or less, 24 hours or less, 23 hours or less, 22 hours or less, 21 hours or less, 20 hours or less, 19 hours or less, 18 hour or less, 17 hours or less, 16 hours or less, 15 hours or less, 14 hour or less, 13 hours or less, or 12 hours or less. In some embodiments, the method from subsetting a source sample to enriching a polynucleotide is performed in from 8 hours to 6, 5, 4, 3, 2, or 1 day, or from 1 day to 6, 5, 4, 3, or 2 days.

In some aspects, the nucleic acid molecules and/or polynucleotides are provided as circular nucleic acid molecules and/or polynucleotides or are circularized during the method. In illustrative embodiments, the nucleic acid molecules and/or polynucleotides are provided as linear nucleic acid molecules and/or polynucleotides and are not circularized during the method. In some embodiments, the nucleic acid molecules and/or polynucleotides transition between linear and circularized at least 1, 2, or 3 times during the method.

In some embodiments, methods provided herein can include 2 or more assembly reactions, for example, 2 or more first assembly reactions that can be performed in parallel. Each assembly reaction can involve assembling 2 or more nucleic acids using any of the methods provided herein as appropriate depending on whether the nucleic acids to be assembled include single-stranded or double-stranded nucleic acid molecules. For example, 2, 3, 4, 5, 6, 7, 8, 9, 10, 11, 12, or more nucleic acid molecules can be assembled in a first assembly reaction or module, and the same or a different number of nucleic acid molecules can be assembled in a second, third, fourth, fifth, sixth, etc. assembly reaction or module, which in illustrative embodiments, are all performed in parallel.

This flexibility of cell-free cloning methods provided herein provides the advantage of breaking up a single assembly reaction into multiple assembly reactions to minimize the production of incorrect, undesirable, or erroneous assembly products. Such assembly reactions can use different assembly technologies in certain illustrative embodiments, to minimize the production of incorrect assembly products. For example, if a nucleic acid molecule to be assembled from single-stranded nucleic acid molecules that contains one or more distinct stretches of identical, similar, or repetitive nucleic acid sequences, in certain illustrative embodiments, portions of such nucleic acid molecules can be first assembled in separate reactions, for example to avoid misassembly. Then, optionally after performance of a cell-free cloning module, such assembled double-stranded polynucleotides can be assembled into larger subsequent polynucleotides using a different assembly technology (e.g., Gibson assembly), which is less prone to producing incorrect assembly products for nucleic acids or polynucleotides to be assembled that have significant region(s) of complementary nucleic acid sequence(s). Thus, an assembly reaction can be split into multiple assembly reactions to reduce incorrect assembly products based on one or more stretches of traditionally problematic sequence, as disclosed elsewhere herein, between nucleic acids or polynucleotides to be assembled.

b. Tagging Nucleic Acid Molecules with Barcodes

As indicated in FIG. 2 and FIG. 3, in illustrative embodiments of vCloning methods provided herein, nucleic acid molecules are tagged with one or more molecular barcodes either before (FIG. 2) or after (FIG. 3) a subsetting or dilution step. Accordingly, as shown in FIG. 2, in some aspects, a method of polynucleotide production comprising a subset withdrawal or dilution step, comprises adding one or more molecular barcodes to the source sample to tag nucleic acid molecules therein. Other aspects, as shown in FIG. 3, provide a method of polynucleotide production comprising a subset withdrawal or dilution step, wherein one or more molecular barcodes are added to the subset or diluted sample to tag nucleic acid molecules therein. Various methods for tagging nucleic acid molecules with molecular barcodes are known and can be used in methods herein. Furthermore, additional details regarding molecular barcodes that can be added to nucleic acids in a tagging step herein, are provided in the Molecular Barcodes section and elsewhere herein.

In some aspects, the method comprises tagging at least one nucleic acid molecule of the source sample or the diluted sample with at least one molecular barcode. In illustrative embodiments, the molecular barcode is a non-degenerate barcode from a set or library of non-degenerative barcodes. In some aspects, the tagging comprises ligating at least one molecular barcode and at least one nucleic acid molecule, such as an assembled nucleic acid molecule of the source sample or the diluted sample. In some aspects, the tagging is performed before the assembly, wherein some portion of the synthesized nucleic acids to be used for assembly, typically a nucleic acid that will be on the end of the assembled nucleic acid molecule, contain one barcode of a set or sets of barcodes. In some aspects, the tagging comprises an amplification reaction, such as a polymerase chain reaction (PCR). In illustrative aspects, the number of unique molecular barcodes or molecular barcode combinations in a set used in methods herein is less than the number of nucleic acid molecules of the source sample. Furthermore, although, in some aspects, the number of unique molecular barcodes or molecular barcode combinations in a set is less than the number of nucleic acid molecules of the diluted sample, typically the number of unique molecular barcodes or barcode combinations in a set used in methods herein is greater than the number of nucleic acid molecules in the diluted sample. In certain illustrative aspects, the number of unique molecular barcodes or molecular barcode combinations is greater than the number of nucleic acid molecules of the diluted sample. In some aspects, the number of unique molecular barcodes or molecular barcode combinations is about the same as the number of nucleic acid molecules of the diluted sample. In some embodiments, the ratio of unique molecular barcodes, or in some subaspects, of unique combinations of molecular barcodes (molecular barcode combinations), to source nucleic acid molecules, such as for example candidate nucleic acid molecules in the source sample is less than, about, exactly, or targeted to be 1:10,000,000, 1:1,000,000, 1,750,000, 1:500,000, 1:250,000, 1:100,000, 1:50,000, 1:25,000, 1:10,000, 1:5,000; 1:2,500, 1:1,000, 1:500, 1:100, or 1:50. In some embodiments, the ratio of unique molecular barcodes, or in some subaspects, of unique combinations of molecular barcodes (molecular barcode combinations), to source nucleic acid molecules, such as for example candidate nucleic acid molecules in the source sample, or nucleic acid molecules or species of the subset (e.g., diluted) sample, is 1:10, 1:5, 1:4, 1:3, 1:2, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes to the number of source nucleic acid molecules or nucleic acid molecules or nucleic acid species of the subset sample. In some embodiments, the ratio of unique molecular barcodes, or in some subaspects, of unique combinations of molecular barcodes in a set used to tag source nucleic acid molecules, to source nucleic acid molecules, such as for example candidate nucleic acid molecules in the source sample or species in the source sample is between 1:1,000 on the low end of the range and $1:1\times10^{18}$, $1:1\times10^{15}$, $1:1\times10^{12}$, $1:1\times10^{9}$, $1:1\times10^{8}$, $1:1\times10^{7}$, $1:1\times10^{6}$, $1:1\times10^{5}$, $1:1\times10^{4}$ on the high end of the range, or between $1:1\times10^{4}$ on the low end of the range and $1:1\times10^{18}$, $1:1\times10^{15}$, $1:1\times10^{12}$, $1:1\times10^{9}$, $1:1\times10^{8}$, $1:1\times10^{7}$, $1:1\times10^{6}$, $1:1\times10^{5}$ on the high end of the range, or between $1:1\times10^{5}$ on the low end of the range and $1:1\times10^{18}$, $1:1\times10^{15}$, $1:1\times10^{12}$, $1:1\times10^{9}$, $1:1\times10^{8}$, $1:1\times10^{7}$, and $1:1\times10^{6}$ on the high end of the range. In some embodiments, the ratio of unique barcode combinations to candidate nucleic acid molecules in the source sample is between $1:1\times10^{4}$ and $1:1\times10^{7}$. In some embodiments, the ratio of unique barcode combinations to candidate nucleic acid molecules in the source sample is between $1:1\times10^{5}$ and $1:1\times10^{7}$. In some embodiments, the ratio of unique barcode combinations to candidate nucleic acid molecules in the source sample is between $1:1\times10^{5}$ and $1:5\times10^{6}$. In some embodiments, the ratio of unique barcode combinations to candidate nucleic acid molecules in the source sample is between $1:6\times10^{5}$ and $1:5\times10^{6}$.

In some embodiments, between 1%, 5%, 10%, 20%, 25%, 30%, or 40% on the low end of the range and 50% on the high end of the range of tagged nucleic acid molecules of a source sample or nucleic acid species of a subset sample are uniquely tagged. In some embodiments, at least 1%, 5%, 10%, 20%, 25%, 30%, 40%, 50%, 60%, 70%, 75% 80%, 85%, 90%, 95%, or 99% of tagged nucleic acid molecules of a source sample or nucleic acid species of a subset sample are uniquely tagged. In illustrative embodiments, at least one nucleic acid species in a subset sample is a uniquely tagged species. Uniquely tagged nucleic acid species are nucleic acid molecules that share the same sequence, including, in some embodiments, the desired nucleic acid sequence and molecular barcode(s) or molecular barcode combination. Thus, two nucleic acid species can have the same desired nucleic acid sequences but different barcodes, the same barcodes but different sequences corresponding to the same desired nucleic acid sequence (or a different desired nucleic acid sequence), or different sequences corresponding to the same desired nucleic acid sequence (or a different desired nucleic acid sequence) and different barcodes. Thus, uniquely tagged nucleic acid species do not share the same molecular barcode or molecular barcode combination with any other nucleic acid species in the same sample, e.g., source sample or subset sample. However, there may be two or more tagged nucleic acid molecules in a uniquely tagged species in the same sample, for example, if two nucleic acid molecules with the same sequence-perfect desired nucleic acid sequence were both tagged with the same molecular barcode or molecular barcode combination.

In some embodiments, between 1%, 5%, 10%, 20%, 25%, 30%, or 40% on the low end and 50% on the high end of the range of tagged nucleic acid molecules of a source sample or nucleic acid species of a subset sample are non-uniquely tagged, also referred to as redundantly tagged.

In some embodiments, the ratio of unique molecular barcodes, or in some subaspects, of unique combinations of molecular barcodes (molecular barcode combinations), to the target number of the subset (e.g., diluted) sample, is about, exactly, or targeted to be 1:10, 1:5, 1:4, 1:3, 1:2, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes. In some embodiments, the target number is based on the number of nucleic acid species that should be sequenced to have a high probability of identifying a nucleic acid species having the desired nucleic acid sequence, and in some embodiments the sequence-perfect desired nucleic acid sequence. In some embodiments, the number of nucleic acid species that should be sequenced is determined based on the error-rate of the source nucleic acid molecules. For example, if the source nucleic acid molecules contain a high number of errors, then a higher number of nucleic acid species in the subset sample may have to be sequenced to have a high probability of identifying a nucleic acid species having the desired nucleic acid sequence, and in some embodiments the sequence-perfect desired nucleic acid sequence. With a higher number of nucleic acid species to be sequenced, the target number of nucleic acid molecules in the subset sample increases, and the number of barcodes used can increase to maintain the same ratio of unique molecular barcodes to nucleic acid species.

In some embodiments, the method comprises a barcoding or tagging reaction which includes adding between 3 and 10,000, between 3 and 9,000, between 3 and 8,000, between 3 and 7,000, between 3 and 6,000, between 3 and 5000, between 3 and 4000, between 3 and 3000, between 3 and 2000, between 3 and 1000, between 3 and 750, between 3 and 500, between 3 and 450, between 3 and 400, between 3 and 384, between 3 and 350, between 3 and 300, between 3 and 250, between 3 and 200, between 3 and 150, between 3 and 100, between 3 and 96, between 3 and 90, between 3 and 80, between 3 and 70, between 3 and 60, between 3 and 50, between 3 and 40, between 3 and 30, between 3 and 20, between 3 and 20, or between 3 and 10 unique molecular barcodes to one or more nucleic acid molecules of the source and/or diluted samples. In some aspects, the method comprises attaching (e.g., in an amplification or ligation reaction) 1, 2, 3, 4, 5,6, 7, 8, 9, or 10 molecular barcodes from 1, 2, 3, 4, 5,6, 7, 8, 9, or 10 or more sets of molecular barcodes, to a single nucleic acid molecule. The set of possible combinations of multiple barcodes that can be attached to a single nucleic acid molecule are referred to herein as combinations of molecular barcodes (also referred to herein as molecular barcode combinations), and the set of possible unique barcode combinations that can be attached to a single nucleic acid molecule are referred to herein as unique combinations of molecular barcodes (also referred to herein as unique molecule barcode combinations). In some embodiments, the unique combination of barcodes is between 3 and 150,000, between 3 and 147,456, between 3 and 200,000, between 3 and 100,000, between 3 and 50,000, between 3 and 36864, between 3 and 25,000, between 3 and 10,000, between 3 and 9,000, between 3 and 8,000, between 3 and 7,000, between 3 and 6,000, between 3 and 5000, between 3 and 4000, between 3 and 3000, between 3 and 2304, between 3 and 2000, between 3 and 1000, between 3 and 750, between 3 and 500, between 3 and 450, between 3 and 400, between 3 and 350, between 3 and 300, between 3 and 250, between 3 and 200, between 3 and 150, between 3 and 100, between 3 and 90, between 3 and 80, between 3 and 70, between 3 and 60, between 3 and 50, between 3 and 40, between 3 and 30, between 3 and 20, between 3 and 20, or between 3 and 10 unique combination of barcodes. In some embodiments, the unique combination of barcodes is between 64 and 15,000, between 64 and 147,456, between 64 and 200,000, between 64 and 100,000, between 64 and 50,000, 64 and 25,000, between 64 and 10,000, between 64 and 9,000, between 64 and 8,000, between 64 and 7,000, between 64 and 6,000, between 64 and 5000, between 64 and 4000, between 64 and 3,000, between 64 and 2304, between 64 and 2000, between 64 and 1000, between 64 and 750, between 64 and 500, between 64 and 450, between 64 and 400, between 64 and 350, between 64 and 300, between 64 and 250, between 64 and 200, between 64 and 150, between 64 and 100, between 64 and 90, between 64 and 80, and between 64 and 70.

In some aspects of any of the methods provided herein that include a tagging reaction, which is typically a step of tagging nucleic acid molecules with barcodes, the step can be performed in solution, e.g., the nucleic acid molecules and polynucleotides are not attached to a solid-phase during the step.

In some aspects of any of the methods provided herein that include a step of tagging nucleic acid molecules with barcodes, the tagging can be part of a multiplex method that comprises tagging different source or subset samples in parallel and combined at later steps. In some embodiments, different source or subset samples barcoded in parallel can be barcoded with different barcodes such that each source or subset sample has unique barcodes on the tagged nucleic acid molecules. In some embodiments, one or more of the source or subset samples contain at one identical barcode on the nucleic acid molecules. In some aspects of any of the methods provided herein that include a step of tagging nucleic acid molecules with barcodes, the tagging can be part of a multiplex method that comprises combining different source or subset samples and barcoding the combined sample. In some embodiments, at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 source or subset samples are combined before tagging. In some embodiments, between 2, 3, 4, 5, 6, 7, 8, 9, 10, 15, 20, 25, 30, 35, 40, 45, 50, 60, 70, 80, or 90 source or subset samples on the low end of the range, and 100 source or subset samples on the high end of the range, are combined before tagging. In some embodiments, between 2, 3, 4, 5, 6, 7, 8, 9, 10, 15, 20, 25, 30, 35, 40, 45, 50, 60, 70, 80, 90, 100, 200, 300, 400, 500, 600, 700, 800, or 900 source or subset samples on the low end of the range and 1,000 source or subset samples on the high end of the range are combined before tagging. In some embodiments, between 2 source or subset samples on the low end of the range, and 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 source or subset samples on the high end of the range, are combined before tagging.

Through the barcode tagging, the population of candidate nucleic acid molecules, or the population of candidate polynucleotides, are transformed into tagged nucleic acid molecules, or a population of candidate tagged nucleic acid molecules, or, in illustrative embodiments, a population of candidate tagged polynucleotides having a desired nucleic acid sequence. In illustrative embodiments, at least one of the populations of candidate polynucleotides comprises or is sequence-perfect with respect to a desired sequence and/or at least one of the populations of candidate tagged polynucleotides comprises a sequence-perfect nucleic acid sequence. In illustrative embodiments, barcodes are attached as part of the assembly reaction that forms the source sample by attaching barcodes to the plurality of assembled nucleic acid molecules.

c. Subsetting (e.g., Diluting) Source Sample

Cell-free cloning/vCloning methods provided herein typically include a step of subsetting, isolating, withdrawing, collecting, sampling or partitioning a subset volume of a source sample to form, create, or yield a subset sample. In illustrative embodiments, this isolating, withdrawing, collecting, sampling, or partitioning involves diluting a portion or subvolume of a source sample to yield a subset sample that is a diluted sample. Such diluting typically occurs as part of forming the subset sample even if a portion of the source sample is not diluted in a diluent, because reagents are typically present or added to the subset volume of the source sample, for example to amplify tagged nucleic acid molecules in the subset sample as provided herein, and optionally to tag sample nucleic acid molecules in the subset sample as provided for some embodiments herein. Such subsetting is typically performed by transferring, or otherwise isolating away from the source sample into the subset (e.g., diluted) sample, a desired or target number, or desired or target number range, as provided herein, of source nucleic acid molecules (i.e., nucleic acids in a source sample) and/or tagged nucleic acid molecules derived therefrom. Such number can depend in certain embodiments, on the number of barcodes that are or will be present on the source nucleic acid molecules, which relates to the number of barcodes in each set of barcodes and the number of sets of barcodes that are or will be present on the nucleic acid molecules, and in illustrative embodiments such that at least some of the tagged nucleic acid species present in the subset (i.e., diluted) sample are uniquely barcoded. Thus, more than one nucleic acid molecule can be uniquely barcoded with the same barcode as long as the rest of the sequences on such nucleic acid molecules are identical. Thus, in certain embodiments, a number or approximate number of source nucleic acid molecules, or tagged nucleic acids derived therefrom, in the source sample is determined and typically a number of barcodes and barcode sets is known. This subsetting (e.g., diluting) step can provide methods herein, the power to effectively produce polynucleotides having a desired sequence, for example at least 1 kb in length polynucleotides having a sequence-perfect desired sequence, in a fraction of the time of prior art methods. In any of the aspects and embodiments herein, tagged nucleic acid molecules are in illustrative embodiments tagged candidate nucleic acid molecules. The exact sequences of candidate nucleic acid molecules have typically not been determined by sequencing. In some embodiments, candidate nucleic acid molecules are generated from synthesis or assembly reactions or isolated from a cell, and in illustrative embodiments generated from synthesis or assembly reactions.

In some aspects, the source sample comprises between about 2 to about $1 \times 10^{15}$ source nucleic acid molecules, and typically comprises about or at least $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, $1 \times 10^{20}$ or $1 \times 10^{21}$, or between $1 \times 10^5$ and $1 \times 10^{21}$, $1 \times 10^{20}$, $1 \times 10^{19}$, $1 \times 10^{18}$, $1 \times 10^{17}$, $1 \times 10^{16}$, $1 \times 10^{15}$, $1 \times 10^{14}$, $1 \times 10^{13}$, $1 \times 10^{12}$, $1 \times 10^{10}$, $1 \times 10^9$, $1 \times 10^8$, $1 \times 10^7$, or $1 \times 10^6$ source nucleic acid molecules, or between $1 \times 10^6$ and $1 \times 10^{21}$, $1 \times 10^{20}$, $1 \times 10^{19}$, $1 \times 10^{18}$, $1 \times 10^{17}$, $1 \times 10^{16}$, $1 \times 10^{15}$, $1 \times 10^{14}$, $1 \times 10^{13}$, $1 \times 10^{12}$, $1 \times 10^{10}$, $1 \times 10^9$, $1 \times 10^8$, or $1 \times 10^7$ source nucleic acid molecules, or between $1 \times 10^9$ and $1 \times 10^{21}$, $1 \times 10^{20}$, $1 \times 10^{19}$, $1 \times 10^{18}$, $1 \times 10^{17}$, $1 \times 10^{16}$, $1 \times 10^{15}$, $1 \times 10^{14}$, $1 \times 10^{13}$, $1 \times 10^{12}$, $1 \times 10^{11}$, or $1 \times 10^{10}$ source nucleic acid molecules, or between $1 \times 10^{12}$ and $1 \times 10^{21}$, $1 \times 10^{20}$, $1 \times 10^{19}$, $1 \times 10^{18}$, $1 \times 10^{17}$, $1 \times 10^{16}$, $1 \times 10^{10}$, $1 \times 10^9$, $1 \times 10^8$, $1 \times 10^7$, $1 \times 10^6$, or $1 \times 10^5$ source nucleic acid molecules. Methods provided herein, can include a step of determining the number of source nucleic acid molecules, or molecules derived therefrom, in the source sample and/or the subset (e.g., diluted) sample.

In some aspects, the diluting comprises diluting the source sample at least 10, 50, 100, 1,000, 5,000, $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, $1 \times 10^{20}$, or $1 \times 10^{21}$ fold depending on the number of source nucleic acid molecules in the source sample and the desired or target number or number range of source nucleic acid molecules in the subset (e.g., diluted) sample. In some aspects, the source sample comprises at least $1 \times 10^6$ source nucleic acid molecules and the desired or target number or number range for the subset (e.g., diluted) sample is between about 1 to about 100,000 source nucleic acid molecules or a target number therein, e.g., from about 5, 10, 15, 20, 25, 30, 35, 40, 45, 50, 60, 70, 80, 90, or 100 source nucleic acid molecules on the low end of the range to about 1000 source nucleic acid molecules on the high end of the range, or a target number therein, from about 100 source nucleic acid molecules on the low end of the range to about $1 \times 10^5$, $1 \times 10^4$, $1 \times 10^3$ source nucleic acid molecules on the high end of the range, or a target number therein, or from about 10, 100, or 250 source nucleic acid molecules on the low end of the range to about $1 \times 10^4$ source nucleic acid molecules on the high end of the range, or a target number therein. In some aspects, the diluted sample comprises about 1 to about 50,000, about 1 to about 25,000, 1 to about 10,000, 1 to about 9000, 1 to about 8000, 1 to about 7000, 1 to about 6000, 1 to about 5000, 1 to about 4000, 1 to about 3000, 1 to about 2500, 1 to about 2000, 1 to about 1500, 1 to about 1000, 1 to about 900, 1 to about 800, 1 to about 700, 1 to about 600, 1 to about 500, 1 to about 400, 1 to about 300, 1 to about 200, 1 to about 100 nucleic acid molecules, 10 to about 50,000, about 10 to about 25,000, 10 to about 10,000, 10 to about 9000, 10 to about 8000, 10 to about 7000, 10 to about 6000, 10 to about 5000, 10 to about 4000, 10 to about 3000, 10 to about 2500, 10 to about 2000, 10 to about 1500, 10 to about 1000, 10 to about 900, 10 to about 800, 10 to about 700, 10 to about 600, 10 to about 500, 10 to about 400, 10 to about 300, 10 to about 200, 10 to about 100, 10 to about 50, 10 to about 25, or 10 to about 20 source nucleic acid molecules, or about 50 to about 1000 source nucleic acid molecules. In some aspects, the subset or diluted sample comprises numbers of source nucleic acid molecules within exactly the ranges recited above. In some aspects, the subset or diluted sample comprises at most 50,000, 25,000, 10,000, 9,000, 8,000, 7,000, 6,000, 5,000, 4,000, 3,000, 2,500, 2,000, 1,500, 1,000, 900, 800, 700, 600, 500, 400, 300, 200, 100, 90, 80, 70, 60, 50, 40, 30, 25, 20, 10, 5, 4, 3, or 2 source nucleic acid molecules. In some embodiments, the subset (e.g., diluted) sample comprises any of the desired or target numbers or ranges of source nucleic acid molecules provided herein above.

In some aspects, dilution of the source sample comprises a serial dilution. In some embodiments, the serial dilution comprises 2, 3, 4, 5, 6, 7, 8, 9, 10, 12, 14, 16, 18, 20, 22, 24, 26, 28, 32, 36, 40, 44, or 48 dilutions performed serially. Such dilutions can include diluting a volume from the source sample in a diluent, such as, for example water or a buffer. Whether or not dilution steps are performed by diluting the source sample in a diluent, in some aspects, diluting includes adding reagents for amplifying and optionally tagging nucleic acids in the subset sample, to a subset volume that includes source nucleic acids isolated away from a source sample. In some aspects, diluting the source sample comprises adding an aqueous and/or an oil-based solution to the source sample, or typically a portion thereof. In some aspects, the diluting comprises partitioning all or typically part of the source sample into one or more partitions. Such partitions are discussed further infra. In some aspects, the dilution and/or partitioning is performed using a microfluidic device.

Methods for polynucleotide production typically comprise withdrawing or otherwise isolating away from the source sample, a subset volume of the source sample to yield a subset sample. In illustrative embodiments, subsetting is performed by diluting a source sample of source nucleic acid molecules to yield a desired or target number or number range of source nucleic acid molecules in the diluted sample. Thus, a diluted sample in any aspect or embodiment herein, can be a subset sample or a partition sample as well. In some aspects of any of the methods provided herein that include molecular barcodes, including as non-limiting examples, methods for producing, enriching, or generating a polynucleotide having a desired sequence, the number of unique molecular barcodes, or in subaspects, the number of unique combinations of molecular barcodes (also referred to herein as molecular barcode combinations), is less than the number of source nucleic acid molecules in the source sample. In some of these, and other aspects, the number of unique molecular barcodes, or in some subaspects the number of unique combinations of molecular barcodes, is greater than the number of source nucleic acid molecules in the diluted sample. In some aspects, the number of unique molecular barcodes, or in some subaspects the number of unique combinations of molecular barcodes, is about the same as the number of source nucleic acid molecules of the diluted sample.

As indicated herein, the sample barcoding in the subset (e.g., diluted) sample does not have to be unique for all source nucleic acid molecules or nucleic acid species in a sample, for example because sequencing of tagged nucleic acid molecules can be performed to differentiate tagged nucleic acid species that have been uniquely tagged versus those that have not. Thus, in illustrative embodiments some of the tagged nucleic acid species in the source sample and/or the subset (e.g. diluted) sample are not uniquely tagged/barcoded (i.e. redundantly tagged/barcoded). In illustrative embodiments, one or more of the tagged nucleic acid species are distinctly tagged with respect to other tagged nucleic acid species (i.e., some of the tagged nucleic acid molecules are distinctly tagged, and some (i.e., others) are not). As indicated herein, in illustrative embodiments, a sufficient number of tagged nucleic acid species in the subset (e.g., diluted) sample are sequenced to assure that a representative molecule from every distinct nucleic acid species in the subset (e.g., diluted) sample is sequenced at least once, and typically multiple times depending on the error rate of the sequencing technology, as discussed herein. Thus, in some aspects, the ratio of unique molecular barcodes, or in some subaspects, of unique combinations of molecular barcodes (molecular barcode combinations), to source nucleic acid molecules or species of the subset (e.g., diluted) sample, is about, exactly, or targeted to be 1:10, 1:5, 1:4, 1:3, 1:2, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes to the number of source nucleic acid molecules or nucleic acid molecules or species of the subset sample. In some aspects, the subsetting (e.g., diluting) is performed to achieve a ratio of unique molecular barcodes to source nucleic acid molecules or nucleic acid species, in the diluted sample such that the probability of having at least one source nucleic acid molecule or nucleic acid species uniquely identified by at least one molecular barcode is 1% or more, 5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 96% or more, 97% or more, 98% or more, 99% or more, 99.5% or more, 99.9% or more, between 1% and 99.9%, between 75% and 99.9%. In some aspects, the ratio of molecular barcodes to source nucleic acid molecules or nucleic acid species in the diluted sample is such that the probability of having at least one source nucleic acid molecule or nucleic acid species uniquely identified by at least one molecular barcode is greater than 90%.

In certain embodiments, the target number is determined, set, and/or calculated based on the number of unique tags, the number of unique barcodes, degenerate barcodes or non-degenerate barcodes, the number of unique barcode combinations or degenerate barcode combinations, or in illustrative embodiments the number of unique non-degenerative barcode combinations in a set of tags or barcodes to be used in a tagging reaction. In certain embodiments, the number of target molecules is determined based on the number of unique tags in a source or subset (e.g. diluted) sample, or based on the number of tagged nucleic acid species in a subset (e.g. diluted) sample. These embodiments can include those in which tagging is performed in a subset (e.g. diluted) sample, or in illustrative embodiments, in a source sample where it may be even more convenient and yield even more consistent results especially in a commercial setting, to tag the much larger number of nucleic acid molecules than in a subset (e.g. diluted) sample. Furthermore, in illustrative embodiments, as disclosed herein, a target number of nucleic acid molecules that are isolated away from a source (e.g. diluted) sample is between 1 and 10,000, 1 and 1,000, 1 and 500, 1 and 400, 2 and 250, 5 and 200, 20 and 150, 50 and 100, 3 and 400, 3 and 384, 3 and 200, 3 and 192, 3 and 100, 3 and 96, 3 and 48, 3 and 25, and 3 and 20. In such embodiments, especially wherein the polynucleotides are non-degenerate, barcodes can be designed such that they are effective as, designed as, qualified as, and well-suited as binding sites for barcode amplification primers, for example under similar or the same amplification conditions, such as annealing temperature, as some, most, almost all or all of the other barcodes in a set. Rules for designing such binding sites and primers for amplifying the same, are known in the art. Since these embodiments are well suited for storage in multi-well plates of primers (e.g. 96-well or 384-well plates), include premade stock primers, they provide illustrative methods that are especially well-suited for high-throughput, automated processing for execution of methods to generate, assemble, tag, identify and enrich polynucleotides having a desired nucleic acid sequence. Pre-made primers, also referred to as pre-made stock primers exist and are available to a user before a method herein, or an assembly, diluting, or sequencing step of a method herein is performed by the user. Such pre-made stock primers can exist for example, in a freezer that is accessible to the user.

In some embodiments, between 2 and 100,000, 2 and 10,000, 2 and 5,000, 2 and 2,500, 2 and 2,000, 2 and 1,000, 2 and 500, 2 and 250, 2 and 100, 2 and 50, 2 and 40, 2 and 30, 2 and 25, 2 and 20, 2 and 10, 2 and 5, 5 and 100, 5 and 50, 5 and 25, 5 and 20, 5 and 10, 10 and 100,000, 10 and 10,000, 10 and 5,000, 10 and 2,500, 10 and 2,000, 10 and 1,000, 10 and 500, 10 and 250, 10 and 100, 10 and 50, 10 and 40, 10 and 30, 10 and 25, 10 and 20, 15 and 50, 15 and 25, 20 and 40, 20 and 30 tags are found in a source sample or a subset (e.g. diluted) sample as part of the tagged nucleic acid molecules or tagged nucleic acid species. Each tag can be a barcode or a combination of two, three, four, five, six, seven, eight, nine or ten barcodes on one or each side of a synthesized or assembled nucleic acid.

In some aspects of any of the methods provided herein that include a step of subsetting a source sample, the subsetting can be part of a multiplex method that comprises combining a portion of at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 different source samples to form a single subset (e.g., dilute) sample. Thus, in some embodiments, the subset sample contains at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 nucleic acid species, in illustrative embodiments, uniquely tagged nucleic acid species, having at least 2, 3, 4, 5, 6, 7, 8, 9, 10, 15, 20, 25, 30, 35, 40, 45, 50, 60, 70, 80, 90, 100 desired sequences, 200, 300, 400, 500, 600, 700, 800, 900, or 1,000.

In some aspects of any of the methods provided herein that include a subsetting (e.g., diluting) the source sample step, the step can be performed in solution, e.g., the nucleic acid molecules and polynucleotides are not attached to a solid-phase during the step. In any aspect or embodiment provided herein that includes a subsetting step, the sequencing results between different subsets from the same source sample are not compared to determine a relative amount of a polynucleotide in the source sample.

c(i). Partitioning Source Sample

In some aspects, the diluting of the source sample comprises partitioning the source sample into one or more partitions. In some aspects, the partitions may be isolated from one another by a carrier fluid, such as a continuous phase of an emulsion, by a solid phase, such as at least one wall of a container, or a combination thereof, among others. In some aspects, the partitions can be droplets disposed in a continuous phase, such that the droplets and the continuous phase collectively form an emulsion. In some aspects, the partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), or the like. Accordingly, the partitions may be formed serially, in parallel, or in batch. In some aspects, the partitions may have any suitable volume or volumes. In some aspects, the partitions may be of substantially uniform volume or may have different volumes. In some aspects, the partitions, when formed, are competent for performing one or more reactions in the partitions. In some aspects, one or more reagents can be added to the partitions after they are formed to render them competent for reaction. In some aspects, the reagents can be added by any suitable mechanism, such as a fluid dispenser, fusion of droplets, or the like. Any of the reagents may be combined with the partitions (or a bulk phase sample) in a macrofluidic or microfluidic environment. In some aspects, each reaction performed in each partition can occur selectively (and/or substantially) in only a subset of the partitions, such as less than about one-half, one-fourth, or one-tenth of the partitions, among others. In some aspects of any of the methods provided herein that include a partitioning a source sample step, the step can be performed in solution, e.g., the nucleic acid molecules and polynucleotides are not attached to a solid-phase during the step. In some aspects of any of the methods provided herein that include a partitioning a source sample step, the partitions can be recombined at a later step in the method.

In some aspects, the source sample can be partitioned into at least 10, 20, 30, 40, 50, 100, 250, 500, 1,000, 2,500, 5,000, 10,000, 25,000, 50,000, 100,000, 250,000, 500,000, 1,000,000, 2,500,000, 5,000,000, or 10,000,000 partitions. In some aspects, the number of partitions depends on the number of nucleic acid molecules in the source sample. In some embodiments, the number of partitions is about the same number as the number of nucleic acid molecules in the source sample. In some aspects, at least one partition comprises at least one nucleic acid molecule of the source sample. In some aspects, at least one partition comprises more than one nucleic acid molecule of the source sample. In some aspects, at least 10%, 15%, 20%, 25%, 30%, 40%, 50%, 60%, 70%, 80%, or 90% of the partitions contain exactly one nucleic acid molecule. In some embodiments, the average number of nucleic acid molecules per partition is less than 1, about 1, more than 1, about 2, or about 3 nucleic acid molecules. In some embodiments, the average number of nucleic acid molecules per partition is between 0 and 2, 0.25 and 1.75, 0.5 and 1.5, 0.75 and 1.25, 0.8 and 1.2, or 0.9 and 1.1 nucleic acid molecules.

In some aspects, each partition comprises between 1 to 100,000 nucleic acid molecules, or any of the numbers of nucleic acid molecules disclosed above with respect to the subset (e.g., diluted) sample. In some aspects, the subset (e.g., diluted) sample comprises a population of at least 10, 20, 30, 40, 50, 100, 250, 500, 1,000, 2,500, 5,000, 10,000, 25,000, 50,000, 100,000, 250,000, 500,000, 1,000,000, 2,500,000, 5,000,000, or 10,000,000 partitions each including one nucleic acid molecule of the source sample.

In some aspects, the dilution and/or partitioning is performed using a microfluidic device. In some aspects, the dilution comprises subsetting a source sample into one or more partitions, wherein each partition comprises 1 to 100,000 nucleic acid molecules, or any of the numbers of nucleic acid molecules disclosed above with respect to the subset (e.g., diluted) sample.

In some aspects, the partitions comprise droplets. In some aspects, droplets can be generated having an average diameter of about, more than about, less than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. In some aspects, the average diameter of the droplets can be about 0.001 microns to about 0.01 microns, about 0.001 microns to about 0.005 microns, about 0.001 microns to about 0.1 microns, about 0.001 microns to about 1 micron, about 0.001 microns to about 10 microns, about 0.001 microns to about 100 microns, about 0.001 microns to about 500 microns, about 0.01 microns to about 0.1 microns, about 0.01 microns to about 1 micron, about 0.01 microns to about 10 microns, about 0.01 microns to about 100 microns, about 0.01 microns to about 500 microns, about 0.1 microns to about 1 micron, about 0.1 microns to about 10 microns, about 0.1 microns to about 100 microns, about 0.1 microns to about 500 microns, about 1 micron to about 10 microns, about 1 micron to about 100 microns, 1 micron to about 500 microns, about 10 microns to about 100 microns, about 10 microns to about 500 microns, or about 100 microns to about 500 microns. In some aspects, droplet volume can be about, more than about, less than about, or at least about 0.001 nl, 0.01 nl, 0.1 nl, 1 nl, 10 nl, 100 nl, 200 nl, 300 nl, 400 nl, 500 nl, 600 nl, 700 nl, 800 nl, 900 nl, or 1 µl.

In some aspects, the droplets are monodisperse droplets. In some aspects, the droplets are generated such that the size of said droplets does not vary by more than plus or minus 5% of the average size of said droplets. In some aspects, the droplets are generated such that the size of said droplets does not vary by more than plus or minus 2% of the average size of said droplets. In some aspects, a droplet generator can generate a population of droplets from a single sample, wherein none of the droplets can vary in size by more than plus or minus 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, 30%, 35%, 40%, 45%, or 50% of the average size of the total population of droplets.

In illustrative embodiments, any aspect or embodiment provided herein that includes a partitioning step, the sequencing results between different partitions from the same source sample are not compared to determine a relative amount or number of a polynucleotide in the source sample.

d. Amplifying Subset (e.g., Diluted) Sample

Methods of certain aspects provided herein include an optional step of amplifying the subset (e.g., diluted) sample. In such step, nucleic acid molecules or tagged nucleic acid molecules of the subset (e.g., diluted) sample are amplified. Thus, the number of molecules of most or all nucleic acid species (sets of identical nucleic acid molecules) is increased, typically by one or more orders of magnitude. Furthermore, because errors can be introduced into amplified nucleic acid molecules during the amplification process, additional typically undesired nucleic acid species can be created. Such amplification step can be performed using virtually any amplification method known in the art, for amplifying a template nucleic acid molecule, typically a population of nucleic acid molecules. In some embodiments, such amplification is performed using the same primer binding sites (e.g., universal primer binding sites), for example that are present outside the potential desired sequence region, on the nucleic acid molecules of the subset (e.g., diluted) sample. In some embodiments, the nucleic acid molecules of the subset (e.g., diluted) sample are amplified using isothermal amplification. In some aspects, an isothermal amplification can comprise Loop-Mediated Isothermal Amplification (LAMP), Whole Genome Amplification (WGA), Strand Displacement Amplification (SDA) Helicase-Dependent Amplification (HDA), Recombinase Polymerase Amplification (RPA), or Nucleic Acid Sequences Based Amplification (NASBA), or amplification of circularized nucleic acid molecules. In some aspects, the isothermal amplification can be performed at a temperature less than or about 25° C., 30° C., 35° C., 37° C., 40° C., 45° C., 50° C., 55° C., 60° C., or 65° C. In some embodiments, the nucleic acid molecules of the subset (e.g., diluted) sample are amplified using polymerase chain reaction (PCR), digital PCR, barcode-targeted PCR, reverse-transcription PCR, quantitative PCR, real-time PCR, isothermal amplification, linear amplification, or isothermal linear amplification, quantitative fluorescent PCR (QF-PCR), multiplex fluorescent PCR (MF-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), bridge PCR (bPCR), picotiter PCR, digital PCR, droplet digital PCR, or emulsion PCR (emPCR). Other suitable amplification methods include ligase chain reaction (LCR (oligonucleotide ligase amplification (OLA)), transcription amplification, cycling probe technology (CPT), molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), transcription mediated amplification (TMA), degenerate oligonucleotide-primed PCR (DOP-PCR), multiple-displacement amplification (MDA), strand displacement amplification (SDA), and nucleic acid based sequence amplification (NABSA), and any combinations thereof. In illustrative embodiments, the nucleic acid molecules of the subset (e.g., diluted) sample are amplified using barcode-targeted PCR. In further illustrative embodiments, the barcodes attached to the nucleic acid molecules are non-degenerate, as disclosed elsewhere herein. The use of a limited number of non-degenerate barcodes allows the design, ordering, and stocking of barcodes, and tags including adapters containing such tags, that are suitable as binding sites for primers used in amplification, such as for PCR. In contrast, degenerate barcodes can include sequences that may not PCR well. Additionally, the use of a limited number of non-degenerate barcodes allows all the corresponding primers to be designed, ordered, pre-made, readily available, in stock, and stored such that they are ready for use immediately after a desired nucleic acid is identified in a method herein. For example, 2 sets of 384 unique barcodes (768 unique barcodes in total) allow 147,456 unique molecular barcodes in combination (384 unique barcodes in set 1×384 unique barcodes in set 2), and all 768 corresponding amplification primers can be easily stored in two 384-well plates. Other amplification methods that can be used herein include those described in U.S. Pat. Nos. 5,242,794; 5,494,810; 4,988,617; and 6,582,938. A skilled artisan will understand how to perform the various PCR methods disclosed above, including adjusting the concentrations of the various PCR components, for example adjusting primer concentrations, including adding primers at different concentrations, and in some embodiments performing linear PCR with one or more primers, before adding additional primers to perform exponential amplification. In some aspects of any of the methods provided herein that include an amplifying the subset (e.g., diluted) sample step, the step can be performed in solution, e.g., the nucleic acid molecules and polynucleotides are not attached to a solid-phase during the step. In some embodiments of any of the methods provided herein that include a step of amplifying the subset (e.g., diluted) sample step, the amplifying can be part of a multiplex method that comprises combining subset samples to form a combined sample before amplifying. In illustrative embodiments, a single subset sample is amplified. In some aspects of any of the methods provided herein that include an amplifying the subset (e.g., diluted) sample step, different subset samples are amplified in parallel and combined at later steps. In some embodiments, different subset samples are combined and amplified together.

In some aspects, a reaction mixture is provided for amplification of circularized nucleic acid molecules. In some aspects, a reaction mixture for amplification of circularized nucleic acid molecules can include: (a) a first enzyme group that catalyzes replication of circular DNA; (b) a second enzyme group that catalyzes an Okazaki fragment maturation and synthesizes two sister circular DNAs constituting a catenane; (c) a third enzyme group that catalyzes a separation of the two sister circular DNAs; and (d) rNTPs and dNTPs. In some aspects, a reaction mixture for assembling or replicating a circularized nucleic acid molecule can be maintained at a temperature of from 20° C. to 50° C. thereby amplifying the circular DNA. In some embodiments, the third enzyme group includes at least two enzymes selected from the group consisting of an enzyme having topoisomerase III activity, an enzyme having topoisomerase IV activity, and an enzyme having RecQ activity. In some embodiments, the first enzyme group includes one or more of an enzyme having DnaA activity, one or more types of nucleoid protein, an enzyme or enzyme group having DNA gyrase activity, a single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III* activity. In some embodiments, the second enzyme group includes one or more of an enzyme having DNA polymerase I activity and an enzyme having DNA ligase activity.

e. Sequencing Subset (e.g., Diluted) Sample

Methods of certain aspects provided herein include an optional step of sequencing to determine if any of the species are uniquely tagged (e.g., barcoded) and include the desired, and in some embodiments sequence-perfect desired, nucleic acid sequence. Such methods include sequencing nucleic acid molecules, typically tagged nucleic acid species, that are present in the subset (e.g., diluted) sample, wherein at least one of the tagged nucleic acid species is a desired uniquely tagged nucleic acid molecule in the subset (e.g., diluted) sample, which in illustrative embodiments comprises a sequence-perfect desired nucleic acid sequence. In illustrative embodiments, at least one copy of each of the nucleic acid species in the subset (e.g., diluted) sample are sequenced. The number of copies of each species sequenced (depth of read) can depend on the accuracy of the sequencing technology utilized. Since the polynucleotides to be sequenced are typically tagged with barcodes (which are typically used for selection as described here), the reads are typically assembled into consensus sequences to identify and discriminate, for example, errors resulting from an amplification step or sequencing, versus errors in source nucleic acid molecules from which the nucleic acid species are derived, compared to a sequence-perfect desired nucleic acid sequence. The method can accommodate virtually any sequencing platform and error rate or error rate mode that platform. Sequencing can be performed to any depth of read to achieve any desired degree of confidence in the base calls for a polynucleotide to determine whether such polynucleotide comprises a desired nucleic acid sequence, especially a sequence-perfect nucleic acid sequence. Accordingly, in some embodiments, sufficient depth of sequencing reads are performed to provide a 90, 95, 98, 99, 99.9, 99.99, or 99.999% confidence in the sequence of a sequenced polynucleotide.

Any of the methods herein can, and typically do, include sequencing. Any nucleic acid sequencing technology known in the art can be used in methods herein to perform such sequencing. In certain non-limiting examples, the nucleic acid sequencing comprises sequencing more than one nucleic acid molecule in parallel, and in illustrative embodiments is next-generation/massively parallel sequencing (e.g., Illumina, San Diego, CA; Ion Torrent—Thermo Fisher, Carlsbad, CA), including for example paired-end sequencing. The nucleic acid sequencing in certain illustrative embodiments, is long-read nucleic acid sequencing. Such long-read nucleic acid sequence can be performed, for example, using single-molecule real-time (SMRT) sequencing (e.g., PacBio, Menlo Park, CA) or nanopore-based sequencing (e.g., Oxford Nanopore Technologies, Oxford, UK).

In some embodiments, sequencing reads generated using any of the sequencers are grouped or binned into a plurality of families based on the sequence information from the molecular barcodes, wherein a family corresponds to a nucleic acid molecule or species from among the tagged nucleic acid molecules or species present in a subset sample. In some embodiments, sequencing reads are grouped or binned into a plurality of families based on the sequences of the nucleic acid molecules corresponding to the desired sequence region. In some embodiments, nucleic acid molecules with the same barcodes and at least some, and in illustrative embodiments all, of the same sequence corresponding to the desired sequence region are grouped or binned into a family. In illustrative embodiments, the sequencing reads are grouped into a plurality of families based on the sequence information from the molecular barcodes and the sequences of the nucleic acid molecules corresponding to the desired sequence region. In some embodiments, sequencing reads from one family are used to generate a consensus sequence for the corresponding nucleic acid species. In some embodiments, errors in sequencing can be determined using other sequencing reads corresponding to the same nucleic acid species, and the errors can be removed from the consensus sequence. In certain illustrative embodiments sequencing analysis is performed by first binning (i.e., grouping) reads by matching them to the intended target (i.e., desired nucleic acid sequence) and then their unique barcode combinations. In certain multiplex embodiments, sample specific barcodes are not used, but rather different initial intended targets (i.e., desired nucleic acid sequences) are binned by primary alignment to the intended target sequences (i.e., desired nucleic acid sequences) to demultiplex the reads. In some embodiments, only high confidence barcode reads are included in the analysis, for example using a filter for which false positives are <5%, 4%, 3%, 2%, or in illustrative embodiments <1%.

In some aspects, the nucleic acid sequencing comprises determining the sequence of at least 1, 2, 3, 4, 5, 10, 25, 50, 100, 500, 1,000, 2,000, 5,000, 10,000, 25,000, 100,000, $1\times10^6$, $1\times10^7$, $1\times10^8$, or $1\times10^9$ polynucleotides, or between 1 and 10, 25, 50, 100, 500, 1,000, 2,000, 5,000, or 10,000 25,000, 100,000, $1\times10^6$, $1\times10^7$, $1\times10^8$, or $1\times10^9$ polynucleotides, or between 100 and 500, 1,000, 2,000, 5,000, or 10,000 25,000, 100,000, $1\times10^6$, $1\times10^7$, $1\times10^8$, or $1\times10^9$ polynucleotides. In some aspects, the nucleic acid sequencing comprises use of a sequencer that can read about 150, 200, 250, 300, 350, 400, 450, 500, 1,000, 5,000, or 10,000 nucleotides (nt) in a single read. In certain illustrative aspects, the nucleic acid sequencing is long-read sequencing and can read between 5,000 nt and 1,000,000 nt, or between 10,000 and 50,000, 100,000, 250,000, 500,000, 1,000,000, 2,500,000, or 5,000,000 nt in a single read.

In some embodiments, the nucleic acid sequencing includes determining the sequence of at least 100, 200, 300, 400, 500, or 750 nucleotides, or 1, 2, 3, 4, 5, 10, 20, 25, 50, 75, 100, 200, 300, 400, 500, 600, 700, 800, 900, 1,000, 1,500, 2,000 kilobases of each of the nucleic acid species sequenced. In some embodiments, the nucleic acid sequencing includes determining the sequence of between 1 kb and 1, 2, 3, 4, 5, 10, 20, 25, 50, 75, 100, 200, 300, 400, 500, 600, 700, 800, 900, 1,000, 1,500, 2,000 kilobases of each of the nucleic acid species sequenced. In some embodiments, the nucleic acid sequencing includes determining the sequence of 95, 96, 97, 98, 99, or 100% of the nucleotides of a nucleic acid, for example a tagged candidate nucleic acid species, or a product polynucleotide that is of any of the lengths provided herein, such as, for example, between 1 KB on the low end or the range, and 2, 3, 4, 5, 10, 20, 25, 50, 75, 100, 200, 300, 400, 500, 600, 700, 800, 900, 1,000, 1,500, 2,000 kB on the high end of the range.

In some aspects the nucleic acid sequencing uses at least or about 10 Amol, 100 Amol, 1 fmol, 10 fmol, 100 fmol, 1 pmol, 10 pmol, or 100 pmol, or between 10 Amol, and 100 Amol, 1 fmol, 10 fmol, 100 fmol, 1 pmol, 10 pmol, or 100 pmol, or between 1 fmol and 10 fmol, 100 fmol, 1 pmol, 10 pmol, or 100 pmol of the nucleic acid molecules in the subset (e.g, dilute sample).

The subsetting of the source sample typically included in illustrative methods provided herein reduces the number of unique nucleic acid molecules, typically to below 1,000,000 target nucleic acid molecules and in illustrative embodiments between 1 and 100,000 target nucleic acid molecules, and in illustrative embodiments between 10 and 10,000 target nucleic acid molecules or other ranges as provided herein. In some embodiments, a short-read sequencer is used and a short-range sequencing reaction is performed, for example using a next-generation system designed to generate short-reads (e.g. between 75 and 300 nucleotides in length). Short-read next generation sequencing systems, such as those from Illumina or Thermo (ion Torrent) are available. In some embodiments, tagmentation and fragment barcoding is used with a next generation sequencing reaction to generate longer assembled sequence reads using a short-read next-generation system.

In illustrative embodiments herein, long-read sequencing (LRS) technologies is performed, typically using a long-read sequencer. With long-read sequencing, as provided in some embodiments herein, read lengths can average at least 500 bases, such as 500 bases to 2 megabases. In some embodiments, the long-read sequencing generates a sequence read that encompasses the entire nucleotide sequence of the nucleic acid molecule, for example the tagged candidate nucleic acid molecule, product polynucleotide, or subsequent polynucleotide. For example, such long read length can be any of the lengths and ranges therein, provided herein for such molecules. For example, the long reads can be from 500 bases, 1 kb, 2 kb, or 10 kb up to 2 megabases, Accordingly, in some embodiments, a nucleic acid sequence is determined of 90, 95, 98, or 99%, or in illustrative embodiments all or an entire, candidate nucleic acid, tagged candidate nucleic acid, nucleic acid species, candidate nucleic acid species, tagged candidate nucleic acid species, polynucleotide, product polynucleotide, or subsequent polynucleotide typically using long read sequencing, typically in a single read, sometimes called a single long read. Such sequencing can be performed using a third generation sequencing system/sequencer.

Accordingly, in some embodiments, sequences are determined for nucleic acids in methods herein, such as for tagged candidate nucleic acid species using long read sequencing (LRS). In some embodiments, LRS is performed using nanopore sequencing or using single-molecule real-time (SMRT) sequencing. Single-molecule real-time sequencing services and/or instruments are available from Pacific Biosciences (PacBio). As indicated, in some embodiments, LRS is performed in methods herein using single-molecule real-time sequencing (SMRT) in a parallelized single molecule DNA sequencing method. Single-molecule real-time sequencing utilizes a zero-mode waveguide (ZMW). A single DNA polymerase enzyme is affixed at the bottom of a ZMW with a single molecule of DNA as a template. The ZMW is a structure that creates an illuminated observation volume that is small enough to observe only a single nucleotide of DNA being incorporated by DNA polymerase. Each of the four DNA bases is attached to one of four different fluorescent dyes. When a nucleotide is incorporated by the DNA polymerase, the fluorescent tag is cleaved off and diffuses out of the observation area of the ZMW where its fluorescence is no longer observable. Thus in such methods herein, a detector typically detects the fluorescent signal of the nucleotide incorporation, and the base call is made according to the corresponding fluorescence of the dye. In other embodiments herein, LRS used to determine the sequence of a nucleic acid in method herein, is performed using nanopore sequencing. Nanopore sequencing, released by Oxford Nanopore Technologies in 2014, works by a different principle: threading the DNA molecule through a 1.5 nm wide bioengineered channel embedded in a biological membrane. Electrical current across the channel depends on which nucleotide is traversing the channel at the time. This variation is used to determine the base sequence of the nucleic acid. In some embodiments, LRS is performed using a long-read sequencer that performs nanopore sequencing, or a variation thereof. In some methods a long-read sequencer capable of sequencing thousands to millions of bases is used, such as Oxford Nanopore. Oxford Nanopore sequencing is a third-generation sequencing technology, that can generate ultra-long reads exceeding 800 kb in a portable device, for example a MinION. Thus, in some embodiments, methods herein determine the sequence of nucleic acids using a third-generation sequencing technology, that can generate ultra-long reads exceeding 800 kb, in non-limiting subembodiments in a portable device. In some embodiments, a long-read sequencer performs single molecule, real time (SMRT) sequencing, or a variation thereof to determine the sequence of a nucleic acids, such as those in nucleic acid species in diluted samples herein. In some embodiments, a long-read sequencer utilizing SMRT sequencing is used. Non-limiting examples of such third-generation sequencers are PacBio RS II. PacBio RS II (Pacific Biosciences, Menlo Park, CA, USA). PacBio RS II is able to sequence single DNA molecules in real-time without means of amplification such as PCR, enabling direct observation of DNA synthesis by DNA polymerase. SMRT technology offers four major advantages compared to first- and second-generation platforms: (1) long read lengths (half of data in reads >20 kb and maximum read length >60 kb, for example read lengths between 10 kb on the low end of the range and 1M kb, 500,000 kb, 250,000 kb, 100,000 kb, 90 kb, 80 kb, 75 kb, and 60 kb on the high end of the range, or between 20 kb on the low end of the range and 1M kb, 500,000 kb, 250,000 kb, 100,000 kb, 90 kb, 80 kb, 75 kb, and 60 kb on the high end of the range, (2) high consensus accuracy (for example >99.999% at 30× in coverage depth, free of systematic errors), (3) low degree of bias (even or relatively even coverage across G+C content), and (4) simultaneous epigenetic characterization (direct detection of DNA base modifications at one-base resolution). These advantages enable resolution and analysis of hard-to-sequence regions in complex genomes.

In some embodiments, third generation sequencing using high-throughput systems allows detection of a sequenced nucleotide immediately after or upon its incorporation into a growing strand, e.g., detection of sequence in real time or substantially real time. In some embodiments, high throughput sequencing third generation sequencing generates at least 1000, 5000, 10,000, 20,000, 30,000, 40,000, 50,000, 100,000, or 500,000 sequence reads per hour. In some embodiments, each read is at least 50, 60, 70, 80, 90, 100, 120, or 150 bases per read. In some embodiments, long-read sequencing can include sequencing that provides a contiguous sequence read of for example, at least 1000 bases, 1500 bases, 2000 bases, 2500 bases, 2500 bases, 3000 bases, 4000 bases, 4500 bases, 5000 bases, 6000 bases, 7000 bases, 8000 bases, 9000 bases, 10,000, 100,000, 200,000, 250,000, 500,000, 750,000, 1,000,000, 1,500,000, or 2,000,000 bases or more depending on the size of the nucleic acid whose sequence is determined.

In some aspects, the number of sequencing reads generated on the sequencer is based on the number of target nucleic acid molecules or species in the dilute or subset sample. In some aspects, the number of sequencing reads generated on the sequencer can be at least 5, 10, 25, 50, 100, 250, 500, 1,000, 5,000, 10,000, 50,000, 100,000, 500,000, or 1,000,000 times the number of unique target nucleic acid molecules or species in the subset sample. In some aspects, the average depth of read per base (the number of times a particular nucleotide base of a particular species is sequenced) for some, most, or all of the bases can be at least 5, 10, 15, 20, 25, 30, 35, 40, 45, 50, 60, 70, 80, 90, 100, 250, 500, or 1,000, 5,000, 10,000, 50,000, 100,000, 500,000, or 1,000,000 for at least 50%, 60%, 70%, 80%, 90%, 95%, 96%, 97%, 98%, 99%, 99.5%, 99.9% or all of the nucleic acid species in the subset sample. In some aspects, the average depth of read for the sequencer can be at least 5, 10, 15, 20, 25, 30, 35, 40, 45, 50, 60, 70, 80, 90, 100, 250, 500, or 1,000. In some aspects, the subset sample can be sequenced in a manner such that there is at least a 90%, 95%, 96%, 97%, 98%, 99%, 99.5%, or 99.9% probability that all of the nucleic acid species in the subset sequence are read in the sequencer. In some embodiments, the subset sample can be sequenced in a manner such that there is at least a 90%, 95%, 96%, 97%, 98%, 99%, 99.5%, or 99.9% probability that all of the subset nucleic acid species in the subset sequence are read wholly or in part at least 5, 10, 25, 50, 100, 250, 500, or 1,000 times in the sequencer. In some aspects, the number of sequencing reads generated on the sequencer can be based at least in part on the number of unique barcodes in the set of barcodes, the number of sets of barcodes, the number of nucleic acid species in the subset sample, the length of the sequencing reads, an error rate of the sequencer used to determine the sequence, and/or a target minimum depth of read for the determining the sequence. The advantageously low number of sample nucleic acid molecules in the subset sample as disclosed herein, which in illustrative embodiments can target fewer than 10,000 sample nucleic acid molecules, reduces the number of sequencing reads necessary to provide high probability that all nucleic acid species in the subset sample have been sequenced enough times to generate a high-quality consensus sequence. As sequencing reagents and runs are relatively expensive, these savings provide a significant advantage over existing technologies.

In some aspects, any of the methods herein can include sequencing advantageously fewer polynucleotides than typical in the art when identifying a desired polynucleotide that is sequence-perfect to the desired nucleic acid sequence. In some embodiments, the method can be performed by sequencing 5 or fewer nucleic acid species. In some embodiments, a method can be performed by sequencing 5,000, 4,000, 3,000, 2,000, 1,750, 1,500, 1,250, 1,000, 900, 800, 700, 600, 500, 400, 300, 200, 150, 125, 100, 90, 80, 75, 70, 65, 60, 55, 50, 45, 40, 35, 30, 25, 20, 15, 10, 9, 8, 7, 6, 5, 4, or 3, or fewer nucleic acid species. In some embodiments, the method can be performed by sequencing 1 nucleic acid species. In some embodiments, the method can have a 95%, 96%, 97%, 98%, 98%, 99%, 99.9%, 99.99%, or 99.999% probability of identifying a desired polynucleotide that is sequence-perfect to the desired nucleic acid sequence when sequencing any of the above numbers of nucleic acid species. In some aspects, the method can have a 95% probability of identifying a desired polynucleotide that is sequence-perfect to the desired nucleic acid sequence when sequencing any of the above numbers of nucleic acid species.

The number of nucleic acid species that should be sequenced to identify the desired polynucleotide that is sequence-perfect to the desired nucleic acid sequence is associated with the length of the desired polynucleotide. In some embodiments, a method including a population of desired polynucleotides having between 500 and 1,999 bp in length, can include sequencing 100, 90, 80, 75, 70, 65, 60, 55, 50, 45, 40, 35, 30, 25, 20, 15, 10, 9, 8, 7, 6, 5, 4, 3, or 2 or fewer nucleic acid species. In some embodiments, a method including a population of desired polynucleotides having between 2,000 and 2,999 bp in length, can include sequencing 200, 150, 125, 100, 90, 80, 75, 70, 65, 60, 55, 50, 45, 40, 35, 30, 25, 20, 15, 10, 9, 8, 7, 6, 5, 4, 3, or 2 or fewer nucleic acid species. In some embodiments, a method including a population of desired polynucleotides having between 3,000 and 50,000 bp in length, can include sequencing 1,000, 900, 800, 700, 600, 500, 400, 300, 200, 150, 125, 100, 90, 80, 75, 70, 65, 60, 55, 50, 45, 40, 35, 30, 25, 20, 15, 10, 9, 8, 7, 6, 5, 4, 3, or 2 or fewer nucleic acid species. In some embodiments, a method including a population of desired polynucleotides having between 50,001 and 100,000 bp in length can include sequencing 2,000, 1,750, 1,500, 1,250, 1,000, 900, 800, 700, 600, 500, 400, 300, 200, 150, 125, 100, 90, 80, 75, 70, 65, 60, 55, 50, 45, 40, 35, 30, 25, 20, 15, 10, 9, 8, 7, 6, 5, 4, 3, or 2 or fewer nucleic acid species. In some embodiments, a method including a population of desired polynucleotides having between 100,001 and 1,000,000 bp in length can include sequencing 5,000, 4,000, 3,000, 2,000, 1,750, 1,500, 1,250, 1,000, 900, 800, 700, 600, 500, 400, 300, 200, 150, 125, 100, 90, 80, 75, 70, 65, 60, 55, 50, 45, 40, 35, 30, 25, 20, 15, 10, 9, 8, 7, 6, 5, 4, 3, or 2 or fewer nucleic acid species. In some aspects, the method can have a 95%, 96%, 97%, 98%, 98%, 99%, 99.9%, 99.99%, or 99.999% probability of identifying a desired polynucleotide that is sequence-perfect to the desired nucleic acid sequence when sequencing any of the numbers of nucleic acid species above for the different length desired nucleic acid sequences. In some aspects, the method can have a 95% probability of identifying a desired polynucleotide that is sequence-perfect to the desired nucleic acid sequence when sequencing any of the numbers of nucleic acid species above for the different length desired nucleic acid sequences.

Multiplexing can also reduce costs associated with sequencing. In some aspects of any of the methods provided herein that include a step of sequencing tagged nucleic acid species, the sequencing can be part of a multiplex method that comprises combining subset samples to form a combined sample before sequencing. In some embodiments, at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 subset samples are combined before sequencing. In some embodiments, between 2, 3, 4, 5, 6, 7, 8, 9, 10, 15, 20, 25, 30, 35, 40, 45, 50, 60, 70, 80, or 90 subset samples on the low end of the range, and 100 subset samples on the high end of the range, are combined before sequencing. In some embodiments, between 2, 3, 4, 5, 6, 7, 8, 9, 10, 15, 20, 25, 30, 35, 40, 45, 50, 60, 70, 80, 90, 100, 200, 300, 400, 500, 600, 700, 800, or 900 subset samples on the low end of the range, and 1,000 subset samples on the high end of the range, are combined before sequencing. In some embodiments, between 2 subset samples on the low end of the range, and 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 subset samples on the high end of the range are combined before sequencing. In some embodiments, sample barcodes are added to the different subset samples before they are combined. In illustrative embodiments, no sample barcodes are used. In such embodiments with no sample barcodes, the different polynucleotides from the different subset samples can be distinguished based on the desired sequences in the sequencing reads. In some embodiments, the subset samples contain different barcodes on the nucleic acid molecules. In some embodiments, one or more of the subset samples contain at least one identical barcode on the nucleic acid molecules.

In some aspects, the method comprises determining whether nucleic acid species, typically tagged nucleic acid species, have the desired nucleic acid sequence. In some aspects, the determined nucleic acid sequence(s) are sequence-perfect, i.e., the sequences do not contain any errors relative to the sequence-perfect desired nucleic acid sequence, and thus a polynucleotide having such a sequence is also referred to herein as a polynucleotide having a sequence-perfect desired nucleic acid sequence. In some aspects, a desired nucleic acid sequence can have 1 or fewer, 2 or fewer, 3 or fewer, 4 or fewer, 5 or fewer, 6 or fewer, 7 or fewer, 8 or fewer, 9 or fewer, 10 or fewer, 15 or fewer, 20 or fewer, 30 or fewer, 40 or fewer, 50 or fewer, or 50 or more errors relative to the sequence-perfect desired nucleic acid sequence. In some embodiments, the enriched population of polynucleotides can include at least 25%, 30%, 40%, 50%, 60%, 70%, 75%, 80%, 85%, 90%, 95%, 96%, 97%, 98%, 99%, 99.5%, 99.9% or 100% of the polynucleotides comprising the desired nucleic acid sequence. In some embodiments, the desired nucleic acid sequence is at least 25%, 30%, 40%, 50%, 60%, 70%, 75%, 80%, 85%, 90%, 95%, 96%, 97%, 98%, 99%, 99.5%, or 99.9% identical to a sequence-perfect desired nucleic acid sequence. In some embodiments, the desired nucleic acid sequence is the sequence-perfect desired nucleic acid having 0 errors, or is a population of polynucleotides wherein at least 25%, 30%, 40%, 50%, 60%, 70%, 75%, 80%, 85%, 90%, 95%, 96%, 97%, 98%, 99%, 99.5%, 99.9% or 100% of the polynucleotides have 0 sequence errors (i.e., are a single nucleic acid species). In some aspects, the method of polynucleotide production comprises selecting 1 or more, 2 or more, 5 or more, 10 or more, 20 or more, 50 or more, 100 or more, 250 or more, 500 or more, 750 or more, 1000 or more, 2000 or more, 3000 or more, 4000 or more, 5000 or more, 10,000 or more polynucleotides for analysis, e.g., sequence-based analysis such as, but not limited to, nucleic acid sequence determination.

f. Enriching (e.g., Isolating) Polynucleotide(s) Having Desired Sequence

Methods of certain aspects provided herein include a step of enriching (e.g., isolating) the polynucleotide, or a population thereof, having the desired, in illustrative embodiments the sequence-perfect desired, nucleic acid sequence from the diluted sample. This typically includes enriching at least one polynucleotide, and in illustrative embodiments a population of polynucleotides from a desired uniquely tagged nucleic acid species, which in illustrative embodiments is a sequence-perfect nucleic acid species with respect to a desired nucleic acid sequence, to generate a population of polynucleotides having the desired nucleic acid sequence. The uniquely tagged nucleic acid species includes tagged nucleic acid molecules that all have the same unique tag (e.g., barcode) sequence and a similar (e.g., 75%, 80%, 90%, 95%, or 99%) or identical desired nucleic acid sequence. Thus, the unique tag is not shared with nucleic acid molecules other than those that have the desired nucleic acid sequence. Such enrichment can include performing an amplification reaction to enrich one or more polynucleotides from the desired tagged nucleic acid species. Any of the amplification methods disclosed herein can be used for enriching the one or more polynucleotides. In illustrative embodiments, a high-fidelity polymerase and/or a high-fidelity PCR kit, such as KAPA HiFi HotStart ReadyMix, are used to reduce or eliminate the number of errors introduced by amplification during enriching. Thus, in some embodiments, one or more primers are added to the subset (e.g., diluted) sample that are used for the amplification to yield the enriched desired, tagged nucleic acid molecule. In some embodiments, one or more primers can be used that include enrichment tags, for example biotin, that bind to a binding partner and allow the amplification products (having incorporated the enrichment tags) to be further enriched using the corresponding binding partner, for example streptavidin, using methods a skilled artisan will understand. The following paragraphs discuss adding primers to the methods herein, and/or reaction mixtures generally, or to specific samples. It will be recognized that such embodiments that include the addition of one or more primers can be applied to any step herein that includes an amplification reaction. In some embodiments, the method of polynucleotide production comprises adding at least one primer complementary to a portion of at least one nucleic acid molecule of the source sample. In some aspects, the method of polynucleotide production comprises adding at least one primer complementary to a portion of at least one nucleic acid molecule of the diluted sample. In some aspects, the method of polynucleotide production comprises adding at least one primer complementary to a portion of at least one polynucleotide. In some aspects, enriching can be performed using hybrid-capture based methods, PCR with 1 or 2 primers that bind to at least a portion of barcodes or the sequence complementary to the barcodes, linear amplification, multiple displacement amplification, rolling circle amplification, ligation-based methods (e.g., selective circularization methods, molecular inversion probes), or any combinations thereof.

In some aspects of any of the method aspects and embodiments provided herein, the method comprises adding at least one primer complementary to at least one barcode, and in illustrative embodiments at least one unique barcode or molecular barcode, to a reaction mixture, and in illustrative embodiments subset sample, to amplify and enrich the nucleic acid molecule or polynucleotide having the desired nucleic acid sequence. In some aspects, the method of polynucleotide production comprises adding at least one primer complementary to at least one adaptor. In some aspects, at least one polynucleotide comprises at least one desired nucleic acid sequence. In some aspects, the method of polynucleotide production further comprises adding at least two different primers to a sample.

In any of the aspects where multiple subset samples have been combined, the primers added can include a portion of the desired sequence. For example, two or more polynucleotides having sequence-perfect desired sequences of different desired sequences can share the same barcode. In such embodiments, a portion of the desired sequence can be included on the primer with the barcode to amplify out different the specific sequence-perfect desired sequence.

In some aspects, multiple primers are added that are complementary to more than one barcode or more than one primer binding site within a molecular barcode, such that barcode-targeted PCR can be performed to enrich and amplify one or more desired nucleic acid molecules or polynucleotides. For example, nested, barcode-targeted PCR can be used to enrich one or more desired nucleic acid molecules or polynucleotides. Nested PCR can include a subsequent round or rounds of PCR amplification using one or more new primers that bind internally, by at least one base pair, to the primers used in a previous round. Nested PCR reduces the number of spurious amplification targets by amplifying, in subsequent reactions, only those amplification products from the previous one that have the correct internal sequence. Reducing spurious amplification targets improves the number of useful measurements that can be obtained, especially in sequencing. Nested PCR typically entails designing primers completely internal to the previous primer binding sites, necessarily increasing the minimum DNA segment size required for amplification. In some embodiments, nested PCR methods that are known in the art, such as one-sided or two-sided nested PCR, can be used to increase the sensitivity of the PCR. In some embodiments, the nested PCR can include using one or more types of nesting PCR, for example: semi-nested PCR, fully nested PCR, heminested PCR, triply hemi-nested PCR, one-sided nested PCR, one-sided PCR, or reverse semi-nested PCR. Accordingly, the number of barcodes on one or two or more tags can be designed to accommodate such PCR reactions. For example, one, two, three or more barcodes (e.g. non-degenerate barcodes from a non-degenerate set of barcodes) can be on one tag that is attached to a candidate nucleic acid molecule on one side of a candidate nucleic acid sequence on that molecule. As another example, one, two, three or more barcodes (e.g. non-degenerate barcodes from a non-degenerate set of barcodes) can be on two tags that are each attached to opposite ends/sides of a candidate nucleic acid molecule outside a candidate nucleic acid sequence on that molecule. Each tag can have the same or a different number of barcodes. The tags can be on a set of pre-made adapter molecules that can each include a tag and in total include an entire set of tags that include one, two, three, or more unique, non-degenerate molecule barcodes, for example. In some embodiments, nested PCR includes amplifying nucleic acid molecules using primers that bind to molecular barcodes on both ends of the nucleic acid molecule. In some embodiments, nested PCR includes amplifying nucleic acid molecules using primers that bind to molecular barcodes on one end of the nucleic acid molecule. In some embodiments, the amplification can include primers that bind to universal primer binding sites. In some embodiments, enriching a desired uniquely tagged nucleic acid species comprises amplifying one or more tagged nucleic acid molecules, and in illustrative embodiments tagged nucleic acid candidate molecules, of desired uniquely tagged nucleic acid species using nested PCR with primers that bind two or more of the at least two barcodes on one side of the tagged nucleic acid molecules, and in illustrative embodiments tagged nucleic acid candidate molecules, of the desired uniquely tagged nucleic acid species in successive PCR reactions to generate the population of polynucleotides or product polynucleotides. In some nested PCR methods, at least one set of primers can be added to a sample, such as a subset (e.g., diluted) sample, that includes a first primer (e.g., forward primer) complementary to at least a portion of an outer barcode and a universal primer complementary to a universal primer binding site located on a tagged nucleic acid molecule on the opposite end and outside of a desired nucleotide sequence, wherein the universal primer site is present on some, many, most, or all nucleic acid molecules in the sample. In some embodiments, at least a second set of primers can be used that includes a second primer complementary to at least a portion of an inner barcode and the primer complementary to the universal primer. In some embodiments, the universal primer site includes some portion of the desired sequence. Such barcode-targeted PCR can be used to enrich and amplify a tagged nucleic acid comprising a desired sequence, such as a sequence-perfect desired sequence, for example identified by long-read sequencing, to generate a polynucleotide having the sequence-perfect desired polynucleotide sequence.

In some embodiments, the number of nucleotides in a primer can be at least 10, 11, 12, 13, 14, 15, 16, 17, 18, 19, 20, 21, 22, 23, 24, 25, 26, 27, 28, 29, 30, 35, 40, 45, or 50 nucleotides. In some embodiments, the number of nucleotides in a primer can be between 10, 11, 12, 13, 14, 15, 16, 17, 18, 19, 20, 21, 22, 23, 24, or 25 nucleotides on the low end of the range and 15, 16, 17, 18, 19, 20, 21, 22, 23, 24, 25, 26, 27, 28, 29, 30, 35, 40, 45, or 50 nucleotides on the high end of the range. In some embodiments, the primers can include 5' tails. In some embodiments, the 5' tails can be at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleotides. In some embodiments, 5' tails added in one amplification can be used in a subsequent PCR. In some embodiments, any of the PCR methods herein can include a pit-stop PCR, wherein the first PCR is performed for 5-20 cycles, for example, 5-15 cycles, 8-12 cycles, or 10 cycles, before a second PCR is performed.

In some aspects of any of the method aspects and embodiments provided herein, the method comprises adding at least one hybrid capture probe that targets at least one barcode, and in illustrative embodiments a unique barcode or molecular barcode, to a reaction mixture for enriching the nucleic acid molecule or polynucleotide having the desired nucleic acid sequence. In such aspects, after hybridizing the hybrid capture probes to the nucleic acid molecules or polynucleotide with the complementary sequence, the other nucleic acid molecules and/or polynucleotides in the subset sample or source sample can be physically removed, such that only the polynucleotide comprising a desired sequence, such as a sequence-perfect desired sequence, for example identified by long-read sequencing, remains and can be enriched, and optionally amplified with primers to any part of the polynucleotide including the unique barcodes or the desired sequence, to generate a polynucleotide having the sequence-perfect desired polynucleotide sequence, In some aspects, the method of polynucleotide production comprises adding at least one hybrid capture probe complementary to at least one adaptor. In some aspects, at least one polynucleotide comprises at least one desired nucleic acid sequence. In some aspects, the method of polynucleotide production further comprises adding at least 2, 3, 4, 5, 6, 7, 8, 9, or 10 different hybrid capture probes. In some embodiments, the hybrid capture probes can be at most 150, 140, 130, 120, 110, 100, 90, 80, 70, 60, 50, 40, 30, 25, or 20 nucleotides in length. In some embodiments, amplification is performed after hybrid capture. In some embodiments, barcode-targeted PCR is used after hybrid capture. In illustrative embodiments, non-targeted PCR is used after hybrid capture.

In some aspects of any of the method aspects and embodiments provided herein, the method comprises adding at least one circularizing primer to a reaction mixture, and in illustrative embodiments source sample or subset sample, for enriching the nucleic acid molecule or polynucleotide having the desired nucleic acid sequence. In some embodiments, the circularizing primer binds the 5' and 3' ends of a nucleic acid molecule to generate an unligated, circularized nucleic acid molecule. In illustrative embodiments, the circularizing primer binds to a barcode sequence of a nucleic acid molecule having the desired, and in illustrative embodiments sequence-perfect desired, nucleic acid sequence on at least one end of the nucleic acid molecule. In some embodiments, the circularizing primer binds to another barcode, a universal primer binding site, or part of the desired sequence at the other end of the nucleic acid molecule having the desired nucleic acid sequence. In some embodiments, ligase is added to the reaction mixture to ligate the unligated, circularized nucleic acid molecule. In illustrative embodiments, the circularizing primer can be added in excess to the reaction mixture. Not to be limited by theory, an excess of circularizing primers can reduce intermolecular ligation events. Ligated, circularized nucleic acid molecules having the desired sequence can then be enriched using exonucleases that degrade the other, linear nucleic acid molecules that were not bound by the circularizing primer. After degradation of the unwanted nucleic acid molecules, the circularized nucleic acid molecule can be enriched (e.g., isolated) using standard techniques and/or amplified using primers complementary to at least a portion of a barcode, universal primers complementary to a universal primer binding site, or primer complementary to the desired sequence. The ligated circularized nucleic acid molecules having the desired sequence can also be enriched by direct amplification using rolling circle PCR.

The enriching (e.g., isolating) steps disclosed above can be used in various combinations that a skilled artisan understands.

The enriched polynucleotides can be processed to remove a portion of the polynucleotide. For example, barcode sequences or universal primer binding sites can be removed from the polynucleotide, leaving the desired sequence without additional sequences. In some embodiments, the additional sequences can be removed by PCR with primers that bind internal to the additional sequences. In some embodiments, the additional sequences can be removed using restriction enzymes, for example Type IIS restriction enzymes, to restriction sites that were included in the oligonucleotides. Generally, the restriction sites will be near one or both ends of a polynucleotide and digestion will result in a polynucleotide having the remainder of the desired sequence with the additional sequences removed. Notably, some sequences that could be considered additional sequences may be removed during earlier steps in the method, for example nested PCR with an inner primer can remove the outer primer binding site in the amplification product.

Certain embodiments of any of the methods provided herein that include an enriching (e.g., isolating) step, are multiplex embodiments wherein polynucleotides can be enriched based on sequencing results from a combined sample that comprises various subset samples made by combining a plurality of individual subset samples, wherein each individual subset sample typically comprises a population of different desired nucleic acid molecules (e.g., with less than 25%, 20%, 10%, 5%, or 1% sequence identity). In illustrative embodiments, the combined sample containing various subset samples is sequenced and the sequencing results are used to enrich polynucleotides from the individual subset samples. Thus, in illustrative embodiments, the polynucleotides are enriched from the subset samples. In other embodiments, the polynucleotides are enriched from the combined sample, or multiple combined samples. In some embodiments, at least one polynucleotide is enriched from the subset sample and another polynucleotide is enriched from a combined sample. In some embodiments, at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1,000 polynucleotides can be enriched from the individual subset samples and/or from the combined sample. For example, subset samples, each subset sample comprising nucleic acid species having a desired sequence, can be combined before sequencing to form a combined sample comprising nucleic acid species comprising a set of desired sequences. In some embodiments, the combined sample contains nucleic acid species with sequence-perfect desired sequences corresponding to each of the desired sequences. In some embodiments, at least one nucleic acid species having one of the desired sequences, and in illustrative embodiments one of the sequence-perfect desired sequences, from the set of desired sequences can be identified that also has a barcode that is unique within the combined sample. In illustrative embodiments, at least one nucleic acid species can be identified for each of the desired sequences that has the desired sequence, and in illustrative embodiments the sequence-perfect desired sequence, and has a barcode that is unique within the combined sample. In such embodiments, a skilled artisan will understand how to use the identified unique barcodes to enrich one or more polynucleotides from each target nucleic acid species using the methods disclosed above. In some embodiments, polynucleotides from at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1,000 target nucleic acid species are enriched from the individual subset samples and/or the combined sample. Such enrichment can include, for example, performing an amplification (e.g., nested barcode-targeted PCR) reaction using one or more universal primers and one, two, or more primers that specifically bind to a barcode sequence of a uniquely tagged nucleic acid species.

Methods herein are capable of producing populations of polynucleotides that after enrichment, contain a higher percent of sequence perfect polynucleotides than prior cell-free methods, especially for polynucleotides that are at least about 1,500, 1,800 or 2,000 nucleotides in length. Accordingly, in some embodiments, at least 25%, 30%, 40%, 50%, 60%, 70%, 75%, 80%, 85%, 90%, 95%, 96%, 97%, 98%, 99%, 99.5%, 99.9% or 100% of the polynucleotides in each population of polynucleotides that is generated after enrichment comprises a respective desired nucleic acid sequence. In some embodiments, the respective desired nucleic acid sequence is at least 25%, 30%, 40%, 50%, 60%, 70%, 75%, 80%, 85%, 90%, 95%, 96%, 97%, 98%, 99%, 99.5%, 99.9% or 100% identical to each respective sequence-perfect desired nucleic acid sequence. In some embodiments, methods provided herein are capable of generating a population of polynucleotides having, or are capable of achieving an error rate or a median error rate of at most 1 error in 10,000, 15,000, 20,000, 25,000, 30,000, 40,000, 50,000, 60,000, 70,000, 80,000, 90,000, 100,000, 110,000, 120,000, 130,000, 140,000, 150,000, 160,000, 170,000, 180,000, 190,000, 200,000, 210,000, 220,000, 230,000, 240,000, 250,000, 300,000, 350,000, 400,000, 450,000, 500,000, 600,000, 700,000, 800,000, or 900,000 nucleotides (1:10,000, 1:15,000, 1:20,000, etc.) in the population of polynucleotides. The number of nucleotide errors in the population is the total number of nucleotide errors when the number of errors in each individual polynucleotide of the population are added together. Thus, for a population of $1 \times 10^6$ polynucleotides, wherein each polynucleotide in the population is 1,000 nucleotides in length, and wherein 20,000 polynucleotides in the population have 1 error each, would have an error rate of 20,000 in $1 \times 10^9$, or simplified to 1 in 50,000 nucleotide errors in the population of polynucleotides.

In some embodiments, the enriching step does not include an error-correction step. In some embodiments, the enriching step can include an error-correction step. Methods for error-correction steps are known in the art. A DNA mismatch-binding protein, MutS (from *Thermus aquaticus*), can be employed to remove failure products from synthetic genes using different strategies (Schofield and Hsieh, 2003; Carr et al., 2004; Binkowski et al., 2005). In some embodiments, the enriching step can include some other strategies (Pogulis et al., 1996; Ling and Robinson, 1997; An et al., 2005; Peng et al., 2006b) use site-directed mutagenesis by overlap extension PCR to correct mistakes, and can be coupled with two or more rounds of cloning and sequencing, as well as additional synthesis of oligonucleotides. Functional selection and identification after gene synthesis is another approach (Xiong et al., 2004b; Smith et al., 2003). Another approach to error correction uses SURVEYOR endonuclease (Transgenomic), a mismatch-specific DNA endonuclease to scan for known and unknown mutations and polymorphisms in heteroduplex DNA. SURVEYOR technology is based on a mismatch-specific DNA endonuclease from celery, Surveyor nuclease, which is a member of the CEL nuclease family of plant DNA endonucleases (Qiu et al., 2004). Surveyor nuclease cleaves with high specificity at the 3' side of any base-substitution mismatch and other distortion site in both DNA strands, including all base substitutions and insertion/deletions up to at least 12 nucleotides. Insertion/deletion mismatches and all base-substitution mismatches can be recognized, with varying efficiency of cleavage based on the mismatch sequence. In one example, Surveyor nuclease technology can be used for mismatch detection in a method involving four steps: (i) optional polynucleotide amplification, e.g. PCR, of desired polynucleotide targets with both mutant/variant and wild-type/desired sequences; (ii) hybridization resulting heteroduplexes comprising mismatches; (iii) treatment of heteroduplexes with Surveyor nuclease to cleave at mismatch sites; and (iv) optional analysis of digested polynucleotide products using the detection/separation platform of choice. The cleavage products resulting from the treatment of heteroduplexes may be subjected to PCA after the error at the cleavage site is chewed out, e.g. by an exonuclease, to generate error depleted products. The mismatch bases can be substantially or in some cases completely removed to produce error-free strands. In some embodiments, the cleaved strands can be reannealed to targets in a pool of polynucleotides and extended. As the frequency of error containing polynucleotides is very low after the initial annealing and cleavage of heteroduplexes removing mismatches, most cleaved strands will anneal to targets with sequences free of error at the site of the initial mismatch. Through extension along the targets, polynucleotides can be resynthesized free of the initial mismatch. Various examples of gene assembly incorporate error correction. For example, the PCR-based accurate synthesis (PAS) protocol can incorporate: design of the gene and oligonucleotides, purification of the oligonucleotides, a first PCR to synthesize segments, a second PCR to assemble the full-length gene, and sequencing and error correction (Xiong et al., 2006). Alternatively, the sample by be subjected to PCR, wherein the cleaved products are not able to participate, thereby diluting the abundance of the error in the sample. The use of the MutSLH complex to remove the majority of errors from PCR fragments is described by Smith et al. (J. Smith and P. Modrich, "Removal of polymerase-produced mutant sequences from PCR products." 1997, PNAS 94:6847-6850), incorporated herein by reference in its entirety. In the absence of DAM methylation, the MutSLH complex can be used to catalyze double-stranded cleavage at (GATC) sites. PCR products can be treated with MutSLH in the presence of ATP.

In some aspects of any of the methods provided herein that include an enriching step, the step can be performed in solution, e.g., the nucleic acid molecules and polynucleotides are not attached to a solid-phase during the step. In some embodiments, the nucleic acid molecules and polynucleotides are cleaved from a solid-phase as part of the enriching step. In some embodiments, nucleic acid molecules and polynucleotides that have errors relative to the desired nucleic acid sequence are cleaved from a solid-phase as part of the enriching step.

g. Methods for Producing a Subsequent Polynucleotide

Also provided herein are methods of producing a subsequent polynucleotide, which method comprises linking one or more polynucleotides produced by the cell-free methods provided herein, typically to produce covalently linked polynucleotides, which in illustrative embodiments are directly linked such that they have the consecutive sequences of the linked polynucleotides. As non-limiting examples, the linked polynucleotides are produced, enriched (e.g., isolated), and/or generated using cell-free methods for producing, enriching, or generating a polynucleotide having a desired sequence provided herein. And the linking is performed, in certain aspects, using any of the assembly methods or technologies provided herein.

Accordingly, in certain embodiments, a cell-free cloning method provided herein (any of which are called vCloning methods herein), includes performing a first assembly module or reaction followed by a cell-free cloning module or reaction on the assembled nucleic acids, followed by a second assembly module or reaction after the cell-free cloning module or reaction, wherein the polynucleotide, typically a population of polynucleotides produced after the second assembly module or reaction, can be considered a subsequent polynucleotide or a population of subsequent polynucleotides. Furthermore, cell-free cloning methods provided herein can include repeatedly performing 2 or more (e.g. 2, 3, 4, 5, 6, 7, 8, 9, 10, 11, 12, etc.) cycles, wherein each cycle includes performance of an assembly module or reaction followed by performance of a cell-free cloning module or reaction. Such cell-free cloning methods can include an optional final assembly module or reaction that is not followed by a cell-free cloning module or reaction. Polynucleotides or populations of polynucleotides produced after a second, third, fourth, etc. assembly in such a cell-free cloning method can be called a subsequent polynucleotide or a population of subsequent polynucleotides herein and can optionally include one or more final enrichment cycles after the final assembly. In some embodiments, such cycle(s) of performing an assembly module or reaction followed by a cell-free cloning module or reaction can be cycle(s) of two or more parallel assembly modules or reactions followed by one or more cell-cloning modules or reactions of the assembled nucleic acids or subsequent polynucleotides of an assembly reaction(s) of a cycle.

As indicated above, the cell-free cloning method in such methods that include 1 or more cycles of an assembly module followed by a cell-free cloning module, can be followed, in some embodiments, by a final assembly module that is not followed by a cell-free cloning module. Thus, such embodiments can include combining a series of nucleic acids, such as oligonucleotides, in a first assembly, which in some embodiments is a primary assembly, or combining subsets of such series of nucleic acids in a parallel set of first assemblies, and after one or more cycles of performing assembly modules followed by cell-free cloning module(s), such cycles are followed by a final assembly module or reaction that is optionally not followed by a cell-free cloning module or reaction, to produce a final population of subsequent polynucleotides. Any of the aspects and embodiments herein can include a primary assembly that generates initial assembly products. In some embodiments, a set of oligonucleotides between 10 and 150, 10 and 175, 10 and 200, 25 and 150, 25 and 175, or 25 and 200 nucleotides in length is assembled to yield two or more initial assembly products. Such initial assembly products can be between 250 and 1000, 250 and 750, 500 and 750, or 500 and 1000 base pairs. In some embodiments, the initial assembly products are ordered from a commercial supplier and the methods herein are used to generate high percentages of sequence-perfect initial assembly products (which can also be called a population of polynucleotides). In some embodiments, the initial assembly products are used in another assembly reaction before the methods herein are used to generate a population of product polynucleotides and optionally a population of subsequent polynucleotides, which can also be referred to herein as a population of subsequence product polynucleotides. Such populations can include a high percentages of sequence-perfect polynucleotides. In some embodiments, methods herein that include 1, 2, 3, 4, 5, or more repeat cycles of any of the diluting, determining the sequence, and enriching steps herein, can start with an initial assembly reaction of oligonucleotides, and then include another assembly reaction using the candidate nucleic acid molecules from the initial assembly, before the first diluting step, to produce the population of product polynucleotides or population of subsequent polynucleotides.

In illustrative embodiments subsequent polynucleotides produced after such a cell-free cloning method can be between 2 times and 1,000 times, 500 times, 100 times, 50 times, 25 times, 20 times, or 10 times, or 5 times larger; or between 5 times and 1,000 times, 500 times, 100 times, 50 times, 25 times, 20 times, or 10 times larger; or between 10 times and 1,000 times, 500 times, 100 times, 50 times, 25 times, or 20 times larger, than the size of one or more, or all, of the nucleic acids used in the first assembly module or reaction of such a cell-free cloning method provided herein. A population of subsequent polynucleotides produced by such a method can have any of the characteristics of such populations of subsequent polynucleotides provided herein. Furthermore, such method, from first assembly through enrichment of the final population of subsequent polynucleotides, in certain embodiments can be performed within 1 day and 7 days, 6 days, 5 days, 4 days, 3 days, or 2 days; or between 2 days and 7 days, 6 days, 5 days, 4 days, or 3 days.

In some aspects, a subsequent polynucleotide produced by certain vCloning methods herein comprises at least one synthetic gene segment, at least one synthetic gene, at least one vector, at least one expression vector, at least one gene cluster, at least one expression cassette, and/or at least one non-coding segment. In some embodiments, the subsequent polynucleotide comprises a promoter and/or an origin of replication. In some embodiments, the vector can be a sequence capable of entering a cell and causing at least a portion of the sequence to be replicated. In some embodiments, the expression vector can be a sequence capable of entering a cell and causing at least a portion of the sequence to be expressed, e.g., transcribed into RNA or translated into a polypeptide, and typically includes a promoter. In some embodiments, the at least one gene cluster can include 2, 3, 4, 5, 6, 7, 8, 9, or 10 or more genes. In illustrative embodiments, the at least one gene cluster can encode similar polypeptides, which in further illustrative embodiments, share a generalized function. In some embodiments, the expression cassette comprises one or more genes and one or more regulatory sequences, which typically includes a promoter. In some embodiments, the non-coding segment can comprise functional non-coding RNA molecules (e.g., transfer RNA, ribosomal RNA, and/or regulatory RNAs), sequences that control transcriptional and translational regulation of protein-coding sequences, scaffold attachment regions, origins of replication, centromeres, and/or telomeres. In some aspects, the subsequent polynucleotide comprises two or more synthetic genes or segments thereof. In some aspects, the subsequent polynucleotide is produced without cells. In some aspects, the method for producing a subsequent polynucleotide produces a subsequent polynucleotide having a desired sequence, and includes a primary assembly step, linking polynucleotides having a desired sequence, for example a sequence-perfect desired sequence, that were produced, enriched, and/or generated using any such method provided herein.

The more polynucleotides that are combined to generate a subsequent polynucleotide, the lower the probability that the subsequent polynucleotide will be sequence-perfect. For example, if 2 polynucleotides, wherein for each, 90% of the molecules are sequence-perfect, are combined to make a subsequent polynucleotide using an error-free assembly method (such that the only errors are from the initial polynucleotides), only 81% of the resulting subsequent polynucleotides would be sequence-perfect, assuming random recombination during assembly (thus, $0.90 \times 0.90 = 0.90^2 = 0.81 \times 100\% = 81\%$). If 10 polynucleotides are combined, wherein for each, 90% of the molecules are sequence-perfect, are combined to make a subsequent polynucleotide (again using a hypothetical error-free assembly method), less than 35% of the subsequent polynucleotides would be sequence-perfect, assuming random recombination during assembly ($0.90^{10} \times 100\% = 34.87\%$). One way to increase the probability that a subsequent polynucleotide has the sequence-perfect desired sequence, especially when many polynucleotides are combined, is to increase the fraction of each starting polynucleotide that is sequence-perfect, for example using the methods disclosed herein to enrich polynucleotides having sequence-perfect desired sequences. For example, when combining 2 or 10 polynucleotides to generate a subsequent polynucleotide, and increasing the probabilities of each of the 2 or 10 polynucleotides being sequence-perfect to 99.9%, the subsequent polynucleotide has a 99.8% probability (starting with 2 polynucleotides ($0.999^2 \times 100\% = 99.8\%$)) and a 99% probability (starting with 10 polynucleotides ($0.999^{10} \times 100\% = 99\%$) of being sequence-perfect. Thus, the methods disclosed herein that efficiently increase the probability of having a sequence-perfect desired sequence for one polynucleotide are especially advantageous for combining multiple polynucleotides into a subsequent polynucleotide. In some embodiments, at least 80%, 85%, 90%, 95%, 96%, 97% 98%, 99%, 99.5%, or 99.9% of the one or more polynucleotides combined in an assembly reaction to generate a subsequent polynucleotide are sequence-perfect. In some aspects, the probability that a subsequent polynucleotide is sequence-perfect is at least 1%, 2%, 3%, 4%, 5%, 10%, 15%, 20%, 25%, 30%, 40%, 50%, 60%, 70%, 75%, 80%, 85%, 90%, 95%, 96%, 97% 98%, 99%, 99.5%, or 99.9%.

In some aspects of any of the methods provided herein, the method is performed at least 2, 3, 4, 5, 6, 7, 8, 9, 10, 15, 20, 25, 30, 40, 50, 60, 70, 80, 90, or 100 times, in certain embodiments as part of a multiplex method as discussed herein, to enrich at least 2, 3, 4, 5, 6, 7, 8, 9, 10, 15, 20, 25, 30, 40, 50, 60, 70, 80, 90, or 100 different polynucleotides, respectively having 2, 3, 4, 5, 6, 7, 8, 9, 10, 15, 20, 25, 30, 40, 50, 60, 70, 80, 90, or 100 different sequence-perfect desired nucleic acid sequences, respectively. In some aspects of any of the methods provided herein at least 2, 3, 4, 5, 6, 7, 8, 9, 10, 15, 20, 25, 30, 40, 50, 60, 70, 80, 90, or 100 different polynucleotides having 2, 3, 4, 5, 6, 7, 8, 9, 10, 15, 20, 25, 30, 40, 50, 60, 70, 80, 90, or 100 different sequence-perfect desired nucleic acid sequences, respectively, are enriched from one subset sample, from 2, 3, 4, 5, 6, 7, 8, 9, 10, 15, 20, 25, 30, 40, 50, 60, 70, 80, 90, or 100 different subset samples, or from one combined sample comprising multiple subset samples. In some embodiments, the sequence-perfect desired polynucleotides are 2, 3, 4, 5, 6, 7, 8, 9, 10, 15, 20, 25, 30, 40, 50, 60, 70, 80, 90, or 100 populations comprising the sequence-perfect desired polynucleotides, wherein the populations comprise at least 95%, 96%, 97%, 98%, 99%, 99.5%, 99.9%, or 100% sequence-perfect desired polynucleotides. In illustrative embodiments, the 2, 3, 4, 5, 6, 7, 8, 9, 10, 15, 20, 25, 30, 40, 50, 60, 70, 80, 90, or 100 populations comprising 2, 3, 4, 5, 6, 7, 8, 9, 10, 15, 20, 25, 30, 40, 50, 60, 70, 80, 90, or 100 sequence-perfect desired polynucleotides, respectively, are assembled into a subsequent polynucleotide having the consecutive nucleotide sequences of the 2, 3, 4, 5, 6, 7, 8, 9, 10, 15, 20, 25, 30, 40, 50, 60, 70, 80, 90, or 100 different sequence-perfect desired polynucleotides. In some aspects of any of the methods provided herein that include generating a subsequent polynucleotide step, the entire method—including assembling at least 2 nucleic acid molecules to form a source sample, tagging nucleic acid molecules, subsetting the source sample, amplifying the subset sample, sequencing the subset sample, enriching polynucleotides from the subset sample, and assembling subsequent polynucleotide that include at least two enriched polynucleotides, can be performed within 1, 2, 3, 4, 5, 6, or 7 days. In illustrative embodiments, the method is performed in between 1 and 2, 3, 4, or 5 days. In some embodiments, subsequent polynucleotides generated using the methods herein can be used to generate a further subsequent polynucleotide.

In some aspects, the subsequent polynucleotide comprises one or more desired nucleic acid sequences. In some aspects, the subsequent polynucleotide comprises one or more nucleic acid molecules each comprising one or more desired nucleic acid sequences. In some aspects, the subsequent polynucleotide comprises one or more assembled nucleic acid molecules, each comprising one or more desired nucleic acid sequences. In some aspects, the subsequent polynucleotide comprises one or more assembled polynucleotides, each comprising one or more desired nucleic acid sequences. In some aspects, the subsequent polynucleotide comprises one or more desired nucleic acid sequences each comprising 1 or less, 2 or less, 3 or less, 4 or less, 5 or less, 6 or less, 7 or less, 8 or less, 9 or less, 10 or less, 15 or less, 20 or less, 30 or less, 40 or less, 50 or less, or 50 or more errors relative to the sequence-perfect desired nucleic acid sequence. In some illustrative embodiments, the subsequent polynucleotide comprises one or more desired nucleic acid sequences that are each sequence-perfect, i.e., have 0 errors relative to the desired nucleic acid sequences.

As indicated herein, a cell-free cloning module provided herein can be performed between an assembly reaction/module, and such cycle(s) of performing an assembly reaction/module followed by a cell-free cloning reaction/module can be repeated one or more times. Such cycle or repeated cycles can be followed by a final assembly reaction of cell-free cloned polynucleotides that is not followed by another cell-free cloning module. The cell-free cloning modules performed in such methods function to enrich for a population of polynucleotides that have a much higher sequence identity to a sequence-perfect nucleic acid sequence than was present immediately after the assembly reaction.

In illustrative embodiments of such cell-free cloning methods provided herein that include performance of at least one cycle of assembly/cell-free cloning followed by a final assembly reaction, the final cell-free cloned polynucleotide, or population thereof, is at least 1 kb, 2 kb, 3 kb, 4 kb, 5 kb, 6 kb, 7 kb, 8 kb, 9 kb, 10 kb, 20 kb, 25 kb, 30 kb, 40 kb, or 50 kb, or between 10 kb and 1 Mb, 500 kb, 250 kb, 200 kb, 100 kb, 50 kb, or 25 kb in length or any of the lengths disclosed herein for subsequent polynucleotides. In certain embodiments, the final cell-free cloned polynucleotide, or population thereof, is too long to be amplified reliably by an amplification method, such as an isothermal amplification method or PCR. In some embodiments of such methods, the nucleic acid molecules assembled in one or more first assembly reactions/modules used in the method are less than ½, ⅓, ¼, ⅕, 1/10, 1/20, 1/25, 1/50, or 1/100 the size of the cell-free cloned polynucleotide. In certain embodiments, the nucleic acid molecules assembled in the first assembly reaction are between 10 bases and 10 kb, 5 kb, or 1 kb, or 500, 250, 200, or 100 bases in length. In certain embodiments, the nucleic acid molecules assembled in one or more first assembly reactions/modules are small enough to be amplified reliably by an amplification method, such as an isothermal amplification method or PCR.

Assembly modules in such cycles of assembly/cell-free cloning can include parallel assembly reactions/modules, which each can be followed by a cell-free cloning module, and then one or more of these cell-free cloned polynucleotides (typically populations of cell-free cloned polynucleotides) can be assembled. Following such cell-free cloning module, or as part of such module, barcodes and/or other adapter sequences can be removed before subsequent assembly reactions/modules. A tagging step is typically included in a next cycle of performing an assembly module followed by a cell-free cloning module provided herein, and such method may include a final assembly module that is not followed by a cell-free cloning module provided herein, to produce a final subsequent polynucleotide.

Thus, a skilled artisan will understand that many variations can be used to produce a subsequent polynucleotide that is an assembly of cell-free cloned polynucleotides. For example, if a 100 kb polynucleotide is desired (e.g. ordered by a customer using a system provided herein), a cell-free process can be used with many combinations of assembly and cell-free cloning modules. For example, 100 bp oligos can be used in 100 first assemblies, which in some embodiments can be primary assemblies, each first assembly including between 2 and 100 of such oligos. Then the products of such first assembly can be subjected to cell-free cloning and then assembled in 5 assemblies performed in parallel followed by cell-free cloning to produce five 20-kb sequence-perfect polynucleotides, then five 20 kb polynucleotides can be assembled into a 100 kb polynucleotide having at least 90%, 95, 99% sequence identity to the sequence-perfect desired sequence.

In certain embodiments, such method for producing a subsequent polynucleotide, including as non-limiting examples, such methods wherein the length of the subsequent polynucleotide is at least 10 kb, is performed in four days or less, three days or less, two days or less, 48 hours or less, 46 hours or less, 44 hours or less, 42 hours or less, 40 hours or less, 38 hours or less, 36 hours or less, 34 hours or less, 32 hours or less, 30 hours or less, 28 hours or less, 26 hours or less, or 24 hours or less.

Since subsequent polynucleotides comprise two or more polynucleotides having a desired sequence, enriched using a method provided herein, they typically have lengths that are larger than, and in certain embodiments, 50%, 75%, 80%, 90%, 95%, 99%, 100% larger, or 1.5, 2, 3, 4, 5, 6, 7, 8, 9, 10, 11, 12, etc. times larger than polynucleotides that were assembled to create the subsequent polynucleotide, depending on the number of polynucleotides that are assembled to form the subsequent polynucleotide. In some aspects, the length of the subsequent polynucleotide is at least 500, 750, 1 kilobase (kb), 2.5 kb, 5 kb, 7.5 kb, 10 kb, 100 kb, 250 kb, 500 kb, 750 kb, 1 megabase (Mb), 2.5 Mb, 5 Mb, 10 Mb, 20 Mb, 30 Mb, 40 Mb, 50 Mb, 75 Mb, 100 Mb, 200 Mb, or 300 Mb. In some embodiments, the length subsequent polynucleotide is from about 0.5 kilobases (kb) to about 500 megabases (Mb), from about or exactly 0.5 kb to 250 Mb, 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, 15 kb, 10 kb, or 5 kb in length. In other embodiments, the length subsequent polynucleotide is from about 1 kb to about 500 Mb, 250 Mb, 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, 15 kb, 10 kb, or 5 kb. In certain illustrative embodiments, the length subsequent polynucleotide is from about 10 kb to 250 Mb, 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, or 15 kb.

In some embodiments, the method for producing a subsequent polynucleotide includes a first assembly reaction or module, a vCloning module, and a second assembly reaction or module, and in illustrative embodiments generates, produces, or enriches a subsequent polynucleotide, or population thereof, wherein at least 75%, 80%, 90%, 95%, 99%, or 100% of the polynucleotides therein, have a nucleic acid sequence that is at least 75%, 80%, 90%, 95%, 99%, 99.9% or 100% sequence-perfect with respect to a desired nucleic acid sequence. In non-limiting examples, the desired nucleic acid sequence is at least 10 kb. In certain illustrative embodiments, such method is a cell-free method performed in between 1 day and 7 days, 6 days, 5 days, 4 days, 3 days or 2 days, or between 2 days and 7 days, 6 days, 5 days, 4 days, or 3 days. In certain illustrative embodiments, the sequencing step in such a method is performed using long-range sequencing.

In some aspects, the method of producing the subsequent polynucleotide comprises selecting 1 or more, 2 or more, 5 or more, 10 or more, 20 or more, 50 or more, 100 or more, 250 or more, 500 or more, 750 or more, 1000 or more, 2000 or more, 3000 or more, 4000 or more, 5000 or more, 10,000 or more polynucleotides and/or subsequent polynucleotides for analysis. In some aspects, the analysis comprises sequence-based analysis as provided herein, such as long-read sequence analysis.

In some aspects, the method of subsequent polynucleotide production comprises adding at least one primer complementary to at least one molecular barcode. In some aspects, at least one subsequent polynucleotide comprises at least one desired nucleic acid sequence. In some aspects, the method of subsequent polynucleotide production further comprises adding at least two different primers. In some aspects, the primers are complementary to more than one molecular barcode, such that barcode-targeted PCR can be performed to enrich and amplify one or more desired nucleic acid sequences. For instance, at least one set of primers can be complementary to an outer barcode and its reverse primer site, and at least a second set of primers can be complementary to an inner barcode and its reverse primer site.

In some aspects, the subsequent polynucleotide is assembled using polymerase cycling assembly (PCA) (Stemmer et al. Gene. 1995 Oct. 16; 164(1):49-53), isothermal assembly, e.g., Gibson assembly (Gibson et al. Nat Methods. 2009 May; 6(5):343-5), ligase cycling reaction (LCR) (Chandran. Methods Mol Biol. 2017; 1472:105-10), overlap extension PCR (overlapping PCR, PCR SOEing, PCR sewing) (Bryksin and Matsumura. Methods Mol Biol. 2013; 1073:31-42), PCR stitching, bacterial recombination, yeast homologous recombination, or circular DNA assembly (e.g., OriCiro® Assembly Kit and OriCiro® Amp Kit) of two or more polynucleotides produced by the methods described herein. In some aspects, the subsequent polynucleotide comprises a subsequent polynucleotide assembled by polymerase cycling assembly (PCA) (Stemmer et al. Gene. 1995 Oct. 16; 164(1):49-53), isothermal assembly, e.g., Gibson assembly (Gibson et al. Nat Methods. 2009 May; 6(5):343-5), ligase cycling reaction (LCR) (Chandran. Methods Mol Biol. 2017; 1472:105-10), overlap extension PCR (overlapping PCR, PCR SOEing, PCR sewing) (Bryksin and Matsumura. Methods Mol Biol. 2013; 1073:31-42), PCR stitching, bacterial recombination, yeast homologous recombination, or circular DNA assembly (e.g., OriCiro® Assembly Kit and OriCiro® Amp Kit) of two or more polynucleotides produced by the methods described herein. In some aspects, the subsequent polynucleotide comprises subsequent polynucleotides that have been produced by the methods described herein that are then further assembled using any of the above methods, e.g., Gibson assembly, of two or more of the subsequent polynucleotides.

h. Removing Adaptors and/or Molecular Barcodes

At any step during or after one of the methods herein, adaptors and/or molecular barcodes can be removed from the polynucleotides of the population of polynucleotides. Thus, in some embodiments of any of the methods herein, the method further comprises removing adaptors and/or molecular barcodes step. In illustrative embodiments, the adaptors and/or molecular barcodes are removed from the polynucleotides of the population of polynucleotides after an enriching step. In further illustrative embodiments, both the adaptors and molecular barcodes are removed. The sequences of such polynucleotides then include only the desired nucleic acid sequence.

Various methods of adaptor removal are known in the art. In some embodiments, the adaptors and/or molecular barcodes are removed using uracil-containing primers. An amplification is performed with the uracil-containing primers such that the amplification products contain uracil. The amplification products are then incubated with a uracil DNA glycosylase (UDG) and DNA glycosylase-lyase Endonuclease VIII such that the uracil bases are removed from the amplification products. Multiple uracils can be included in the primers such that the resulting segments after the uracil bases are removed are short enough that the segments melt off, leaving a single-stranded overhang. The single-stranded overhang can then be truncated using methods known in the art, for example, using the Klenow fragment. Thus, in some embodiments the removing adaptors and/or molecular barcodes step can include an amplifying step including uracil-containing primers, a uracil-base removing step including a uracil DNA glycosylase (UDG) and DNA glycosylase-lyase Endonuclease VIII, and a removing a single-stranded overhang step including a nuclease, for example, the Klenow fragment. A similar method can be used with deoxyinosine-containing primers and endonuclease V. Thus, in some embodiments the removing adaptors and/or molecular barcodes step can include an amplifying step including deoxyinosine-containing primers, a deoxyinosine-base removing step including an Endonuclease V, and a removing a single-stranded overhang step including a nuclease, for example, the Klenow fragment. Type IIS restriction enzymes can also be used to remove adaptors and/or molecular barcodes. A skilled artisan understands how to use any of the methods in the art to remove adaptors and/or molecular barcodes of the methods of the present disclosure.

i. Automated Production System

Any of the methods herein can be partially or fully automated. Thus, any one or more of the steps of such method can be performed using automation. In some embodiments, the method includes the use of a robotic fluid-handling system, microfluidic system, and/or nanofluidic system for one or more of the steps of the method, for example, the assembly, tagging, subsetting (e.g., diluting). In some embodiments, the method includes the use of a computer system to control the automated production system. In some embodiments, the computer system is configured to control the automated production system. In some embodiments, a desired nucleic acid sequence is entered into a computer system and the computer system controls the automated production system to generate a population of polynucleotides. In illustrative embodiments, more than one desired nucleic acid sequences are entered into a computer system and the computer system controls the automated production system to generate populations of polynucleotides corresponding to each desired nucleic acid sequence. The desired nucleic acid sequences can include any of the embodiments related to desired nucleic acid sequence disclosed herein, for example, traditionally difficult sequences, and the populations of polynucleotides can include any of the embodiments related to populations of polynucleotides disclosed herein.

j. Quality Thresholds

A skilled artisan using the methods and compositions disclosed herein can generate populations of desired polynucleotides (populations of polynucleotides having the desired nucleic acid sequence) with high percentages of polynucleotides having the desired nucleic acid sequence, and in illustrative embodiments the sequence-perfect desired nucleic acid sequence. This is possible even with desired polynucleotides having desired nucleic acid sequences that were previously difficult to synthesize and enrich reliably in a cell-free system. A quality threshold can be included in any of the methods herein. A quality threshold can be the minimum percentage of nucleic acid molecules in the population of polynucleotides, and in illustrative embodiments product polynucleotides, that comprise a sequence that is sequence-perfect to the desired nucleic acid sequence. Alternatively, the quality threshold can be a minimum error rate of the sequences of the population of polynucleotides, and in illustrative embodiments product polynucleotides. The quality threshold can be calculated by sequencing at least 10 polynucleotides from the population of polynucleotides, and calculating the percentage of sequenced polynucleotides that include a region that is sequence identical to the desired nucleic acid sequence or calculating the error rate. In some embodiments, at least 15, 20, 25, 30, 35, 40, 50, 60, 70, 80, 90, 100, 150, 200, 250, 500, 750, or 1,000 desired polynucleotides can be sequenced to calculate the quality threshold. In some aspects, the polynucleotides can include sequences beyond the desired nucleic acid sequence. In illustrative embodiments, any excess sequence beyond the desired nucleic acid sequence is removed. In some aspects, the quality threshold can be calculated based on the error rate of a polymerase used to amplify a single sequence-perfect nucleic acid molecule or desired polynucleotide.

In some aspects, a method including a population of polynucleotides can include one or more quality thresholds that depends on the length of the desired nucleic acid sequence of the desired polynucleotides of the population. In some aspects, for desired polynucleotides between 500 and 1,999 bp in length, the quality threshold can be 95%, 96%, 97%, 98%, 98.5%, 99%. 99.5%, 99.6%, 99.7%, 99.8%, 99.9%, 99.99%, or 99.999%. In some aspects, for desired polynucleotides between 2,000 and 2,999 bp in length, the quality threshold can be 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 3,000 and 50,000 bp in length, the quality threshold can be 80%, 81%, 82%, 83%, 84%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 50,001 and 100,000 bp in length, the quality threshold can be 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 100,001 and 1,000,000 bp in length, the quality threshold can be 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

In illustrative embodiments, a method of fulfilling an order for a population of desired polynucleotides can include desired polynucleotides of the population that are:
  i) between 500 and 1,999 bp in length, and wherein the quality threshold is 98%;
  ii) between 2,000 and 2,999 bp in length, and wherein the quality threshold is 95%; or
  iii) between 3,000 and 50,000 bp in length, and wherein the quality threshold is 92%.

In some aspects, the quality threshold is the error rate in the sequences of the population of polynucleotides. The error rate in the population of polynucleotides can be calculated as the number of errors per a specific number of base pairs (e.g, 1 error per 10,000 total base pairs in the population of polynucleotides (1:10,000). For desired nucleic acid sequences in populations of polynucleotides that are shorter than the error rate, multiple polynucleotides may have to be read to identify one error. For example, if the error rate is 1:10,000, and the desired nucleic acid sequence is 2,000 bp in length, on average one error will be found per 5 polynucleotides (1 error per 10,000 bp=1 error per (5 polynucleotides×2,000 bp/polynucleotide)). If, in contrast, the desired nucleic acid sequence is 10,000 bp in length, on average one error will be found on each polynucleotide (1 error per 10,000 bp=1 error per (1 polynucleotide×10,000 bp/polynucleotide). Thus, lower error rates lead to higher percentages of polynucleotides having the desired nucleic acid sequence, but the percentage is dependent on the length of the desired nucleic acid sequence.

In any of the aspects and embodiments herein that include a population of polynucleotide having a desired nucleic acid sequence, the sequences in the population can have an error rate of 1:10,000, 1:15,000, 1:20,000, 1:25,000, 1:30,000, 1:35,000, 1:40,000, 1:45,000, 1:50,000, 1:60,000, 1:70,000, 1:80,000, 1:90,000, 1:100,000, 1:110,000, 1:120,000, 1:130,000, 1:140,000, 1:150,000, 1:160,000, 1:170,000, 1:180,000, 1:190,000, 1:200,000, 1:210,000, 1:220,000, 1:230,000, 1:240,000, 1:250,000, 1:300,000, 1:350,000, 1:400,000, 1:450,000, 1:500,000, 1:600,000, 1:700,000, 1:800,000, or 1:900,000 or lower. In some embodiments, the sequences in the population can have an error rate that is greater than 1:1,000,000, 1:2,000,000, 1:3,000,000, 1:4,000,000, or 1:5,000,000. In some embodiments, the sequences in the population can have an error rate between 1:10,000, 1:15,000, 1:20,000, 1:25,000, 1:30,000, 1:35,000, 1:40,000, 1:45,000, 1:50,000, 1:60,000, 1:70,000, 1:80,000, 1:90,000, and 1:100,000 on the low end of the range and 1:30,000, 1:35,000, 1:40,000, 1:45,000, 1:50,000, 1:60,000, 1:70,000, 1:80,000, 1:90,000, 1:100,000, 1:110,000, 1:120,000, 1:130,000, 1:140,000, 1:150,000, 1:160,000, 1:170,000, 1:180,000, 1:190,000, 1:200,000, 1:210,000, 1:220,000, 1:230,000, 1:240,000, 1:250,000, 1:300,000, 1:350,000, 1:400,000, 1:450,000, 1:500,000, 1:600,000, 1:700,000, 1:800,000, or 1:900,000 on the high end of the range. In illustrative embodiments any of the compositions and methods herein that include a population of polynucleotide having a desired nucleic acid sequence or a population of desired polynucleotides, the sequences in the population can have an error rate of 1:30,000 or lower. In illustrative embodiments, the error rate is 1:60,000 or lower.

k. Reproducibility Thresholds

In addition to generating populations of desired polynucleotides with high percentages of polynucleotides having the desired nucleic acid sequence, and in illustrative embodiments the sequence-perfect desired nucleic acid sequence, e.g., with a high quality threshold, the methods and compositions disclosed herein are capable of generating a population of desired polynucleotides reproducibly, e.g., with a high reproducibility threshold. Thus, in some aspects, a method includes a quality threshold at a reproducibility threshold, wherein the reproducibility threshold is the minimum percent success rate, e.g., the minimum percent success rate of generating a population of desired polynucleotides. The minimum percent success rate is calculated based on the number of successful attempts at generating a population of desired polynucleotides at the quality threshold and the total number of attempts at generating the population of desired polynucleotides. In some aspects, the number of attempts used to calculate the minimum percent success rate, and therefore the reproducibility threshold, can be at least 5, 10, 15, 20, 25, 30, 35, 40, 45, 50, 60, 70, 80, 90, or 100 attempts. In some aspects, the number of attempts used to calculate the minimum percent success rate, and therefore the reproducibility threshold, can be 5, 10, 15, 20, 25, 30, 35, 40, 45, 50, 60, 70, 80, 90, or 100 attempts.

In some aspects, a method can include one or more quality thresholds at a reproducibility threshold depending on the length of the desired nucleic acid sequence of the desired polynucleotides of the population. In some aspects, for desired polynucleotides between 500 and 1,999 bp in length, the quality threshold can be 95%, 96%, 97%, 98%, 98.5%, 99%. 99.5%, 99.6%, 99.7%, 99.8%, 99.9%, 99.99%, or 99.999%. In some aspects, for desired polynucleotides between 500 and 1,999 bp in length, the reproducibility threshold can be 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 500 and 1,999 bp in length, the quality threshold can be 98% and the reproducibility threshold can be 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

In some aspects, a method can include one or more quality thresholds at a reproducibility threshold depending on the length of the desired nucleic acid sequence of the desired polynucleotides of the population. In some aspects, for desired polynucleotides between 2,000 and 2,999 bp in length, the quality threshold can be 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 2,000 and 2,999 bp in length, the reproducibility threshold can be 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 2,000 and 2,999 bp in length, the quality threshold can be 95% and the reproducibility threshold can be 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

In some aspects, for desired polynucleotides between 3,000 and 50,000 bp in length, the quality threshold can be 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 3,000 and 50,000 bp in length, the reproducibility threshold can be 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 3,000 and 50,000 bp in length, the quality threshold can be 92% and the reproducibility threshold can be 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

In some aspects, for desired polynucleotides between 50,001 and 100,000 bp in length, the quality threshold can be 65%, 70%, 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 50,001 and 100,000 bp in length, the reproducibility threshold can be 60%, 65%, 70%, 75%, 80%, 85%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 50,001 and 100,000 bp in length, the quality threshold can be 85% and the reproducibility threshold can be 60%, 65%, 70%, 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

In some aspects, for desired polynucleotides between 100,001 and 1,000,000 bp in length, the quality threshold can be 70%, 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 100,001 and 1,000,000 bp in length, the reproducibility threshold can be 50%, 55%, 60%, 65%, 70%, 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%. In some aspects, for desired polynucleotides between 100,001 and 1,000,000 bp in length, the quality threshold can be 75% and the reproducibility threshold can be 50%, 55%, 60%, 65%, 70%, 75%, 80%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

In illustrative embodiments, a method can include desired polynucleotides of the population that are:
i) between 500 and 1,999 bp in length, and wherein the quality threshold is 98% and wherein the reproducibility threshold is 98%;
ii) between 2,000 and 2,999 bp in length, and wherein the quality threshold is 95% and wherein the reproducibility threshold is 95%; or
iii) between 3,000 and 50,000 bp in length, and wherein the quality threshold is 92% and wherein the reproducibility threshold is 92%.

In some embodiments, a method of generating a population of polynucleotides or fulfilling an order for a population of desired polynucleotides can include one or more quality thresholds at a reproducibility threshold, wherein the quality threshold is any of the error rate disclosed herein and the reproducibility threshold is 60%, 65%, 70%, 75%, 80%, 85%, 85%, 86%, 87%, 88%, 89%, 90%, 91%, 92%, 93%, 94%, 95%, 96%, 97%, 98%, 98.5%, 99%. 99.5%, 99.6%, 99.7%, 99.8%, 99.9%, 99.99%, or 99.999%.

l. Rapid Generation of Polynucleotides

In addition to easily generating populations of desired polynucleotides with high percentages of polynucleotides having the desired nucleic acid sequence, and in illustrative embodiments the sequence-perfect desired nucleic acid sequence, using the methods and compositions disclosed herein, a skilled artisan can generate the populations of desired polynucleotides in advantageously short amounts of time. Thus, in some aspects, a method herein can be performed in less than 7 days. In some aspects, the method is performed in 14, 13, 12, 11, 10, 9, 8, 7, 6, 5, 4, 3, 2, or 1 day or less. In some aspects, a method of fulfilling an order is performed in between 1 day and 14, 13, 12, 11, 10, 9, 8, 7, 6, 5, 4, 3, or 2 days. In some aspects, a method is performed in between 2 days and 14, 13, 12, 11, 10, 9, 8, 7, 6, 5, 4, or 3 days. In some aspects, a method is performed in between 2 days and 7 days. In some aspects, a method is performed in between 3 days and 14, 13, 12, 11, 10, 9, 8, 7, 6, 5, or 4 days. In some aspects, a method is performed in between 5 days and 14, 13, 12, 11, 10, 9, 8, 7, or 6 days.

III. Methods of Fulfilling Orders

The methods disclosed herein provide a fast method of generating a highly enriched population of polynucleotide having a desired nucleic acid sequence. These methods allow a faster ordering process, such that a customer can order a polynucleotide having a desired nucleic acid sequence and the order can be fulfilled in an advantageously short time, without the cumbersome use of cell cloning or other techniques. The methods herein that refer to fulfilling an order, can also refer to methods of completing, preparing, or satisfying an order, or methods of producing a population. Thus, in one aspect provided herein, is a method of fulfilling (or completing, preparing, or satisfying) an order for a population of desired polynucleotides, the method comprising:
  a) receiving an order for the population of desired polynucleotides from a customer, wherein the desired polynucleotide has a desired nucleic acid sequence; and
  b) fulfilling (or completing, preparing, or satisfying) the order by generating the population of desired polynucleotides with a quality threshold, wherein the quality threshold is the minimum percentage of nucleic acid molecules in the population of desired polynucleotides that comprise a sequence that is sequence-perfect to the desired nucleic acid sequence.

As fulfilling an order includes generating a population of desired polynucleotides (i.e., population of polynucleotide having the desired nucleic acid sequence), any of the methods herein that include an order can include any of the aspects and embodiments related to producing a population of polynucleotide. In illustrative embodiments, the method can be performed using a cell-free method. In illustrative embodiments, the method can be performed using an automated production system, as disclosed elsewhere herein. In illustrative embodiments, the desired polynucleotides can be template-free polynucleotides.

In some aspects, the method can further include a shipping step, wherein the population of desired polynucleotides is shipped to the customer. In such embodiments, the shipping can be performed using any shipping company capable of shipping the population of desired polynucleotides. In some embodiments, the shipping is performed in a temperature-controlled manner, such that the population of desired polynucleotides is kept with 5° C. of a desired temperature. In some embodiments, the desired temperature can be 25° C., 20° C., 15° C., 10° C., 5° C., 0° C., −5° C., −10° C., −15° C., or −20° C. In some aspects, the method can further include a receiving step, wherein the customer receives the population of desired polynucleotides. In some aspects, the method can further include a lyophilization step. In some embodiments, the population of desired polynucleotides can be lyophilized before being shipped to and/or received by the customer.

A skilled artisan understands how any of the polynucleotides disclosed elsewhere herein, or any of the characteristics of the polynucleotides disclosed elsewhere herein, can be used in any of the aspects and embodiments here that include a method for fulfilling, completing, preparing, or satisfying an order. In some aspects, a method for ordering can include using tagged nucleic acid molecules. In some aspects, the tagged nucleic acid molecules can include unique barcodes. Thus, in some aspects, a method of ordering can include a tagged sample comprising a plurality of tagged nucleic acid molecules, wherein the tagged nucleic acid molecules each comprise at least a portion of the desired nucleic acid sequence and further comprise one or more barcodes, wherein at least some of the tagged nucleic acid molecules are uniquely tagged nucleic acid species, wherein tagged nucleic acid species are tagged nucleic acid molecules with identical nucleic acid sequences.

A skilled artisan understands how any of the methods for polynucleotide production, for producing or generating a polynucleotide or a population of polynucleotides, for production of such a polynucleotide or population, or in certain illustrative embodiments, a method of cell-free cloning of such a polynucleotide or population can be used in any of the aspects and embodiments here that include a method for fulfilling, completing, preparing, or satisfying an order. In some embodiments, the method of ordering includes vCloning, as disclosed elsewhere herein.

In some aspects, a method of fulfilling an order can include one or more of: a cell-free method; or an automated production system. Various embodiments are set forth in the section below and can be combined in any manner.

The methods and compositions disclosed herein are capable of generating a population of desired polynucleotides having desired nucleic acid sequences that in total, or segments of which were previously believed in the art to be difficult to synthesize, assemble, and/or otherwise generate, as discussed in more detail herein. Thus, in some aspects, a desired sequence in a method of fulfilling (or completing, preparing, or satisfying) an order includes desired nucleic acid sequences that are or comprise a traditionally problematic sequence, as disclosed elsewhere herein.

In some aspects that include a shipping step and/or a delivering or receiving step, the time from receiving the order to shipping and/or delivering the population of desired polynucleotides can be performed in less than 10 days. In some aspects, the time from receiving the order to shipping and/or delivering the population of desired polynucleotides is less than 21, 20, 19, 18, 17, 16, 15, 14, 13, 12, 11, 10, 9, 8, 7, 6, 5, 4, or 3 days. In some aspects, the time from receiving the order to shipping and/or delivering the population of desired polynucleotides is performed in between 2 days and 14, 13, 12, 11, 10, 9, 8, 7, 6, 5, 4, or 3 days. In some aspects, the time from receiving the order to shipping and/or delivering the population of desired polynucleotides is performed in between 2 days and 10 days. In some aspects, the time from receiving the order to shipping and/or delivering the population of desired polynucleotides is performed in between 3 days and 21, 20, 19, 18, 17, 16, 15, 14, 13, 12, 11, 10, 9, 8, 7, 6, 5, or 4 days. In some aspects, the time from receiving the order to shipping and/or delivering the population of desired polynucleotides is performed in between 5 days and 21, 20, 19, 18, 17, 16, 15, 14, 13, 12, 11, 10, 9, 8, 7, or 6 days.

IV. Nucleic Acid Molecules and Polynucleotides

In some aspects, the combined lengths of the different sequences of the nucleic acid molecules of the source sample is at least 2, 3, 4, 5, 10, 15, 20, 30, 40, 50, 60, 90, 100, 200, 300, 400, 500, 750, 1,000, 2,500, 5,000, 7,500, 10,000, 100,000, 250,000, 500,000, 750,000, 1,000,000, 2,500,000, 5,000,000, 10,000,000, 20,000,000, 30,000,000, 40,000,000, 50,000,000, 75,000,000, 100,000,000, 200,000,000, or 300,000,000 bases. In some aspects, the combined lengths of the different sequences of the nucleic acid molecules of the source sample is from about 0.1 kilobases (kb) to about 500 megabases (Mb), about 0.1 kb to about 250 Mb, about 0.1 kb to about 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, 15 kb, 10 kb, or 5 kb, or about 0.01 kb to about 30 kb, about 0.1 kb to about 30 kb, about 0.5 kb to about 100 Mb, 75 Mb, 50 Mb, 25 Mb, 20 Mb, 15 Mb, 10 Mb, 5 Mb, 500 kb, 250 kb, 100 kb, 75 kb, 50 kb, 30 kb, 20 kb, 10 kb, 5 kb, or 4 kb. In some aspects, the combined lengths of the different sequences of the nucleic acid molecules of the source sample is from about 0.1 kb to about 30 kb in length.

In some aspects, the lengths of the polynucleotides having a desired sequence are at least 500, 750, 1,000, 2,500, 5,000, 7,500, 10,000, 100,000, 250,000, 500,000, 750,000, 1,000, 000, 2,500,000, 5,000,000, 10,000,000, 20,000,000, 30,000, 000, 40,000,000, 50,000,000, 75,000,000, 100,000,000, 200, 000,000, or 300,000,000 bases. In some aspects, the lengths of the polynucleotides having a desired sequence is from about 0.1 kilobases (kb) to about 500 megabases (Mb), about 0.1 kb to about 250 Mb, about 0.1 kb to about 100 Mb, 75 Mb, 50 Mb, 25 Mb, 20 Mb, 15 Mb, 10 Mb, 5 Mb, 500 kb, 250 kb, 100 kb, 75 kb, 50 kb, 25 kb, 20 kb, 15 kb, 10 kb, or 5 kb, or about 0.01 kb to about 30 kb, about 0.1 kb to about 30 kb, about 0.5 kb to about 100 Mb, 75 Mb, 50 Mb, 25 Mb, 20 Mb, 15 Mb, 10 Mb, 5 Mb, 500 kb, 250 kb, 100 kb, 75 kb, 50 kb, 30 kb, 20 kb, 10 kb, 5 kb, or 4 kb. In some aspects, the lengths of the polynucleotides having a desired sequence is from about 0.1 kb to about 30 kb in length.

In some aspects, the nucleic acid molecules of the source sample and/or the diluted sample comprise DNA. In some aspects, the nucleic acid molecules of the source sample and/or the diluted sample comprise RNA. In some aspects, the nucleic acid molecules of the source sample and/or the diluted sample comprise synthetic nucleic acids, naturally occurring sources, or both synthetic and natural sequences. In some aspects, the nucleic acid molecules of the source sample and/or the diluted sample comprise PCR product(s). In some aspects, the nucleic acid molecules of the source sample and/or the diluted sample comprise nucleic acids isolated from a biological sample containing a variety of other components, such as proteins, lipids and non-template nucleic acids. In some aspects, the nucleic acid molecules of the source sample and/or the diluted sample comprise nucleic acids can be obtained from any cellular material, obtained from an animal, plant, bacterium, fungus, or any other cellular organism. In some aspects, the nucleic acid molecules of the source sample and/or the diluted sample comprise nucleic acids can be obtained from biological samples. In some aspects, the nucleic acid molecules of the source sample and/or the diluted sample comprise nucleic acids obtained from viral particles or preparations. In some aspects, the nucleic acid molecules of the source sample and/or the diluted sample comprise nucleic acids obtained directly from an organism or from a biological sample obtained from an organism, e.g., from blood, urine, cerebrospinal fluid, seminal fluid, saliva, sputum, stool and tissue. For instance, any tissue or body fluid specimen may be used as a source for nucleic acid for use with the present disclosure. In some aspects, the nucleic acid molecules of the source sample and/or the diluted sample comprise nucleic acid molecules isolated from cultured cells, such as a primary cell culture or a cell line. In some aspects, the nucleic acid molecules of the source sample and/or the diluted sample comprise nucleic acids from cells or tissues that are infected with a virus or other intracellular pathogen. In some aspects, the nucleic acid molecules of the source sample and/or the diluted sample comprise total RNA extracted from a biological specimen, a cDNA library, viral, or genomic DNA. In some aspects, the nucleic acid molecules of the source sample and/or the diluted sample comprise one or more gene fragments.

In some aspects, the nucleic acid molecules of the source sample and/or the diluted sample comprise one or more polynucleotides and/or one or more subsequent polynucleotides produced by the methods described herein. In some aspects, the nucleic acid molecules of the source sample and/or the diluted sample comprise nucleic acids synthesized by the assembly of two or more nucleic acids, for example using any of the assembly methods disclosed herein. In some aspects, the nucleic acid molecules of the source sample and/or the diluted sample comprise a fragment isolated from a gel. In some aspects, the nucleic acid molecules of the source sample and/or the diluted sample comprise an amplification product, e.g., a PCR product. In illustrative aspects, the nucleic acid molecules of the source sample and/or the diluted sample comprise an amplification product. In such aspects, the nucleic acid molecules and polynucleotides can be template-free nucleic acid nucleic acid molecules or polynucleotides. Such template-free nucleic acid molecules and polynucleotides can include nucleic acid molecules and polynucleotides where no single, initial template nucleic acid molecule was amplified to generate the entire desired nucleic acid sequence. In some embodiments, source nucleic acid molecules or polynucleotides having a desired nucleic acid sequence are generated by assembling nucleic acid molecules without performing an amplification from a single initial template nucleic acid molecule that generates in the entire desired nucleic acid sequence. Such template-free nucleic acid molecules and polynucleotides can, and typically are, amplified later in the methods disclosed herein, but there is no single, initial template from which the entire desired nucleic acid sequence is generated. In some embodiments, the desired nucleic acid sequence can be a non-natural sequence. Such non-natural sequences include nucleic acid sequences that do not naturally occur, for example, e.g., a sequence that does not occur in any DNA or RNA sequences from any kingdom of life (Animalia, Plantae, Fungi, Protista, Archaea, and Bacteria) or virus.

a. Adapters

In some aspects, at least one nucleic acid molecule of the source sample comprises at least one adapter. In some aspects, at least one adapter is attached to the 5' and/or the 3' end of at least one nucleic acid molecule. In some aspects, a variety of types of adaptors can be used in the methods and kits described herein. For example, in some aspects, an adaptor can comprise double stranded sequence. In some aspects, an adaptor with double stranded sequence can comprise one blunt end. In some aspects, an adaptor with double stranded sequence comprises two blunt ends. In some aspects, an adaptor with double stranded sequence can comprise one 3' overhang. In some aspects, an adaptor with double stranded sequence can comprise two 3' overhangs. In some aspects, an adaptor with double stranded sequence can comprise one 5' overhang. In some aspects, an adaptor with double stranded sequence can comprise two 5' overhangs. In some aspects, an adaptor with double stranded sequence can comprise a 5' overhang and a 3' overhang. In some aspects, an adaptor comprises only single stranded nucleic acid. In some aspects, when an adaptor has one or more overhangs, the overhang can be about, more than about, less than about, or at least about 1, 2, 3, 4, 5, 6, 7, 8, 9, 10, 11, 12, 13, 14, 15, 16, 17, 18, 19, or 20 bases. For example, a 3' overhang can be about, more than about, less than about, or at least about 1, 2, 3, 4, 5, 6, 7, 8, 9, 10, 11, 12, 13, 14, 15, 16, 17, 18, 19, or 20 bases. In some aspects, a 5' overhang can be about, more than about, at least about, or less than about 1, 2, 3, 4, 5, 6, 7, 8, 9, 10, 11, 12, 13, 14, 15, 16, 17, 18, 19, or 20 bases. In some aspects, if an adaptor comprises two overhangs, the overhangs can comprise the same or different number of bases. In some aspects, the longest strand of an adaptor can be about, more than about, less than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 bases. In some aspects, if an adaptor comprises a double-stranded portion, the double stranded portion can be about, more than about, at least about, or less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base-pairs. In some aspects, the longest strand of an adaptor can be about, more than about, less than about, or at least about 1,2,3,4,5,6,7,8,9,10,11,12,13,14,15,16,17,18, 19,20,21,22,23,24,25,26,27,28,29,30,31,32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 bases. In some aspects, if an adaptor comprises a double-stranded portion, the double stranded portion can be about, more than about, at least about, or less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base-pairs.

In some aspects, an adaptor can comprise exo-nucleotides and/or restriction sites. In some embodiments, the exo-nucleotides can be degradable by glycosylases. In some embodiments, the restriction sites can be Type IIS restriction sites. A skilled artisan will understand how to incorporate any appropriate exo-nucleotides or restriction sites known in the art. The exo-nucleotides and restriction sites can be used for later processing of enriched polynucleotides to remove additional sequences.

In some aspects, an adaptor can comprise double stranded nucleic acid. In some aspects, an adaptor comprises double stranded DNA. In some aspects, an adaptor comprises double stranded RNA. In some aspects, an adaptor comprises a DNA/RNA hybrid duplex. In some aspects, an adaptor comprises single stranded nucleic acid. In some aspects, an adaptor comprises single stranded RNA. In some aspects, an adaptor comprises single stranded DNA. In some aspects, an adaptor comprises single stranded RNA and DNA. In some aspects, when an adaptor comprises double stranded sequence, one strand of the adaptor comprises only DNA and one strand of the adaptor can comprise only RNA. In some aspects, a first strand comprises DNA and RNA and a second strand comprises DNA only. In some aspects, a first stand comprises DNA and RNA, and a second strand comprises RNA only. In some aspects, if a strand of an adaptor comprises both DNA and RNA, the DNA can be 5' of the RNA or the DNA and be 3' or the RNA. In some aspects, an adaptor is single stranded and comprises DNA and RNA, and the DNA is 5' of the RNA or 3' of the RNA. In some aspects, an adaptor comprises a hairpin (or hairpin loop). In some aspects, a hairpin comprises DNA and/or RNA. In some aspects, the number of non-base-paired bases in a loop of a hairpin is about, more than about, or at least about 4, 5, 6, 7, 8, 9, 10, 11, 12, 13, 14, 15, 16, 17, 18, 19, 20, 21, 22, 23, 24, 25, 26, 27, 28, 29, or 30 bases. In some aspects, the number of non-base-paired bases in a loop of a hairpin is about 4 to about 8, about 4 to about 10, about 4 to about 14, about 4 to about 16, about 4 to about 20, about 4 to about 24, about 4 to about 26, or about 4 to about 30 bases. In some aspects, the length of the stem (base-paired portion) of the adaptor can be about, more than about, or at least about 4, 5, 6, 7, 8, 9, 10, 11, 12, 13, 14, 15, 16, 17, 18, 19, 20, 21, 22, 23, 24, 25, 26, 27, 28, 29, or 30 base-pairs. In some aspects, a hairpin adaptor is ligated to only one end of a polynucleotide. In some aspects, a first hairpin adaptor is ligated to one end of a polynucleotide and a second hairpin adaptor is ligated to the other end of the polynucleotide. In some aspects, the hairpin adaptors that are ligated to each end of a polynucleotide can comprise the same nucleic acid sequence or different nucleic acid sequence. In some aspects, the hairpin adaptors that ligate to each end of a polynucleotide can have barcodes, and the barcodes can be the same or different. In some aspects, a hairpin adaptor that ligates to one end of a polynucleotide can have a barcode, and a hairpin adaptor that ligates to the other end of a polynucleotide can lack a barcode. In some aspects, adaptors are ligated to polynucleotides such that multiple adaptors and polynucleotides are interspersed.

In some aspects, an adaptor comprises no barcodes. In some aspects, an adaptor comprises one or more barcodes. In some aspects, an adaptor has one or more ends that lack a 5' phosphate residue. In some aspects, an adaptor comprises at least a portion of at least one molecular barcode. In some aspects, an adaptor comprises a partial barcode sequence, and assembly of two or more barcodes results in a complete barcode sequence. In some aspects, an adaptor is used as a primer site. In some aspects, an adaptor is used during nucleic acid sequencing. In some aspects, an adaptor comprises sequences used in sequencing, and in illustrative embodiments, next-generation sequencing, for example, as primer binding sites for sequencing primers.

b. Molecular Barcodes

In some aspects, at least one nucleic acid molecule of the source sample and/or the subset (e.g., diluted) sample comprises at least one molecular barcode. In illustrative embodiments, the molecular barcode is a non-degenerate barcode from a set or library of non-degenerative barcodes. Non-degenerate barcodes and sets and libraries thereof, are barcodes and sets and libraries thereof, with predefined, predetermined, and known sequences before the barcodes are synthesized, i.e, typically there are no N residues in the barcode sequences of the set, where N can be any of the possible nucleotides typically randomly selected. In other words, typically, non-degenerative barcodes are from a set or library of non-degenerative barcodes, that do not have any N residue where a nucleotide at that position is randomly selected and/or all 4 possible nucleotides at that N residue are present in the barcode set/library. A fully degenerate barcode and a set and library thereof, has random nucleotides (e.g., NNNNNNN). A partially degenerate barcode (e.g., NNNANTN), and a set and library thereof, has some residues that are N residues. In some embodiments of methods, compositions, and kits herein, the barcodes are fully degenerate barcodes from a set of fully degenerate barcodes. In some embodiments barcodes are partially degenerate barcodes from a set or library of partially degenerate barcodes. In illustrative embodiments, the barcodes are non-degenerate barcodes from a non-degenerative set or library, and thus have a predefined sequence. In some embodiments, a barcode is a partially degenerate barcode, from a library or set of partially degenerate barcodes having 1 N residue (i.e., is not a poly N degenerate barcode), or 2 N residues, or having less than all, 75%, 50%, 25%, 10%, 5%, or 1%, degenerate positions compared to all positions on the corresponding barcode.

In some aspects, at least one molecular barcode is linked to the 5' and/or the 3' end of at least one nucleic acid molecule. In some aspects, the 5' and/or 3' end of at least one nucleic acid molecule is tagged with at least one molecular barcode. In some aspects, only the 5' end of at least one nucleic acid molecule is tagged with at least one molecular barcode. In some aspects, only the 3' end of at least one nucleic acid molecule is tagged with at least one molecular barcode.

In some aspects, the methods of polynucleotide production described herein comprise adding 96, 192, 384, between 3 and 10,000, between 3 and 9,000, between 3 and 8,000, between 3 and 7,000, between 3 and 6,000, between 3 and 5000, between 3 and 4000, between 3 and 3000, between 3 and 2000, between 3 and 1000, between 3 and 750, between 3 and 500, between 3 and 450, between 3 and 400, between 3 and 384, between 3 and 350, between 3 and 300, between 3 and 250, between 3 and 200, between 3 and 150, between 3 and 100, between 3 and 96, between 3 and 90, between 3 and 80, between 3 and 70, between 3 and 60, between 3 and 50, between 3 and 40, between 3 and 30, between 3 and 20, between 3 and 20, between 3 and 10, between 10 and 1000, between 10 and 500, between 10 and 250, between 10 and 200, between 10 and 100, or between 10 and 50 unique molecular barcodes to one or more nucleic acid molecules during an assembly reaction, or to the source and/or diluted samples, or the source or diluted sample comprise nucleic acid molecules or nucleic acid species, respectively, that include such numbers of barcodes. Such unique molecular barcodes can form a set of molecular barcodes. In some aspects, the methods of polynucleotide production described herein comprises attaching (e.g., in an amplification or ligation reaction) one, two, three, four, five, six, seven, eight, nine, or ten molecular barcodes from 1, 2, 3, 4, 5,6, 7, 8, 9, or 10 or more sets of molecular barcodes, to a single nucleic acid molecule. The set of possible combinations of multiple barcodes that can be attached to a single nucleic acid molecule are referred to herein as combinations of molecular barcodes (also referred to herein as molecular barcode combinations), and the set of possible unique barcode combinations that can be attached to a single nucleic acid molecule are referred to herein as unique combinations of molecular barcodes (also referred to herein as unique molecule barcode combinations). For example, attaching two barcodes to a nucleic acid molecule, where each barcode is selected from a set of 10 barcodes, provides 100 barcode combinations (10 barcodes×10 barcodes=100 barcode combinations). In some embodiments, the Hamming distance between any two barcodes in a set, or in multiple sets of barcodes to be combined into a molecular barcode, is at least 1, 2, 3, 4, 5, 6, 7, 8, 9 or 10. In illustrative embodiments, the Hamming distance is at least 5. In some aspects, a molecular barcode is about, more than about, less than about, at least about, more than, less than, or exactly 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases or bases pairs. In some aspects, a barcode is about 4 to about 6 bases or bp, about 4 to about 7 bases or bp, about 4 to about 8 bases or bp, about 4 to about 9 bases or bp, about 4 to about 10 bases or bp, about 4 to about 12 bases or bp, about 4 to about 14 bases or bp, about 4 to about 16 bases or bp, about 4 to about 18 bases or bp, about 4 to about 20 bases or bp, about 5 to about 10 bases or bp, about 5 to about 15 bases or bp, about 5 to about 20 bases or bp, about 5 to about 25 bases or bp, about 5 to about 30 bases or bp, about 5 to about 35 bases or bp, about 5 to about 40 bases or bp, about 5 to about 50 bases or bp, about 5 to about 60 base or bp, about 5 to about 70 bases or bp, about 5 to about 80 bases or bp, about 5 to about 90 bases or bp, about 5 to about 100 bases or bp, about 5 to about 125 bases or bp, about 5 to about 150 bases or bp, about 5 to about 175 bases or bp, about 5 to about 200 bases or bp, about 10 to about 15 bases or bp, about 10 to about 20 bases or bp, about 10 to about 25 bases or bp, about 10 to about 30 bases or bp, about 10 to about 35 bases or bp, about 10 to about 40 bases or bp, about 10 to about 50 bases or bp, about 10 to about 60 base or bp, about 10 to about 70 bases or bp, about 10 to about 80 bases or bp, about 10 to about 90 bases or bp, about 10 to about 100 bases or bp, about 10 to about 125 bases or bp, about 10 to about 150 bases or bp, about 10 to about 175 bases or bp, or about 10 to about 200 bases or bp, or exactly any of these lengths. In some aspects, the length of the molecular barcodes is from about 10 nucleotides to about 200 or 10 nucleotides to 200 nucleotides.

In some aspects, bases in a barcode are contiguous. In some aspects, bases in a barcode are noncontiguous. In some aspects, a molecular barcode can be double stranded in an adaptor. In some aspects, a molecular barcode is single stranded in an adaptor. In some aspects, a molecular barcode can comprise double stranded and single stranded sequence in an adaptor. In some aspects, an adaptor can comprise about, more than about, at least about, or less than about 1, 2, 3, 4, 5, 6, 7, 8, 9, or different molecular barcodes. In some aspects, if an adaptor comprises more than one molecular barcode, the molecular barcodes can be separated from each other by about, more than about, or at least about 1, 2, 3, 4, 5, 6, 7, 8, 9, 10, 11, 12, 13, 14, 15, 16, 17, 18, 19, or 20 bases or base pairs on the adaptor. In some aspects, the molecular barcodes are used as both unique molecular identifiers (UMI) during nucleic acid sequencing-based analyses and the molecular barcodes are used as a part of an amplification reaction, such as used as primer binding sites for barcode-targeted PCR. In some aspects, the molecular barcodes are used as unique molecular identifiers (UMI) during long-range sequencing such as nanopore-based nucleic acid sequencing. In some aspects, the molecular barcodes are used to multiplex samples for nucleic acid sequencing, either by using a single, distinguishable barcode per sample, or in illustrative embodiments, by using a different set of barcodes in each sample, or the same set of barcodes in some, most, or all samples, but using all or a portion of a desired polynucleotide sequence for each sample as well, to distinguish samples. In some embodiments, adaptors comprising barcodes are attached to source nucleic acid molecules in an assembly reaction or in a diluted sample.

In some aspects, the molecular barcodes comprise one or more variable sequences. In some aspects, the molecular barcodes comprise one or more static sequences and one or more variable sequences. In some aspects, two or more molecular barcodes comprise complementary overlapping sequences. In some aspects, the molecular barcodes are degenerate molecular barcodes. In certain illustrative aspects, the molecular barcodes are non-degenerate molecular barcodes. In some aspects, the molecular barcodes are synthesized by a commercial vendor, e.g., IDT. In some aspects, the molecular barcodes contain 1% or less errors in the nucleobase sequence as compared to the sequence-perfect nucleobase sequence of the molecular barcodes. In some aspects, molecular barcodes comprising one or more errors that are used to tag are not selected during barcode-targeted PCR as, for example, no primer complementary to the molecular barcode comprising one or more errors is used.

Commercially available kits comprising barcodes and/or adaptors with barcodes can be used in the methods described herein. For example, a kit comprising barcodes can comprise any commercially available kit that comprises barcodes compatible with a nanopore-based sequencer, such as a nanopore-based sequencer produced by Oxford Nanopore Technologies. For example, such barcodes can include those found in the Native Barcoding Expansion 1-12 Kit and Rapid Barcoding Kit as sold by Oxford Nanopore Technologies. Moreover, a kit comprising adaptors with barcodes can include the ENCORE™ 384 Multiplex System (NUGEN™) which can comprise 384 molecularly barcoded library adaptors. The ENCORE™ NGS Multiplex Library Systems for ION TORRENT™ can comprise adaptors with barcodes that can be ligated to fragments. The ENCORE™ Complete RNA-Seq IL Multiplex System 1-8 (NUGEN™) and ENCORE™ Complete RNA-Seq IL Multiplex System 9-16 (NUGEN™) can provide barcoded adaptors for multiplex sequencing. The ENCORE™ Complete RNA-Seq DR Multiplex system 1-8 (NUGEN™) and ENCORE™ Complete RNA-Seq DR Multiplex system 9-16 (NUGEN™) can provide a dedicated read (DR) barcode design. Examples of kits with adaptors with barcodes from LIFE TECHNOLOGIES™ include 5500 SOLiD™ Fragment Library Barcode Adaptors 1-16, 5500 SOLiD™ Fragment Library Barcode Adaptors 1-96, 5500 SOLiD™ Fragment Library Barcode Adaptors 17-32, 5500 SOLiD™ Fragment Library Barcode Adaptors 33-48, 5500 SOLiD™ Fragment Library Barcode Adaptors 49-64, 5500 SOLiD™ Fragment Library Barcode Adaptors 65-80, 5500 SOLiD™ Fragment Library Barcode Adaptors 81-96, 5500 SOLiD™ Fragment Library Core Kit, 5500 SOLiD™ Fragment Library Standard Adaptors, LIBRARY BUILDER™ Fragment Core Kit for 5500 Genetic Analysis Systems, SOLiD™ Fragment Library Barcoding Kit 1-96, SOLiD™ Fragment Library Barcoding Kit Module 17-32, SOLiD™ Fragment Library Barcoding Kit Module 33-48, SOLiD™ Fragment Library Barcoding Kit Module 49-64, SOLiD™ Fragment Library Barcoding Kit Module 65-80, SOLiD™ Fragment Library Barcoding Kit Module 81-96, SOLiD™ RNA Barcoding Kit, Module 1-16, SOLiD™ RNA Barcoding Kit, Module 1-48, SOLiD™ RNA Barcoding Kit, Module 1-96, SOLiD™ RNA Barcoding Kit, Module 17-32, SOLiD™ RNA Barcoding Kit, Module 33-48, SOLiD™ RNA Barcoding Kit, Module 49-64, SOLiD™ RNA Barcoding Kit, Module 49-96, SOLiD™ RNA Barcoding Kit, Module 65-80, or SOLiD™ RNA Barcoding Kit, Module 81-96. Other commercially available kits with adaptors with barcodes include SureSelect AB Barcode Adaptor Kit (AGILENT TECHONOLOGIES), Bio Scientific's AIR™ Barcoded Adapters, NEXTFLEX™ DNA Barcodes, ILLUMINA™ TRUSEQ™ RNA and DNA Sample Preparation Kits, RAINDANCE™ Technologies DEEPSEQ™ FFPE solution, NEBNEX™ Multiplex Oligos for ILLUMNIA™ (Index Primers 1-12), or NEBNEX™ Multiplex Small RNA Library Prep set for ILLUMINA™ (Index Primers 1-12).

In some aspects, a nucleic acid and/or a polynucleotide can receive a barcode by being ligated to an adaptor comprising a barcode. In some aspects, the ligation can involve use of one or more ligases. In some aspects, a barcode can be attached to a nucleic acid and/or a polynucleotide by amplification with a primer comprising a barcode. In some aspects, a barcode can be adjacent to a primer binding site. In some aspects, a barcode can be 0 or about 1, 2, 3, 4, 5, 6, 7, 8, 9, 10, 11, 12, 13, 14, 15, 16, 17, 18, 19, or 20 bases 3' of a primer binding (annealing, hybridization) site.

In some aspects, a barcode, and in illustrative embodiments a molecular barcode, can be assembled from at least two separate nucleic acids, such as during a DNA assembly process. In some aspects, a barcode can be assembled from at least two separate nucleic acids by a PCR-based method, such as any of the PCR methods provided herein. In some aspects, a barcode can be assembled from at least two separate nucleic acids by a ligation-based method. A skilled artisan will understand other methods known in the art to generate barcodes. In some aspects, the at least two separate nucleic acids can contain an outer barcode (OBC) and an inner barcode (IBC) on separate nucleic acids. In such aspects, the assembled barcode will include the OBC and the IBC. In some aspects, a plurality of barcodes can be formed or assembled using the at least two separate nucleic acids. In such aspects, the at least two separate nucleic acids can include at least 5, 10, 15, 20, 25, 30, 35, 40, 45, or 50 separate nucleic acids. In some aspects, the at least two separate nucleic acids can include at least 5, 10, 15, 20, 25, 30, 35, 40, 45, or 50 OBCs. In some aspects, the at least two separate nucleic acids can include at least 5, 10, 15, 20, 25, 30, 35, 40, 45, or 50 IBCs. In some aspects, the combinations of OBCs and IBCs can provide at least 25, 50, 100, 200, 300, 400, 500, 600, 700, 800, 900, or 1,000 unique barcodes.

In some aspects, the methods of polynucleotide production described herein further comprise adding primers complementary to one or more molecular barcodes. In some aspects, the methods of polynucleotide production described herein further comprise detecting at least one molecular barcode. In some aspects, the barcodes are used for barcode-targeted PCR. For example, a barcode-targeted PCR can be performed comprising two amplification reactions: a first amplification reaction that targets a first molecular barcode, and a second amplification reaction that targets a second molecular barcode. Such barcode-targeted PCR is used in some aspects, to enrich and amplify one or more desired nucleic sequences.

In some aspects, each of one or more molecular barcodes are positioned to the 5' of a nucleic acid molecule which was tagged with the one or more molecular barcodes. In some aspects, each of one or more molecular barcodes are positioned to the 3' of a nucleic acid molecule which was tagged with the one or more molecular barcodes. In some aspects, each of the 5' and 3' sides of a nucleic acid molecule is tagged with one or more molecular barcodes. The 5' strand and the 3' strand can be either the 5' end or the 3' end of positive or negative strand of a nucleic acid molecule of any type, e.g., single stranded, double-stranded, double-stranded with a single strand overhang, etc.

c. Oligonucleotides

In some aspects, the methods of polynucleotide production described herein comprise source samples that include one or more oligonucleotides, which are typically synthetic oligonucleotides, which can be for example between 10 and 100, 250, 500, or 1,000 kb in length. In some aspects, the one or more oligonucleotides comprise commercially synthesized oligonucleotides, such as, for example, kits comprising barcodes and/or adaptors described supra. In some aspects, the oligonucleotides comprise at least one molecular barcode. In some aspects, the oligonucleotides comprise at least one adapter. In some aspects, the methods of polynucleotide production described herein further comprise tagging at least one nucleic acid molecule of the source sample with at least one oligonucleotide. In some aspects, the tagging comprises ligating at least one oligonucleotide to at least one nucleic acid molecule of the source sample. In some aspects, the tagging comprises linking at least one oligonucleotide to at least one nucleic acid molecule of the source sample. In some aspects, the oligonucleotides are primers. In some aspects, the oligonucleotides contain primer sites.

In some aspects, the methods of polynucleotide production described herein further comprise adding one or more oligonucleotides to the diluted sample. In some aspects, the one or more oligonucleotides comprise commercially synthesized oligonucleotides, such as, for example, kits comprising barcodes and/or adaptors described supra. In some aspects, the methods of polynucleotide production described herein further comprise tagging at least one nucleic acid molecule of the diluted sample with at least one oligonucleotide. In some aspects, the tagging comprises ligating at least one oligonucleotide to at least one nucleic acid molecule of the diluted sample. In some aspects, the tagging comprises linking at least one oligonucleotide to at least one nucleic acid molecule of the diluted sample. In some aspects, the oligonucleotides are primers. In some aspects, the oligonucleotides contain primer sites.

In some aspects, the methods of polynucleotide production described herein further comprise adding at least one primer complementary to at least one oligonucleotide. In some aspects, the methods of polynucleotide production described herein comprises tagging a single nucleic acid molecule with at least one, two, three, four, five, six, seven, eight, nine, or ten oligonucleotides.

In some aspects, the oligonucleotides, e.g., adaptors, e.g., molecular barcodes, are used as a part of one or more amplification reactions. In some aspects, the amplification reactions comprise isothermal amplification, including any of the isothermal amplifications disclosed above with respect to amplification of the subset (e.g., diluted) sample. In some aspects, the amplification reactions comprise polymerase chain reactions (PCR), including any of the PCR amplifications disclosed above with respect to amplification of the subset (e.g., diluted) sample.

d. Adapted Polynucleotides

In some aspects, the polynucleotide comprises at least one adaptor. In some aspects, the polynucleotides comprises at least one adaptor and at least one molecular barcode. In some aspects, the polynucleotide comprises at least one adaptor and/or at least one molecular barcode wherein optionally either or both of the adaptor and/or molecular barcodes can serve as primer sites.

Figure 4A:
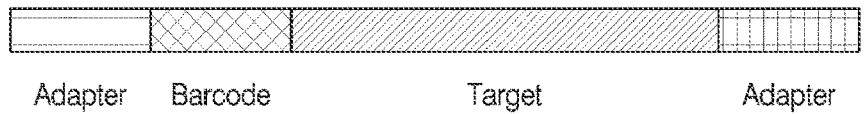
FIG. 4A-FIG. 4Q present schematic representations of various different arrangements of target sequences, barcodes, and/or adapters in accordance with the present disclosure.
Figure 4B:
Figure 4C:
Figure 4D:
Figure 4E:
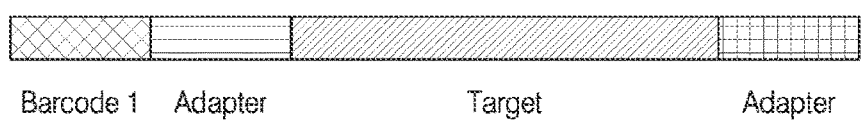
Figure 4F:
Figure 4G:
Figure 4H:
Figure 4I:
Figure 4J:
Figure 4K:
Figure 4L:
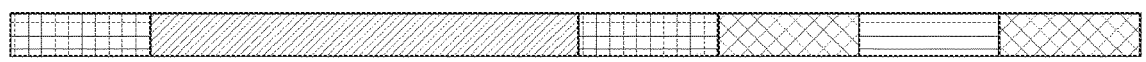
Figure 4M:
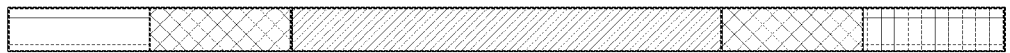
Figure 4N:
Figure 4O:
Figure 4P:
Figure 4Q:

A skilled artisan could determine the various combinations of two or more adapters and barcodes that could be attached to desired nucleic acid molecules in methods herein to generate polynucleotides having desired nucleic acid sequences. As non-limiting examples, in some embodiments, the polynucleotide comprises in 5' to 3' order: adapter 1-molecular barcode 1-nucleic acid molecule-adapter 2; adapter 1-molecular barcode 1-nucleic acid molecule-molecular barcode 2-adapter 2; adapter 1-molecular barcode 1-molecular barcode 2-nucleic acid molecule-adapter 2; molecular barcode 1-adapter 1-nucleic acid molecule-adapter 2; molecular barcode 1-adapter 1-nucleic acid molecule-adapter 2-molecular barcode 2; molecular barcode 1-molecular barcode 2-adapter 1-nucleic acid molecule-adapter 2; adapter 1-molecular barcode 1-adapter 2-nucleic acid molecule-adapter 3; adapter 1-molecular barcode 1-adapter 2-nucleic acid molecule-molecular barcode 2-adapter 3; adapter 1-molecular barcode 1-molecular barcode 2-adapter 2-nucleic acid molecule-adapter 3; molecular barcode 1-adapter 1-adapter 2-nucleic acid molecule-adapter 3; molecular barcode 1-adapter 1-adapter 2-nucleic acid molecule-adapter 3-molecular barcode 2; molecular barcode 1-molecular barcode 2-adapter 1-adapter 2-nucleic acid molecule-adapter 3. In some aspects, at least two of adapter 1, adapter 2, and adapter 3 have the same sequence. In some aspects, adapter 1, adapter 2, and adapter 3 are the same sequence. In some aspects, at least two of adapter 1, adapter 2 and adapter 3 are different sequences. In some aspects, adapter 1, adapter 2, and adapter 3 are different sequences. In some aspects, the polynucleotide comprises in 5' to 3' order an arrangement as presented in FIGS. 4A-4Q.

e. Traditionally Difficult Sequences

In some embodiments, a desired nucleic acid sequence of the current disclosure can include one or more problematic sequences that traditionally have made synthesizing, assembling, and/or generating the sequence more difficult. For example, in some embodiments, the traditionally difficult, challenging, or problematic sequences can include one or more of a low GC content, a high GC content, homopolymeric run(s), repeat sequence(s), including but not limited to inverted repeats and/or tandem repeats, low sequence complexity, and/or have secondary structure. Such nucleic acid sequences, or segments of polynucleotides containing such nucleic acid sequences, can be referred to herein as noteworthy sequences, synthetic sequences, segments, or synthetic segments; difficult to generate sequences, synthetic sequences, segments, or synthetic segments; problematic sequences, synthetic sequences, segments, or synthetic segments; historically or traditionally problematic sequences, synthetic sequences, segments, or synthetic segments; difficult sequences, synthetic sequences, segments or synthetic segments; historically or traditionally difficult sequences, synthetic sequences, segments or synthetic segments; or historically or traditionally difficult to generate sequences, synthetic sequences, segments or synthetic segments. A skilled artisan will understand that although previous dogma in the art is that such sequences are particularly difficult to synthesize, assemble or otherwise generate, the disclosed methods, kits, and compositions are able to synthesize some of these sequences that are particularly difficult to synthesize.

In some embodiments, a traditionally problematic sequence comprises one or more of:

i) a low GC content;
ii) a high GC content;
iii) a homopolymeric run of As or Ts;
iv) a homopolymeric run of Gs or Cs;
v) a repeat sequence;
vi) low sequence complexity; and/or
vii) secondary structure.

In some embodiments, low GC content is a GC content of 40%, 35%, 30%, 25%, 20%, 15%, 10%, or 5% or less of a segment of at least 25, 30, 35, 40, 45, 50, 75, 100, 150, 200, 300, 400, 500, 600, 700, 800, 900, or 1,000 nucleotides or an entire desired nucleic acid sequence or polynucleotide. In some embodiments, low GC content is a GC content of 25% or less of a segment of at least 25, 30, 35, 40, 45, 50, 75, 100, 150, 200, 300, 400, 500, 600, 700, 800, 900, or 1,000 nucleotides or an entire desired nucleic acid sequence or polynucleotide. In some embodiments, high GC content is a GC content of 60%, 65%, 70%, 75%, 80%, 85%, 90%, or 95% or more of a segment of at least 25, 30, 35, 40, 45, 50, 75, 100, 150, 200, 300, 400, 500, 600, 700, 800, 900, or 1,000 nucleotides or an entire desired nucleic acid sequence or polynucleotide. In some aspects, high GC content is a GC content of 75% or more of a segment of at least 25, 30, 35, 40, 45, 50, 75, 100, 150, 200, 300, 400, 500, 600, 700, 800, 900, or 1,000 nucleotides or an entire desired nucleic acid sequence or polynucleotide. In some embodiments, the GC content of a segment of a desired nucleic acid sequence or polynucleotide is measured in a segment that is at least 25, 30, 35, 40, 45, 50, 75, 100, 150, 200, 300, 400, 500, 600, 700, 800, 900, 1,000, 2,000, 3,000, 4,000, 5,000, 6,000, 7,000, 8,000, 9,000, or 10,000 nucleotides. In some embodiments, the GC content is measured in a segment between 25, 30, 35, 40, 45, 50, 100, 150, 200, 300, 400, 500, 600, 700, 800, 900, and 1,000 nucleotides on the low end of the range and 50, 75, 100, 150, 200, 300, 400, 500, 600, 700, 800, 900, 1,000, 2,000, 3,000, 4,000, 5,000, 6,000, 7,000, 8,000, 9,000, or 10,000 nucleotides on the high end of the range.

In some aspects, the traditionally problematic sequence can include a homopolymeric run. In some embodiments, the homopolymeric run can be a homopolymeric run of As or Ts. In some embodiments, the homopolymeric run of As or Ts can be at least 3, 4, 5, 6, 7, 8, 9, 10, 11, 12, 13, 14, or 15 As or Ts. In some embodiments, the homopolymeric run of As or Ts can be at least 10 As or Ts. In some embodiments, the homopolymeric run can be a homopolymeric run of Gs or Cs. In some embodiments, the homopolymeric run of Gs or Cs can be at least 3, 4, 5, 6, 7, 8, 9, 10, 11, 12, 13, 14, or 15 Gs or Cs. In some embodiments, the homopolymeric run of As or Ts can be at least 6 Gs or Cs.

In some aspects, the traditionally problematic sequence can include one or more repeat sequences. In some aspects, a repeat sequence can have a length of at least 3, 4, 5, 6, 7, 8, 9, 10, 15, 20, 25, 30, 35, 40, 45, or 50 nucleotides. In some aspects, a repeat sequence can be repeated at least 2, 3, 4, 5, 6, 7, 8, 9, 10, 11, 12, 13, 14, or 15 times. In some aspects, a repeat sequence can have a length of at least 8 nucleotides that is repeated at least 2, 3, 4, 5, 6, 7, 8, 9, 10, 11, 12, 13, 14, or 15 times. In some aspects, a repeat sequence can have a length of at least 8 nucleotides that is repeated at least 5 times. In some aspects, a repeat sequence can have a length of at least 15 nucleotides that is repeated at least 2, 3, 4, 5, 6, 7, 8, 9, 10, 11, 12, 13, 14, or 15 times. In some aspects, a repeat sequence can have a length of at least 15 nucleotides that is repeated at least 2 times. In some embodiments, the repeat sequence can be a tandem repeat sequence, wherein the repeats are directly adjacent to each other. In some embodiments, a repeat sequence can be an inverted repeat sequence, wherein the repeat sequence is followed downstream by its reverse complement. In some embodiments, an inverted repeat sequence only occurs 1 time. In some embodiments, the inverted repeat sequence can be at least 4, 5, 6, 7, 8, 9, 10, 11, 12, 13, 14, 15, 16, 17, 18, 19, 20, 25, 30, 35, 40, 45, or 50 nucleotides in length. In some embodiments, the inverted repeat sequence can be at least 2, 3, 4, 5, 6, 7, 8, 9, 10, 11, 12, 13, 14, or 15 times.

In some embodiments, the desired nucleic acid sequence can have low sequence complexity. Sequence complexity can be measured using various methods. For example, sequence complexity can be measured using information entropy (Shannon, ACM SIGMOBILE Mobile Computing and Communications Review, vol. 5, no. 1, pp. 3-55, 2001), Kolmogorov complexity (Li and Vitanyi, An introduction to Kolmogorov complexity and its applications, New York, 2009), or statistical complexity (Feldman and Crutchfield, Physics Letters A, vol. 238, no. 4, pp. 244-252, 1998; Lopez-Ruiz et al, Physics Letters A, vol. 209, no. 5, pp. 321-326, 1995) (Monge and Crespo-Marino, DOI: 10.1109/IWOBI.2014.6913941). Appropriate values can be set to categorize sequences as low, medium, or high sequence complexity. In some embodiments, the Complexity program can be used to identify sequences with low complexity (Nucleic Acids Res. 2004 Jul. 1; 32(Web Server issue): W628-33).

In some embodiments, the desired nucleic acid sequence can include a sequence that forms a secondary structure. In some embodiments, the secondary structure can include one or more of a stem, hairpin (also referred to as a stem-loop), internal loop, or pseudoknot, each of which can include, for example, between 3, 4, 5, 6, 7, 8, 9, 10, 11, 12, 13, 14, or 15 nucleotides on the low end of the range and 7, 8, 9, 10, 11, 12, 13, 14, 15, 20, 25, 30, 35, 40, 45, 50, 60, 70, 80, 90, or 100 nucleotides on the high end of the range, or at least 3, 4, 5, 6, 7, 8, 9, 10, 11, 12, 13, 14, 15, 20, 25, 30, 35, 40, 45, 50, 60, 70, 80, 90, or 100 nucleotides. A pseudoknot can include at least two stem-loop structures in which half of one stem is intercalated between the two halves of another stem. In some embodiments, a desired nucleic acid sequence can include a low, medium, or high secondary structure percentage. The secondary structure percentage can be defined as the percentage of 50 nucleotide segments across a sequence that have a predicted folding melting temperature above 65° C. The low, medium, and high categories of secondary structure percentages can depend on the GC content of the desired nucleic acid sequence. For a given GC content range, sequences within the 0-33rd percentile of the secondary structure percentage distribution are defined as low secondary structure, sequences with the 34-66th percentiles are defined as medium secondary structure, and sequences with the 67-99th percentiles are defined as high secondary structure. In some embodiments, traditionally problematic sequences with secondary structure can have a medium or high secondary structure. In some embodiments, traditionally problematic sequences with secondary structure can have a high secondary structure.

In some embodiments the desired traditional problematic nucleic acid sequence comprises one or more of:
i) a GC content 25% or less for a stretch of at least 25, 30, 35, 40, 45, 50, 75, 100, 150, 200, 300, 400, 500, 600, 700, 800, 900, or 1,000 nucleotides of, or for an entire desired nucleic acid sequence;
ii) a GC content of 75% or more for a stretch of at least 25, 30, 35, 40, 45, 50, 75, 100, 150, 200, 300, 400, 500, 600, 700, 800, 900, or 1,000 nucleotides of, or for an entire desired nucleic acid sequence;
iii) a homopolymeric run of 10 or more As or Ts;
iv) a homopolymeric run of 6 or more Gs or Cs;
v) a repeat sequence of at least 6 nucleotides that is repeated 5 times;
vi) a repeat sequence of at least 8 nucleotides that is repeated at least 2 times;

vii) a repeat sequence comprising a tandem repeat sequence;
viii) an inverted repeat sequence of at least 6 nucleotides;
ix) low sequence complexity; or
x) a sequence with a polynucleotide secondary structure comprising at least 10, 11, 12, 13, 14, 15, 20, 25, 30, 35, 40, 45, 50, 60, 70, 80, 90, or 100 nucleotides.

V. Populations of Nucleic Acid Molecules and Polynucleotides and Pluralities Thereof Populations of nucleic acid molecules or polynucleotides are aspects of the disclosure herein, including populations in the source or subset (e.g., dilute) samples. In one aspect, provided herein is a population of nucleic acid molecules and molecular barcodes, wherein the ratio of nucleic acid molecules to different sequences in the molecular barcodes (e.g., unique molecular barcodes) is at most $1:1.6 \times 10^{18}$ or greater. In some embodiments, the ratio of unique molecular barcodes, or in some subaspects, of unique combinations of molecular barcodes, to source nucleic acid molecules or species of a source sample, is at most, about, exactly, or targeted to be $1:1.6 \times 10^{18}$, $1:1 \times 10^{18}$, $1:1 \times 10^{17}$, $1:1 \times 10^{16}$, $1:1 \times 10^{15}$, $1:1 \times 10^{14}$, $1:1 \times 10^{13}$, $1:1 \times 10^{12}$, $1:1 \times 10^{11}$, $1:1 \times 10^{10}$, $1:1 \times 10^{9}$, $1:1 \times 10^{8}$, $1:1 \times 10^{7}$, $1:1 \times 10^{6}$, 1:1×100,000, 1:1×10,000, 1:1×1,000, 1:100, 1:10, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes to the number of source nucleic acid molecules or species of the source sample. In some embodiments, the ratio of unique molecular barcodes, or in some subaspects, of unique combinations of molecular barcodes, to source nucleic acid molecules or species of a source sample, is between $1:1.6 \times 10^{18}$, $1:1 \times 10^{18}$, $1:1 \times 10^{17}$, $1:1 \times 10^{16}$, $1:1 \times 10^{15}$, $1:1 \times 10^{14}$, $1:1 \times 10^{13}$, $1:1 \times 10^{12}$, $1:1 \times 10^{11}$, $1:1 \times 10^{10}$, $1:1 \times 10^{9}$, $1:1 \times 10^{8}$, $1:1 \times 10^{7}$, or $1:1 \times 10^{6}$ on the low end of the range and $1:1 \times 10^{16}$, $1:1 \times 10^{15}$, $1:1 \times 10^{14}$, $1:1 \times 10^{13}$, $1:1 \times 10^{12}$, $1:1 \times 10^{11}$, $1:1 \times 10^{10}$, $1:1 \times 10^{9}$, $1:1 \times 10^{8}$, $1:1 \times 10^{7}$, $1:1 \times 10^{6}$, 1:1×100,000, 1:1×10,000, 1:1×1,000, 1:100, 1:10, 1:1, 2:1, 3:1, 4:1, 5:1, 10:1, 20:1, 50:1, 100:1, 1,000:1, or 10,000:1 on the high end of the range. In some embodiments, the ratio of unique molecular barcodes, or in some subaspects, of unique combinations of molecular barcodes, to source nucleic acid molecules, such as for example candidate nucleic acid molecules or species in the source sample is between 1:1,000 on the low end of the range and $1:1 \times 10^{18}$, $1:1 \times 10^{15}$, $1:1 \times 10^{12}$, $1:1 \times 10^{9}$, $1:1 \times 10^{8}$, $1:1 \times 10^{7}$, $1:1 \times 10^{6}$, $1:1 \times 10^{5}$, $1:1 \times 10^{4}$ on the high end of the range, or between $1:1 \times 10^{4}$ on the low end of the range and $1:1 \times 10^{18}$, $1:1 \times 10^{15}$, $1:1 \times 10^{12}$, $1:1 \times 10^{9}$, $1:1 \times 10^{8}$, $1:1 \times 10^{7}$, $1:1 \times 10^{6}$, $1:1 \times 10^{5}$ on the high end of the range, or between $1:1 \times 10^{5}$ on the low end of the range and $1:1 \times 10^{18}$, $1:1 \times 10^{15}$, $1:1 \times 10^{12}$, $1:1 \times 10^{9}$, $1:1 \times 10^{8}$, $1:1 \times 10^{7}$, and $1:1 \times 10^{6}$ on the high end of the range. In some embodiments, the ratio of unique barcode combinations to candidate nucleic acid molecules in the source sample is between $1:1 \times 10^{4}$ and $1:1 \times 10^{7}$. In some embodiments, the ratio of unique barcode combinations to candidate nucleic acid molecules in the source sample is between $1:1 \times 10^{5}$ and $1:1 \times 10^{7}$. In some embodiments, the ratio of unique barcode combinations to candidate nucleic acid molecules in the source sample is between $1:1 \times 10^{5}$ and $1:5 \times 10^{6}$. In some embodiments, the ratio of unique barcode combinations to candidate nucleic acid molecules in the source sample is between $1:5 \times 10^{5}$ and $1:5 \times 10^{6}$.

In some embodiments, the ratio of unique molecular barcodes, or in some subaspects, of unique combinations of molecular barcodes (molecular barcode combinations), to nucleic acid molecules or species in a subset (e.g., diluted) sample, is about, exactly, or targeted to be 1:10, 1:5, 1:4, 1:3, 1:2, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes to the number of source nucleic acid molecules or nucleic acid molecules or nucleic acid species of the subset sample. A skilled artisan understands the aspects including a population of nucleic acid molecules or polynucleotides can include other aspects and embodiments provided herein, for example, the number of unique molecular barcodes, or combinations of unique molecular barcodes, in the ratios disclosed above can include any of the number of unique molecular barcodes, or combinations of unique molecular barcodes disclosed elsewhere herein.

In another aspect, provided herein is a population of polynucleotides having a desired nucleic acid sequence (population of desired polynucleotides), wherein the sequences in the population of polynucleotides can have an error rate of 1:10,000 (1 error per 10,000 nucleotides), 1:15,000, 1:20,000, 1:25,000, 1:30,000, 1:35,000, 1:40,000, 1:45,000, 1:50,000, 1:60,000, 1:70,000, 1:80,000, 1:90,000, 1:100,000, 1:110,000, 1:120,000, 1:130,000, 1:140,000, 1:150,000, 1:160,000, 1:170,000, 1:180,000, 1:190,000, 1:200,000, 1:210,000, 1:220,000, 1:230,000, 1:240,000, 1:250,000, 1:300,000, 1:350,000, 1:400,000, 1:450,000, 1:500,000, 1:600,000, 1:700,000, 1:800,000, or 1:900,000 or lower. The error rate can be determined relative to the sequence-perfect desired nucleic acid sequence. In some embodiments, the sequences in the population can have an error rate that is greater than 1:1,000,000, 1:2,000,000, 1:3,000,000, 1:4,000,000, or 1:5,000,000. In some embodiments, the sequences in the population can have an error rate between 1:10,000, 1:15,000, 1:20,000, 1:25,000, 1:30,000, 1:35,000, 1:40,000, 1:45,000, 1:50,000, 1:60,000, 1:70,000, 1:80,000, 1:90,000, and 1:100,000 on the low end of the range and 1:30,000, 1:35,000, 1:40,000, 1:45,000, 1:50,000, 1:60,000, 1:70,000, 1:80,000, 1:90,000, 1:100,000, 1:110,000, 1:120,000, 1:130,000, 1:140,000, 1:150,000, 1:160,000, 1:170,000, 1:180,000, 1:190,000, 1:200,000, 1:210,000, 1:220,000, 1:230,000, 1:240,000, 1:250,000, 1:300,000, 1:350,000, 1:400,000, 1:450,000, 1:500,000, 1:600,000, 1:700,000, 1:800,000, or 1:900,000 on the high end of the range. In illustrative embodiments any of the compositions and methods herein that include a population of polynucleotide having a desired nucleic acid sequence or a population of desired polynucleotides, the sequences in the population can have an error rate of 1:30,000 or lower. In illustrative embodiments, the error rate is 1:60,000 or lower. A skilled artisan understands the aspects including a population of nucleic acid molecules or polynucleotides can include other aspects and embodiments provided herein.

The populations of polynucleotides generated using the methods herein are themselves aspects. Thus, in one aspect provided herein is a population of polynucleotides generated using any of the methods disclosed herein. The populations of polynucleotides can include any of the aspects and embodiments herein.

The methods herein can be used to generate populations of polynucleotides that include traditionally difficult sequences, as disclosed elsewhere herein. In one aspect, provided herein is a population of polynucleotides, wherein the polynucleotides include a desired nucleic acid sequence, and wherein the desired nucleic acid sequence is a traditionally difficult sequence and comprises one or more of:
i) a low GC content;
ii) a high GC content;

iii) a homopolymeric run of As or Ts;
iv) a homopolymeric run of Gs or Cs;
v) a repeat sequence;
vi) low sequence complexity; and/or
vii) secondary structure.

VI. Kits and Commercial Systems

In some aspects, described herein are kits comprising one or more containers containing molecular barcodes for use with the methods described herein, and one or more containers of a reagent for diluting a source sample. In some aspects, the kit comprises between 3 and 10,000, between 3 and 9,000, between 3 and 8,000, between 3 and 7,000, between 3 and 6,000, between 3 and 5000, between 3 and 4000, between 3 and 3000, between 3 and 2000, between 3 and 1000, between 3 and 750, between 3 and 500, between 3 and 450, between 3 and 400, between 3 and 350, between 3 and 300, between 3 and 250, between 3 and 200, between 3 and 150, between 3 and 100, between 3 and 90, between 3 and 80, between 3 and 70, between 3 and 60, between 3 and 50, between 3 and 40, between 3 and 30, between 3 and 20, between 3 and 20, or between 3 and 10 unique molecular barcodes. In some aspects, the molecular barcodes comprise one or more variable sequences. In some aspects, the molecular barcodes comprise one or more static sequences and one or more variable sequences. In some aspects, the kit further comprises primers complementary to the one or more molecular barcodes. In some aspects, two or more molecular barcodes comprise complementary overlapping sequences. In some aspects, at least one molecular barcode comprises at least one adapter. In some aspects, at least one adapter comprises at least one molecular barcode. In some aspects, the length of the molecular barcodes is from about 10 nucleotides to about 200 nucleotides. In some aspects, the molecular barcodes are sequence verified molecular barcodes. In some aspects, the molecular barcodes are non-degenerate molecular barcodes. In some aspects, the molecular barcodes contain 1% or less errors as compared to the sequence-perfect nucleic acid sequence of a given molecular barcode.

In certain aspects, provided herein is a commercial system that comprises a functionality for placing an order for one or more polynucleotides having a desired nucleic acid sequence, in illustrative embodiments a sequence-perfect desired nucleic acid sequence. Upon receiving the order, the system initiates performance of any of the methods provided herein for producing, generating, or enriching a polynucleotide having a desired nucleic acid sequence, a method for polynucleotide production of such a polynucleotide, or in certain illustrative embodiments, a method of cell-free cloning of such a polynucleotide. For example, the initiating can be performed by one or more automated systems that design oligonucleotides that can be used as inputs in such method. For example, the system can identify not only the precise sequence of each oligonucleotide having a portion of the desired nucleic acid sequence, but can additionally identify specific additional sequences with certain related functionality for such methods as provided herein, such as a specific pool(s) of barcode sequences, primer binding sequences, and sequencing primer binding sequences.

Exemplary Embodiments

Provided in this Exemplary Embodiments section are non-limiting exemplary aspects and embodiments provided herein and further discussed throughout this specification. For the sake of brevity and convenience, all aspects and embodiments disclosed herein and all of the possible combinations of the disclosed aspects and embodiments are not listed in this section. Additional embodiments and aspects are provided in other sections herein. Furthermore, it will be understood that embodiments are provided that are specific embodiments for many aspects, as discussed in this entire disclosure. It is intended in view of the full disclosure herein, that any individual embodiment recited below or in this full disclosure can be combined with any aspect recited below or in this full disclosure where it is an additional element that can be added to an aspect or because it is a narrower element for an element already present in an aspect. Such combinations are discussed more specifically in other sections of this detailed description.

In one aspect, provided herein is a method of generating a population of product polynucleotides, wherein the method comprises:
a. diluting a subvolume of a source sample comprising candidate nucleic acid molecules to form a diluted sample having a target number of the candidate nucleic acid molecules isolated from the source sample, wherein the diluted sample comprises one or more tagged candidate nucleic acid species derived from one or more of the candidate nucleic acid molecules, wherein each nucleic acid molecule of a candidate nucleic acid species has an identical nucleic acid sequence comprising the nucleic acid sequence of the one or more candidate nucleic acid molecules from which it was derived and a tag comprising at least one barcode from a set of barcodes,
b. determining the sequence of at least some of the tagged candidate nucleic acid species; and
c. enriching a desired uniquely tagged nucleic acid species by amplifying one or more candidate nucleic acid molecules of the desired uniquely tagged nucleic acid species, using one or more primers that bind to one or more barcodes on the tag associated with the candidate nucleic acid molecules of the desired uniquely tagged nucleic acid species to generate a population of product polynucleotides.

In one aspect, provided herein is a method of generating a population of product polynucleotides, wherein the method comprises:
a. diluting a subvolume of a source sample to form a diluted sample having a target number of the tagged candidate nucleic acid molecules isolated from the source sample, wherein each tagged candidate nucleic acid molecule has a tag comprising one or more barcodes,
wherein the diluted sample comprises one or more tagged candidate nucleic acid species derived from one or more of the tagged candidate nucleic acid molecules, wherein each nucleic acid molecule of a tagged candidate nucleic acid species has an identical nucleic acid sequence comprising the nucleic acid sequence of the one or more tagged candidate nucleic acid molecules from which it was derived;
b. determining the sequence of at least some of the tagged candidate nucleic acid species, wherein at least 1 of the tagged candidate nucleic acid species is a desired uniquely tagged nucleic acid species; and
c. enriching the desired uniquely tagged nucleic acid species by amplifying one or more tagged candidate nucleic acid molecules of the desired uniquely tagged nucleic acid species to generate the population of product polynucleotides.

In some aspects, provided herein is a method of generating a population of polynucleotides, wherein the method comprises:
  a. assembling at least two nucleic acid molecules separately in each of a set of initial sources of nucleic acid molecules to produce a set of source samples;
  b. diluting a subset volume of the set of source samples to form a set of diluted samples each having a target number of tagged candidate nucleic acid molecules isolated from each of the set of source samples,
  c. combining a portion of each diluted sample in the set of diluted samples to form a combined diluted sample, wherein the combined diluted sample comprises tagged candidate nucleic acid species derived from one or more of the tagged candidate nucleic acid molecules from each diluted sample of the set of diluted samples, wherein each nucleic acid molecule of a tagged candidate nucleic acid species has an identical nucleic acid sequence comprising the nucleic acid sequence of the one or more tagged candidate nucleic acid molecules from which it was derived;
  d. determining the sequence of at least some of the tagged candidate nucleic acid species from each of the diluted samples in the combined diluted sample, wherein at least 1 of the tagged nucleic acid species from each diluted sample is a desired uniquely tagged nucleic acid species, wherein the desired uniquely tagged nucleic acid species comprise a sequence-perfect desired nucleic acid sequence;
  e. enriching the desired uniquely tagged species from each diluted sample of the set of diluted samples by amplifying in each diluted sample of the set of one or more tagged nucleic acid molecules of the desired uniquely tagged nucleic acid species using one or more primers that bind one or more barcodes on the tagged candidate nucleic acid molecules of the desired uniquely tagged nucleic acid species to generate a set of populations of product polynucleotides; and
  f. assembling the set of populations of polynucleotides to form a population of subsequent product polynucleotides.

In another aspect, provided herein is a method of generating a population of product polynucleotides, wherein the method comprises:
  a. diluting a subvolume of a source sample comprising at least $1\times10^4$, $1\times10^5$ or $1\times10^6$ tagged candidate nucleic acid molecules to form a diluted sample having a target number of the tagged candidate nucleic acid molecules isolated from the source sample, wherein each tagged candidate nucleic acid molecule has a tag comprising at least one barcode, for example non-degenerate barcode, from a set of a number between any of the ranges provided herein for such a set, for example between 3 to 200 unique (e.g. non-degenerate) barcodes,
  wherein the diluted sample comprises one or more tagged candidate nucleic acid species derived from one or more of the tagged candidate nucleic acid molecules, wherein each nucleic acid molecule of a tagged candidate nucleic acid species has an identical nucleic acid sequence comprising the nucleic acid sequence of the one or more tagged candidate nucleic acid molecules from which it was derived, and wherein in illustrative embodiments at least one of the tagged candidate nucleic acid species in the diluted sample is uniquely tagged;
  b. determining the sequence of at least some of the tagged candidate nucleic acid species, wherein typically at least 1 of the tagged candidate nucleic acid species is a desired uniquely tagged nucleic acid species, wherein in illustrative embodiments the desired uniquely tagged nucleic acid species comprises a sequence-perfect desired nucleic acid sequence; and
  c. enriching the desired uniquely tagged nucleic acid species by amplifying one or more tagged candidate nucleic acid molecules of the desired uniquely tagged nucleic acid species to generate the population of product polynucleotides, wherein the target number of the tagged candidate nucleic acid molecules isolated from the source sample is a number within any of the ranges provided herein for a target number, for example between 10 and 400 nucleic acid molecules, and wherein the desired and in illustrative embodiments, sequence-perfect desired nucleic acid sequence is within any of the length ranges provided herein for such sequence, for example 1 kb to 50 kb in length.

In another aspect with non-limiting illustrative values, provided herein is a method of generating a population of product polynucleotides, wherein the method comprises:
  a. diluting a subvolume of a source sample comprising at least $1\times10^4$, $1\times10^5$ or $1\times10^6$ candidate nucleic acid molecules to form a diluted sample having a target number of the candidate nucleic acid molecules isolated from the source sample, wherein the target number is between 10 and 400,
  wherein the diluted sample comprises one or more tagged candidate nucleic acid species derived from one or more of the candidate nucleic acid molecules, wherein each nucleic acid molecule of a candidate nucleic acid species has an identical nucleic acid sequence comprising the nucleic acid sequence of the one or more candidate nucleic acid molecules from which it was derived and a tag comprising a combination of at least one or two, for example, barcodes, for example non-degenerate barcodes, selected from a set of unique (e.g.) non-degenerate barcodes;
  b. determining the sequence of at least some of the tagged candidate nucleic acid species, in illustrative embodiments using long read sequencing, wherein at least 1 of the tagged candidate nucleic acid species is a desired uniquely tagged nucleic acid species, wherein the desired uniquely tagged nucleic acid species comprises in illustrative embodiments, a sequence-perfect desired nucleic acid sequence; and
  c. enriching a desired uniquely tagged nucleic acid species by amplifying one or more candidate nucleic acid molecules of the desired uniquely tagged nucleic acid species, using one or more primers that bind to one or more barcodes on the tag associated with the candidate nucleic acid molecules of the desired uniquely tagged nucleic acid species to generate a population of product polynucleotides, wherein in illustrative embodiments the desired (e.g. sequence-perfect desired) nucleic acid sequence is any of the length provided herein, such as 1 kb to 50 kb in length, and wherein in illustrative embodiments the enriching the desired uniquely tagged nucleic acid species comprises amplifying one or more tagged candidate nucleic acid molecules of the desired uniquely tagged nucleic acid species using nested PCR with primers that bind two or more of the at least two barcodes on one side of the tagged candidate nucleic acid molecules of the desired uniquely tagged nucleic acid species in successive PCR reactions to generate the population of product polynucleotides.

In another aspect, provided herein is a method of generating a population of polynucleotides, wherein the method comprises:
  a. assembling at least two nucleic acid molecules separately in each of a set of initial sources of nucleic acid molecules to produce a set of source samples each comprising at least $1\times10^4$, $1\times10^5$ or $1\times10^6$ tagged candidate nucleic acid molecules;
  b. diluting a subvolume each source sample of the set of source samples to form a set of diluted samples each having a target number of tagged candidate nucleic acid molecules isolated from each source sample in the set of source samples, wherein each tagged candidate nucleic acid molecule has a tag comprising a combination of at least two non-degenerate barcodes from a set of in illustrative embodiments between 3 to 200 unique, and in illustrative embodiments non-degenerate, barcodes, and wherein in illustrative embodiments the target number of the tagged candidate nucleic acid molecules isolated from the source sample is between 10 and 400 nucleic acid molecules;
  c. combining a portion of each diluted sample in the set of diluted samples to form a combined diluted sample, wherein the combined diluted sample comprises tagged candidate nucleic acid species derived from one or more of the tagged candidate nucleic acid molecules from each diluted sample of the set of diluted samples, wherein each nucleic acid molecule of a tagged candidate nucleic acid species has an identical nucleic acid sequence comprising the nucleic acid sequence of the one or more tagged candidate nucleic acid molecules from which it was derived, and wherein at least one of the tagged candidate nucleic acid species from each diluted sample in the combined diluted sample is uniquely tagged;
  d. determining the sequence of at least some of the tagged candidate nucleic acid species from each of the diluted samples in the combined diluted sample using long-read sequencing, wherein at least 1 of the tagged nucleic acid species from each diluted sample in the combined diluted sample is a desired uniquely tagged nucleic acid species, wherein in illustrative embodiments the desired uniquely tagged nucleic acid species comprise a sequence-perfect desired nucleic acid sequence;
  e. enriching the desired uniquely tagged nucleic acid species from each diluted sample of the set of diluted samples by amplifying in each diluted sample of the set of one or more tagged candidate nucleic acid molecules of the desired uniquely tagged nucleic acid species using one or more primers that bind one or more barcodes on the tagged candidate nucleic acid molecules of the desired uniquely tagged nucleic acid species to generate a set of populations of product polynucleotides; and
  f. assembling the set of populations of polynucleotides to form a population of subsequent product polynucleotides, wherein in illustrative embodiments the sequence-perfect desired nucleic acid sequence of each desired nucleic acid is between 50 kb and 1 Mb in length.

In some embodiments, the determining the sequence includes long-read sequencing, wherein the entire sequence of the tagged candidate nucleic acid molecules, product polynucleotides, or subsequent polynucleotides are determined.

In some embodiments, the nucleic acid sequence is determined for less than $1\times10^6$ tagged candidate nucleic acid species. In some embodiments, the nucleic acid sequence is determined for between 10 and 100,000 tagged candidate nucleic acid species. In some embodiments, the nucleic acid sequence is determined for all the nucleic acid species in the diluted sample.

In some embodiments, the sequence-perfect desired nucleic acid sequence comprises a segment having one or more of the following:
  i) a GC content 25% or less for a stretch of at least 25 nucleotides of, or for the entire desired nucleic acid sequence;
  ii) a GC content of 75% or more for a stretch of at least 25 nucleotides of, or for the entire desired nucleic acid sequence;
  iii) a homopolymeric run of 10 or more As or Ts;
  iv) a homopolymeric run of 6 or more Gs or Cs;
  v) a repeat sequence of at least 6 nucleotides that is repeated 5 times;
  vi) a repeat sequence of at least 8 nucleotides that is repeated at least 2 times;
  vii) a repeat sequence comprising a tandem repeat sequence;
  viii) an inverted repeat sequence of at least 6 nucleotides;
  ix) low sequence complexity; or
  x) a sequence with a polynucleotide secondary structure comprising a stem, hairpin, internal loop, or pseudoknot and/or a high secondary structure percentage.

In some embodiments, the desired nucleic acid sequence comprises a GC content 25% or less for a stretch of at least 25 nucleotides of, or for the entire desired nucleic acid sequence. In some embodiments, the desired nucleic acid sequence comprises a GC content of 75% or more for a stretch of at least 25 nucleotides of, or for the entire desired nucleic acid sequence. In some embodiments, the desired nucleic acid sequence comprises a homopolymeric run of 10 or more As or Ts. In some embodiments, the desired nucleic acid sequence comprises a homopolymeric run of 6 or more Gs or Cs. In some embodiments, the desired nucleic acid sequence comprises a repeat sequence of at least 6 nucleotides that is repeated 5 times. In some embodiments, the desired nucleic acid sequence comprises a repeat sequence of at least 8 nucleotides that is repeated at least 2 times. In some embodiments, the desired nucleic acid sequence comprises a repeat sequence of at least 10 nucleotides that is repeated at least 2 times. In some embodiments, the desired nucleic acid sequence comprises a repeat sequence of at least 15 nucleotides that is repeated at least 2 times. In some embodiments, the desired nucleic acid sequence comprises a repeat sequence of at least 25 nucleotides that is repeated at least 2 times. In some embodiments, the desired nucleic acid sequence comprises a repeat sequence of at least 50 nucleotides that is repeated at least 2 times. In some embodiments, the desired nucleic acid sequence comprises a repeat sequence of at least 100 nucleotides that is repeated at least 2 times. In some embodiments, the desired nucleic acid sequence comprises a repeat sequence comprising a tandem repeat sequence. In some embodiments, the desired nucleic acid sequence comprises an inverted repeat sequence of at least 6 nucleotides. In some embodiments, desired nucleic acid sequence comprises a low sequence complexity. In some embodiments, the desired nucleic acid sequence is a traditionally difficult to generate sequence. In some embodiments, the traditionally difficult to generate sequence comprises a traditionally difficult to generate segment of at least 100 base pairs in length. In some embodiments, the desired nucleic acid sequence comprises a secondary structure and wherein the secondary structure is a stem, hairpin, internal loop, or a pseudoknot and/or a high secondary structure percentage. In some embodiments, the desired nucleic acid sequence comprises a sequence with a polynucleotide secondary structure comprising a stem, hairpin, internal loop, or pseudoknot and/or a high secondary structure percentage.

In some embodiments, the source sample comprises at least $1 \times 10^7$ tagged candidate nucleic acid molecules, and wherein the ratio of unique non-degenerate barcode combinations in tags, to candidate nucleic acid molecules in the source sample is between $1:1 \times 10^4$ and $1:1 \times 10^7$.

In some embodiments, the method is capable of achieving a median error rate of at most 1 in 10,000. In some embodiments, the method is capable of achieving a median error rate of at most 1 in 30,000. In some embodiments, the method is capable of achieving a median error rate of at most 1 in 30,000 and wherein the sequence-perfect desired nucleic acid sequence is 2.5 kb to 10 kb in length.

In some embodiments, the sequence-perfect desired nucleic acid sequence is 2.5 kb to 50 kb in length and at least 90% of the product polynucleotides in the population of product polynucleotides have the sequence-perfect desired nucleic acid sequence.

In some embodiments, the source nucleic acid molecules have a length, and wherein said length is between 0.2 kilobases (kb) and 1 kb. In some embodiments, less than 25% of the nucleic acid molecules or the tagged nucleic acid molecules in the source sample are sequence-perfect with respect to a corresponding portion of the desired nucleic acid sequence.

In some embodiments, the target number is determined based on the number of unique non-degenerate barcodes in the set of unique, non-degenerate barcodes or unique non-degenerate barcode combinations selected from the set of unique, non-degenerate barcodes, and wherein the target number is less than the number of unique non-degenerate barcodes in the unique, degenerate set of barcodes or unique non-degenerate barcode combinations selected from the set of non-degenerate barcodes.

In some embodiments, the source sample comprises a set of tags having between 64 to and 10,000 unique combinations of at least two of the non-degenerate barcodes. In some embodiments, the tagging comprises ligating an adapter comprising the tag to the candidate nucleic acid molecules in the source sample or in the dilute sample.

In some embodiments, wherein at least one step of the method is automated. In some embodiments, steps a to c of the above aspects are performed in 1-3 days. In some embodiments, the method from step a to step c is performed in from 8 hours to 6 days. In some embodiments, the steps a to f are performed in 3 to 6 days.

In some embodiments, each tagged candidate nucleic acid molecule has a tag comprising a combination of at least two of the non-degenerate barcodes, and the enriching the desired uniquely tagged nucleic acid species comprises amplifying one or more tagged candidate nucleic acid molecules of the desired uniquely tagged nucleic acid species using nested PCR with primers that bind two or more of the at least two barcodes on one side of the tagged candidate nucleic acid molecules of the desired uniquely tagged nucleic acid species in successive PCR reactions to generate the population of product polynucleotides.

In some embodiments, at least one of the tagged nucleic acid species in the diluted sample is not uniquely barcoded. In some embodiments, at least one of the tagged nucleic acid sequence in the diluted sample is uniquely barcoded.

In some embodiments, the enriching the desired uniquely tagged nucleic acid species comprises amplifying one or more tagged candidate nucleic acid molecules of the desired uniquely tagged nucleic acid species using nested PCR with primers that bind two or more of the at least two barcodes on one side of the tagged candidate nucleic acid molecules of the desired uniquely tagged nucleic acid species in successive PCR reactions to generate the population of product polynucleotides. In some embodiments, the enriching is performed using pre-made primers. In some embodiments, each tagged candidate nucleic acid molecule has a tag comprising a combination of at least two barcodes on one side of the candidate nucleic acid molecule, and wherein the enriching the desired uniquely tagged nucleic acid species comprises amplifying one or more tagged candidate nucleic acid molecules of the desired uniquely tagged nucleic acid species using nested PCR with primers that bind two or more of the at least two barcodes on one side of the tagged candidate nucleic acid molecules of the desired uniquely tagged nucleic acid species in successive PCR reactions to generate the population of product polynucleotides.

In some embodiments, the method further comprises assembling and tagging two or more initial assembly products of between 250 and 750 nucleotides in length to form the tagged candidate nucleic acid molecules in the source sample. In some embodiments, the method further comprises an initial assembly reaction comprising assembling a set of oligonucleotides between 10 and 150 nucleotides in length to yield the two or more initial assembly products. In some embodiments, no diluting or determining the sequence is performed before the assembling and tagging the two or more initial assembly products.

In some embodiments, the assembling the set of population of polynucleotides to form the population of subsequent polynucleotides is performed using polymerase cycling assembly (PCA), isothermal assembly, circular DNA assembly, ligase cycling reaction (LCR), bacterial recombination, yeast homologous recombination, overlap extension PCR are used to generate a subsequent polynucleotide. In some embodiments, the assembling the set of populations of polynucleotides to form a population of subsequent product polynucleotides is performed at an isothermal temperature and comprises a reaction mixture comprising a 5' exonuclease, a polymerase, and a DNA ligase. In some embodiments, the assembling the set of populations of polynucleotides to form a population of subsequent product polynucleotides is performed at an isothermal temperature using circular DNA assembly and a reaction mixture comprising:

(a) a first enzyme group that catalyzes replication of circular DNA;
(b) a second enzyme group that catalyzes an Okazaki fragment maturation and synthesizes two sister circular DNAs constituting a catenane;
(c) a third enzyme group that catalyzes a separation of the two sister circular DNAs; and
(d) rNTPs and dNTPs.

In some embodiments, the first enzyme group comprises one or more of an enzyme having DnaA activity, one or more types of nucleoid protein, an enzyme or enzyme group having DNA gyrase activity, a single-strand binding protein (SSB), an enzyme having DNA helicase activity, an enzyme having DNA helicase loader activity, an enzyme having DNA primase activity, an enzyme having DNA clamp activity, and an enzyme or enzyme group having DNA polymerase III* activity. In some embodiments, the second enzyme group comprises one or more of an enzyme having DNA polymerase I activity and an enzyme having DNA ligase activity. In some embodiments, the third enzyme group comprises at least two enzymes selected from the group consisting of an enzyme having topoisomerase III activity, an enzyme having topoisomerase IV activity, and an enzyme having RecQ activity.

In some embodiments, the ratio of unique non-degenerative barcode combinations in tags, to candidate nucleic acid molecules in the source sample is between $1:1\times10^4$ and $1:1\times10'$.

In some embodiments, the method is a multiplex method performed by combining a portion of each of at least 2 different diluted samples to form a combined sample, wherein the multiplex method comprises determining the sequences in the same sequencing run, of at least some of the tagged nucleic acid species in the combined sample, wherein said tagged nucleic acid species are from, or derived from nucleic acid molecules from each of the at least 2 different diluted samples, and wherein the enriching comprises enriching at least 1 population of polynucleotides from each of the at least 2 different diluted samples.

In some embodiments, the method is performed at least 2 times to enrich 2 different polynucleotides having 2 different sequence-perfect desired nucleic acid sequences. In some embodiments, the method is performed at least 3 times to enrich 3 different polynucleotides having 3 different sequence-perfect desired nucleic acid sequences. In some embodiments, the sequence-perfect desired polynucleotides are 3 populations comprising the sequence-perfect desired polynucleotides, and wherein the populations comprise at least 95% sequence-perfect desired polynucleotides. In some embodiments, the method further comprises linking one or more sequence-perfect desired polynucleotides to generate a subsequent polynucleotide. In some embodiments, the subsequent polynucleotide comprises at least one synthetic gene segment, at least one synthetic gene, at least one vector, at least one expression vector, at least one gene cluster, or at least one expression cassette.

In one aspect, provided herein is a method of generating a polynucleotide, or a population of polynucleotides, wherein the method includes:
  a. subsetting (e.g., diluting) a source sample comprising at least 2, and in illustrative embodiments at least $1\times10^5$ source nucleic acid molecules and/or tagged nucleic acid molecules derived therefrom, to form a subset sample by isolating a target number of the source nucleic acid molecules and/or the tagged nucleic acid molecules away from the source sample,
  wherein the subset sample comprises one or more tagged nucleic acid species derived from one or some of the source nucleic acid molecules, wherein the tagged nucleic acid molecules from each tagged nucleic acid species have an identical nucleic acid sequence,
  wherein at least some of the tagged nucleic acid species in the subset sample are uniquely tagged source nucleic acid molecules;
  b. determining the sequence of at least some of the tagged nucleic acid species, wherein at least 1 of the tagged nucleic acid species is a desired uniquely tagged nucleic acid species, wherein the desired uniquely tagged nucleic acid species comprises the desired nucleic acid sequence; and
  c. enriching the polynucleotide having the desired nucleic acid sequence from the subset sample by enriching one or more polynucleotides of the desired uniquely tagged nucleic acid species, to generate the polynucleotide or the population of polynucleotides.

In certain illustrative embodiments, the target number of source nucleic acid molecules and/or tagged nucleic molecules isolated away from the source sample is between 10 and 100,000 nucleic acid molecules. In certain illustrative embodiments, at least 25%, 30%, 40%, 50%, 60%, 70%, 75%, 80%, 90%, 95%, 99%, or 100% of the polynucleotides in the population of polynucleotides generated by the method comprise the desired nucleic acid sequence. In some embodiments, the desired nucleic acid sequence is at least 25%, 30%, 40%, 50%, 60%, 70%, 75%, 80%, 90%, 95%, 99%, or 100% identical to a sequence-perfect desired nucleic acid sequence. In certain embodiments, the subsetting the source sample is diluting the source sample. In certain illustrative embodiments, an amplification is performed in the diluted sample to generate the one or more tagged nucleic acid species.

In certain illustrative embodiments, the target number of source nucleic acid molecules and/or tagged nucleic molecules isolated away from the source sample is between 10 and 100,000 nucleic acid molecules. In certain illustrative embodiments, at least 25%, 30%, 40%, 50%, 60%, 70%, 75%, 80%, 90%, 95%, 99%, or 100% of the polynucleotides in the population of polynucleotides generated by the method comprise the desired nucleic acid sequence, and the desired nucleic acid sequence is at least 25%, 30%, 40%, 50%, 60%, 70%, 75%, 80%, 90%, 95%, 99%, or 100% identical to a sequence-perfect desired nucleic acid sequence. In certain embodiments, the subsetting the source sample is diluting the source sample. In certain illustrative embodiments, an amplification is performed in the diluted sample to generate the one or more tagged nucleic acid species.

In any of the aspects, in some embodiments although the barcodes can be fully or partially degenerate barcodes from a library or set of fully or partially degenerate barcodes, in illustrative embodiments the barcodes are non-degenerate barcodes of a library or set of non-degenerate barcodes.

In certain illustrative embodiments, the method further includes before the subsetting (e.g., diluting) step: assembling at least two nucleic acid molecules of an initial source of nucleic acid molecules to produce the source sample of nucleic acid molecules. Such assembling can include, for example, performing an assembly reaction in a reaction mixture comprising a plurality of nucleic acid molecules, to generate a plurality of assembled nucleic acid molecules, a population of candidate nucleic acid molecules, or a population of candidate polynucleotides, some, most, or all of which typically have a desired nucleic acid sequence. Thus, such assembled nucleic acid molecules, can be the source nucleic acid molecules and can provide source nucleic acid species. In illustrative some embodiments, the assembled nucleic acid molecules include at least some (e.g. 10%, 20%, 25%, 50%, 75% or more) nucleic acid molecules that are at least 75%, 80%, 90%, 95%, 99% or in illustrative embodiments 100% sequence-perfect with respect to the desired nucleic acid sequence.

In some illustrative embodiments, the method includes performing the assembly, the polynucleotide or population of polynucleotides having the desired nucleic acid sequence are between 5 kb and 50 kb in length, the determining the sequence is performed using long-read sequencing, the method is performed in between 8 hours and 2 days, and/or the nucleic acid molecules do not enter a cell during the method. In further illustrative embodiments of such a method, the method is performed in between 8 hours and 1 day, or between 12 hours and 1 day, or between 1 and 2 days.

In some embodiments, the method is an automated, partially automated, or fully automated method. In some embodiments, at least one, two, three, four, most, some, or all of the steps of the method are automated. In some embodiments, each tagged molecule includes one or more barcodes from a set of between 2, 10, 20, 100, or 1,000 and $1 \times 10^6$ barcodes. In some embodiments of any of the methods and compositions herein, the ratio of unique barcodes or barcode combinations in a set of tags to candidate nucleic acid molecules in the source sample is between $1:1 \times 10^4$ and $1:1 \times 10^7$. In some embodiments, the ratio of unique barcodes or barcode combinations in a set of tags to candidate nucleic acid molecules in the source sample is between $1:1 \times 10^5$ and $1:1 \times 10^7$. In some embodiments, the ratio of unique barcodes or barcode combinations in a set of tags to candidate nucleic acid molecules in the source sample is between $1:1 \times 10^5$ and $1:5 \times 10^6$. In some embodiments, the ratio of unique barcodes or barcode combinations in a set of tags to candidate nucleic acid molecules in the source sample is between $1:6 \times 10^5$ and $1:5 \times 10^6$.

In some embodiments, the ratio of unique molecular barcodes, or in some subaspects, of unique combinations of molecular barcodes (molecular barcode combinations), to source nucleic acid molecules or species of the subset (e.g., diluted) sample, is about, exactly, or targeted to be 1:10, 1:5, 1:4, 1:3, 1:2, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes to the number of source nucleic acid molecules, or nucleic acid molecules or species of the subset sample. In some embodiments, less than 95%, 90%, 80%, 75%, 70%, 65%, 60%, 55%, 50%, 45%, 40%, 35%, 30%, 25%, 20%, 15%, 10%, 5%, 4%, 3%, 2%, or 1%, or between 1% on the low end of the range and 2%, 3%, 4%, 5%, 10%, 15%, 20%, 25%, 30%, 35%, 40%, 45%, 50%, 55%, 60%, 65%, 70%, 75%, 80%, 90%, 95%, 96%, 97%, 98%, or 99%, on the high end of the range, or between 1%, 2%, 3%, 4%, 5%, 10%, 15%, 20%, 25%, 30%, 35%, 40%, or 45% on the low end of the range and 50% on the high end of the range, or between 25% and 75% or 50%, or between 50% and 90%, 80%, or 75%, or between 75% and 95%, 90%, or 80% of the nucleic acid molecules or species in the source sample have at least 75%, 80%, 90%, 95%, or 99% identity, or in illustrative embodiments, are sequence-perfect, with respect to a corresponding portion of the desired nucleic acid sequence.

In some aspects of any of the methods provided herein, the method is performed in from 8 hours to 6, 5, 4, 3, 2, or 1 day, or from 1 day to 6, 5, 4, 3, or 2 days. In some aspects of any of the methods provided herein, the method is performed in solution, e.g., the nucleic acid molecules and/or polynucleotides are not attached to a solid-phase during the method. In some aspects of any of the methods provided herein, the method is performed on a microfluidic device.

In another aspect, provided herein is a population of product polynucleotides, wherein the population of product polynucleotides is generated using a method disclosed herein. In some embodiments, the error rate of the sequences of the population of product polynucleotides is 1 error per 10,000, 15,000, 20,000, 25,000, 30,000, 35,000, 40,000, 45,000, 50,000, 60,000, 70,000, 80,000, 90,000, 100,000, 110,000, 120,000, 130,000, 140,000, 150,000, 160,000, 170,000, 180,000, 190,000, 200,000, 210,000, 220,000, 230,000, 240,000, 250,000, 300,000, 350,000, 400,000, 450,000, 500,000, 600,000, 700,000, 800,000, or 900,000 nucleotides or lower. In some embodiments, the error rate of the sequences of the population of product polynucleotides is more than 1 error per 1,000,000, 2,000,000, 3,000,000, 4,000,000, or 5,000,000 nucleotides. In some embodiments, the error rate of the sequences of the population of product polynucleotides is between 1 error per 30,000 nucleotides and 1 error per 900,000 nucleotides.

In another aspect, provided herein is a population of polynucleotides, wherein the population of polynucleotides each comprise a desired nucleic acid sequence, wherein the error rate of the sequences of the desired nucleic acid sequences relative to a sequence-perfect nucleic acid sequence is between 1 error per 10,000, 15,000, 20,000, 25,000, 30,000, 35,000, 40,000, 45,000, 50,000, 60,000, 70,000, 80,000, 90,000, and 100,000 nucleotides on the low end of the range and 1 error per 110,000, 120,000, 130,000, 140,000, 150,000, 160,000, 170,000, 180,000, 190,000, 200,000, 210,000, 220,000, 230,000, 240,000, 250,000, 300,000, 350,000, 400,000, 450,000, 500,000, 600,000, 700,000, 800,000, or 900,000 nucleotides on the high end of the range. In some embodiments, the error rate of the sequences of the desired nucleic acid sequences relative to a sequence-perfect nucleic acid sequence is between 1 error per 30,000 nucleotides on the low end of the range and 1 error per 110,000, 120,000, 130,000, 140,000, 150,000, 160,000, 170,000, 180,000, 190,000, 200,000, 210,000, 220,000, 230,000, 240,000, 250,000, 300,000, 350,000, 400,000, 450,000, 500,000, 600,000, 700,000, 800,000, or 900,000 nucleotides on the high end of the range. In some embodiments, the error rate of the sequences of the desired nucleic acid sequences relative to a sequence-perfect nucleic acid sequence is between 1 error per 60,000 nucleotides on the low end of the range and 1 error per 110,000, 120,000, 130,000, 140,000, 150,000, 160,000, 170,000, 180,000, 190,000, 200,000, 210,000, 220,000, 230,000, 240,000, 250,000, 300,000, 350,000, 400,000, 450,000, 500,000, 600,000, 700,000, 800,000, or 900,000 nucleotides on the high end of the range.

In another aspect, provided herein is a method of fulfilling an order for a population of product polynucleotides, the method comprising:
  a) receiving an order for the population of product polynucleotides from a customer, wherein the product polynucleotide has a desired nucleic acid sequence; and
  b) fulfilling the order by generating the population of product polynucleotides with a quality threshold, wherein the quality threshold is the minimum error rate in the sequences of the population of product polynucleotides relative to a sequence-perfect desired nucleic acid sequence, and wherein the quality threshold is 1 error per 30,000 nucleotides.

In some embodiments, the quality threshold is 1 error per 60,000 nucleotides. In some embodiments, the method from receiving the order to fulfilling the order is performed in between 1 and 6 days. In some embodiments, the population of product polynucleotides is generated using the method according to any one of the methods provided herein.

In some embodiments, the nucleic acid molecules of the source sample include DNA. In some embodiments, the nucleic acid molecules of the source sample include RNA. In some embodiments, the nucleic acid molecules of the source sample include non-natural nucleotides. In some embodiments, the at least one polynucleotide includes at least one desired nucleic acid sequence. In some embodiments, the nucleic acid molecules in the source sample include cellular DNA. In some embodiments, the nucleic acid molecules in the source sample include cellular RNA. In some embodiments, the nucleic acid molecules in the source sample include synthetic nucleic acid molecules. In further embodiments, the synthetic nucleic acid molecules include synthetic oligonucleotides. In some embodiments, the lengths of the nucleic acid molecules of the source sample are from about 0.2 kilobases (kb) to about 50 kb, for example 0.2 kb to 40 kb, 30 kb, 20 kb, or 10 kb. In some embodiments, the method includes adding one or more oligonucleotides to the source sample. In further embodiments, the one or more oligonucleotides include commercially synthesized oligonucleotides. In some embodiments, the oligonucleotides include at least one molecular barcode. In some embodiments, the oligonucleotides include at least one adapter.

In some embodiments, the method further includes before the subsetting: assembling at least two nucleic acid molecules of an initial source of nucleic acid molecules to produce the source sample of nucleic acid molecules. In some embodiments, the initial source of nucleic acid molecules are chemically synthesized oligonucleotides of between 20 and 5,000 nucleotides, for example between 50 and 1,000 nucleotides. In some embodiments, the assembling at least two nucleic acid molecules of an initial source of nucleic acid molecules is an assembly method for assembling single-stranded nucleic acid molecules. In some embodiments, the desired polynucleotide is between 100 and 10,000 nucleotides in length, for example between 500 and 5,000 nucleotides in length. In some embodiments, the polynucleotide having the desired nucleic acid sequence is between 1,000 nucleotides and 50,000 nucleotides in length. In some embodiments, the assembly can be performed using polymerase cycling assembly (PCA), isothermal assembly, e.g., Gibson assembly, ligase cycling reaction (LCR), overlap extension PCR (overlapping PCR, PCR SOEing, PCR sewing), PCR incorporating 5' sequences, PCR stitching, or any combination of these methods. In some aspects of any of the methods provided herein that include an assembling nucleic acid molecules step, the step can be performed in solution, e.g., the nucleic acid molecules and polynucleotides are not attached to a solid-phase during the step.

In some embodiments, the nucleic acid molecules or species of the subset sample include DNA. In some embodiments, the nucleic acid molecules or species of the subset sample include RNA. In some embodiments, the nucleic acid molecules or species of the subset sample include non-natural nucleotides. In some embodiments, the subset sample includes between 100 to 100,000 nucleic acid molecules or species. In some embodiments, the subset sample includes about 1 to about 50,000, about 1 to about 25,000, 1 to about 10,000, 1 to about 9000, 1 to about 8000, 1 to about 7000, 1 to about 6000, 1 to about 5000, 1 to about 4000, 1 to about 3000, 1 to about 2500, 1 to about 2000, 1 to about 1500, 1 to about 1000, 1 to about 900, 1 to about 800, 1 to about 700, 1 to about 600, 1 to about 500, 1 to about 400, 1 to about 300, 1 to about 200, 1 to about 100 nucleic acid molecules, 10 to about 50,000, about 10 to about 25,000, 10 to about 10,000, 10 to about 9000, 10 to about 8000, 10 to about 7000, 10 to about 6000, 10 to about 5000, 10 to about 4000, 10 to about 3000, 10 to about 2500, 10 to about 2000, 10 to about 1500, 10 to about 1000, 10 to about 900, 10 to about 800, 10 to about 700, 10 to about 600, 10 to about 500, 10 to about 400, 10 to about 300, 10 to about 200, 10 to about 100 nucleic acid molecules, or about 50 to about 1000 nucleic acid molecules or species. In some embodiments, the subset sample includes about 50 to about 1000 nucleic acid molecules or species.

In some embodiments, the subsetting comprises diluting the source sample at least 10, 50, 100, 1,000, 5,000, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, $1\times10^{20}$, or $1\times10^{21}$ fold depending on the number of source nucleic acid molecules in the source sample and the desired or target number or number range of source nucleic acid molecules in the subset (e.g., diluted) sample. In some aspects, the source sample comprises at least $1\times10^6$ source nucleic acid molecules and the desired or target number or number range for the subset (e.g., diluted) sample is between about 1 to about 100,000 source nucleic acid molecules or a target number therein, e.g., from about 5, 10, 15, 20, 25, 30, 35, 40, 45, 50, 60, 70, 80, 90, or 100 source nucleic acid molecules on the low end of the range to about 1000 source nucleic acid molecules on the high end of the range, or a target number therein, from about 100 source nucleic acid molecules on the low end of the range to about $1\times10^5$, $1\times10^4$, $1\times10$ source nucleic acid molecules on the high end of the range, or a target number therein, or from about 10, 100, or 250 source nucleic acid molecules on the low end of the range to about $1\times10$ source nucleic acid molecules on the high end of the range, or a target number therein. In some aspects, the diluted sample comprises about 1 to about 50,000, about 1 to about 25,000, 1 to about 10,000, 1 to about 9000, 1 to about 8000, 1 to about 7000, 1 to about 6000, 1 to about 5000, 1 to about 4000, 1 to about 3000, 1 to about 2500, 1 to about 2000, 1 to about 1500, 1 to about 1000, 1 to about 900, 1 to about 800, 1 to about 700, 1 to about 600, 1 to about 500, 1 to about 400, 1 to about 300, 1 to about 200, 1 to about 100 nucleic acid molecules, 10 to about 50,000, about 10 to about 25,000, 10 to about 10,000, 10 to about 9000, 10 to about 8000, 10 to about 7000, 10 to about 6000, 10 to about 5000, 10 to about 4000, 10 to about 3000, 10 to about 2500, 10 to about 2000, 10 to about 1500, 10 to about 1000, 10 to about 900, 10 to about 800, 10 to about 700, 10 to about 600, 10 to about 500, 10 to about 400, 10 to about 300, 10 to about 200, 10 to about 100 source nucleic acid molecules, or about 50 to about 1000 source nucleic acid molecules. In some aspects, the subset or diluted sample comprises numbers of source nucleic acid molecules within exactly the ranges recited above. In some aspects, the subset or diluted sample comprises at most 50,000, 25,000, 10,000, 9,000, 8,000, 7,000, 6,000, 5,000, 4,000, 3,000, 2,500, 2,000, 1,500, 1,000, 900, 800, 700, 600, 500, 400, 300, 200, 100, 90, 80, 70, 60, 50, 40, 30, or 25 source nucleic acid molecules. In some embodiments, the subset (e.g., diluted) sample comprises any of the desired or target numbers or ranges of source nucleic acid molecules provided hereinabove. In some embodiments, subsetting the source sample includes a serial dilution.

In some embodiments, subsetting the source sample includes adding an aqueous and/or an oil-based solution to the source sample to subset the source sample into two or more partitions such that the subset sample includes two or more partitions. In some embodiments, at least one partition has one nucleic acid molecule of the source sample. In some embodiments, at least one partition includes more than one nucleic acid molecule of the source sample. In some embodiments, the partitions can be droplets. In further embodiments, the subset sample includes a population of at least 10, 20, 30, 40, 50, 100, 250, 500, 1,000, 2,500, 5,000, 10,000, 25,000, 50,000, 100,000, 250,000, 500,000, 1,000, 000, 2,500,000, 5,000,000, or 10,000,000 partitions. In some embodiments, the partitions each include one nucleic acid molecule of the source sample. In some embodiments, at least 10%, 15%, 20%, 25%, 30%, 40%, 50%, 60%, 70%, 80%, or 90% of the partitions contain exactly one nucleic acid molecule. In some embodiments, the average number of nucleic acid molecules or species per partition is less than 1, about 1, more than 1, about 2, or about 3 nucleic acid molecules or species. In some embodiments, the average number of nucleic acid molecules or species per partition is between 0 and 2, 0.25 and 1.75, 0.5 and 1.5, 0.75 and 1.25, 0.8 and 1.2, or 0.9 and 1.1 nucleic acid molecules or species. In some embodiments, the lengths of the nucleic acid molecules of the subset sample are from about 0.2 kb to about 30 kb, from about 1 kb to about 30 kb, or about 5 kb to about 30 kb.

In some aspects of any of the methods provided herein that include a subsetting (e.g., diluting) or a partitioning the source sample step, the step can be performed in solution, e.g., the nucleic acid molecules and polynucleotides are not attached to a solid-phase during the step. In some aspects of any of the methods provided herein that include a step of subsetting a source sample, the subsetting can be part of a multiplex method that comprises combining a portion of at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 different source samples to form the subset (e.g., dilute) sample. Thus, in some embodiments, the subset sample contains at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 polynucleotides having at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 desired sequences. In certain embodiments of any aspect or embodiment provided herein that includes a subsetting or partitioning step, the sequencing results between different partitions from the same source sample are not compared to determine a relative amount of a polynucleotide in the source sample.

In some embodiments, the method includes tagging at least one nucleic acid molecule of the source sample or subset sample with at least one oligonucleotide, e.g., at least one barcode. In some embodiments, the 5' and/or 3' end of at least one nucleic acid molecule is tagged with at least one molecular barcode. In some embodiments, only the 5' end of at least one nucleic acid molecule is tagged with at least one molecular barcode. In some embodiments, only the 3' end of at least one nucleic acid molecule is tagged with at least one molecular barcode. In some embodiments, at least one nucleic acid molecule of the source sample includes at least one adapter. In further embodiments, at least one adapter is attached to the 5' and/or the 3' end of at least one nucleic acid molecule. In some embodiments, at least one nucleic acid molecule of the source sample includes at least one or more molecular barcodes. In some embodiments, at least one molecular barcode is attached to the 5' and/or the 3' end of at least one nucleic acid molecule. In some embodiments, the method further includes adding one or more molecular barcodes to the source sample. In further embodiments, the method includes tagging nucleic acid molecules of the source sample with at least one molecular barcode. In further embodiments, the tagging includes ligating at least one molecular barcode and at least one nucleic acid molecule of the source sample. In some embodiments, the number of unique molecular barcodes is less than the number of nucleic acid molecules or species of the source sample. In further embodiments, the number of unique molecular barcodes is greater than the number of nucleic acid molecules or species of the subset sample. In further embodiments, the number of unique molecular barcodes is about the same as the number of nucleic acid molecules or species of the subset sample. In some embodiments, the number of unique combinations of molecular barcodes is about the same as the number of nucleic acid molecules or species of the subset sample. In some embodiments, the ratio of unique molecular barcodes, or in some subaspects, of unique combinations of molecular barcodes (molecular barcode combinations), to source nucleic acid molecules or species of the subset (e.g., diluted) sample, is about, exactly, or targeted to be 1:10, 1:5, 1:4, 1:3, 1:2, 1:1, 2:1, 3:1, 4:1, 5:1, 10:1, 20:1, 50:1, 100:1, 1,000:1, or 10,000:1 or a greater ratio of unique molecular barcodes, or unique combinations of barcodes to the number of source nucleic acid molecules or nucleic acid molecules or species of the subset sample. In some embodiments, the number of unique combinations of molecular barcodes is less than the number of nucleic acid molecules or species of the source sample. In some embodiments, the number of unique combinations of molecular barcodes is greater than the number of nucleic acid molecules or species of the subset sample. In some embodiments of any aspect or embodiment herein, the method can include adding between 3 and 10,000, between 3 and 9,000, between 3 and 8,000, between 3 and 7,000, between 3 and 6,000, between 3 and 5000, between 3 and 4000, between 3 and 3000, between 3 and 2000, between 3 and 1000, between 3 and 750, between 3 and 500, between 3 and 450, between 3 and 400, between 3 and 350, between 3 and 300, between 3 and 250, between 3 and 200, between 3 and 150, between 3 and 100, between 3 and 90, between 3 and 80, between 3 and 70, between 3 and 60, between 3 and 50, between 3 and 40, between 3 and 30, between 3 and 20, between 3 and 20, between 3 and 10, between 15 and 400, between 15 and 350, between 15 and 300, between 15 and 250, between 15 and 200, between 15 and 150, between 15 and 100, between 15 and 90, between 15 and 80, between 15 and 70, between 15 and 60, between 15 and 50, between 15 and 40, between 15 and 30, between 20 and 400, between 20 and 350, between 20 and 300, between 20 and 250, between 20 and 200, between 20 and 150, between 20 and 100, between 20 and 90, between 20 and 80, between 20 and 70, between 20 and 60, between 20 and 50, between 20 and 40, or between 20 and 30 unique molecular barcodes. In some embodiments, one, two, three, four, five, six, seven, eight, nine, or ten molecular barcodes can be attached to a single nucleic acid molecule. In some embodiments, the method includes adding one or more molecular barcodes to the subset sample. In further embodiments, the method includes tagging at least one nucleic acid molecule of the subset sample with at least one oligonucleotide, for example a molecular barcode. In further embodiments, the tagging includes ligating at least one molecular barcode to at least one nucleic acid molecule of the subset sample. In some embodiments, the tagging includes a polymerase chain reaction (PCR). In some embodiments, the target number is determined based on the number of unique barcodes in the one or more sets of barcodes and the number of barcodes attached to each tagged nucleic acid molecule such that at least one of the tagged nucleic acid molecules or species in the subset sample is uniquely barcoded and at least one of the tagged nucleic acid molecules or species in the subset sample is not uniquely barcoded. In some embodiments, the target number is determined based at least in part on the number of unique barcodes in each set of barcodes, the number of sets of barcodes, the number of nucleic acid molecules or species in the source sample, an error rate of the sequencer used to determine the sequence, and/or a target minimum depth of read for the determining the sequence.

In some aspects of any of the methods provided herein that include a step of tagging nucleic acid molecules with barcodes, the step can be performed in solution, e.g., the nucleic acid molecules and polynucleotides are not attached to a solid-phase during the step. In some aspects of any of the methods provided herein that include a step of tagging nucleic acid molecules with barcodes, the tagging can be part of a multiplex method that comprises tagging different source or subset samples in parallel and combined at later steps. In some embodiments, different source or subset samples barcoded in parallel can be barcoded with different barcodes such that each source or subset sample has unique barcodes on the tagged nucleic acid molecules or species. In some embodiments, one or more of the source or subset samples contain at one identical barcode on the nucleic acid molecules or species.

In some aspects of any of the methods provided herein that include a step of tagging nucleic acid molecules with barcodes, the tagging can be part of a multiplex method that comprises combining different source or subset samples and barcoding the combined sample. In some embodiments, at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 source or subset samples are combined before tagging. In some embodiments, between 2, 3, 4, 5, 6, 7, 8, 9, 10, 15, 20, 25, 30, 35, 40, 45, 50, 60, 70, 80, or 90 subset samples on the low end of the range and 100 source or subset samples on the high end of the range are combined before tagging. In some embodiments, between 2, 3, 4, 5, 6, 7, 8, 9, 10, 15, 20, 25, 30, 35, 40, 45, 50, 60, 70, 80, 90, 100, 200, 300, 400, 500, 600, 700, 800, or 900 source or subset samples on the low end of the range and 1,000 source subset samples on the high end of the range are combined before tagging In some embodiments, between 2 source or subset samples on the low end of the range and 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 source or subset samples on the high end of the range are combined before tagging.

In some embodiments, the method further comprises a step of amplifying the subset sample. In some embodiments, the nucleic acid molecules of the subset (e.g., diluted) sample are amplified using isothermal amplification. In some aspects, an isothermal amplification can comprise Loop-Mediated Isothermal Amplification (LAMP), Whole Genome Amplification (WGA), Strand Displacement Amplification (SDA) Helicase-Dependent Amplification (HDA), Recombinase Polymerase Amplification (RPA), or Nucleic Acid Sequences Based Amplification (NASBA), In some aspects, the isothermal amplification can be performed at a temperature less than or about 25° C., 30° C., 35° C., 37° C., 40° C., 45° C., 50° C., 55° C., 60° C., or 65° C. In some embodiments, the nucleic acid molecules of the subset (e.g., diluted) sample are amplified using polymerase chain reaction (PCR), digital PCR, barcode-targeted PCR, reverse-transcription PCR, quantitative PCR, real-time PCR, isothermal amplification, linear amplification, or isothermal linear amplification, quantitative fluorescent PCR (QF-PCR), multiplex fluorescent PCR (MF-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), bridge PCR (bPCR), picotiter PCR, digital PCR, droplet digital PCR, or emulsion PCR (emPCR). Other suitable amplification methods include ligase chain reaction (LCR (oligonucleotide ligase amplification (OLA)), transcription amplification, cycling probe technology (CPT), molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), transcription mediated amplification (TMA), degenerate oligonucleotide-primed PCR (DOP-PCR), multiple-displacement amplification (MDA), strand displacement amplification (SDA), and nucleic acid based sequence amplification (NABSA), and any combinations thereof. Other amplification methods that can be used herein include those described in U.S. Pat. Nos. 5,242,794; 5,494,810; 4,988,617; and 6,582,938. In some aspects of any of the methods provided herein that include an amplifying the subset (e.g., diluted) sample step, the step can be performed in solution, e.g., the nucleic acid molecules and polynucleotides are not attached to a solid-phase during the step. In some aspects of any of the methods provided herein that include a step of amplifying the subset (e.g., diluted) sample step, the amplifying can be part of a multiplex method that comprises combining subset samples to form a combined sample before amplifying. In illustrative embodiments, a single subset sample is amplified. In some aspects of any of the methods provided herein that include an amplifying the subset (e.g., diluted) sample step, different subset samples are amplified in parallel and combined at later steps. In some embodiments, different subset samples are combined and amplified together.

Provided herein in one aspect is a method of generating a population of product polynucleotides, wherein the method comprises:

a. diluting a subvolume of a source sample comprising at least $1 \times 10^6$ tagged candidate nucleic acid molecules to form a diluted sample having a target number of the tagged candidate nucleic acid molecules isolated from the source sample, wherein each tagged candidate nucleic acid molecule has a tag comprising a combination of at least two non-degenerate barcodes, and wherein each non-degenerate barcode is selected from a set of between 3 to 200 unique, non-degenerative barcodes, wherein the diluted sample comprises one or more tagged candidate nucleic acid species derived from one or more of the tagged candidate nucleic acid molecules, wherein each nucleic acid molecule of a tagged candidate nucleic acid species has an identical nucleic acid sequence comprising the nucleic acid sequence of the one or more tagged candidate nucleic acid molecules from which it was derived, and wherein at least one of the tagged candidate nucleic acid species in the diluted sample is uniquely tagged;

b. determining the sequence of at least some of the tagged candidate nucleic acid species, wherein at least 1 of the tagged candidate nucleic acid species is a desired uniquely tagged nucleic acid species, wherein the desired uniquely tagged nucleic acid species comprises a sequence-perfect desired nucleic acid sequence; and c. enriching the desired uniquely tagged nucleic acid species by amplifying one or more tagged candidate nucleic acid molecules of the desired uniquely tagged nucleic acid species to generate the population of product polynucleotides, wherein the target number of the tagged candidate nucleic acid molecules isolated from the source sample is between 10 and 400 nucleic acid molecules, and wherein the sequence-perfect desired nucleic acid sequence is 1 kb to 500,000 kb, 1 kb to 100,000 kb, 1 kb to 1,000 kb, 1 kb to 100 kb, or 1 kb to 50 kb in length.

In some embodiments, any method herein is a cell-free method.

In some embodiments, the target number is determined based on the number of unique non-degenerate barcodes in the set of unique, non-degenerate barcodes, or based on the number of unique non-degenerate barcode combinations selected from the set of unique, non-degenerate barcodes.

In some embodiments, determining the sequence is performed using long read sequencing. In some embodiments, at least one step of the method is automated. In some embodiments, the steps are performed in 1, 2 or 3 days or 1-3 days. In some embodiments, the source sample comprises at least $1\times10^7$ tagged candidate nucleic acid molecules. In some embodiments, the ratio of unique non-degenerate barcode combinations in tags to candidate nucleic acid molecules in the source sample is between $1:1\times10^4$ and $1:1\times10'$. In some embodiments, a median error rate of at most 1 in 10,000 is capable of being achieved.

In some embodiments, enriching the desired uniquely tagged nucleic acid species comprises amplifying one or more tagged candidate nucleic acid molecules of the desired uniquely tagged nucleic acid species using nested PCR with primers that bind two or more of the at least two non-degenerate barcodes on one side of the tagged candidate nucleic acid molecules of the desired uniquely tagged nucleic acid species in successive PCR reactions to generate the population of product polynucleotides. In some embodiments, method is capable of achieving a median error rate of at most 1 in 30,000. In some embodiments, the sequence-perfect desired nucleic acid sequence is 2.5 kb to 50 kb in length and wherein at least 90% of the product polynucleotides in the population of product polynucleotides have the sequence-perfect desired nucleic acid sequence. In some embodiments, the source sample comprises at least $1\times10^7$ tagged candidate nucleic acid molecules, and wherein the ratio of unique non-degenerate barcode combinations in tags to candidate nucleic acid molecules in the source sample is between $1:1\times10^5$ and $1:1\times10^7$. In some embodiments, enriching the desired uniquely tagged nucleic acid species further comprising assembling and tagging two or more initial assembly products of between 250 kb and 750 kb to form the tagged candidate nucleic acid molecules in the source sample. In some embodiments, enriching the desired uniquely tagged nucleic acid species further comprises an initial assembly reaction comprising assembling a set of oligonucleotides between 10 and 150 nucleotides in length to yield the two or more initial assembly products. In some embodiments, the enriching is performed using pre-made primers. In some embodiments, there is no diluting or sequence determination performed before assembling and tagging the two or more initial assembly products. In some embodiments, the ratio of unique non-degenerate barcode combinations in tags to candidate nucleic acid molecules in the source sample is between $1:1\times10^4$ and $1:1\times10^7$. In some embodiments, the method is capable of achieving a median error rate of at most 1 in 30,000. In some embodiments, the sequence-perfect desired nucleic acid sequence is 2.5 kb to 10 kb in length.

In another aspect, provided herein is a method of generating a population of polynucleotides comprises
a. diluting a subvolume of a source sample comprising at least $1\times10^6$ tagged candidate nucleic acid molecules, to form a diluted sample having a target number of the tagged candidate nucleic acid molecules isolated from the source sample, wherein each tagged candidate nucleic acid molecule has a tag comprising a combination of at least two non-degenerate barcodes, and wherein each non-degenerate barcode is selected from a set of unique, non-degenerate barcodes, wherein the diluted sample comprises one or more tagged candidate nucleic acid species derived from one or more of the tagged candidate nucleic acid molecules, wherein each nucleic acid molecule of a tagged candidate nucleic acid species has an identical nucleic acid sequence comprising the nucleic acid sequence of the one or more tagged candidate nucleic acid molecules from which it was derived, wherein at least one of the tagged candidate nucleic acid species in the diluted sample is uniquely tagged, and wherein the target number is determined based on the number of unique non-degenerate barcodes or barcode combinations selected from the set of unique non-degenerate barcodes, and wherein the target number is less than the number of unique non-degenerate barcodes in the set of unique, non-degenerate barcodes or the unique barcode combinations selected from the set of unique non-degenerate barcodes;
b. determining the sequence of at least some of the tagged candidate nucleic acid species, wherein at least 1 of the tagged candidate nucleic acid species is a desired uniquely tagged nucleic acid species, wherein the desired uniquely tagged nucleic acid species comprises a sequence-perfect desired nucleic acid sequence; and
c. enriching the desired uniquely tagged nucleic acid species by amplifying one or more tagged candidate nucleic acid molecules of the desired uniquely tagged nucleic acid species using primers that bind two or more of the at least two barcodes on the desired uniquely tagged nucleic acid species, to generate the population of product polynucleotides,
wherein the target number is between 10 and 1,000 nucleic acid molecules, and wherein the sequence-perfect desired nucleic acid sequence is 1 kb to 50 kb in length.

In some embodiments, the determining the sequence is performed using long read sequencing, and the barcodes are non-degenerate barcodes. In some embodiments, at least one step of the method is automated. In some embodiments, the source sample comprises at least $1\times10^7$ tagged candidate nucleic acid molecules. In some embodiments, the source sample comprises a set of between 3 to 200 unique barcodes.

In some embodiments, each tagged candidate nucleic acid molecule has a tag comprising a combination of at least two barcodes on one side of the candidate nucleic acid molecule. In some embodiments, the enriching the desired uniquely tagged nucleic acid species comprises amplifying one or more tagged candidate nucleic acid molecules of the desired uniquely tagged nucleic acid species using nested PCR with primers that bind two or more of the at least two barcodes on one side of the tagged candidate nucleic acid molecules of the desired uniquely tagged nucleic acid species in successive PCR reactions to generate the population of product polynucleotides.

In some embodiments, the method is capable of achieving a median error rate of at most 1 in 30,000.

In some embodiments, the sequence-perfect desired nucleic acid sequence is 2.5 kb to 50 kb in length. In some embodiments, at least 90% of the product polynucleotides in the population of product polynucleotides have the sequence-perfect desired nucleic acid sequence.

In some embodiments, the source sample comprises at least $1\times10^7$ tagged candidate nucleic acid molecules, and wherein the ratio of unique barcode combinations in tags to candidate nucleic acid molecules in the source sample is between $1:1\times10^5$ and $1:1\times10^7$.

In some embodiments, the method further comprises assembling and tagging two or more initial assembly products of between 250 kb and 750 kb to form the tagged candidate nucleic acid molecules in the source sample.

In some embodiments, the method further comprises an initial assembly reaction comprising assembling a set of oligonucleotides between 10 and 150 nucleotides in length to yield the two or more initial assembly products.

In some embodiments, enriching is performed using pre-made primers. In some embodiments, no diluting or determining the sequence is performed before the assembling and tagging the two or more initial assembly products, wherein the ratio of unique barcode combinations in tags to candidate nucleic acid molecules in the source sample is between $1:1\times10^4$ and $1:1\times10^7$. In some embodiments, the method is capable of achieving a median error rate of at most 1 in 30,000, and wherein the sequence-perfect desired nucleic acid sequence is 2.5 kb to 10 kb in length.

In one embodiment, a cell-free method of generating a population of polynucleotides comprises
  a. assembling at least two nucleic acid molecules separately in each of a set of initial sources of nucleic acid molecules to produce a set of source samples each comprising at least $1\times10^6$ tagged candidate nucleic acid molecules,
  b. diluting a subvolume of each source sample in the set of source samples to form a set of diluted samples each having a target number of tagged candidate nucleic acid molecules isolated from each source sample in the set of source samples, wherein each tagged candidate nucleic acid molecule has a tag comprising one or more barcodes selected from a set of between 3 to 200 unique barcodes.
  c. combining a portion of each diluted sample in the set of diluted samples to form a combined diluted sample, wherein the combined diluted sample comprises tagged candidate nucleic acid species derived from one or more of the tagged candidate nucleic acid molecules from each diluted sample of the set of diluted samples, wherein each nucleic acid molecule of a tagged candidate nucleic acid species has an identical nucleic acid sequence comprising the nucleic acid sequence of the one or more tagged candidate nucleic acid molecules from which it was derived, and wherein at least one of the tagged candidate nucleic acid species from each diluted sample in the combined diluted sample is uniquely tagged;
  d. determining the sequence of at least some of the tagged candidate nucleic acid species from each of the diluted samples in the combined diluted sample using long-read sequencing, wherein at least 1 of the tagged candidate nucleic acid species from each diluted sample in the combined diluted sample is a desired uniquely tagged nucleic acid species, wherein the desired uniquely tagged nucleic acid species comprise a sequence-perfect desired nucleic acid sequence;
  e. enriching the desired uniquely tagged nucleic acid species from each diluted sample of the set of diluted samples by amplifying in each diluted sample of the set one or more tagged candidate nucleic acid molecules of the desired uniquely tagged nucleic acid species using one or more primers that bind one or more barcodes in the tagged candidate nucleic acid molecules of the desired uniquely tagged nucleic acid species to generate a set of populations of product polynucleotides, and
  f. assembling the set of populations of polynucleotides to form a population of subsequent product polynucleotides, wherein the sequence-perfect desired nucleic acid sequence of each desired nucleic acid is between 50 kb and 1 Mb in length.

In some embodiments, the assembling the set of population of polynucleotides is performed using circular DNA assembly.

In some embodiments, the steps are performed in 3 to 6 days.

In some embodiments, each tagged candidate nucleic acid molecule has a tag comprising a combination of at least two barcodes on one side of the candidate nucleic acid molecule. In some embodiments, enriching the desired uniquely tagged nucleic acid species comprises amplifying one or more tagged candidate nucleic acid molecules of the desired uniquely tagged nucleic acid species using nested PCR with primers that bind two or more of the at least two barcodes on one side of the tagged candidate nucleic acid molecules of the desired uniquely tagged nucleic acid species in successive PCR reactions to generate the population of product polynucleotides.

In some embodiments, the method is capable of achieving a median error rate of at most 1 in 30,000.

In some embodiments, assembling at least two nucleic acid molecules comprising assembling and tagging two or more initial assembly products of between 250 kb and 750 kb to form the tagged candidate nucleic acid molecules in the source sample.

In some embodiments, the method further comprises an initial assembly reaction comprising assembling a set of oligonucleotides between 10 and 150 nucleotides in length to yield the two or more initial assembly products.

In some embodiments, the enriching is performed using pre-made primers. In some embodiments, wherein no diluting or determining the sequence is performed before the assembling and tagging the two or more initial assembly products, wherein the ratio of unique barcode combinations in tags to candidate nucleic acid molecules in each source sample of the set of source samples is between $1:1\times10^4$ and $1:1\times10^7$. In some embodiments, the method is capable of achieving a median error rate of at most 1 in 30,000.

In some embodiments, the source sample comprises a set of tags having between 64 to and 10,000 of the unique combinations of at least two non-degenerate barcodes.

In some embodiments of any method herein, the method is a multiplex method performed by combining a portion of each of at least 2, 3, 4, 5, 10, 15, or 20 or more different diluted samples to form a combined sample. In some embodiments, the multiplex method comprises determining the sequences in the same sequencing run, of at least some, most, almost all, or all, or 10%, 20%, 25%, 50%, 75%, 80%, 90%, 95%, 96%, 97%, 98%, 99%, 99.9% or 100% of the tagged nucleic acid species in the combined sample. In some embodiments, the tagged nucleic acid species are from, or derived from nucleic acid molecules from each of the at least 2, 3, 4, 5, 10, 15, or 20 or more different diluted samples. In some embodiments, the enriching comprises enriching at least population of polynucleotides from each of the at least 2, 3, 4, 5, 10, 16, or 20 different diluted samples.

In some embodiments, the method further includes detecting one or more desired nucleic acid sequences. In some embodiments, the method of the prior aspect or embodiment further includes selecting 1 or more, 2 or more, 5 or more, 10 or more, 20 or more, 50 or more, 100 or more, 250 or more, 500 or more, 750 or more, 1000 or more, 2000 or more, 3000 or more, 4000 or more, 5000 or more, 10,000 or more polynucleotides for analysis. In some embodiments, the method includes detecting at least one molecular barcode. In further embodiments, the detecting includes detecting the sequence of at least one molecular barcode. In some embodiments, the polynucleotide sequence is determined by nucleic acid sequencing. In some embodiments, the nucleic acid sequencing includes determining the sequence of at least one polynucleotide. Any nucleic acid sequencing technology known in the art can be used in methods herein to perform such sequencing. In some embodiments, the nucleic acid sequencing comprises sequencing more than one nucleic acid molecule in parallel, and in illustrative embodiments is next-generation/massively parallel sequencing (e.g., Illumina, San Diego, CA; Ion Torrent-Thermo Fisher, Carlsbad, CA), including for example paired-end sequencing. In illustrative embodiments, the nucleic acid sequencing is long-read nucleic acid sequencing. In some embodiments, the long-read nucleic acid sequencing can be performed, for example, using single-molecule real-time (SMRT) sequencing (e.g., PacBio, Menlo Park, CA) or the sequencing comprises nanopore-based sequencing (e.g., Oxford Nanopore Technologies, Oxford, UK). In other embodiments, virtual long reads are constructed using methods known to those skilled in the art. In some embodiments, the long-read nucleic acid sequencing can be performed using virtual long-read sequencing.

In some embodiments, the sequence is determined for less than $1 \times 10^6$ tagged nucleic acid molecules or species, for example between 2 and 10,000,000 tagged nucleic acid molecules or species, for example between 2 and 5,000,000, 5, and 1,000,000, 10 and 100,000, 10 and 1,000, 10 and 100, or 100 and 100,000 tagged nucleic acid molecules or species. In some embodiments, the determining the sequence is performed to a depth of read to achieve at least a 95%, 96%, 97% 98%, 99%, 99.5%, or 99.9% confidence that a sequence of the enriched polynucleotide is sequence-perfect with respect to the desired nucleic acid sequence. In some aspects, the number of sequencing reads generated on the sequencer can be at least 5, 10, 25, 50, 100, 250, 500, 1,000, 5,000, 10,000, 50,000, 100,000, 500,000, or 1,000,000 times the number of unique target nucleic acid molecules or species in the subset sample. In some aspects, the average depth of read per base (the number of times a particular nucleotide base of a particular species is sequenced) for some, most, or all of the bases can be at least 5, 10, 15, 20, 25, 30, 35, 40, 45, 50, 60, 70, 80, 90, 100, 200, 250, 500, or 1,000, 5,000, 10,000, 50,000, 100,000, 500,000, or 1,000,000 for at least 50%, 60%, 70%, 80%, 90%, 95%, 96%, 97%, 98%, 99%, 99.5%, 99.9% or all of the nucleic acid species in the subset sample. In some aspects, the average depth of read for the sequencer can be at least 5, 10, 15, 20, 25, 30, 35, 40, 45, 50, 60, 70, 80, 90, 100, 250, 500, or 1,000. In some embodiments, each polynucleotide in the subset sample is sequenced. In some aspects of any of the methods provided herein that include a step of sequencing tagged nucleic acid molecules or species, the sequencing can be part of a multiplex method that comprises combining subset samples before sequencing. In some embodiments, at least 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 subset samples are combined before sequencing. In some embodiments, between 2, 3, 4, 5, 6, 7, 8, 9, 10, 15, 20, 25, 30, 35, 40, 45, 50, 60, 70, 80, or 90 subset samples on the low end of the range and 100 subset samples on the high end of the range are combined before sequencing. In some embodiments, between 2, 3, 4, 5, 6, 7, 8, 9, 10, 15, 20, 25, 30, 35, 40, 45, 50, 60, 70, 80, 90, 100, 200, 300, 400, 500, 600, 700, 800, or 900 subset samples on the low end of the range and 1,000 subset samples on the high end of the range are combined before sequencing. In some embodiments, between 2 subset samples and 3, 4, 5, 6, 7, 8, 9, 10, 15, 20, 25, 30, 35, 40, 45, 50, 60, 70, 80, 90, 100, 200, 300, 400, 500, 600, 700, 800, 900, or 1,000 subset samples are combined before sequencing. In some embodiments, sample barcodes are added to the different subset samples before they are combined. In illustrative embodiments, no sample barcodes are used. In such embodiments with no sample barcodes, the different polynucleotides from the different subset samples can be distinguished based on the desired sequences in the sequencing reads. In some embodiments, the subset samples contain different barcodes on the nucleic acid molecules or species. In some embodiments, one or more of the subset samples contain at one identical barcode on the nucleic acid molecules or species.

In some embodiments, the enriching includes adding at least one primer complementary to at least one oligonucleotide. In some embodiments, one or more primers can be used that include enrichment tags. In some embodiments, the enrichment tag can be biotin. A skilled artisan will understand how to use enrichment tags to further purify amplified polynucleotides. In some embodiments, the enriching includes adding at least one primer complementary to a portion of at least one polynucleotide. In some embodiments, the enriching includes adding at least one primer complementary to a portion of at least one nucleic acid molecule of the source sample. In some embodiments, the enriching includes adding at least one primer complementary to a portion of at least one nucleic acid molecule of the subset sample. In some embodiments, the enriching includes adding at least two different primers. In illustrative embodiments, the enriching includes adding primers complementary to at least a portion of one or more molecular barcodes. In further embodiments, the primers are complementary to more than one molecular barcode. In some embodiments, the enriching is performed using barcode-targeted amplification. In illustrative embodiments, the enriching is performed using nested, barcode-targeted amplification, wherein the nesting is performed using at least two primers that bind to different primer binding sites on the one or more barcodes on the desired tagged nucleic acid molecule. In some embodiments, the nested amplification is one-sided nested amplification. In some embodiments, a method of producing a subsequent polynucleotide, for example as provided below, includes linking one or more enriched polynucleotides. In some aspects of any of the methods provided herein that include an enriching step, different tagged nucleic acid molecules or species can be enriched from the same subset sample. In some embodiments, the enriching the polynucleotide having the desired nucleic acid sequence includes generating the polynucleotide having the desired nucleic acid sequence by removing the tag from the desired tagged nucleic acid molecule. In some aspects of any of the methods provided herein that include an enriching step, the step can be performed in solution, e.g., the nucleic acid molecules and polynucleotides are not attached to a solid-phase during the step. In some aspects of any of the methods provided herein that include an enriching step, target nucleic acid molecules can be enriched from a subset sample based on sequencing results from a combined sample that comprises two or more subset samples. In some embodiments, at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1,000 target nucleic acid molecules or species and/or polynucleotides can be enriched from the individual subset samples and/or the combined sample. In some embodiments, the individual subset samples and/or the combined sample contain nucleic acid molecules or species polynucleotides with sequence-perfect desired sequences corresponding to each of the desired sequences. In some embodiments, at least one nucleic acid molecule or species and/or polynucleotide having one of the desired sequences, and in illustrative embodiments one of the sequence-perfect desired sequences, from the set of desired sequences can be identified that also has a barcode that is unique within the individual subset samples and/or the combined sample. In illustrative embodiments, at least one nucleic acid molecule or species and/or polynucleotide can be identified for each of the desired sequences that has the desired sequence, and in illustrative embodiments the sequence-perfect desired sequence, and has a barcode that is unique within the individual subset samples and/or the combined sample. In such embodiments, a skilled artisan will understand how to use the identified unique barcodes to enrich each target nucleic acid molecule or polynucleotide using the methods disclosed above.

In some embodiments, the method is performed at least 2, 3, 4, 5, 6, 7, 8, 9, or 10 times to enrich 2, 3, 4, 5, 6, 7, 8, 9, 10, 15, 20, 25, 30, 40, 50, 60, 70, 80, 90, or 100 different polynucleotides having 2, 3, 4, 5, 6, 7, 8, 9, 10, 15, 20, 25, 30, 40, 50, 60, 70, 80, 90, or 100 different desired, in some embodiments sequence-perfect desired, nucleic acid sequences, or to enrich at least 2, 3, 4, 5, 6, 7, 8, 9, 10, 15, 20, 25, 30, 40, 50, 60, 70, 80, 90, or 100 different populations of polynucleotides having 2, 3, 4, 5, 6, 7, 8, 9, 10, 15, 20, 25, 30, 40, 50, 60, 70, 80, 90, or 100 different desired, in some embodiments sequence-perfect, desired, nucleic acid sequences. In some embodiments, at least 25%, 30%, 40%, 50%, 60%, 70%, 75%, 80%, 85%, 90%, 95%, 96%, 97%, 98%, 99%, 99.5%, 99.9% or 100% of the polynucleotides in each population comprises a respective desired nucleic acid sequence. In some embodiments, the respective desired nucleic acid sequence is at least 25%, 30%, 40%, 50%, 60%, 70%, 75%, 80%, 85%, 90%, 95%, 96%, 97%, 98%, 99%, 99.5%, or 99.9% identical to each respective sequence-perfect desired nucleic acid sequence. In some embodiments, at least 90%, 95%, 96%, 97%, 98%, 99%, 99.5%, or 99.9% of the polynucleotides in each of the populations are sequence-perfect desired polynucleotides.

In any of the aspects or embodiments provided herein, at least 2 different desired polynucleotides enriched using the methods provided herein are assembled into a subsequent polynucleotide having the nucleotide sequences of the at least 2 different polynucleotides. In some embodiments, the 2, 3, 4, 5, 6, 7, 8, 9, 10, 15, 20, 25, 30, 40, 50, 60, 70, 80, 90, or 100 populations including desired polynucleotides are assembled into a subsequent polynucleotide having the consecutive nucleotide sequences of the 2, 3, 4, 5, 6, 7, 8, 9, 10, 15, 20, 25, 30, 40, 50, 60, 70, 80, 90, or 100 different desired polynucleotides.

In some embodiments, the subsequent polynucleotide includes at least one synthetic gene segment, at least one synthetic gene, at least one vector, at least one expression vector, at least one gene cluster, at least one expression cassette, and/or at least one non-coding segment. In some embodiments, the subsequent polynucleotide comprises a promoter and/or an origin of replication. In some embodiments, the vector can be a sequence capable of entering a cell and causing at least a portion of the sequence to be replicated. In some embodiments, the expression vector can be a sequence capable of entering a cell and causing at least a portion of the sequence to be expressed, e.g., transcribed into RNA or translated into a polypeptide, and typically includes a promoter. In some embodiments, the gene cluster can include 2 or more genes, for example 3, 4, 5, 6, 7, 8, 9, or 10 or more genes. In illustrative embodiments, the gene cluster can encode similar polypeptides, which in further illustrative embodiments, share a generalized function. In some embodiments, the expression cassette comprises one or more genes and one or more regulatory sequences, which typically includes a promoter. In some embodiments, the non-coding segment can comprise functional non-coding RNA molecules (e.g., transfer RNA, ribosomal RNA, and/or regulatory RNAs), sequences that control transcriptional and translational regulation of protein-coding sequences, scaffold attachment regions, origins of replication, centromeres, and/or telomeres. In some embodiments, the subsequent polynucleotide includes two or more synthetic genes or segments thereof. In some embodiments, the subsequent polynucleotide is between 10 kb and 1 Mb in length. In some embodiments, assembly of the subsequent polynucleotide is performed using polymerase cycling assembly (PCA), isothermal assembly, ligase cycling reaction (LCR), overlap extension PCR, PCR incorporating 5' sequences, PCR stitching, bacterial recombination, yeast homologous recombination, or circular DNA assembly. In illustrative embodiments, the subsequent polynucleotide is produced without cells. In some illustrative embodiments, the subsequent polynucleotide having the desired nucleic acid sequence is between 10 kb and 1 Mb in length, the determining the sequence is performed using long-read sequencing, the method is performed in between 8 hours and 6 days, and/or the nucleic acid molecules do not enter a cell during the method. In further illustrative embodiments of such a method, the method is performed in less than 7, 6, 5, 4, 3, 2, or 1 day, or between 8 hours and 4, 3, 2 or 1 days, or between the 12 hours and 4, 3, 2, or 1 day, or between 1 and 3 or 2 days.

In certain illustrative embodiments, a method provided herein is not a diagnostic method that involves preparing a population of diluted samples and counting the number of diluted samples that include or do not include one or more target nucleic acids.

In another aspect, provided herein is a method of polynucleotide production, the method including the following:
  a. providing a source sample of nucleic acid molecules;
  b. adding adapters and molecular barcodes to the nucleic acid molecules source sample;
  c. tagging at least one nucleic acid molecule with at least one adapter and/or at least one molecular barcode to yield a tagged source sample including at least one tagged nucleic acid molecule; and
  d. subsetting the source sample to yield a subset sample including at least one tagged nucleic acid molecule, which subset sample includes between about 1 to about 100,000 nucleic acid molecules.

In another aspect, provided herein is a method of polynucleotide production, the method including the following:
  a. providing a source sample of nucleic acid molecules;
  b. subsetting the source sample to yield a subset sample which includes between about 1 to about 100,000 nucleic acid molecules;
  c. adding adapters and molecular barcodes to the nucleic acid molecules of the subset sample; and
  d. tagging at least one nucleic acid molecule of the subset sample with at least one adapter and/or at least one molecular barcode to yield at least one tagged nucleic acid molecule.

In another aspect, provided herein is a method of polynucleotide production, the method including the following:
  a. providing a source sample of nucleic acid molecules;
  b. adding adapters and molecular barcodes to the nucleic acid molecules source sample;

c. tagging at least one nucleic acid molecule with at least one adapter and/or at least one molecular barcode to yield a tagged source sample including at least one tagged nucleic acid molecule;
d. subsetting the source sample to yield a subset sample including at least one tagged nucleic acid molecule, which subset sample includes between about 1 to about 100,000 nucleic acid molecules; and
e. determining the sequence of one or more polynucleotides.

In another aspect, provided herein is a method of polynucleotide production, the method including the following:
a. providing a source sample of nucleic acid molecules;
b. subsetting the source sample to yield a subset sample which includes between about 1 to about 100,000 nucleic acid molecules;
c. adding adapters and molecular barcodes to the nucleic acid molecules of the subset sample;
d. tagging at least one nucleic acid molecule of the subset sample with at least one adapter and/or at least one molecular barcode to yield at least one tagged nucleic acid molecule; and
e. determining the sequence of one or more polynucleotides.

In another aspect, provided herein is a method of polynucleotide production, the method including the following:
a. providing a source sample of nucleic acid molecules;
b. adding adapters and molecular barcodes to the nucleic acid molecules source sample;
c. tagging at least one nucleic acid molecule with at least one adapter and/or at least one molecular barcode to yield a tagged source sample including at least one tagged nucleic acid molecule;
d. subsetting the source sample to yield a subset sample including at least one tagged nucleic acid molecule, which subset sample includes between about 1 to about 100,000 nucleic acid molecules;
e. determining the sequence of one or more polynucleotides; and
f. performing one or more barcode-targeted polymerase chain reactions.

In another aspect, provided herein is a method of polynucleotide production, the method including the following:
a. providing a source sample of nucleic acid molecules;
b. subsetting the source sample to yield a subset sample which includes between about 1 to about 100,000 nucleic acid molecules;
c. adding adapters and molecular barcodes to the nucleic acid molecules of the subset sample;
d. tagging at least one nucleic acid molecule of the subset sample with at least one adapter and/or at least one molecular barcode to yield at least one tagged nucleic acid molecule;
e. determining the sequence of one or more polynucleotides; and
f. performing one or more barcode-targeted polymerase chain reactions.

In some embodiments, a nucleic acid sequence of a polynucleotide in any of the methods, kits, or compositions herein, can be a historically difficult to generate sequence. In some embodiments, a traditionally difficult to generate sequence comprises:
i) a low GC content;
ii) a high GC content;
iii) a homopolymeric run of As or Ts;
iv) a homopolymeric run of Gs or Cs;
v) a repeat sequence;
vi) low sequence complexity; and/or
vii) secondary structure.

In some embodiments a desired difficult to generate sequence comprises one or more of:
i) a GC content 25% or less for a stretch of at least 25, 30, 35, 40, 45, 50, 75, 100, 150, 200, 300, 400, 500, 600, 700, 800, 900, or 1,000 nucleotides of, or for an entire desired nucleic acid sequence;
ii) a GC content of 75% or more for a stretch of at least 25, 30, 35, 40, 45, 50, 75, 100, 150, 200, 300, 400, 500, 600, 700, 800, 900, or 1,000 nucleotides of, or for an entire desired nucleic acid sequence;
iii) a homopolymeric run of 10 or more As or Ts;
iv) a homopolymeric run of 6 or more Gs or Cs;
v) a repeat sequence of at least 6 nucleotides that is repeated 5 times;
vi) a repeat sequence of at least 8 nucleotides that is repeated at least 2 times;
vii) a repeat sequence comprising a tandem repeat sequence;
viii) an inverted repeat sequence of at least 6 nucleotides;
ix) low sequence complexity; or
x) a sequence with a polynucleotide secondary structure comprising at least 25, 30, 35, 40, 45, 50, 75, 100, 150, 200, 300, 400, 500, 600, 700, 800, 900, or 1,000 nucleotides.

Any aspects or embodiments provided herein, including the above aspects and embodiments, can be combined with one or more of any of the other aspects or embodiments provided herein, which a skilled artisan will understand.

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1: Polynucleotide Production

In the present example, populations of polynucleotides having the desired nucleic acid sequences were produced using molecular barcodes and a dilution step as follows.

Figure 5:
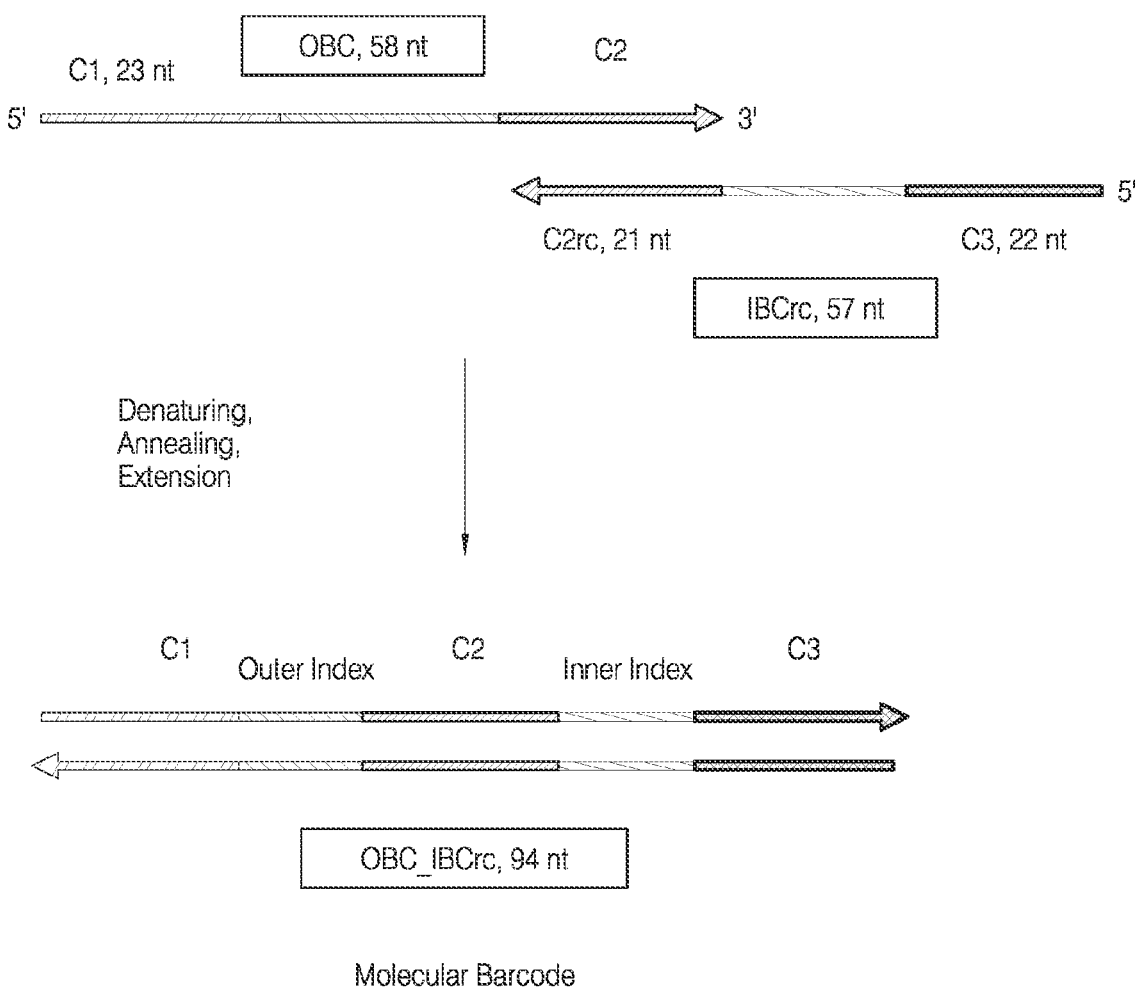
FIG. 5 presents a schematic of barcode assembly in accordance with Example 1. OBC=outer barcode; IBC=inner barcode; nt=nucleotides; C1=connector (linker) 1; C2=connector (linker) 2; C3=connector (linker) 3; and rc=reverse compliment.

FIG. 5 presents a schematic representation of the molecular barcode assembly process used in the present example. Molecular barcodes were assembled from pre-synthesized oligonucleotides. In particular, 22 non-degenerate outer barcodes (OBCs), 20 non-degenerate inner barcodes (IBCs), and their respective complementary ("rc") strands, were synthesized by a commercial supplier and then purified using HPLC-based purification. The concentrations of the OBCs and IBCs were then normalized to 50 uM, and assembly reactions of OBCs and IBCs were prepared by pooling together the OBCs and IBCs to be assembled in IDTE buffer (pH 8.0) and adjusting the pooled OBC/IBC mixture to a final concentration of 1 uM.

The 22 OBCs and 20 IBCs were then assembled into 440 unique molecular barcode combinations (with a minimum Hamming distance of 5 between any 2 OBC or any 2 IBC barcodes) by annealing and extension reactions using the following reaction conditions:

TABLE 1

| Barcode Assembly Reaction Components | Reaction 1, μl | Reaction 2, μl |
|---|---|---|
| Nuclease free H20 | 10.5 | 7.5 |
| 2x KAPA HiFi HotStart ReadyMix | 12.5 | 12.5 |
| 22 OBC pool, 1 uM | 1 | 2.5 |
| 20 IBC rc pool, 1 uM | 1 | 2.5 |
| Total vol. | 25 | 25 |
| Final conc. OBC/IBC rc | 40 fmol/ul | 100 fmol/ul |

TABLE 2

| Step | Temperature | Duration | Ramp |
|---|---|---|---|
| Denaturation | 95° C. | 5 min | ramp 0.1 C/s |
| Annealing | 60° C. | 10 min | ramp 0.1 C/s |
| Extension | 72° C. | 10 min | |
| Hold | 4° C. | Forever | |

Following the molecular barcode combination assembly reaction, 100-500 fmol of unpurified product were loaded onto a 4% agarose gel for analysis. The expected size of the assembled molecular barcode combinations was 94 bp. The gel was loaded as described in Table 3 below:

TABLE 3

| Gel Lane | Input |
|---|---|
| 5 | 100 fmol Reaction 1 |
| 6 | 200 fmol Reaction 1 |
| 7 | 100 fmol Reaction 2 |
| 8 | 250 fmol Reaction 2 |
| 9 | 500 fmol Reaction 2 |
| 10 | 50 bp Ladder |

Figure 6:
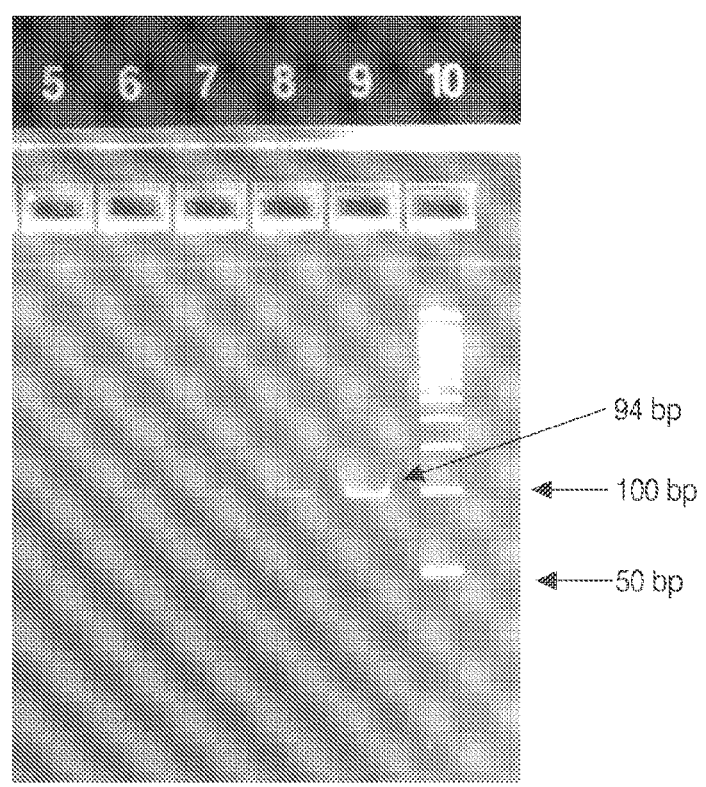
FIG. 6 presents an image of a 4% agarose gel of various different assembled molecular barcodes in accordance with Example 1. Lane 5=100 fmol molecular barcode, 40 nM stock concentration; Lane 6=200 fmol molecular barcode, 40 nM stock concentration; Lane 7=100 fmol molecular barcode, 100 nM stock concentration; Lane 8=250 fmol molecular barcode, 100 nM stock concentration; Lane 9=500 fmol molecular barcode, 100 nM stock concentration; and Lane 10=50 bp ladder.

Referring now to FIG. 6, the expected 94 bp band of the assembled molecular barcode combinations was observed in two reactions of each 40 nM and 100 nM barcode concentrations in lanes 6-9.

Figure 7:
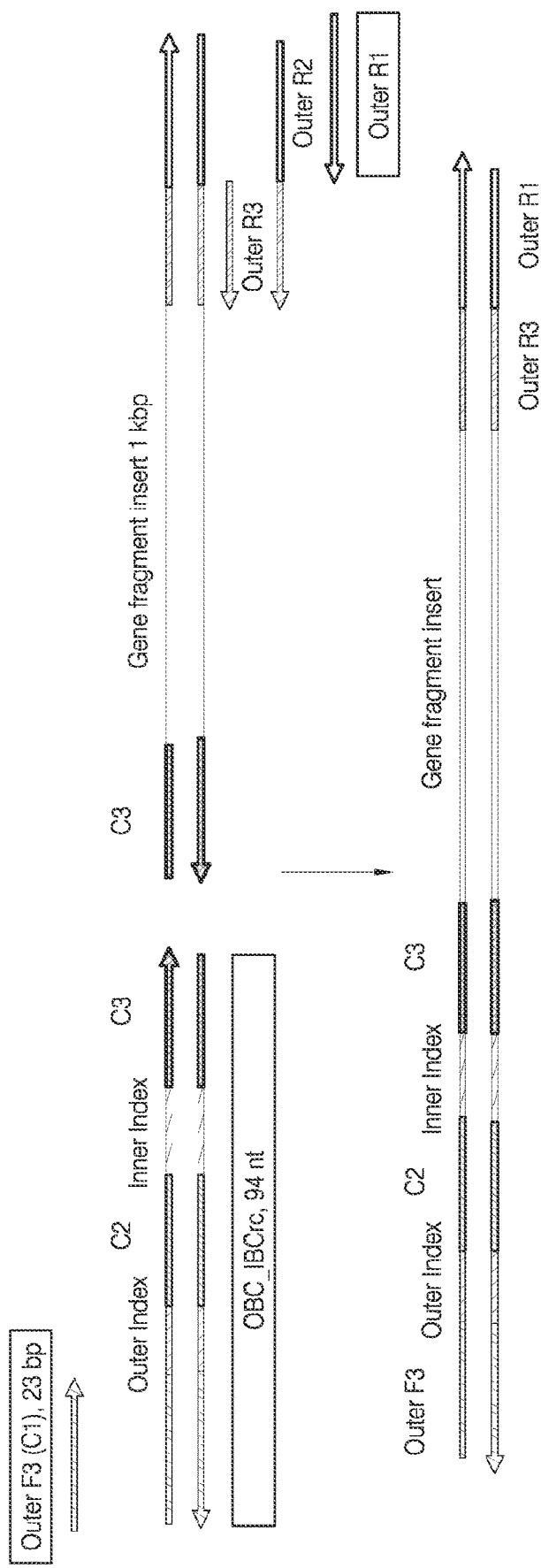
FIG. 7 presents a schematic representation of tagging a gene fragment with molecular barcodes in accordance with Example 1. nt=nucleotides; C1=connector (linker) 1; C2=connector (linker) 2; C3=connector (linker) 3; rc=reverse compliment; Outer Index=outer barcode; Inner Index=inner barcode; OBC=outer barcode; IBC=inner barcode; Outer R1=outer reverse primer site 1; and Outer R3=outer reverse primer site 3.

Following gel-based analysis, the molecular barcode combinations were diluted from 40 fmol/ul to 1 fmol/ul. The molecular barcode combinations (OBC/IBC rc) were then used in a barcoding sample to tag an assembled 774 bp gene fragment (A6) and 1069 bp gene fragment (GF2B), which were synthesized by a commercial provider, to generate tagged nucleic acid molecules. The tagging was performed using a PCA (polymerase chain assembly) reaction for each clonal gene fragment, a schematic of which is presented in FIG. 7. Briefly, equal fmol (1 fmol) of the preassembled molecular barcode combinations, the outer R1 primer, and the gene fragment were mixed with KAPA HiFi HotStart ReadyMix in the barcoding sample as presented in Table 4:

TABLE 4

| PCA Reaction Component | Stock conc. | ul/rxn |
|---|---|---|
| Nuclease free H2O | | 4.5 |
| 2x KAPA HiFi HotStart ReadyMix | | 12.5 |
| OBCs/IBCrc barcodes | 1 nM | 1 |
| Outer R1 primer | 1 nM | 1 |
| Gene fragments (A6 or GF2B) | 1 nM | 1 |
| After 5 cycles, add outer primers | | |
| Outer F3, 10 uM | | 2.5 |
| Outer R1, 10 uM | | 2.5 |
| Total vol. | | 25 |

TABLE 5

| First 5-8 cycles | | |
|---|---|---|
| Step 1 | 95° C. | 3 min |
| Step 2 | 98° C. | 20 s |
| Step 3 | 60° C. | 20 s |
| Step 4 | 72° C. | 30 s |
| Repeat step 2-4 for 5-8 cycles | | |
| Final extension | 72° C. | 1 min |
| Add outer primers | | |
| Step 1 | 95° C. | 1 min |
| Step 2 | 98° C. | 20 s |
| Step 3 | 60° C. | 20 s |
| Step 4 | 72° C. | 30 s |
| Repeat step 2-4 for 25 cycles | | |
| Final extension | 72° C. | 1 min |

Figure 8:
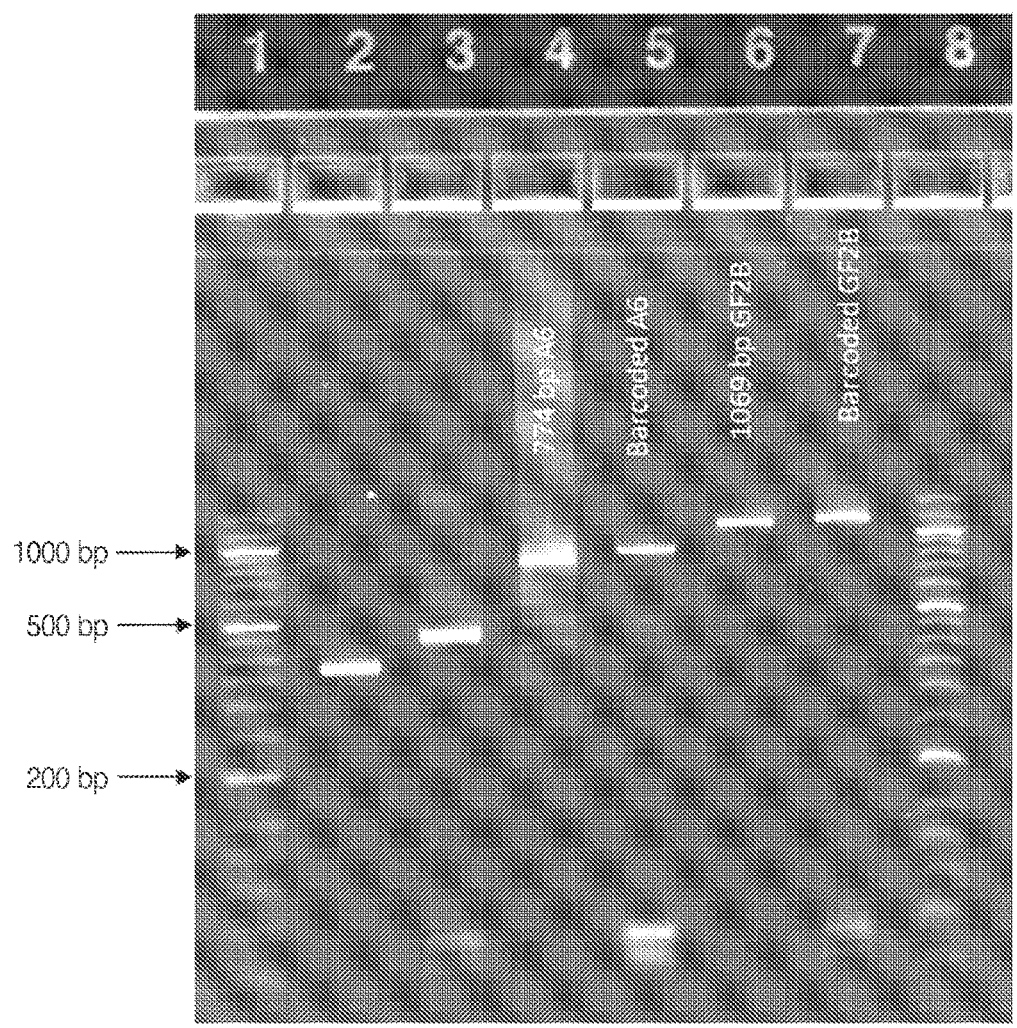
FIG. 8 presents an image of a 2% agarose gel of tagged gene fragments in accordance with Example 1. Lane 1=50 bp E gel ladder; Lane 2=470 bp size control; Lane 3=25 PCR cycles; 1 fmol of each barcode, outer R1, and eblock gene fragment; Lane 4=25 PCR cycles; 5 fmol of each barcode, outer R1, and eblock gene fragment; Lane 5=25 PCR cycles; 10 fmol of each barcode, outer R1, and eblock gene fragment; Lane 6=35 PCR cycles; 1 fmol of each barcode, outer R1, and eblock gene fragment; Lane 7=35 PCR cycles; 5 fmol of each barcode, outer R1, and eblock gene fragment; Lane 8=35 PCR cycles; 10 fmol of each barcode, outer R1, and eblock gene fragment; Lane 9=470 bp size control; Lane 10=369 bp size control; and Lane 11=sizing ladder.

Thus, 440 unique barcode combinations were used to tag approximately $6 \times 10^8$ nucleic acid molecules in the barcoding sample. As indicated in Table 5, following 5 cycles, 25 pmol of the outer primers F3 and R1 were added, and amplification was performed for an additional 25 cycles to produce a source sample comprising the amplification products (i.e., tagged nucleic acid molecules). After amplification, 2 ul of the unpurified amplification products were loaded onto a 2% E-Gel EX agarose gel (Thermo Fisher Scientific) to visualize the amplified product size (FIG. 8). The gel lanes were loaded as described in Table 6.

TABLE 6

| Gel Lane | Input |
|---|---|
| 1 | E gel sizing ladder |
| 4 | 774 bp gene fragment A6 |
| 5 | Tagged A6 gene fragment, expected length is 870 bp |
| 6 | 1069 bp gene fragment GF2B |
| 7 | Tagged GF2B gene fragment, expected length is 1141 bp |

Referring now to FIG. 8, bands of ~870 bp and ~1141 bp were observed in lanes 5 and 7, respectively, which corresponded to the expected full length amplification products.

After amplification, a quantitation step was performed to measure the concentration of nucleic acid molecules in the unpurified amplification product. The product was diluted 10-fold to increase quantitation accuracy. The amount of nucleic acid molecules in the diluted sample was measured using a Qubit dsDNA HS assay in triplicates.

Next, the unpurified amplification products containing the tagged nucleic acid molecules of A6 or GF2B were each further diluted by a factor of $10^8$-$10^9$ to provide three diluted samples containing approximately 10, 50 or 100 tagged nucleic acid molecules, which included various tagged nucleic acid species, giving a ratio of molecular barcode combinations to source nucleic acid molecules of 1:44, 1:8.8, and 1:4.4, respectively. The diluted samples were subsequently amplified by PCR with Outer F3 and Outer R1 primer using the following conditions:

TABLE 7

| PCR Reaction Component | μl/reaction |
|---|---|
| Nuclease free H2O | 10 |
| 2xKAPA HiFi HotStart ReadyMix | 12.5 |
| Outer F3, 10 uM | 0.75 |
| Outer R1, 10 uM | 0.75 |
| Template: (10/50/100 molecules dilution pool) | 1 |
| Total vol. | 25 |

TABLE 8

| Cycling profile | | |
|---|---|---|
| Step 1 | 95° C. | 3 min |
| Step 2 | 98° C. | 20 s |
| Step 3 | 65° C. | 20 s |
| Step 4 | 70° C. | 30 s |
| Repeat step 2-4 | 30 cycles | |
| Final extension | 72° C. | 1 min |
| Hold | 4° C. | Forever |

The amplification products of the diluted samples were purified by using AMPure beads with 0.6× bead to sample ratio. The yield and concentration were quantified using a Qubit dsDNA HS assay.

Figure 9:
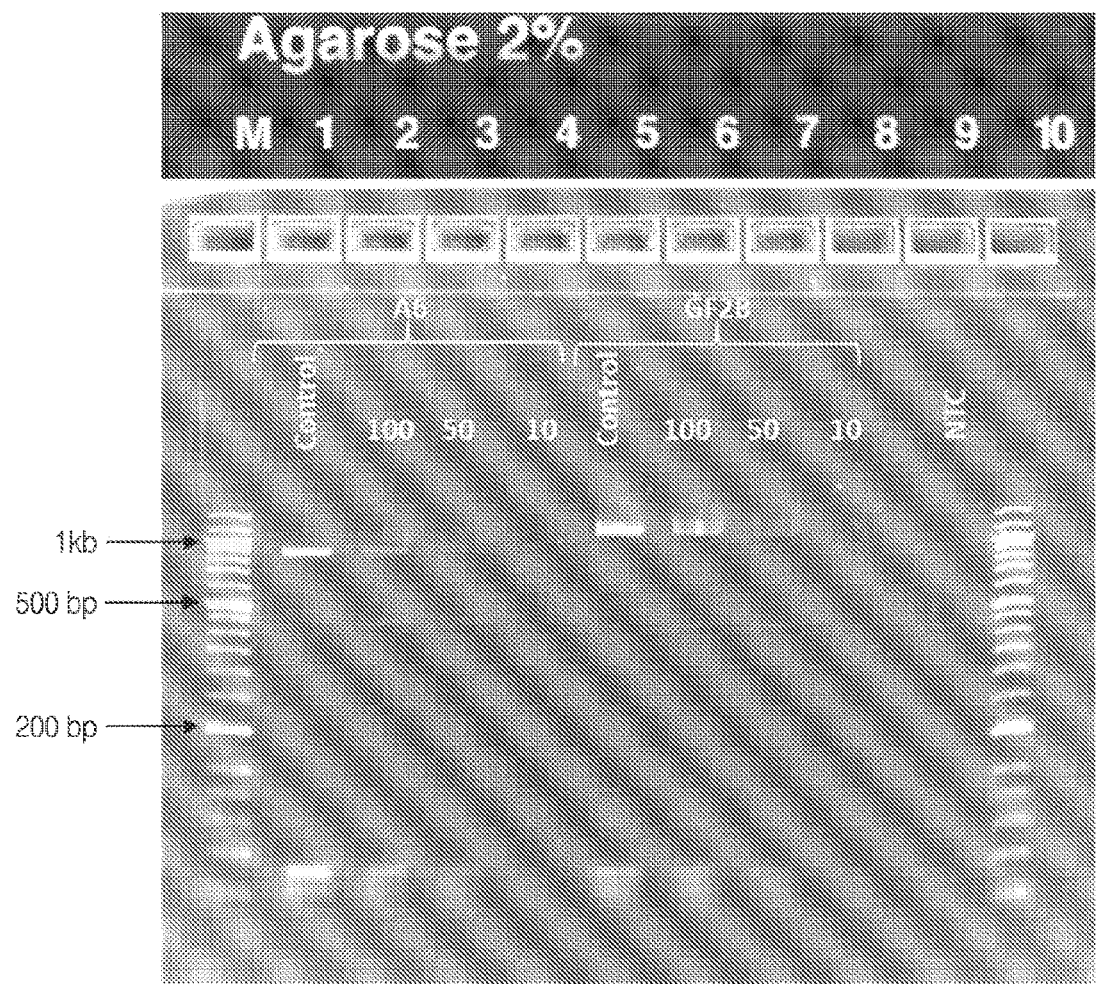
FIG. 9 presents an image of a 2% agarose gel of amplification products of 400 and 4000 molecule molecular barcode-tagged gene fragment pools, which amplification products were produced by dilutions followed by PCR in accordance with Example 1. Lane 1=Blank; Lane 2=Blank; Lane 3=Ladder; Lane 4=369 bp control; Lane 5=470 bp control; Lane 6=400 molecule dilution amplification product; Lane 7=4000 molecule dilution amplification product; and Lane 8=Ladder.

The amplification products were loaded onto a 2% E-Gel EX agarose gel (Thermo Fisher Scientific) to visualize the amplified product size (FIG. 9). The gel lanes were loaded as described in Table 9.

TABLE 9

| Gel Lane | Input |
|---|---|
| 1 | A6 control, 870 bp |
| 2 | 100 molecule dilution amplification product for A6 |
| 3 | 50 molecule dilution amplification product for A6 |
| 4 | 10 molecule dilution amplification product for A6 |
| 5 | GF2B control, 1141 bp |
| 6 | 100 molecule dilution amplification product for GF2B |
| 7 | 50 molecule dilution amplification product for GF2B |
| 8 | 10 molecule dilution amplification product for GF2B |
| 9 | Non template control |

Referring now to FIG. 9, the expected 870 bp and 1141 bp fragments were observed for both the 50 molecule dilution amplification products (Lanes 3 and 7 in FIG. 9) and the 100 molecule dilution amplification product (Lanes 2 and 6 in FIG. 9).

The 50 molecule dilution amplification products for each gene fragment were then used for nanopore-based nucleic acid sequencing. In particular, a combined sample containing amplified tagged nucleic acid molecules from A6 and GF2B was sequenced using the Oxford Nanopore sequencer as follows. 100 fmol of the 50 molecule dilution amplification products of the A6 (50 fmol) and GF2B (50 fmol), which contained approximately 1 fmol ($6 \times 10^8$ molecules) of each of the approximately 100 tagged nucleic acid species (50 A6 species and 50 GF2B species) (a large enough number to ensure sufficient depth of read to construct consensus sequences with no or minimal errors for each of the tagged nucleic acid species) were combined and used to prepare an Oxford Nanopore library using the sequencing ligation kit according to the manufacturer's protocol. Then, 20 fmol of the prepared multiplexed library, containing approximately 0.2 fmol ($1 \times 10^8$ molecules) of each of the initial 100 species (50 A6 species and 50 GF2B species, amplified from the initial approximately 50 molecules of both the A6 and GF2B targets), were loaded onto the Flongle flow-cell, and sequencing was performed by following the manufacturer's instructions.

Briefly, sequencing analysis was performed by first binning reads based on similarity to the desired nucleic acid sequences (A6 or GF2B) and then based on unique barcode combinations to generate joint desired nucleic acid sequence-barcode bins (joint target-barcode bins). Note, sample barcodes were not used for demultiplexing, rather the A6 and GF2B samples were binned by initial alignment to the desired nucleic acid sequences to demultiplex them. Only high confidence barcode combination reads were included in the analysis, using a filter for which false positives are <1%. The joint target-barcode bins were then used to generate individual consensus sequences from the alignment of all the reads within each bin. For each of the joint target-barcode bins, the consensus sequence was generated using a custom pipeline comprised of well-documented analysis software. Briefly, the consensus sequence was generated by aligning the reads in a joint target-barcode bin to their respective desired nucleic acid sequence (i.e., A6 or GF2B; using minimap2) and the overlapping bases at each gene position were compiled (bcftools mpileup). The identity and quality of the compiled bases were used to generate the consensus sequence(s), and variants from the target gene sequence, i.e., errors, were identified with high sensitivity (bcftools call). The resulting dataset contained an average of 540 reads and 240 reads for each uniquely tagged nucleic acid species of the A6 and GF2B genes, respectively. Due to the long reads obtainable on a nanopore sequencer (typically at least 10 kb), most reads spanned the full length of the DNA fragments (max ~1 kb), thus the depth of read per base was essentially equivalent to the number of reads. From the analysis, the A6 desired nucleic acid sequence and the GF2B desired nucleic acid sequence were represented by 15 and 46 uniquely tagged consensus sequences, respectively. Of those consensus sequences, 3 were error-free A6 desired nucleic acid sequences and 31 were error-free GF2B desired nucleic acid sequences (FIGS. 10A and 10B). The remaining consensus sequences had 1 or more errors. Based on the sequencing results, fourteen uniquely tagged nucleic acid species were selected for barcode-targeted PCR.

Barcode-targeted PCR of the selected tagged nucleic acid species (as shown in FIGS. 10A and 10B) proceeded as follows. Fourteen uniquely tagged nucleic acid species, with each representing a single population of molecules (i.e., no apparent mixture of distinct species within the limits of detection of the Oxford Nanopore sequencer and our current error models on that system which can reliably distinguish the presence of an alternative species present at a level 10% or greater), were selected, 5 from the A6 tagged nucleic acid species (of which 3 were sequence perfect and 2 contained 1 error), and 9 from the GF2B tagged nucleic acid species (of which all 9 were sequence perfect) (see Table 13 and FIGS. 10A and 10B). Each of the tagged nucleic acid species was amplified from the amplified product in each of the 2 diluted and subsequently amplified samples described above, using the corresponding OBC primers (Table 13 and FIGS. 10A and 10B) and a universal Outer R1 primer. The PCR reaction components and cycling conditions are shown in Tables 10 and 11.

TABLE 10

| PCR Reaction Component | µl/reaction | Final Conc. |
|---|---|---|
| Nuclease free H2O | 10 | |
| 2x KAPA HiFi HotStart ReadyMix | 12.5 | 1x |
| Outer R1, 10 uM | 0.75 | 0.3 uM |
| OBC primers, 10 uM | 0.75 | 0.3 uM |
| 50 molecule dilution pool amplification product, input concentration 1 fmol/ul | 1 | |
| Total vol. | 25 | |

TABLE 11

| Cycling Profile | | |
|---|---|---|
| Step 1 | 95° C. | 3 min |
| Step 2 | 98° C. | 20 s |
| Step 3 | 65° C. | 20 s |
| Step 4 | 72° C. | 30 s |
| Repeat step 2-4 | 25 cycles | |
| Final extension | 72° C. | 1 min |
| Hold | 4° C. | Forever |

Figure 11:
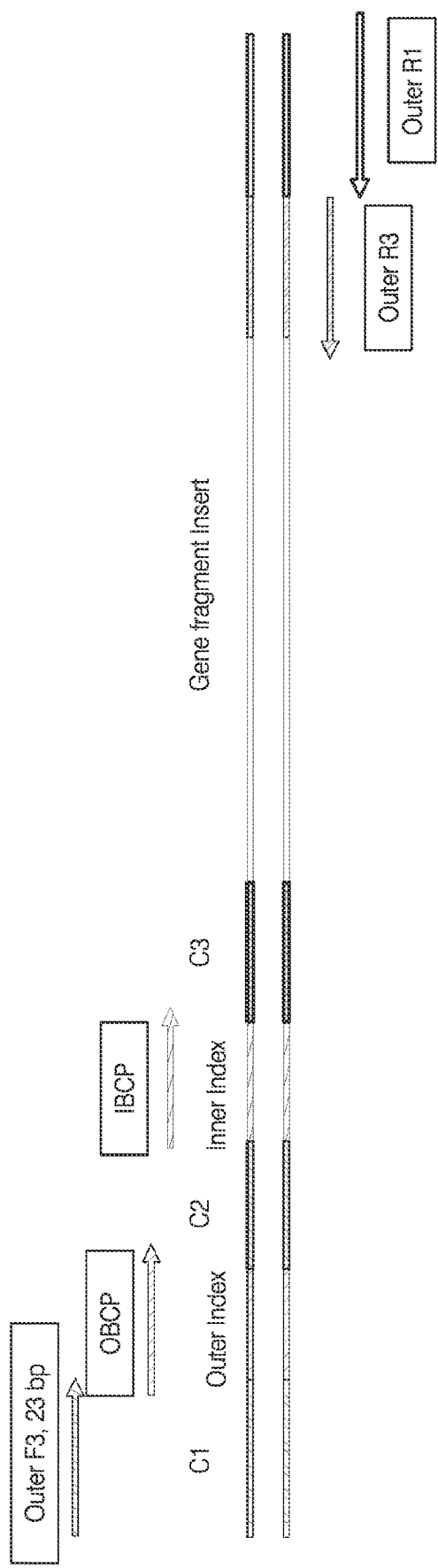
FIG. 11 presents a schematic representation of a tagged gene fragment in accordance with Example 1. C1=connector (linker) 1; C2=connector (linker) 2; C3=connector (linker) 3; Outer Index=outer barcode; Inner Index=inner barcode; OBCP=primer complementary to the outer barcode; IBCP=primer complementary to the inner barcode; Outer R1=outer reverse primer site 1; and Outer R3=outer reverse primer site 3.

Referring now to FIG. 11, FIG. 11 generally illustrates the position of the barcode-targeting primers that were used for the barcode-targeted PCR.

The expected size of each product produced by the barcode-targeted PCR with each primer pair was as follows:

TABLE 12

| Primer Pair | Expected Size of A6 Amplified Product | Expected Size of GF2B Amplified Product |
|---|---|---|
| C3_Outer R1 | 774 bp | 1069 bp |
| F3_Outer R1 | 870 bp | 1141 bp |
| OBCP_Outer R1 | 849 bp | 1116 bp |
| IBCP_Outer R1 | 814 bp | 1085 bp |
| IBCP_Outer R3 | 790 bp | 1041 bp |

After the barcode-targeted PCR reactions, 2 ul of each amplified product was diluted 1:10 and subsequently loaded to a 2% E-Gel EX agarose gel (Thermo Fisher Scientific) to visualize the amplification products. The expected amplification product size was 1116 bp for GF2B and 849 bp for A6.

The gel was loaded as follows:

TABLE 13

| Gel Lane | Gene Fragment | Input |
|---|---|---|
| 1 | | E gel sizing Ladder |
| 2 | GF2B | OBC primer 13 |
| 3 | GF2B | OBC primer 21 |
| 4 | GF2B | OBC primer 22 |
| 5 | GF2B | OBC primer 13 |
| 6 | GF2B | OBC primer 10 |
| 7 | GF2B | OBC primer 4 |
| 8 | GF2B | OBC primer 6 |
| 9 | GF2B | OBC primer 18 |
| 10 | GF2B | OBC primer 6 |
| 11 | GF2B | GF2B control |
| 12 | | E gel sizing Ladder |
| 13 | A6 | OBC primer 20 |

TABLE 13-continued

| Gel Lane | Gene Fragment | Input |
|---|---|---|
| 14 | A6 | OBC primer 20 |
| 15 | A6 | OBC primer 16 |
| 16 | A6 | OBC primer 12 |
| 17 | A6 | OBC primer 10 |
| 18 | A6 | OBC primer 10 |
| 19 | | NTC |
| 20 | A6 | A6 control |
| 21 | | Blank |
| 22 | | Blank |

Figure 12:
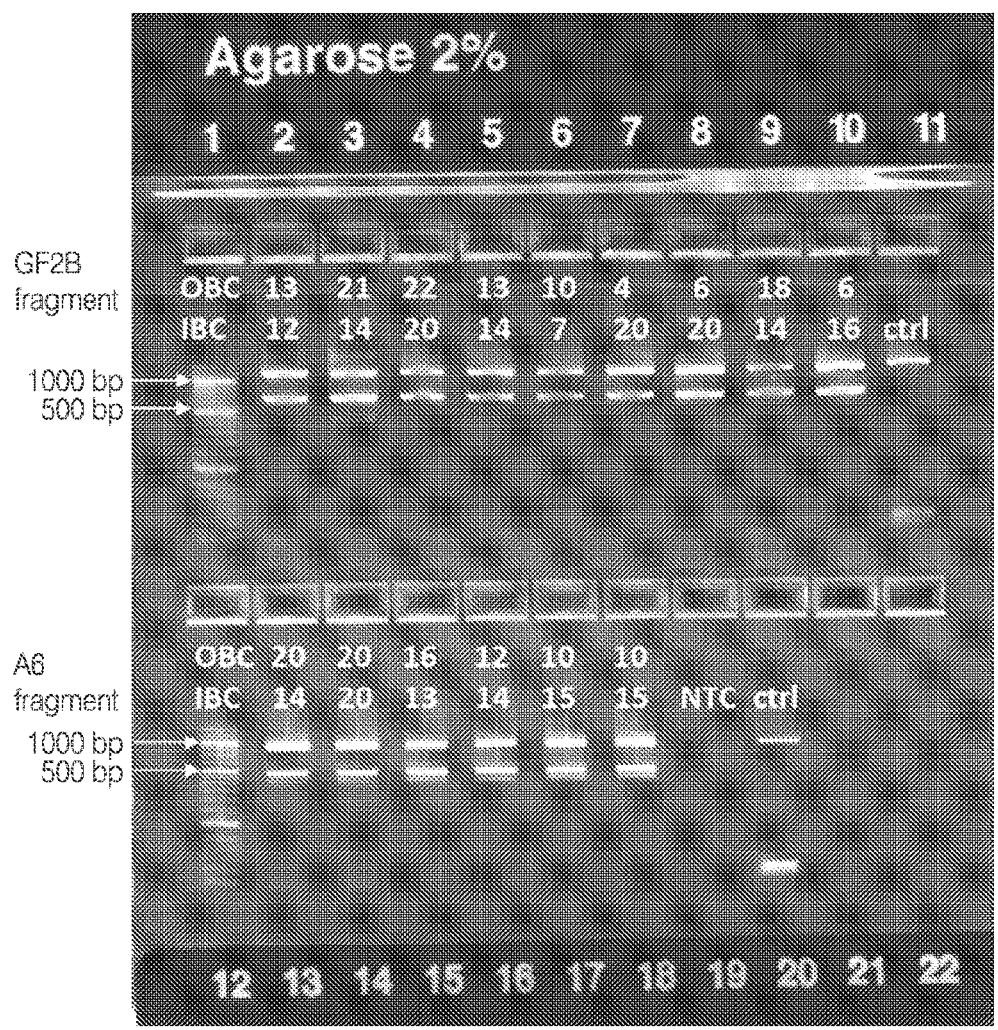
FIG. 12 presents an image of a 2% agarose gel of amplification products of barcode-targeted PCR in accordance with Example 1. Lane 1=Ladder; Lane 2=420 bp control; Lane 3=OBC primer 3; Lane 4=OBC primer 4; Lane 5=OBC primer 4; Lane 6=OBC primer 10; Lane 7=OBC primer 22; Lane 8=OBC primer 22; Lane 9=Ctrl OBC 1; Lane 10=NTC OBC3; Lane 11=369 bp control; Lane 12=Ladder; Lane 13=OBC primer 12; Lane 14=OBC primer 14; Lane 15=OBC primer 14; Lane 16=OBC primer 17; Lane 17=OBC primer 19; Lane 18=OBC primer 9; Lane 19=OBC primer 19; Lane 20=NTC OBC3; Lane 21=Ctrl OBC 3; and Lane 22=369 bp control.

Referring now to FIG. 12, the expected 1116 bp fragment was observed in each of lanes 1-10 for GF2B and the expected 849 bp fragment was observed in each of lanes 13-17 for A6 when using the indicated OBC primer.

After the first barcode-targeted PCR, the amplified products were diluted by 100-fold, and 1 ul each diluted amplification product was used for a second barcode-targeted PCR with the corresponding IBC primers and universal Outer R3 primer (i.e., nested PCR). The PCR reaction and cycling conditions were as follows:

TABLE 14

| PCR Reaction Component | µl/reaction | Final Conc. |
|---|---|---|
| Nuclease free H20 | 10 | |
| 2x KAPA HiFi HotStart Ready mix | 12.5 | 1x |
| Outer R3, 10 uM | 0.75 | 0.3 uM |
| IBC primers, 10 uM | 0.75 | 0.3 uM |
| OBC primer dial out PCR product 1:100 dilution | 1 | |
| Total vol. | 25 | |

TABLE 15

| Cycling Profile | | |
|---|---|---|
| Step 1 | 95° C. | 3 min |
| Step 2 | 98° C. | 20 s |
| Step 3 | 70° C. | 20 s |
| Step 4 | 72° C. | 30 s |
| Repeat step 2-4 | 30 cycles | |
| Final extension | 72° C. | 1 min |
| Hold | 4° C. | Forever |

Figure 13:
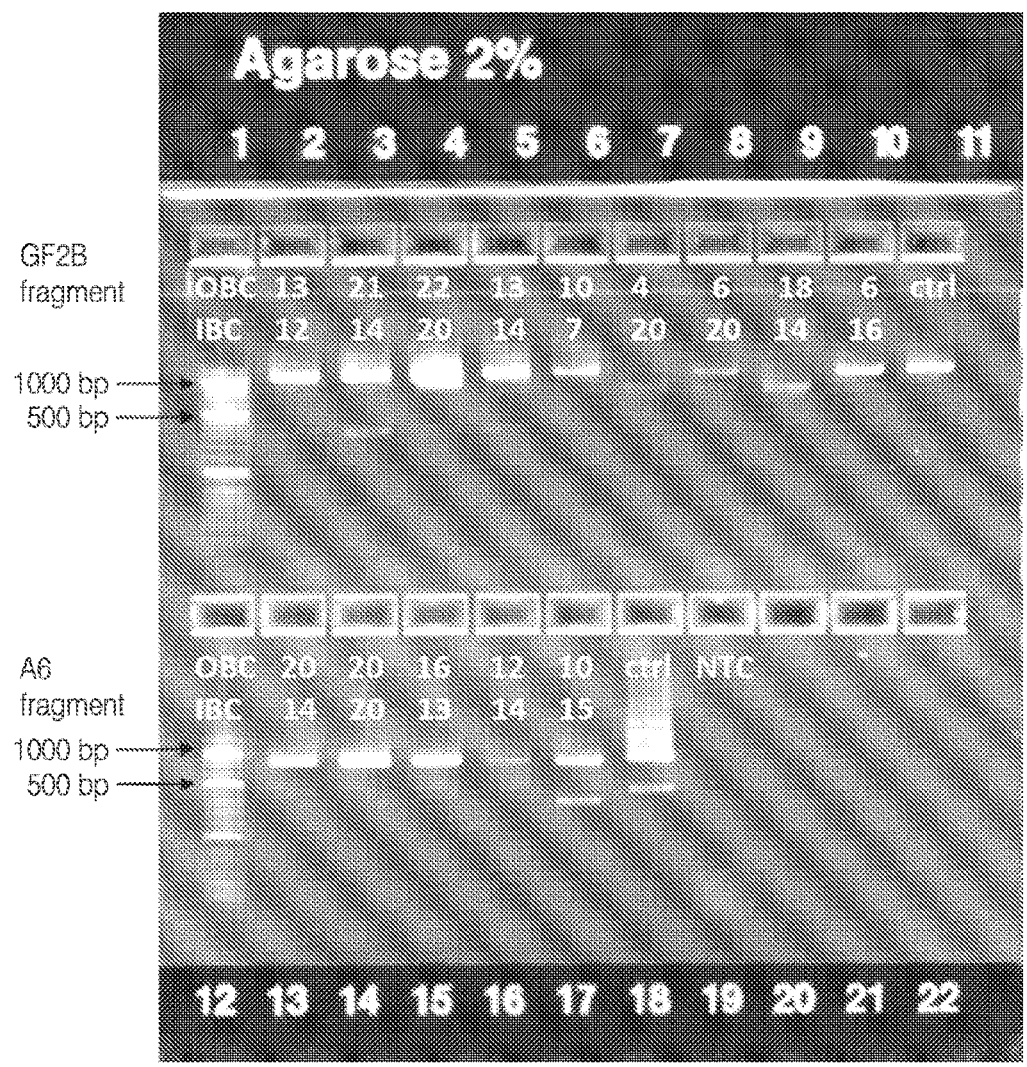
FIG. 13 presents an image of a 2% agarose gel of amplification products of barcode-targeted PCR in accordance with Example 1. Lane 1=Ladder; Lane 2=IBC primer 14, 12; Lane 3=IBC primer 15; Lane 4=IBC primer 2; Lane 5=IBC primer 20; Lane 6=IBC primer 18; Lane 7=IBC primer 19; Lane 8=Ctrl IBC 2; Lane 9=NTC; Lane 10=IBC2; Lane 11=369 bp control; Lane 12=Ladder; Lane 13=IBC primer 11, 10; Lane 14=IBC primer 13; Lane 15=IBC primer 5; Lane 16=IBC primer 13; Lane 17=IBC primer 17; Lane 18=IBC primer 16; Lane 19=Ctrl IBC 1; Lane 20=NTC; and Lane 21=IBC7.

After the barcode-targeted PCR reactions, the amplification products were purified using 0.8x AMPure beads, and then 2 ul of each purified amplified product was diluted 1:10 prior to loading onto a 2% E-Gel EX agarose gel (Thermo Fischer Scientific) to visualize the amplification products (FIG. 13). The expected amplification product size was 1041 bp for GF2B and 790 bp for A6.

The gel was loaded as follows:

TABLE 16

| Gel Lane | Gene fragment | Input |
|---|---|---|
| 1 | | E gel sizing Ladder |
| 2 | GF2B | IBC primer 12 (OBC 13) |
| 3 | GF2B | IBC primer 14 (OBC 21) |
| 4 | GF2B | IBC primer 20 (OBC 22) |
| 5 | GF2B | IBC primer 14 (OBC 13) |
| 6 | GF2B | IBC primer 7 (OBC 10) |
| 7 | GF2B | IBC primer 20 (OBC 4) |
| 8 | GF2B | IBC primer 20 (OBC 6) |
| 9 | GF2B | IBC primer 14 (OBC 18) |

TABLE 16-continued

| Gel Lane | Gene fragment | Input |
|---|---|---|
| 10 | GF2B | IBC primer 16 (OBC 6) |
| 11 | GF2B | GF2B control |
| 12 | | E gel sizing Ladder |
| 13 | A6 | IBC primer 14 (OBC 20) |
| 14 | A6 | IBC primer 20 (OBC 20) |
| 15 | A6 | IBC primer 13 (OBC 16) |
| 16 | A6 | IBC primer 14 (OBC 12) |
| 17 | A6 | IBC primer 15 (OBC 10) |
| 18 | A6 | A6 control |
| 19 | | NTC |
| 20 | | Blank |
| 21 | | Blank |
| 22 | | Blank |

Referring now to FIG. 13, the expected 1041 bp fragment was observed in each of lanes 1-10 for GF2B and the expected 790 bp fragment was observed in each of lanes 13-17 for A6 when using the indicated IBC primer.

After the barcode-targeted PCR, four resulting amplified nucleic acid species from the barcode-targeted PCR, two each from A6 and GF2B, were selected for sequence confirmation using nanopore-based nucleic acid sequencing on the Oxford Nanopore Sequencer and analyzed in a manner similar to that described above. Each uniquely tagged bin had a read depth >750×, and from these reads, consensus sequence(s) were generated also as above and any errors were identified.

Figure 14:
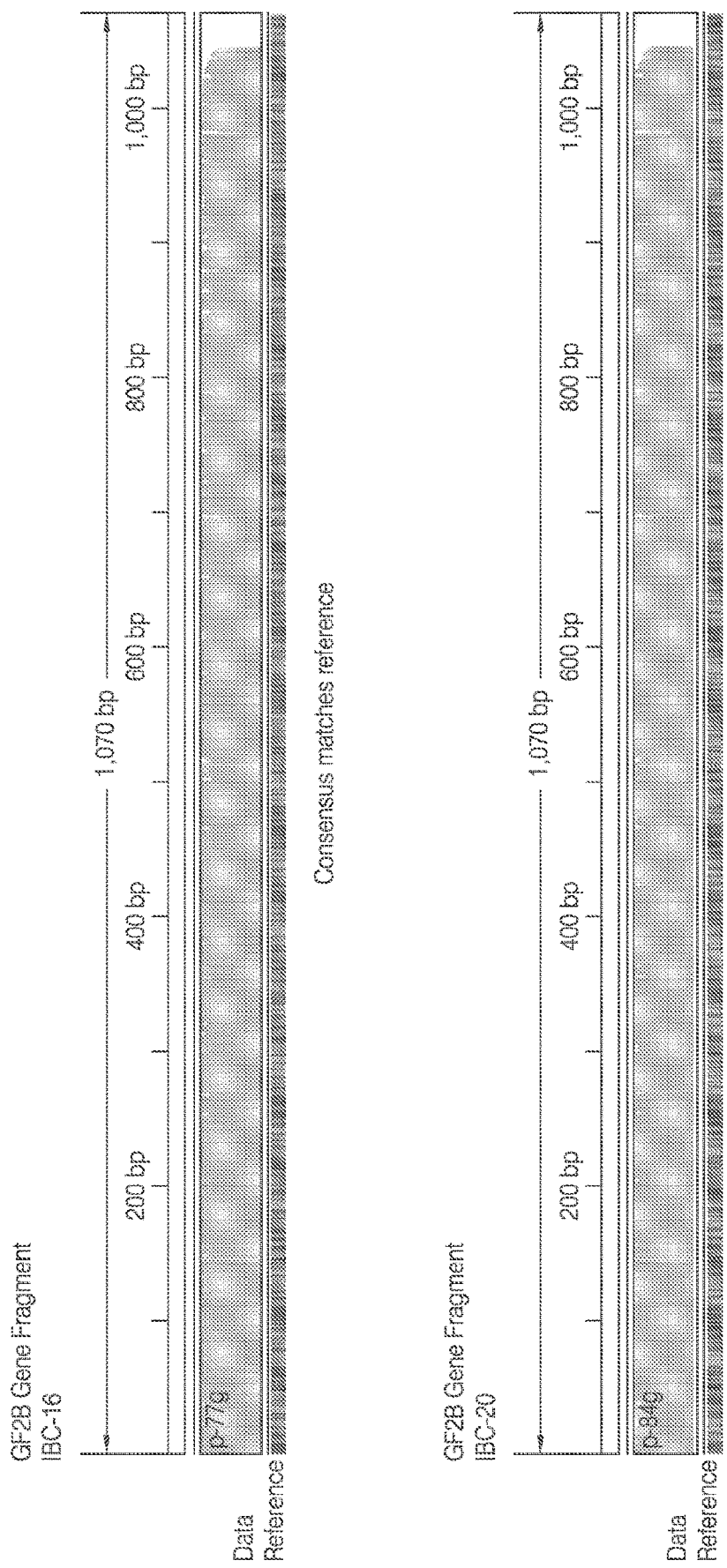
FIG. 14 presents a sequencing readout of two different selected polynucleotides, each with no errors compared to the desired polynucleotide sequence ("sequence-perfect"), in accordance with Example 1.
Figure 15:
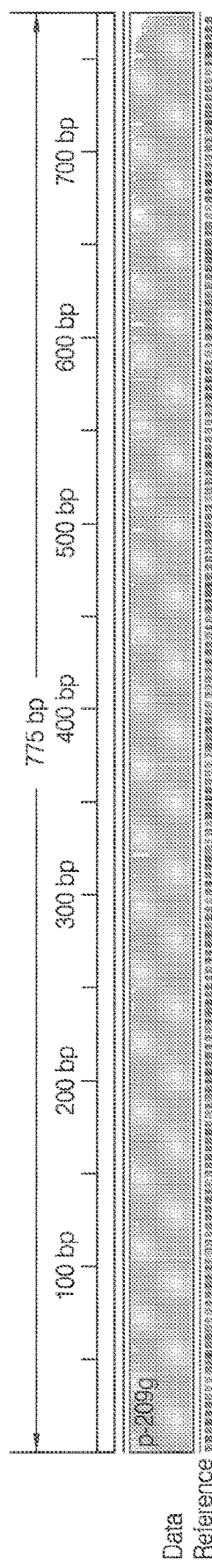
FIG. 15 presents a sequencing readout of two different selected polynucleotides, each with one error as compared to the desired polynucleotide sequence, in accordance with Example 1.
Figure 15:
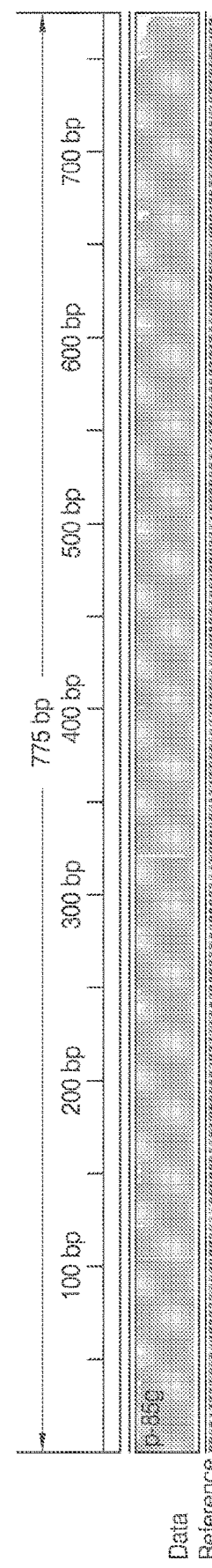

The analysis verified that each of the IBC barcode-targeted PCR products (amplified nucleic acid species) was sequence-perfect or had the same error observed before barcode-targeted PCR process. The visualized data is shown in FIGS. 14 and 15. Specifically, sequencing analysis showed that the amplified product from the 2 selected GF2B species (amplified with nested barcode-targeted PCR using primers to OBC 6 and IBC 16 or OBC 22 and IBC 20) had been successfully amplified from the diluted and amplified sample and that the highly enriched samples each contained a single tagged nucleic acid species that was error free to within the limit of detection of the sequencing method and the consensus reads that were construct it (FIG. 14). Likewise, sequencing analysis showed that the A6 tagged nucleic acid species amplified with nested barcode-targeted PCR using primers to OBC 20 and IBC 14 was also error free, as expected from the previous sequencing data (FIG. 15, top). The second A6 tagged nucleic acid species was selected specifically because it contained a single base deletion. After nested barcode-targeted PCR using primers to OBC 20 and IBC 20, it was found to have been successfully amplified from the diluted and amplified sample. The sequenced data showed that the amplification reaction contained a single tagged nucleic acid species, within the limits of the detection of the sequencer and the method used to construct the consensus sequence, and contained the same previously identified single base deletion previously observed upon sequencing the corresponding diluted and amplified sample (FIG. 15, bottom).

Example 2: Polynucleotide Production Compared to Commercial Suppliers

In the present example, populations of polynucleotides from 45 different desired nucleic acid sequences, ranging from 300 bp to 5,556 bp, were generated using vCloning methods herein, including tagging the nucleic acid molecules with molecular barcodes or combinations of molecular barcodes and diluting tagged nucleic acid molecules similar to Example 1. The nucleic acid sequences of the polynucleotides were also submitted to two established commercial providers (Commercial Provider 1 and 2) to determine which sequences were acceptable for synthesis with or without traditional cloning. Both providers included cutoffs based on length, but some sequences that were within the length limitation were nonetheless rejected. A subset of the accepted sequences were submitted to Commercial Provider 2 for non-clonal synthesis, and successful synthesis from Commercial Provider 2 was compared to the methods herein.

The sequences were characterized using various online tools. The 45 different desired nucleic acid sequences (SEQ ID NOs:2-46) included various sizes (300 bp to 5,556 bp), GC contents (33% to 65%), numbers of homopolymeric runs (0 to 4 runs), numbers of repeats at least 8 nucleotides in length (2 to 326 repeats), numbers of repeats at least 10 nucleotides in length (0 to 247 repeats), numbers of repeats at least 15 nucleotides in length (0 to 5 repeats) (SEQ ID NO:37 had a repeat 46-nucleotides in length), numbers of inverted repeats at least 10 nucleotides in length (0 to 2 inverted repeats), numbers of sets of tandem repeats (0 to 4 sets), and secondary structure (categorized as low, medium, or high according to methods herein). Various characteristics of the different sequences are provided in Table 17.

TABLE 17

| SEQ ID NO | Length (bp) | % GC | Homopolymeric runs (10 As/Ts or 6 Cs/Gs) | Repeats (at least 8 nt.) | Repeats (at least 10 nt.) | Repeats (at least 15 nt.) | Inverted repeats (at least 10 nt.) | Sets of Tandem repeats | Secondary Structure |
|---|---|---|---|---|---|---|---|---|---|
| 2 | 300 | 48% | 0 | 2 | 1 | 0 | 0 | 0 | Medium |
| 3 | 1521 | 59% | 0 | 27 | 2 | 0 | 0 | 0 | Low |
| 4 | 3207 | 39% | 0 | 104 | 7 | 0 | 0 | 0 | Medium |
| 5 | 4094 | 54% | 0 | 118 | 5 | 0 | 0 | 1 | Medium |
| 6 | 3075 | 56% | 0 | 109 | 10 | 0 | 1 | 1 | High |
| 7 | 4205 | 56% | 1 | 376 | 8 | 0 | 0 | 1 | High |
| 8 | 4950 | 46% | 2 | 146 | 14 | 0 | 0 | 1 | High |
| 9 | 5178 | 52% | 0 | 161 | 11 | 0 | 1 | 0 | Medium |
| 10 | 4940 | 50% | 2 | 158 | 23 | 0 | 0 | 1 | Low |
| 11 | 5052 | 33% | 0 | 366 | 47 | 0 | 2 | 0 | Low |
| 12 | 5430 | 37% | 0 | 371 | 40 | 1 | 0 | 2 | Medium |
| 13 | 5556 | 40% | 2 | 321 | 37 | 0 | 0 | 2 | High |
| 14 | 5361 | 57% | 3 | 207 | 13 | 0 | 0 | 3 | High |
| 15 | 5349 | 58% | 4 | 224 | 18 | 0 | 1 | 4 | Low |
| 16 | 5394 | 60% | 2 | 285 | 30 | 1 | 0 | 1 | Medium |
| 17 | 4983 | 61% | 0 | 266 | 32 | 0 | 0 | 0 | High |
| 18 | 1269 | 34% | 0 | 25 | 1 | 0 | 0 | 0 | Low |

TABLE 17-continued

| SEQ ID NO | Length (bp) | % GC | Homopolymeric runs (10 As/Ts or 6 Cs/Gs) | Repeats (at least 8 nt.) | Repeats (at least 10 nt.) | Repeats (at least 15 nt.) | Inverted repeats (at least 10 nt.) | Sets of Tandem repeats | Secondary Structure |
|---|---|---|---|---|---|---|---|---|---|
| 19 | 1134 | 39% | 0 | 11 | 1 | 1 | 0 | 0 | Medium |
| 20 | 951 | 38% | 0 | 16 | 0 | 0 | 0 | 1 | High |
| 21 | 1224 | 41% | 0 | 18 | 1 | 0 | 0 | 0 | Medium |
| 22 | 963 | 52% | 0 | 6 | 0 | 0 | 1 | 0 | Medium |
| 23 | 1141 | 54% | 0 | 8 | 1 | 0 | 0 | 1 | Medium |
| 24 | 1133 | 59% | 0 | 17 | 1 | 0 | 0 | 0 | High |
| 25 | 1380 | 65% | 0 | 36 | 4 | 0 | 0 | 0 | High |
| 26 | 2070 | 39% | 0 | 41 | 3 | 0 | 0 | 1 | Low |
| 27 | 2073 | 39% | 0 | 41 | 4 | 0 | 1 | 0 | Medium |
| 28 | 2039 | 37% | 1 | 52 | 3 | 0 | 2 | 2 | High |
| 29 | 2289 | 45% | 1 | 49 | 4 | 0 | 0 | 0 | Low |
| 30 | 1990 | 47% | 0 | 29 | 3 | 0 | 1 | 0 | Medium |
| 31 | 2172 | 54% | 0 | 55 | 4 | 0 | 0 | 3 | High |
| 32 | 2112 | 59% | 2 | 63 | 10 | 1 | 0 | 1 | Low |
| 33 | 2169 | 59% | 0 | 60 | 7 | 0 | 0 | 0 | Medium |
| 34 | 1968 | 60% | 0 | 41 | 4 | 0 | 1 | 1 | High |
| 35 | 2934 | 37% | 0 | 10 | 6 | 0 | 1 | 1 | High |
| 36 | 3180 | 44% | 0 | 102 | 13 | 1 | 2 | 2 | Low |
| 37 | 3603 | 52% | 0 | 100 | 19 | 5 | 2 | 2 | Medium |
| 38 | 3156 | 58% | 0 | 114 | 10 | 0 | 0 | 1 | Low |
| 39 | 3090 | 59% | 0 | 89 | 9 | 0 | 1 | 0 | Medium |
| 40 | 3903 | 40% | 0 | 317 | 16 | 0 | 0 | 0 | High |
| 41 | 4008 | 44% | 1 | 140 | 9 | 0 | 1 | 1 | Low |
| 42 | 4032 | 59% | 0 | 169 | 10 | 0 | 0 | 0 | Low |
| 43 | 4023 | 58% | 0 | 151 | 12 | 0 | 1 | 1 | Medium |
| 44 | 4260 | 60% | 0 | 167 | 10 | 0 | 1 | 0 | High |
| 45 | 3205 | 65% | 1 | 118 | 11 | 0 | 2 | 2 | High |
| 46 | 4374 | 37% | 0 | 195 | 17 | 0 | 2 | 3 | Medium |

300 bp to 1 kb nucleic acids spanning the nucleic acid sequences of each of the 45 desired nucleic acid sequences were ordered from Commercial Provider 1, and individual assembly reactions were performed for each desired nucleic acid sequence using splice overhang extension. The 300 bp to 1 kb nucleic acids were believed to be the products of an initial assembly reaction performed by Commercial Provider 1. The assembled nucleic acids (also referred to herein as source nucleic acid molecules), which typically included around 300,000,000 source nucleic acid molecules, were tagged with similar a number of molecular barcodes or combinations of molecular barcodes as in Example 1. The tagged source nucleic acid molecules were then diluted to similar target numbers as in Example 1. Tagged nucleic acid molecules in dilute samples were then amplified, pooled, and analyzed using long-read sequencing. Nucleic acid molecules having the desired nucleic acid sequences (sequence-perfect desired nucleic acid sequences) and unique tags were identified and amplified from the dilute sample using the unique molecular barcodes, similar to Example 1. After sequencing, as little as 1.32% of the tagged nucleic acid molecules in the dilute sample had the sequence-perfect desired nucleic acid sequence. Notably, the tagged nucleic acid molecules with the sequence-perfect desired nucleic acid sequence were then amplified using primers that bound to the unique molecular barcodes from the tagged nucleic acid molecules in the sequence-perfect reads, thus enriching the tagged nucleic acid molecules with the sequence-perfect nucleic acid sequence.

The 45 desired nucleic acid sequences were checked for acceptance of synthesis at Commercial Providers 1 and 2. For non-clonal synthesis, both providers only accepted 10 of the 45 desired nucleic acid sequences for synthesis (Table 18). Even using traditional cloning, Commercial Provider 2 would accept only 35 of the 45 desired nucleic acid sequences for synthesis (Table 18). 3 of the 10 accepted desired nucleic acid sequences were submitted to Commercial Provider 2 for non-clonal whole-sequence synthesis (SEQ ID NOs:3, 19, and 25) and 6 fragments from 5 desired nucleic acid sequences (nucleotides 1,075 to 1,521 of SEQ ID NO:3 with a proprietary adaptor sequence at the 3' end), nucleotides 635 to 1,422 of SEQ ID NO:17, nucleotides 2,167 to 2,869 of SEQ ID NO:17, nucleotides 1,382 to 2,039 of SEQ ID NO:28 with a proprietary adaptor sequence at the 3' end, nucleotides 255 to 1,345 of SEQ ID NO:42, and nucleotides 650 to 1,327 of SEQ ID NO:45) for non-clonal fragment synthesis. Table 18 shows the results for these experiments. For Commercial Provider 2, successful synthesis was defined as delivery, and a blank means the sequence was not submitted for synthesis. For Example 2 Methods, successful synthesis was defined as synthesis of the desired nucleic acid sequence with the correct consensus sequence.

TABLE 18

| | Commercial Provider 1 Met Criteria for Synthesis | Commercial Provider 2 | | | | Example 2 Methods Successful Synthesis |
|---|---|---|---|---|---|---|
| SEQ ID NO | | Met Criteria for Non-Clonal Synthesis | Met Criteria for Clonal Synthesis | Successful Non-clonal Gene Synthesis | Successful Non-clonal Fragment Synthesis | |
| 2 | Yes | Yes | Yes | | | Yes |
| 3 | No | Yes | Yes | Yes | Yes | Yes |
| 4 | No | No | Yes | | | Yes |

TABLE 18-continued

| | Commercial Provider 1 Met Criteria for Synthesis | Commercial Provider 2 | | | | Example 2 Methods Successful Synthesis |
|---|---|---|---|---|---|---|
| SEQ ID NO | | Met Criteria for Non-Clonal Synthesis | Met Criteria for Clonal Synthesis | Successful Non-clonal Gene Synthesis | Successful Non-clonal Fragment Synthesis | |
| 5 | No | No | Yes | | | Yes |
| 6 | No | No | Yes | | | Yes |
| 7 | No | No | Yes | | | Yes |
| 8 | No | No | Yes | | | Yes |
| 9 | No | No | No | | | Yes |
| 10 | No | No | No | | | Yes |
| 11 | No | No | No | | | Yes |
| 12 | No | No | No | | | Yes |
| 13 | No | No | No | | | Yes |
| 14 | No | No | No | | | Yes |
| 15 | No | No | No | | | Yes |
| 16 | No | No | No | | | Yes |
| 17 | No | No | Yes | | Yes (2 fragments) | Yes |
| 18 | Yes | Yes | Yes | | | Yes |
| 19 | No | Yes | Yes | Yes | | Yes |
| 20 | Yes | Yes | Yes | | | Yes |
| 21 | Yes | Yes | Yes | | | Yes |
| 22 | Yes | Yes | Yes | | | Yes |
| 23 | Yes | Yes | Yes | | | Yes |
| 24 | Yes | Yes | Yes | | | Yes |
| 25 | No | Yes | Yes | Yes | | Yes |
| 26 | Yes | No | Yes | | | Yes |
| 27 | Yes | No | Yes | | | Yes |
| 28 | No | No | Yes | | Yes | Yes |
| 29 | No | No | No | | | Yes |
| 30 | No | No | Yes | | | Yes |
| 31 | No | No | No | | | Yes |
| 32 | No | No | Yes | | | Yes |
| 33 | Yes | No | Yes | | | Yes |
| 34 | No | No | Yes | | | Yes |
| 35 | No | No | Yes | | | Yes |
| 36 | No | No | Yes | | | Yes |
| 37 | No | No | Yes | | | Yes |
| 38 | No | No | Yes | | | Yes |
| 39 | No | No | Yes | | | Yes |
| 40 | No | No | Yes | | | Yes |
| 41 | No | No | Yes | | | Yes |
| 42 | No | No | Yes | | Yes | Yes |
| 43 | No | No | Yes | | | Yes |
| 44 | No | No | Yes | | | Yes |
| 45 | No | No | Yes | | No | Yes |
| 46 | No | No | Yes | | | Yes |

As shown in Table 18, populations of polynucleotides with the desired nucleic acid sequence (correct consensus sequence) were generated for all 45 desired nucleic acid sequences using the methods of this example. In contrast, non-clonal synthesis by Commercial Provider 2 was only able to successfully deliver 8 of the 9 sequences submitted. Furthermore, Commercial Providers 1 and 2 were unable to even accept 35 of the sequences for synthesis, and even traditional cloning offered by Commercial Provider 2 would not accept 10 of the sequences for synthesis. This example demonstrates the vast superiority of the methods herein for identifying and enriching nucleic acid molecules having the desired nucleic acid sequence (e.g., the sequence-perfect desired nucleic acid sequence).

Example 3: Error-Rates of Polynucleotide Production

In the present example, populations of polynucleotides from 36 different proprietary desired nucleic acid sequences, ranging from 831 bp to 5,587 bp, were generated using vCloning methods herein, including tagging the nucleic acid molecules with molecular barcodes or combinations of molecular barcodes and diluting tagged nucleic acid molecules similar to Example 1. The nucleic acid sequences of the polynucleotides were also submitted to a commercial provider (Commercial Provider 2 from Example 2) for synthesis, and successful synthesis for the sequences were compared to the methods herein.

The 36 different desired nucleic acid sequences included various sizes (831 bp to 5,587 bp), GC contents (38.2% to 55.9%), numbers of homopolymeric runs (0 to 2 runs), numbers of repeats at least 8 nucleotides in length (6 to 287 repeats), numbers of repeats at least 10 nucleotides in length (0 to 37 repeats), numbers of repeats at least 15 nucleotides in length (0 to 2 repeats) (including one sequence with a repeat of $10^9$ nucleotides in length that was successfully synthesized), numbers of inverted repeats at least 10 nucleotides in length (0 to 2 inverted repeats), numbers of sets of tandem repeats (0 to 5 sets), and secondary structure (categorized as low, medium, or high according to methods herein). Characteristics of the different sequences are provided in Table 19.

TABLE 19

| Sequence | Length (bp) | % GC | Homopolymeric runs of 10 As/Ts or 6 Cs/Gs | Repeats (at least 8 nt.) | Repeats (at least 10 nt.) | Repeats (at least 15 nt.) | Inverted repeats (at least 10 nt.) | Sets of Tandem Repeats | Secondary Structure |
|---|---|---|---|---|---|---|---|---|---|
| 1 | 4506 | 40.8 | 0 | 287 | 37 | 0 | 1 | 2 | Low |
| 2 | 4506 | 38.2 | 0 | 170 | 3 | 0 | 0 | 1 | Low |
| 3 | 4506 | 38.2 | 0 | 169 | 4 | 0 | 0 | 1 | Low |
| 4 | 3359 | 39.7 | 1 | 129 | 7 | 0 | 1 | 0 | Low |
| 5 | 5587 | 41 | 0 | 227 | 25 | 1 | 1 | 5 | Low |
| 6 | 2524 | 42.1 | 2 | 49 | 6 | 0 | 0 | 0 | Low |
| 7 | 4038 | 45.9 | 1 | 119 | 10 | 0 | 0 | 0 | Low |
| 8 | 2765 | 39.5 | 0 | 79 | 6 | 0 | 1 | 0 | Low |
| 9 | 1442 | 40.7 | 0 | 19 | 2 | 0 | 0 | 1 | Low |
| 10 | 3128 | 42.3 | 0 | 89 | 12 | 0 | 1 | 1 | Low |
| 11 | 2508 | 39.1 | 0 | 66 | 6 | 0 | 1 | 0 | Low |
| 12 | 1119 | 40.8 | 1 | 21 | 3 | 0 | 0 | 2 | Low |
| 13 | 991 | 52.3 | 0 | 6 | 1 | 1 | 1 | 1 | Medium |
| 14 | 1036 | 47.1 | 0 | 6 | 2 | 1 | 0 | 1 | Medium |
| 15 | 1045 | 48.1 | 0 | 7 | 1 | 1 | 0 | 2 | Medium |
| 16 | 2033 | 43.7 | 0 | 42 | 5 | 2 | 0 | 3 | Low |
| 17 | 1260 | 52.7 | 1 | 10 | 1 | 1 | 0 | 1 | Medium |
| 18 | 1218 | 49.8 | 0 | 8 | 1 | 1 | 0 | 1 | Medium |
| 19 | 831 | 40.8 | 0 | 7 | 1 | 1 | 0 | 2 | Low |
| 20 | 3463 | 50.4 | 0 | 87 | 10 | 2 | 2 | 5 | Medium |
| 21 | 1605 | 41.2 | 0 | 27 | 0 | 0 | 0 | 1 | Low |
| 22 | 2010 | 52.8 | 0 | 20 | 15 | 1 | 0 | 1 | Medium |
| 23 | 1701 | 55.9 | 0 | 17 | 4 | 1 | 1 | 2 | Medium |
| 24 | 1692 | 52.3 | 0 | 24 | 2 | 1 | 0 | 1 | Medium |
| 25 | 1683 | 48.6 | 0 | 13 | 1 | 1 | 0 | 1 | Low |
| 26 | 2526 | 47.2 | 0 | 46 | 5 | 1 | 1 | 0 | Medium |
| 27 | 1866 | 51.9 | 0 | 37 | 9 | 0 | 1 | 2 | Medium |
| 28 | 1872 | 50.4 | 0 | 61 | 6 | 0 | 1 | 2 | Medium |
| 29 | 1896 | 49.2 | 0 | 40 | 10 | 0 | 0 | 2 | Medium |
| 30 | 1932 | 49.6 | 0 | 23 | 2 | 0 | 0 | 2 | Medium |
| 31 | 2472 | 45.4 | 0 | 49 | 3 | 0 | 0 | 2 | Low |
| 32 | 906 | 55.6 | 0 | 9 | 0 | 0 | 0 | 1 | High |
| 33 | 1557 | 50.6 | 0 | 30 | 4 | 0 | 0 | 1 | Medium |
| 34 | 1461 | 55.7 | 0 | 27 | 3 | 0 | 0 | 2 | Medium |
| 35 | 4920 | 49.2 | 1 | 191 | 21 | 2 | 2 | 4 | Low |
| 36 | 2848 | 52 | 0 | 76 | 7 | 0 | 0 | 2 | Medium |

300 bp to 1 kb nucleic acid molecules spanning the nucleic acid sequences of each of the 36 desired nucleic acid sequences were ordered from Commercial Provider 1 and individual assembly reactions were performed for each desired nucleic acid sequence using splice overhang extension. The assembled nucleic acid molecules (also referred to herein as source nucleic acid molecules), which were believed to be the product of an initial assembly performed by Commercial Provider 1, were tagged with a similar number of molecular barcodes or combinations of molecular barcodes as in Example 1. The tagged source nucleic acid molecules were then diluted to similar target numbers as in Example 1. Tagged nucleic acid molecules in dilute samples were then amplified, pooled, and analyzed using long-read sequencing. Nucleic acid molecules having desired nucleic acid sequences (e.g., sequence-perfect desired nucleic acid sequences) and unique tags were identified and amplified from the dilute sample using the unique molecular barcodes, similar to Example 1.

The 36 desired nucleic acid sequences were submitted to Commercial Provider 2 for synthesis. For Commercial Provider 2, successful synthesis was defined as delivery of the sequence. For Example 3 Methods, successful synthesis was defined as synthesis of the desired nucleic acid sequence with the correct consensus sequence. Populations of polynucleotides with the desired nucleic acid sequence (correct consensus sequence) were generated for 33 out of the 36 desired nucleic acid sequences (91.7%) using the methods of this example. In contrast, Commercial Provider 2 was only able to successfully generate 28 of the 36 sequences submitted (77.8%). Notably, the vCloning methods, which included e.g. tagging and diluting steps were able to successfully generate populations of polynucleotides for every desired nucleic acid sequence that Commercial Provider 2 accepted for synthesis (and more that were not accepted) while Commercial Provider 2 was unable to even generate all of the sequences it accepted for synthesis.

TABLE 20

| | Commercial | Example 3 Methods | |
|---|---|---|---|
| Sequence | Provider 2 Successful Synthesis | Successful Synthesis | % Molecules Sequence-Perfect |
| 1 | Yes | Yes | 97.0% |
| 2 | Yes | Yes | 99.0% |
| 3 | Yes | Yes | 98.0% |
| 4 | No | Yes | 98.0% |
| 5 | No | Yes | 98.0% |
| 6 | No | Yes | 96.0% |
| 7 | Yes | Yes | 98.0% |
| 8 | Yes | Yes | 98.0% |
| 9 | No | Yes | 98.0% |
| 10 | No | No | N/A |
| 11 | Yes | Yes | 97.0% |
| 12 | Yes | Yes | 97.0% |
| 13 | Yes | Yes | 98.0% |
| 14 | Yes | Yes | 99.0% |
| 15 | Yes | Yes | 97.0% |
| 16 | No | No | N/A |
| 17 | Yes | Yes | 93.0% |
| 18 | Yes | Yes | 97.0% |
| 19 | Yes | Yes | 98.0% |

TABLE 20-continued

| Sequence | Commercial Provider 2 Successful Synthesis | Example 3 Methods | |
|---|---|---|---|
| | | Successful Synthesis | % Molecules Sequence-Perfect |
| 20 | No | Yes | 92.0% |
| 21 | Yes | Yes | 97.0% |
| 22 | Yes | Yes | 98.0% |
| 23 | Yes | Yes | 96.0% |
| 24 | Yes | Yes | 97.0% |
| 25 | Yes | Yes | 97.0% |
| 26 | Yes | Yes | 89.0% |
| 27 | Yes | Yes | 98.0% |
| 28 | Yes | Yes | 98.0% |
| 29 | Yes | Yes | 97.0% |
| 30 | Yes | Yes | 95.0% |
| 31 | Yes | Yes | 97.0% |
| 32 | Yes | Yes | 96.0% |
| 33 | Yes | Yes | 98.0% |
| 34 | Yes | Yes | 96.0% |
| 35 | No | No | N/A |
| 36 | Yes | Yes | 97.0% |

Figure 16:
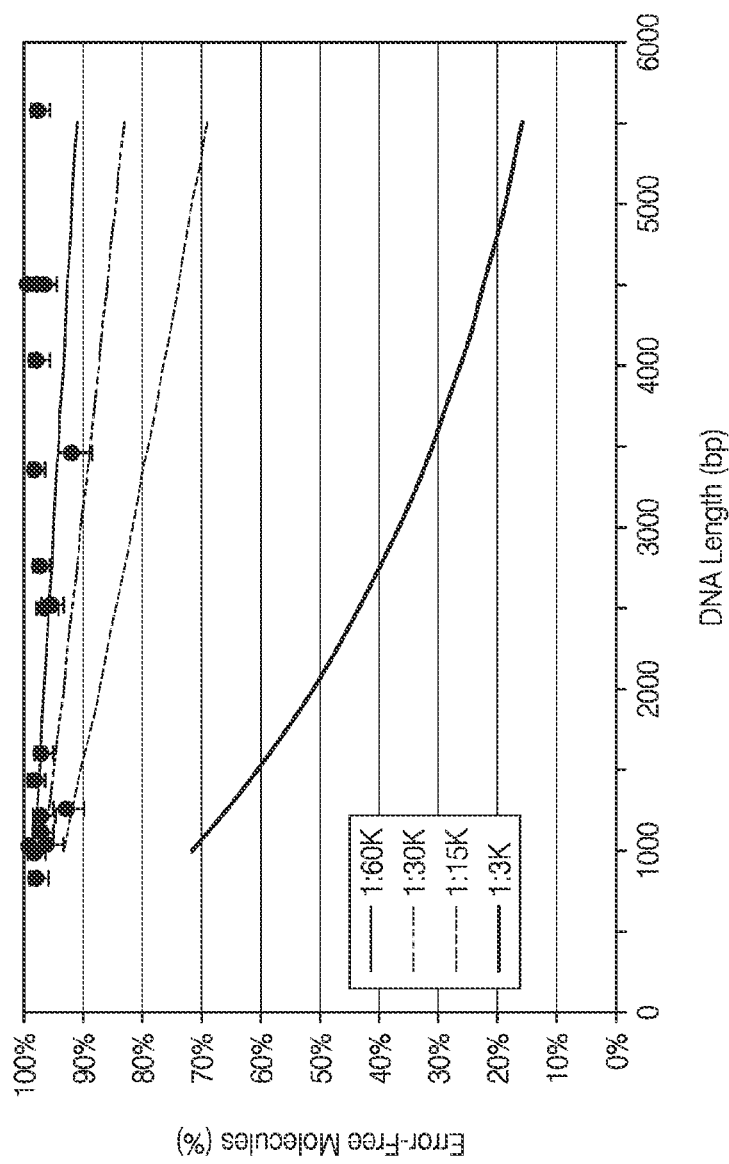
FIG. 16 presents a graph showing the percentage of error-free molecules (e.g., polynucleotides having a sequence-perfect desired nucleic acid sequence) in populations of polynucleotides versus the lengths of the desired nucleic acid sequences.

The percentage of polynucleotides having the corresponding sequence-perfect desired nucleic acid sequence was calculated for each of the 36 populations of polynucleotides generated using the tagging and diluting methods of this example. As shown in Table 20, populations of polynucleotides with the desired nucleic acid sequence (correct consensus sequence) were generated for 33 out of the 36 desired nucleic acid sequences using the methods of this example. In contrast, Commercial Provider 2 was only able to successfully deliver 28 out of the 36 desired nucleic acid sequences. Furthermore, the vCloning methods herein were able to generate all populations of desired nucleic acid sequences that Commercial Provider 2 could, and an additional 5 more. For the populations of polynucleotides generated using vCloning, the percentage of polynucleotides having the sequence-perfect desired nucleic acid sequence were determined using sequencing. The percentages of polynucleotides having the sequence-perfect desired nucleic acid sequence went from 89.0% to 99.0%, with an average of 96.8% and a standard deviation of 2.0% between the populations. The median percentage of polynucleotides having the sequence-perfect desired nucleic acid sequence of the populations was 97.0%. FIG. 16 shows graphically the percentage of polynucleotides having the sequence-perfect desired nucleic acid sequence (error-free molecules) in the populations of polynucleotides for each desired nucleic acid sequence versus the length of DNA of the desired nucleic acid sequence, with error bars denoting the 90% confidence intervals based on the binomial distribution. The percentage of sequence-perfect desired nucleic acid molecules was relatively consistent across the wide range of lengths of the desired nucleic acid sequences, from less than 1 kb to over 5.5 kb. The theoretical yield of percent sequence-perfect desired nucleic acid molecules was laid over for various error rates. The 1:3K line shows the theoretical yield of percent error-free molecules at different lengths of desired nucleic acid sequences using an error rate of 1 error per 3,000 bases (1:3K), the error rate associated with current commercial providers performing non-clonal synthesis. The populations of polynucleotides having the desired nucleic acid sequences using the tagging and diluting methods provided in this example have much higher percentages of error-free molecules. Corresponding lines for error rates of 1:15,000, 1:30,000, and 1:60,000 are also included. Based on the graph, the error rate associated with the methods herein appear to be at most 1 error per 60,000 bases.

In addition to the long-read sequencing performed during and after synthesis, the sequences of populations of polynucleotides including 9 out of the 36 desired nucleic acid sequences were independently verified using traditional cloning by a third party. For each of the 9 desired nucleic acid sequences, 4 bacterial clones were generated, and isolated DNA from the clones was sequenced. All 36 clones (4 clones each for the 9 desired nucleic acid sequence) were 100% sequence-perfect. The 95% binomial confidence interval for 100% (36/36) is 0.9026-1.0000 (90.26%-100%). This result independently validates the performance to at least 90.26% sequence-perfect, and the ability to statistically validate even better performance was only limited by the sample size.

This example demonstrates the methods provided herein are able to generate populations of polynucleotides with a very high percentage of the polynucleotides having the sequence-perfect desired nucleic acid sequence and shows the vastly decreased error rate achieved using these methods versus methods currently available from commercial providers.

Example 4: Polynucleotide Production in Small Samples

In the present example, a population of polynucleotides having a desired nucleic acid sequence is produced using vCloning methods herein, including, for example, molecular barcodes and a dilution step as follows. A desired nucleic acid sequence having a length from 1 kb to 5 kb is selected for synthesis. The desired nucleic acid sequence is analyzed and oligonucleotides that span the entire desired nucleic acid sequence are ordered from a commercial supplier. If short oligonucleotides are ordered, a first assembly (with an optional vCloning step to increase the percentage of sequence-perfect desired polynucleotides) can be performed to generate longer nucleic acid molecules (500-1,000 nucleotides in length). However, nucleic acids of 500-1,000 nucleotides can be ordered directly from commercial suppliers who perform an initial assembly reaction. The nucleic acids are combined in a source sample for an assembly reaction and assembled using any of the methods provided herein. A target number of assembled nucleic acid molecules in the source sample are subset (e.g., sampled or diluted) into a subset sample. The nucleic acid molecules in the subset sample are tagged at both ends with nucleic acids that include molecular barcodes and universal primer binding sites using ligation. The ratio of unique molecular barcodes to nucleic acid molecules in the subset sample is at least 3:1, for example, 4:1, 5:1, 6:1, 7:1, 8:1, 9:1, or 10:1. The tagged nucleic acid molecules are amplified using universal primers that bind to the universal primer binding sites included on the nucleic acids. The amplified tagged nucleic acid molecules are then prepared for sequencing and sequenced to generate sequence reads. The sequencing is performed using a long-read sequencer. The sequences reads are analyzed to identify tagged nucleic acid molecules with the desired nucleic acid sequence, which in some cases is the sequence-perfect desired nucleic acid sequence. The molecular barcodes corresponding to a uniquely tagged sequence-perfect desired nucleic acid molecule are determined. Barcode-targeted PCR is used to specifically amplify the tagged sequence-perfect desired nucleic acid molecule, thereby enriching the desired nucleic acid sequence and generating a population of polynucleotides having a desired nucleic acid sequence.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

What is claimed is:

1. A method of generating a population of polynucleotides, wherein the method comprises:
   (a) separately in each of a set of initial sources of nucleic acid molecules comprising the nucleic acid molecules and a set of between 3 to 1000 unique, non-degenerate barcodes, performing a tagging reaction to produce a set of source samples each comprising at least $1\times10^6$ tagged candidate nucleic acid molecules, wherein each of the tagged candidate nucleic acid molecules comprises a tag comprising one or more of the non-degenerate barcodes;
   (b) diluting a subvolume of each source sample of the set of source samples to form a set of diluted samples each having a target number of the tagged candidate nucleic acid molecules isolated from each source sample in the set of source samples, wherein the target number of the tagged candidate nucleic acid molecules isolated from each source sample is between 10 and 2000 nucleic acid molecules;
   (c) combining a portion of each diluted sample in the set of diluted samples to form a combined diluted sample, wherein the combined diluted sample comprises tagged candidate nucleic acid species derived from one or more of the tagged candidate nucleic acid molecules from each diluted sample of the set of diluted samples, wherein the nucleic acid molecules of each tagged candidate nucleic acid species have an identical nucleic acid sequence comprising the nucleic acid sequence of the one or more tagged candidate nucleic acid molecules from which it was derived, and wherein at least one of the tagged candidate nucleic acid species from each diluted sample in the combined diluted sample is uniquely tagged;
   (d) determining the sequence of at least some of the tagged candidate nucleic acid species from each of the diluted samples in the combined diluted, wherein at least 1 of the tagged candidate nucleic acid species from each diluted sample in the combined diluted sample is a desired uniquely tagged nucleic acid species, wherein the desired uniquely tagged nucleic acid species comprise a sequence-perfect desired nucleic acid sequence; and
   (e) enriching the desired uniquely tagged nucleic acid species from each diluted sample of the set of diluted samples by amplifying in each diluted sample one or more tagged candidate nucleic acid molecules of the desired uniquely tagged nucleic acid species using one or more primers that bind one or more of the barcodes on the tagged candidate nucleic acid molecules of the desired uniquely tagged nucleic acid species to generate a set of populations of product polynucleotides.

2. The method of claim 1, wherein the source sample comprises at least $1\times10^7$ tagged candidate nucleic acid molecules, and wherein the ratio of unique non-degenerate barcode combinations in tags, to candidate nucleic acid molecules in the source sample is between $1:1\times10^4$ and $1:1\times10^7$.

3. The method of claim 2, wherein at least 90% of the product polynucleotides in the population of product polynucleotides have the sequence-perfect desired nucleic acid sequence.

4. The method of claim 1, wherein the target number is determined based on the number of unique non-degenerate barcodes in the set of unique, non-degenerate barcodes or unique nondegenerate barcode combinations selected from the set of unique, non-degenerate barcodes, and wherein the target number is less than the number of unique non-degenerate barcodes in the set of unique, non-degenerate barcodes or unique non-degenerate barcode combinations selected from the set of non-degenerate barcodes.

5. The method of claim 1, wherein one or more of the tagged candidate nucleic acid molecules comprise a tag comprising a combination of at least two of the unique, non-degenerate barcodes and the enriching the desired uniquely tagged nucleic acid species comprises amplifying the one or more tagged candidate nucleic acid molecules of the desired uniquely tagged nucleic acid species using nested PCR with primers that bind two or more of the at least two non-degenerate barcodes on one side of the one or more tagged candidate nucleic acid molecules of the desired uniquely tagged nucleic acid species in successive PCR reactions to generate the population of product polynucleotides.

6. The method of claim 1, wherein the enriching is performed using pre-made primers.

7. The method of claim 1, wherein the sequence is determined for less than $1\times10^6$ tagged candidate nucleic acid species.

8. The method of claim 1, wherein the sequence is determined for between 10 and 100,000 tagged candidate nucleic acid species.

9. The method of claim 1, wherein the nucleic acid sequence is determined for each tagged candidate nucleic acid species in the diluted sample.

10. The method of claim 1, wherein the determining the sequence is performed to an average depth of read of at least 30 per base per tagged candidate nucleic acid species.

11. The method of claim 1, wherein the nucleic acid molecules in the initial sources of nucleic acid molecules have a length, and wherein said length is between 0.2 kilobases (kb) and 1 kb.

12. The method of claim 1, wherein the desired uniquely tagged nucleic acid sequence comprises one or more selected from the group consisting of:
    (i) a secondary structure and wherein the secondary structure is a stem, hairpin, internal loop, or a pseudoknot and/or a high secondary structure percentage,
    (ii) a GC content 25% or less for a stretch of at least 25 nucleotides of, or for the entire desired nucleic acid sequence,
    (iii) a GC content of 75% or more for a stretch of at least 25 nucleotides of, or for the entire desired nucleic acid sequence,
    (iv) a homopolymeric run of 10 or more As or Ts,
    (v) a homopolymeric run of 6 or more Gs or Cs,
    (vi) a repeat sequence of at least 6 nucleotides that is repeated 5 times,
    (vii) a repeat sequence of at least 8 nucleotides that is repeated at least 2 times,
    (viii) a repeat sequence comprising a tandem repeat sequence, and
    (ix) an inverted repeat sequence of at least 6 nucleotides.

13. The method of claim 1, wherein at least one of the non-degenerate barcodes is not unique to one of the tagged candidate nucleic acid species in the diluted sample.

14. The method of claim 1, further comprising removing the tag from the populations of product polynucleotides.

15. The method of claim 1, wherein at least one of the nucleic acid molecules of the set of initial source sample comprises at least one adapter.

16. The method of claim 15, wherein at least one adapter is attached to a 5' end and/or a 3' end of at least one of the nucleic acid molecules of the set of initial source samples.

17. The method of claim 1, wherein the tagging reaction comprises adding the one or more of the non-degenerate barcodes to the nucleic acid molecules by Splicing by Overhang Extension (SOE) or Polymerase Cycling Assembly (PCA).

18. The method of claim 1, further comprising:
assembling the set of populations of product polynucleotides to form a population of subsequent product polynucleotides, wherein each subsequent product polynucleotide is between 1 kb and 50 kb in length.

19. The method of claim 18, wherein the assembling the set of population of product polynucleotides to form the population of subsequent polynucleotides is performed using a method selected from the group consisting of: (i) polymerase cycling assembly (PCA), and (ii) isothermal assembly.

20. The method of claim 1, further comprising, before the tagging reaction, performing an assembly reaction comprising assembling two or more of the nucleic acid molecules in at least one of the initial sources.

21. The method of claim 1, further comprising, concurrently with the tagging reaction, performing an assembly reaction comprising assembling two or more of the nucleic acid molecules in at least one of the initial sources.

22. The method of claim 1, wherein the tagged candidate nucleic acid molecules have a length between 0.2 kilobases (kb) and 50 kb.

23. The method of claim 20, wherein the assembly reaction comprises the assembling the two or more of the nucleic acid molecules by SOE or PCA.

24. The method of claim 21, wherein the assembly reaction comprises the assembling the two or more of the nucleic acid molecules by SOE or PCA.

25. The method of claim 1, wherein, prior to determining the sequence of at least some of the tagged candidate nucleic acid species, amplifying the tagged candidate nucleic acid species.

26. The method of claim 1, wherein the determining the sequence comprises long-read sequencing.

27. The method of claim 18, wherein the assembling the set of population of product polynucleotides to form the population of subsequent polynucleotides is performed using circular DNA assembly.

28. The method of claim 18, wherein the assembling the set of population of product polynucleotides to form the population of subsequent polynucleotides is performed using ligase cycling reaction (LCR).

29. The method of claim 18, wherein the assembling the set of population of product polynucleotides to form the population of subsequent polynucleotides is performed using a method selected from the group consisting of (i) bacterial recombination, and (ii) yeast homologous recombination.

30. The method of claim 18, wherein the assembling the set of population of product polynucleotides to form the population of subsequent polynucleotides is performed using overlap extension PCR.

* * * * *